(12) United States Patent
Preyer et al.

(10) Patent No.: US 11,702,482 B2
(45) Date of Patent: Jul. 18, 2023

(54) TWIN IMMUNE CELL ENGAGER

(71) Applicant: Revitope Limited, Hertfordshire (GB)

(72) Inventors: Martin Preyer, Somerville, MA (US); Allison Colthart, Everett, MA (US); Pamela Weinstein, Cambridge, MA (US); Patrick Wiencek, Cambridge, MA (US); Emma Geiger, Cambridge, MA (US); Werner Meier, Burlington, MA (US)

(73) Assignee: Revitope Limited, Hertfordshire (GB)

(*) Notice: Subject to any disclaimer, the term of this patent is extended or adjusted under 35 U.S.C. 154(b) by 347 days.

(21) Appl. No.: 16/715,621

(22) Filed: Dec. 16, 2019

(65) Prior Publication Data

US 2020/0190213 A1    Jun. 18, 2020

Related U.S. Application Data

(60) Provisional application No. 62/780,770, filed on Dec. 17, 2018.

(51) Int. Cl.
| C07K 16/32 | (2006.01) |
| C07K 16/30 | (2006.01) |
| A61P 35/00 | (2006.01) |

(52) U.S. Cl.
CPC .............. *C07K 16/32* (2013.01); *A61P 35/00* (2018.01); *C07K 16/30* (2013.01); *C07K 2317/31* (2013.01); *C07K 2317/73* (2013.01); *C07K 2319/035* (2013.01); *C07K 2319/74* (2013.01)

(58) Field of Classification Search
CPC combination set(s) only.
See application file for complete search history.

(56) References Cited

U.S. PATENT DOCUMENTS

| 5,610,281 | A | 3/1997 | Brenner et al. |
| 5,844,093 | A | 12/1998 | Kettleborough et al. |
| 5,877,293 | A | 3/1999 | Adair et al. |
| 6,790,939 | B2 | 9/2004 | Reiter et al. |
| 6,969,517 | B2 | 11/2005 | Gillies et al. |
| 7,378,091 | B2 | 5/2008 | Gudas et al. |
| 7,531,174 | B2 | 5/2009 | Sanicola-Nadel et al. |
| 7,632,499 | B2 | 12/2009 | Davies et al. |
| 7,790,165 | B2 | 9/2010 | Zhou et al. |
| 7,867,734 | B2 | 1/2011 | Nakano et al. |
| 7,871,613 | B2 | 1/2011 | Kinoshita et al. |
| 8,039,597 | B2 | 10/2011 | Raitano et al. |
| 8,309,093 | B2 | 11/2012 | Gudas et al. |
| 8,318,163 | B2 | 11/2012 | Appleton et al. |
| 8,877,893 | B2 | 11/2014 | Springer et al. |
| 9,994,646 | B2 | 6/2018 | Christensen et al. |
| 10,035,856 | B2 | 7/2018 | Cobbold |
| 2004/0086503 | A1 | 5/2004 | Cohen et al. |
| 2004/0214235 | A1 | 10/2004 | Mori et al. |
| 2005/0054019 | A1 | 3/2005 | Michaud et al. |
| 2006/0062786 | A1 | 3/2006 | Salcedo et al. |
| 2007/0031414 | A1 | 2/2007 | Adams |
| 2007/0196376 | A1 | 8/2007 | Raeber et al. |
| 2008/0044419 | A1 | 2/2008 | Yayon |
| 2008/0069816 | A1 | 3/2008 | Yazaki et al. |
| 2008/0138898 | A1 | 6/2008 | Zhou et al. |
| 2008/0311134 | A1 | 12/2008 | Junutula et al. |
| 2009/0148436 | A1 | 6/2009 | LaVallie et al. |
| 2009/0175796 | A1 | 7/2009 | Raitano et al. |
| 2009/0175860 | A1 | 7/2009 | Stover et al. |
| 2009/0175866 | A1 | 7/2009 | Yayon et al. |
| 2009/0181034 | A1 | 7/2009 | Gudas et al. |
| 2009/0202546 | A1 | 8/2009 | Harris et al. |
| 2010/0008906 | A1 | 1/2010 | Glaser et al. |
| 2010/0183618 | A1 | 7/2010 | Hasegawa et al. |
| 2010/0278838 | A1 | 11/2010 | Kinch et al. |
| 2010/0298545 | A1 | 11/2010 | Kinch et al. |
| 2010/0330107 | A1 | 12/2010 | Gudas et al. |

(Continued)

FOREIGN PATENT DOCUMENTS

| EP | 0488061 A2 | 6/1992 |
| WO | 1998045331 A2 | 10/1998 |

(Continued)

OTHER PUBLICATIONS

Brinkmann et al (The making of bispecific antibodies, mAbs, vol. 9, Jan. 10, 2017). (Year: 2017).*
Suzuki et al (2012) (1L-23 directly enhances the proliferative and invasive activities of colorectal carcinoma, Oncology Letters, 2012). (Year: 2012).*
Egan et al (2016) (Novel multi-specific heterodimeric antibody format allowing modular assembly of variable domain fragments, mAbs vol. 9 Oct. 27, 2016). (Year: 2016).*
Shah GD et al. Rationale for the development of IMC-3G3, a fully human immunoglobulin G subclass 1 monoclonal antibody targeting the platelet-derived growth factor receptor alpha. Cancer. 116(4 Suppl):1018-26 (2010).

(Continued)

*Primary Examiner* — Laura B Goddard
*Assistant Examiner* — Sarah A Alsomairy
(74) *Attorney, Agent, or Firm* — McNeill Baur PLLC

(57) ABSTRACT

A Twin Immune Cell Engager (TWICE) is a kit or composition for treating cancer comprising a first component and second component. Each component comprises a targeting moiety that binds a tumor antigen expressed by the cancer or an antigen expressed by a non-cancer cell in the tumor microenvironment. In some embodiments, the first and second components each comprise an immune cell binding domain capable of immune cell binding activity when binding the immune cell binding domain in the other component, and a complementary binding domain capable of binding to a complementary antigen when binding the complementary binding domain in the other component. In some embodiments, the first and/or second components comprise a complementary functional domain with activity when targeted to the cancer cell or its microenvironment.

21 Claims, 29 Drawing Sheets

Specification includes a Sequence Listing.

(56) References Cited

U.S. PATENT DOCUMENTS

| | | |
|---|---|---|
| 2011/0028696 A1 | 2/2011 | Cardarelli et al. |
| 2012/0258119 A1 | 10/2012 | Renner et al. |
| 2016/0002356 A1 | 1/2016 | Christensen et al. |

FOREIGN PATENT DOCUMENTS

| | | | |
|---|---|---|---|
| WO | 2004032962 A1 | 4/2004 | |
| WO | 2003064606 A3 | 2/2005 | |
| WO | 2007062466 A1 | 6/2007 | |
| WO | 2007065027 A2 | 6/2007 | |
| WO | 2008143666 A2 | 11/2008 | |
| WO | 2008122551 A9 | 2/2009 | |
| WO | 2009068204 A1 | 6/2009 | |
| WO | 2009089004 A1 | 7/2009 | |
| WO | 2009032949 A3 | 12/2009 | |
| WO | 2010001585 A1 | 1/2010 | |
| WO | 2010111018 A1 | 9/2010 | |
| WO | 2010142990 A1 | 12/2010 | |
| WO | 2011119979 A2 | 9/2011 | |
| WO | 2013104804 A3 | 11/2013 | |
| WO | 2017087789 A1 | 5/2017 | |
| WO | 2017106462 A1 | 6/2017 | |
| WO | 2018020000 A1 | 2/2018 | |
| WO | 2018087172 A1 | 5/2018 | |
| WO | 2018224443 A1 | 12/2018 | |
| WO | WO-2018224443 A1 * | 12/2018 | ............... A61P 29/00 |

OTHER PUBLICATIONS

Shan, "99mTc-labeled succinimidyl-6-hydrazinonicotinate hydrochloride (SHNH)-conjugated visilizumab," Molecular Imaging and Contrast Agent Database (MICAD), 6 pages, 2009 (updated 2010).
Shangguan et al., "Aptamers evolved from live cells as effective molecular probes for cancer study," PNAS 103(32):11838-11843 (2006).
Sheng Q et al. An activated ErbB3/NRG1 autocrine loop supports in vivo proliferation in ovarian cancer cells. Cancer Cell. 17(3):298-310 (2010).
Shi et al., "Latent TGF-β and activation," Nature 474(7351):343-349 (2011).
Shimabukuro-Vornhagen et al., "Cytokine release syndrome," Journal for ImmunoTherapy of Cancer 6(56):1-14 (2018).
Sievers EL et al. Selective ablation of acute myeloid leukemia using antibody-targeted chemotherapy: a phase I study of an anti-CD33 calicheamicin immunoconjugate Blood 93:3678-84 (1999).
Starlets D et al. Cell surface CD74 initiates a signaling cascade leading to cell proliferation and survival. Blood 107:4807-16 (2006).
Stein R et al. CD74: A New Candidate Target for the Immunotherapy of B-Cell Neoplasms Clin Cancer Res 13(18):5556s-5563s (2007).
Stein R et al., "Anti-proliferative activity of a humanized anti-CD74 monoclonal antibody, hLL1, on B-cell malignancies," Blood 104:3705-11 (2004).
Stiff PJ et al. Anti-CD33 monoclonal antibody and etoposide/ cytosine arabinoside combinations for the ex vivo purification of bone marrow in acute nonlymphocytic leukemia. Blood 77 (2): 355-362 (1991).
Strop P et al., "Generating bispecific human IgG1 and IgG2 antibodies from any antibody pair," J. Mol. Biol. 420, 204-219 (2012), Abstract.
Su CC et al. CD30 Is Involved in Inhibition of T-Cell Proliferation by Hodgkin's Reed-Sternberg Cells, Cancer Res 64(6): 2148-2152 (2004).
Suvas S et al. Distinct role of CD80 and CD86 in the regulation of the activation of B cell and B cell lymphoma. J Biol Chem 277: 7766-7775 (2002).
Tai-YT et al. Anti-CS1 humanized monoclonal antibody HuLuc63 inhibits myeloma cell adhesion and induces antibody-dependent cellular cytotoxicity in the bone marrow milieu. Blood 112(4):1329-1337 (2008).
Tang X et al. Anti-TCR antibody treatment activates a novel population of nonintestinal CD8 alpha alpha+ TCR alpha beta+ regulatory T cells and prevents experimental autoimmune encephalomyelitis. J Immunol. 178(10):6043-50 (2007).
Thie H et al. Rise and Fall of an Anti-MUC1 Specific Antibody. PLoS One. Jan. 14, 2011;6(1):e15921.
Thompson HR et al. Tumor B7-H1 Is Associated with Poor Prognosis in Renal Cell Carcinoma Patients with Long-term Follow-up. Cancer Res 66(7):3381-3385 (2006).
Torphy et al., "Newly Emerging Immune Checkpoints: Promises for Future Cancer Therapy," Int. J. Mol. Sci. 18(2642):1-13 (2017).
Toshiro I et al. Analysis of the Role of Negative T Cell Costimulatory Pathways in CD4 and CD8 T Cell-Mediated Alloimmune Responses In Vivo. JImmunol, 174: 6648-6656 (2005).
Travis et al., "TGF-β Activation and Function in Immunity," Annu Rev Immunol. 32:51-82 (2014).
Tsushima F et al. Interaction between B7-H1 and PD-1 Determines Initiation and Reversal of T-Cell Anergy. Blood 110(10): 180-185 (2007).
Uckun FM et al. "Temporal association of CD40 antigen expression with discrete stages of human B-cell ontogeny and the efficacy of anti-CD40 immunotoxins against clonogenic B-lineage acute lymphoblastic leukemia as well as B-lineage non-Hodgkin's lymphoma cells," Blood 76 (12) 2449-2456 (1990).
Van Rhee F et al. Combinatorial efficacy of anti-CS1 monoclonal antibody elotuzumab (HuLuc63) and bortezomib against multiple myeloma. Mol Cancer Ther. 8(9): 2616-2624 (2009).
Vazquez-Lombardi et al., "Challenges and opportunities for non-antibody scaffold drugs," Drug Discov Today, 13 pages (2015).
Vazquez-Lombardi et al., "Molecular Engineering of Therapeutic Cytokines," Antibodies 2:426-451 (2013).
Verma-B. et al. TCR Mimic Monoclonal Antibody Targets a Specific Peptide/HLA Class I Complex and Significantly Impedes Tumor Growth In Vivo Using Breast Cancer Models J Immunol. 184: 2156-2165 2010.
Vincenti, F. What's in the pipeline? New immunosuppressive drugs in transplantation. Am J Transplant 2:898-903 (2002) (abstract).
Von Kreudenstein et al., "Improving biophysical properties of a bispecific antibody scaffold to aid developability: quality by molecular design," mAbs; 5:646-54 (2013).
Vyth-Dreese FA et al. Localization in situ of costimulatory molecules and cytokines in B-cell non-Hodgkin's lymphoma. Immunology 94: 580-586 (1998).
Whiteside et al., "Emerging Opportunities and Challenges in Cancer Immunotherapy," Clin Cancer Res 22(8):1845-1856 (2016).
WHO Drug Information, International Nonproprietary Names for Pharmaceutical Substances (INN) vol. 24, No. 2, 2010 INN_PL103.
Witzig TE et al. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma. J Clin Oncol 20:2453-6 (2003) (abstract).
Wu et al., "Reprogramming the tumor microenvironment: tumor-induced immunosuppressive factors paralyze T cells," OncoImmunology 4:7:e1016700, 14 pages (2015).
Wu et al., "Trispecific antibodies enhance the therapeutic efficacy of tumor-directed T cells through T cell receptor co-stimulation," Nat Cancer 1, 86-98 (2019).
Xu C et al. Human anti-CXCR4 antibodies undergo VH replacement, exhibit functional V-region sulfation, and define CXCR4 antigenic heterogeneity. J Immunol 179(4): 2408-2418 (2007).
Xu et al., "Production of bispecific antibodies in 'knobs-intoholes' using a cell-free expression system," mAbs, 7:1, 231-242 (2015).
Yang et al., "Tumor-associated macrophages: from basic research to clinical application," Journal of Hematology & Oncology 10:58, 12 pages (2017).
Zambello R et al. Analysis of TNF-receptor and ligand superfamily molecules in patients with lymphoproliferative disease of granular lymphocytes. Blood 96:647-54 (2000).
Zegers et al., "RadiotherapyCombinedwith the Immunocytokine L19-IL2 Provides Long-lasting Antitumor Effects," Clin Cancer Res; 21(5):1151-1161 ( 2015).

(56) References Cited

OTHER PUBLICATIONS

Zhang, "CD73: A novel target for cancer immunotherapy," Cancer Res. 70(16):6407-6411 (2010).

Zhu et al., "Progress in Aptamer-Mediated Drug Delivery Vehicles for Cancer Targeting and Its Implications in Addressing Chemotherapeutic Challenges," Theranostics 4(9):931-944 (2014).

Ziani et al., "Alteration of the Antitumor immune Response by Cancer-Associated Fibroblasts," 9(414):1-14 (2018).

Exley MA et al. Selective activation, expansion, and monitoring of human iNKT cells with a monoclonal antibody specific for the TCR alpha-chain CDR3 loop. Eur J Immunol. 38(6):1756-66 (2008).

Fischer T et al. Reassessment of CXCR4 chemokine receptor expression in human normal and neoplastic tissues using the novel rabbit monoclonal antibody UMB-2. PLoS One. 3(12):e4069 (2008).

Fossella V et al. Phase II trial of BB-10901 (huN901-DM1) given weekly for four consecutive weeks every 6 weeks in patients with relapsed SCLC and CD56-positive small cell carcinoma. J Clin Oncol 23(16_suppl): 7159-7159 (2005) (abstract).

Franke, et al., "Cell Surface Receptor-Targeted Therapy of Acute Myeloid Leukemia: A Review," Cancer Biother Radiopharm 2000, 15:459-76, Abstract.

Garrett J et al. Antibodies specifically targeting a locally misfolded region of tumor associated EGFR, PNAS 2009, Supplemental Information, 7 pages.

Gassmann P et al. CXCR4 regulates the early extravasation of metastatic tumor cells in vivo. Neoplasia. 11(7):651-61. (2009).

Gerber, et al., "Antibody drug-conjugates targeting the tumor vasculature," mAbs 1:247-253 (2009).

Goff L et al. Phase I study of pf-03446962, a fully human mab against alk 1, a TGFbeta receptor involved in tumor angiogenesis J Clin Oncol 28(15 suppl):3034 (2010) (abstract).

Guckel B et. Anti-CD2 antibodies induce T cell unresponsiveness in vivo. J Exp Med 174:957, (1991).

Gulley et al., "Preliminary results from a phase 1 trial of M7824 (MSB0011359C), a bifunctional fusion protein targeting PD-L1 and TGF-β, in advanced solid tumors," J. Clin Oncol 35(15) suppl:3006 (2017).

Gunasekaran et al., "Enhancing Antibody Fc Heterodimer Formation through Electrostatic Steering Effects," Journal of Biological Chemistry 285(25):19637-46 (2010).

Guo, et al., "Therapeutic cancer vaccines: past, present, and future," Adv Cancer Res. 119:421-475 (2013).

Haanen, "Converting Cold into Hot Tumors by Combining Immunotherapies," Cell 170:1055-56 (2017).

Hamanishi J et al. Programmed cell death 1 ligand 1 and tumor infiltrating CD8 T lymphocytes are prognostic factors of human ovarian cancer. Proc Natl Acad Sci 105(9):3360-65 (2007).

Han et al., "TGF-β signaling and its targeting for glioma treatment," Am J. Cancer Res 5(3):945-955 (2015).

Harris et al., "Immuno-oncology combinations: raising the tail of the survival curve," Cancer Biol Med 13(2):171-193 (2016).

Hauswirth AW et al. The Target Receptor Siglec-3 (CD33) Is Expressed on AML Stem Cells in a Majority of All Patients with AML Blood 106 (11): 4324 (2005)(abstract).

Henderikx H et al. Human Single-Chain Fv Antibodies to MUC1 Core Peptide Selected from Phage Display Libraries Recognize Unique Epitopes and Predominantly Bind Adenocarcinoma, Cancer Research 58:4324-4332, Oct. 1998.

Herbst et al., "Predictive correlates of response to the anti-PD-L1 antibody MPDL3280A in cancer patients," Nature 515(7528):563-567 (2014).

Herbst R et al. B-cell depletion in vitro and in vivo with an afucosylated anti-CD19 antibody. J Pharmacol Exp Ther 335:213-22 (2010).

Herold KC et al. Treatment of patients with new onset Type 1 diabetes with a single course of anti-CD3 mAb Teplizumab preserves insulin production for up to 5 years. Clin Immunol. 132(2):166-73 (2009).

Hsi ED et al. CS1, a potential new therapeutic antibody target for the treatment of multiple myeloma. Clin Cancer Res. 14(9): 2775-2784 (2008).

Huang et al., "Cancer-associated fibroblasts in digestive tumors," World J Gastroenterol 20(47):17804-17818 (2014).

Hulkkonen J et al. Surface antigen expression in chronic lymphocytic leukemia: clustering analysis, interrelationships and effects of chromosomal abnormalities. Leukemia 16:178-185 (2002).

Hu-Lowe et al., "Targeting Activin Receptor-Like Kinase 1 (ALK1) Inhibits Angiogenesis and Tumorigenesis Through a Mechanism of Action Complementary to Anti-VEGF Therapies," Cancer Res 71(4):1362-1373 (2011).

Ishida M et al. Differential expression of PD-L1 and PD-L2, ligands for an inhibitory receptor PD-1, in the cells of lymphohematopoietic tissues. Immunol Lett 84(1):57-62 (2002).

Israel BF et al. Anti-CD70 antibodies: a potential treatment for EBV+ CD70-expressing lymphoma., Mol Cancer Ther 4(12):2037-2044 (2005).

Iwai Y et al. Involvement of PD-L1 on tumor cells in the escape from host immune system and tumor immunotherapy by PD-L1 blockade. Proc Natl Acad Sci 19(19):12293-12297 (2002).

Johnson NA et al. Diffuse large B-cell lymphoma: reduced CD20 expression is associated with an inferior survival. Blood 113:3773-3780 (2009).

Kaminski MS et al. Radioimmunotherapy with iodine (131)I tositumomab for relapsed or refractory B-cell non-Hodgkin lymphoma: updated results and long-term follow-up of the University of Michigan experience. Blood 96:1259-66 (2000).

Kansas GS et al. Transmembrane signals generated through MHC class II, CD19, CD20, CD39, and CD40 antigens induce LFA-1-dependent and independent adhesion in human B cells through a tyrosine kinase-dependent pathway. J Immunol 147:4094-4102 (1991) (abstract).

Kater AP et al. CD40 stimulation of B-cell chronic lymphocytic leukaemia cells enhances the anti-apoptotic profile, but also Bid expression and cells remain susceptible to autologous cytotoxic T-lymphocyte attack. Br J Haematol 127:404-415 (2004) (abstract).

Khan et al., "Microbead Arrays for the Analysis of ErbB Receptor Tyrosine Kinase Activation and Dimerization in Breast Cancer Cells," ASSAY and Drug Development Technologies 8(1):27-36 (2010).

Knee et al., "Rationale for anti-GITR cancer immunotherapy," European Journal of Cancer 67:1-10 (2016).

Kobold et al., "Rationale for Combining Bispecific T Cell Activating Antibodies With Checkpoint Blockade for Cancer Therapy," Frontiers in Oncology 8(285):1-8 (2018).

Koenecke C et al. In vivo application of mAb directed against the gammadelta TCR does not deplete but generates "invisible" gammadelta T cells. Eur J Immunol. 39(2):372-9 (2009).

Kreitman RJ et al. Efficacy of the anti-CD22 recombinant immunotoxin BL22 in chemotherapy-resistant hairy-cell leukemia. N Engl J Med 345:241-47 (2001).

Kuhn C et al. Human CD3 transgenic mice: preclinical testing of antibodies promoting immune tolerance. Sci Transl Med. 3(68):68ra10 (Feb. 2011).

Kuhn et al., "Therapeutic anti-CD3 monoclonal antibodies: From bench to bedside," Immunotherapy 8(8), 889-906 (2016).

Latchman YE et al. PD-L1-deficient mice show that PD-L1 on T cells, antigen-presenting cells, and host tissues negatively regulates T cells. Proc Natl Acad Sci 101(29):10691-10696 (2004).

Latinne D et al. An anti-CD2 mAb induces immunosuppression and hyporesponsiveness of CD2+ human T cells in vitro. Int Immunol 8:1113 (1996)(abstract).

Lavasani S et al. Monoclonal antibody against T-cell receptor alphabeta induces self-tolerance in chronic experimental autoimmune encephalomyelitis. Scand J Immunol. 65(1):39-47 (2007).

Lee HT et al., "Molecular mechanism of PD-1/PD-L1 blockade via anti-PD-L1 antibodies atezolizumab and durvalumab," Sci Rep 7:5532 (2017).

Lee JK et al. CS1 (CRACC, CD319) induces proliferation and autocrine cytokine expression on human B lymphocytes. J Immunol 179:4672-4678 (2007).

(56) References Cited

OTHER PUBLICATIONS

Lee-Hoeflich et al., "A Central Role for HER3 in HER2-Amplified Breast Cancer: Implications for Targeted Therapy," Cancer Res 68(14):5878-5887 (2008).
Lens SM et al. Aberrant expression and reverse signalling of CD70 on malignant B cells. Br J Haematol 106: 491-503 (1999).
Leonard JW et al. A phase I/II study of galiximab (an anti-CD80 monoclonal antibody) in combination with rituximab for relapsed or refractory, follicular lymphoma. Ann Oncol 18(7):1216-1223 (2007).
Li et al., "Inhibition of Cell Proliferation by an Anti-EGFR Aptamer," PLoS One 6(6):1-10 (2011).
Löffek "Transforming of the Tumor Microenvironment: Implications for TGF-β Inhibition in the Context of Immune-Checkpoint Therapy," Journal of Oncology, ARticle ID 9732939, 9 pages (2018).
Loizos N et al. Targeting the platelet-derived growth factor receptor alpha with a neutralizing human monoclonal antibody inhibits the growth of tumor xenografts: implications as a potential therapeutic target. Mol Cancer Ther. 4(3):369-79 (2005).
"Scholar Rock Demonstrates that Highly Specific TGFβ1 Inhibition Combined with Anti-PDI Drives Tumor Regression and Survival Benefit in Preclinical Models of Primary Resistance to Checkpoint Blockade Therapy," Scholar Rock http://www.scholarrock.com/platform/publications/ 3 pages (2018).
"Supracellular Activation—A New Way to Target Disease," Scholar Rock 2019.
"Tumor Associated Macrophages as a Novel Target for Cancer Therapy," Amgen, 8 pages (2017).
Ahern et al., "Co-administration of RANKL and CTLA4 Antibodies Enhances Lymphocyte-Mediated Antitumor Immunity in Mice," Clin Cancer Res 23(19):5789-5802 (2017).
Akashi-T et al. Chemokine receptor CXCR4 expression and prognosis in patients with metastatic prostate cancer. Cancer Sci 99(3):539-542 (2008).
Amlot PL et al. A phase I study of an anti-CD22-deglycosylated ricin A chain immunotoxin in the treatment of B-cell lymphomas resistant to conventional therapy. Blood 82:2624-2633 (1993).
Antonia et al., "Safety and antitumour activity in a phase 1b study of combined checkpoint blockade with anti-PD-L1 (durvalumab) and anti-CTLA4 (tremelimumab) in non-small cell lung cancer," Lancet Oncol. 17(3):299-308 (2016).
Atwell et al., "Stable heterodimers from remodeling the domain interface of a homodimer using a phage display library," Journal of Molecular Biology 270:26-35 (1997).
Baitsch et al. "The three main stumbling blocks for anticancer T cells," Trends Immunol. 33(7):364-72 (2012).
Barnett et al., "Targeted Therapy for Cancer-Associated Fibroblasts: Are We There Yet?" JNCI Natl Cancer Inst 110(1):11-13 (2018).
Barth-S et al. Ki-4(scFv)-ETA', a new recombinant anti-CD30 immunotoxin with highly specific cytotoxic activity against disseminated Hodgkin tumors in SCID mice. Blood 95 (12): 3909-3914 (2000).
Bedinger et al., "Development and characterization of human monoclonal antibodies that neutralize multiple TGFb isoforms," MABS 8(2):389-404 (2016).
Blanc V et al. SAR3419: An Anti-CD19-Maytansinoid Immunoconjugate for the Treatment of B-Cell Malignancies. Clin Cancer Res 17(20):6448-6458 (2011).
Blank C et al. Blockade of PD-L1 (B7-H1) augments human tumor-specific T cell responses in vitro. Int J Cancer 119:317-327 (2006) (abstract).
Brahmer JR et al. Phase I study of single-agent anti-programmed death-1 (MDX-1106) in refractory solid tumors: safety, clinical activity, pharmacodynamics, and immunologic correlates. J Clin Oncol 28:3167-3175 (2010).
Brennen et al., "Rationale Behind Targeting Fibroblast Activation Protein-Expressing Carcinoma-Associated Fibroblasts as a Novel Chemotherapeutic Strategy," Mol Cancer Ther 11(2):257-266 (2012).

Brischwein K., et al., "MT110: A novel bispecific single-chain antibody construct with high efficacy in eradicating established tumors," Mol Immunol 43(8):1129-43 (2006), Abstract.
Broil K et al. CD137 Expression in Tumor Vessel Walls: High Correlation with Malignant Tumors. Am J Clin Pathol 115(4)543-549 (2001).
Bromberg JS et al. Anti-CD2 monoclonal antibodies alter cell-mediated immunity in vivo. Transplantation 51:219 (1991) (abstract).
Buchbinder et al., "CTLA-4 and PD-1 Pathways Similarities, Differences, and Implications of Their Inhibition," American Journal of Clinical Oncology 39(1):98-106 (2016).
Bullock TN et al. Induction of CD70 on dendritic cells through CD40 or TLR stimulation contributes to the development of CD8+ T cell responses in the absence of CD4+ T cells. J Immunol 174:710-7 (2005).
Burton JD et al. CD74 Is Expressed by Multiple Myeloma and Is a Promising Target for Therapy. Clin Cancer Res 10(19):6606-6611 (2004).
Campbell JJ et al. Unique subpopulations of CD56+ Nk and NK-T peripheral blood lymphocytes identified by chemokine receptor expression repertoire. J Immunol 166(11):6477-82 (2001).
Carnahan J et al. Epratuzumab, a humanized monoclonal antibody targeting CD22: characterization of in vitro properties. Clin Cancer Res 9(10 Pt 2):3982S-90S (2003) (abstract).
Caron PC et al. Biological and Immunological Features of Humanized M195 (Anti-CD33) Monoclonal Antibodies. Cancer Res 52(24): 6761-6767 (1992).
Carter P et al. Humanization of an anti-p185HER2 antibody for human cancer therapy. Proc Natl Acad Sci U S A. 89(10):4285-9 1992.
Chang CH et al. Effective therapy of human lymphoma xenografts with a novel recombinant ribonuclease/anti-CD74 humanized IgG4 antibody immunotoxin. Blood 106:4308-14 (2005).
Chatenoud-L et al. CD3-specific antibodies: a portal to the treatment of autoimmunity. Nat Rev Immunol 7(8):622-32 (2007). Epub Jul. 20, 2007. (abstract).
Chen et al., "Molecular mechanisms of T cell co-stimulation and co-inhibition," Nat Rev Immunol. 13(4):227-242 (2013).
Chen et al., "Molecular Pathways: Next-Generation Immunotherapy-Inhibiting Programmed Death-Ligand 1 and Programmed Death-1," Clin Cancer Res 18(24):6580-6588 (2012).
Cho EY et al. Immunohistochemical study of the expression of adhesion molecules in ovarian serous neoplasms. Pathol Int 56(2):62-70 (2006) (abstract).
Chung WC et al., CREB Mediates Prostaglandin F2α-Induced MUC5AC Overexpression, J Immunol. 182(4):2349-56 (2009).
Coiffier B et al. Rituximab in combination with CHOP improves survival in elderly patients with aggressive non-Hodgkin's lymphoma. Semin Oncol 29(2 Suppl 6):18-22 (2002) (abstract).
Conrad ML et al. TCR and CD3 antibody cross-reactivity in 44 species. Cytometry A. 71(11):925-33 (2007).
Cooke et al., "EFab domain substitution as a solution to the light-chain pairing problem of bispecific antibodies," mAbs 10(8):1248-1259 (2018).
Cooper MA et al. Human natural killer cells: a unique innate immunoregulatory role for the CD56(bright) subset. Blood 97(10):3146-51 (2001).
Cordone I et al. Diagnostic relevance of peripheral blood Immunocytochemistry in hairy cell leukemia. J Clin Pathol 48:955-960 (1995).
D'Arena G et al. Quantitative flow cytometry for the differential diagnosis of leukemic B-cell chronic lymphoproliferative disorders. Am J Hemat 64:275-281 (2000) (abstract).
Da Costa L et al. Immunoscintigraphy in Hodgkin's disease and anaplastic large cell lymphomas: results in 18 patients using the iodine radiolabeled monoclonal antibody HRS-3. Ann Oncol. Sep;3 Suppl 4: 53-7 (1992)(abstract).
Daifotis et al., "Anti-CD3 clinical trials in type 1 diabetes mellitus," Clin Immunol. 149(3):268-78, Abstract (2013).
Davis et al., "SEED bodies: fusion proteins based on strand-exchange engineered domain (SEED) CH3 heterodimers in an Fc

(56) References Cited

OTHER PUBLICATIONS analogue platform for asymmetric binders or immunofusions and bispecific antibodies," Protein Engineering, Design & Selection 23(4):195-202 (2010).
De Groot et al., "The anti-tumor effect of RANKL inhibition in malignant solid tumors—A systematic review," Cancer Treatment Reviews 62:18-28 (2018).
De Maria A et al. Revisiting human natural killer cell subset function revealed cytolytic CD56(dim)CD16+ NK cells as rapid producers of abundant IFN-gamma on activation. Proc Natl Acad Sci 108:728-32 (2011).
De Sousa Linhares et al., "Not All Immune Checkpoints Are Created Equal," Frontiers in Immunology 9(1909):1-15 (2018).
Dean et al., "Combination therapies in the context of anti-CD3 antibodies for the treatment of autoimmune diseases," Swiss Med Wkly 142:w13711, 31 pages (2012).
Deetz CO et al. Gamma interferon secretion by human Vgamma2Vdelta2 T cells after stimulation with antibody against the T-cell receptor plus the Toll-Like receptor 2 agonist Pam3Cys. Infection and Immunity. 74(8):4505-4511 (2006).
Dogan A et al. Follicular lymphomas contain a clonally linked but phenotypically distinct neoplastic B-cell population in the interfollicular zone Blood 91: 4708-4714 (1998).
Dolloff NG et al. Human bone marrow activates the Akt pathway in metastatic prostate cells through transactivation of the alpha-platelet-derived growth factor receptor. Cancer Res. 67(2):555-62 (2007).
Dong H et al. Costimulating aberrant T cell responses by B7-H1 autoantibodies in rheumatoid arthritis. J Clin Invest 111:363-370 (2003).
Dorfman DM et al. In vivo expression of B7-1 and B7-2 by follicular lymphoma cells can prevent induction of T-cell anergy but is insufficient to induce significant T-cell proliferation. Blood 90: 4297-4306 (1997).
Luqman M et al. The antileukemia activity of a human anti-CD40 antagonist antibody, HCD122, on human chronic lymphocytic leukemia cells Blood 112(3):711-720 (2008).
Lyu et al., "Generating Cell Targeting Aptamers for Nanotheranostics Using Cell-SELEX," Theranostics 6 (9):1440-1452 (2016).
Maddipatla-S et al. Augmented Antitumor Activity against B-Cell Lymphoma by a Combination of Monoclonal Antibodies Targeting TRAIL-R1 and CD20. Clin Cancer Res 13(15):4556-4564 (2007).
Maeda-N. Susceptibility of human T-cell leukemia virus type I-infected cells to humanized anti-CD30 monoclonal antibodies in vitro and in vivo. Cancer Sci 101(1):224-30 (2010) (epub Sep. 8, 2009) (abstract).
Mancuso P, et al. Validation of a standardized method for enumerating circulating endothelial cells and progenitors: flow cytometry and molecular and ultrastructural analyses Clin Cancer Res 15:267-73 (2009).
Marin-Acevedo et al., "Next generation of immune checkpoint therapy in cancer: new developments and challenges," Journal of Hematology & Oncology 11(39):1-20 (2018).
Martlnez-Torrecuadrada J et al. Targeting the extracellular domain of fibroblast growth factor receptor 3 with human single-chain Fv antibodies inhibits bladder carcinoma cell line proliferation. Clin Cancer Res 11(17):6280-90 (2005).
Martinhoe, O. et al. Expression, mutation and copy number analysis of platelet-derived growth factor receptor A (PDGFRA) and its ligand PDGFA in gliomas. Br J Cancer 101:973-982 (2009).
Masharani UB and Becker J. Teplizumab therapy for type 1 diabetes. Expert Opin Biol Ther. 10(3):459-65 (2010).
Matthews JB et al. Clinical Trials of Transplant Tolerance: Slow But Steady Progress. Am J Transplant 3:794-803 (2003).
McLaughlin P et al. Rituximab chimeric anti-CD20 monoclonal antibody therapy for relapsed indolent lymphoma: half ol patients respond to a four-dose treatment program. J Clin Oncol 16:2825-33 (1998) (abstract).
Melero I et al. Monoclonal antibodies against the 4-1BB T-cell activation molecule eradicate established tumors. Nat Med 3:682-5 (1997) (abstract).

Melter M et al. Ligation of CD40 induces the expression of vascular endothelial growth factor by endothelial cells and monocytes and promotes angiogenesis in vivo. Blood 96:3801-3808 (2000).
Mirisola-V. et al. CXCL12/SDF1 expression by breast cancers is an independent prognostic marker of disease-free and overall surviva., Eur J Cancer 45(14):2579-87 (2009) (abstract).
Moore et al., "A novel bispecific antibody format enables simultaneous bivalent and monovalent co-engagement of distinct target antigens," mAbs 3, 546-557 (2011).
Moulin et al., "Structures of a pan-specific antagonist antibody complexed to different isoforms of TGFβ reveal structural plasticity of antibody-antigen interactions," Protein Science 23:1698-1707 (2014).
Naeem S et al. Bone marrow involvement in systemic ALK+ anaplastic large cell lymphoma: morphological resemblance with Hodgkin's lymphoma. J Coll Physicians Surg Pak 16(2):148-9 (2006) (abstract).
Nasreen M et al. In vivo treatment of class II MHC-deficient mice with anti-TCR antibody restores the generation of circulating CD4 T cells and optimal architecture of thymic medulla. J Immunol. 171(7):3394-400 (2003).
Ni "Non-Redundant Roles of New Immune Checkpoints in Cancer Evasion," Immunotherapy 3(3):1000145 (2017).
Niu L et al. Cytokine-mediated disruption of lymphocyte trafficking, hemopoiesis, and induction of lymphopenia, anemia, and thrombocytopenia in anti-CD137-treated mice. J Immunol. 178(7): 4194-4213 (2007).
Movellino et al., "A listing of human tumor antigens recognized by T cells," Cancer Immunol Immunother. 54(3):187-207 (2005), Abstract.
Oh et al., "TGF-β: Guardian of T Cell Function," J. Immunol. 191(8):3973-3979 (2013).
Olafsen T et al. Characterization of engineered anti-p185HER-2 (scFv-CH3)2 antibody fragments (minibodies) for tumor targeting, Protein Engineering, Design & Selection 17(4):315-323, 2004.
Otsuka S and Bebb G. The CXCR4/SDF-1 Chemokine Receptor Axis. J Thorac Oncol. 3: 1379-1383 (2008).
Palazon A et al. Agonist anti-CD137 mAb act on tumor endothelial cells to enhance recruitment of activated T lymphocytes. Cancer Res. 71(3):801-11 (Feb. 2011).
Park et al., "Future prospects of immune checkpoint blockade in cancer: from response prediction to overcoming resistance," Experimental & Molecular Medicine 50(109):1-13 (2018).
Parmiani et al., "Unique Human Tumor Antigens: Immunobiology and Use in Clinical Trials," J Immunol. 178:1975-9 (2007).
Pavoni E. et al., Selection, affinity maturation, and characterization of a human scFv antibody against CEA protein, BMC Cancer, Feb. 6:41 (2006).
Pessano S et al. The T3/T cell receptor complex: antigenic distinction between the two 20-kd T3 (T3-6 and T3-E) subunits. EMBO Journal 4(2):337-344 (1985).
Pinto A et al. Human eosinophils express functional CD30 ligand and stimulate proliferation of a Hodgkin's disease cell line. Blood 88 (9) 3299-3305 (1996).
Pogue et al., "Targeting Attenuated Interferon-α to Myeloma Cells with a CD38 Antibody Induces Potent Tumor Regression with Reduced Off-Target Activity," PLoS One 11(9):e0162472 (2016).
Pogue et al., :Targeting attenuated cytokines to tumor cells results in robust tumor killing with significantly reduced off-target activity: Anti-CD38-Attenukine, Cytokine 76(1):66 (2015).
Poh et al., "Targeting Macrophages in Cancer: From Bench to Bedside," Frontiers in Oncology 8(49):1-16 (2018).
Przepiorka D et al. A phase II study of BTI-322, a monoclonal anti-CD2 antibody, for treatment of steroid-resistant acute graft-versus-host disease. Blood 92: 4066-4071 (1998).
Ranheim EA et al, Expression of CD27 and its ligand, CD70, on chronic lymphocytic leukemia B cells. Blood 85: 3556-65 (1995).
Reschke M et al. HER3 is a determinant for poor prognosis in melanoma. Clin Cancer Res. 14(16):5188-97 (2008).
Richards J et al. Phase I evaluation of humanized OKT3: toxicity and immunomodulatory effects of hOKT3gamma4. Cancer Res. 59(9):2096-10. (1999).

(56) References Cited

OTHER PUBLICATIONS

Ridgway et al., "'Knobs-into-holes' engineering of antibody CH3 domains for heavy chain heterodimerization," Protein Eng 9(7):617-621 (1996).

Ries et al., "Targeting Tumor-Associated Macrophages with Anti-CSF-1R Antibody Reveals a Strategy for Cancer Therapy," Cancer Cell 25:846-859 (2014).

Rinderknecht M et al. Phage-Derived Fully Human Monoclonal Antibody Fragments to Human Vascular Endothelial Growth Factor-C Block Its Interaction with VEGF Receptor-2 and 3, PLoS One, Aug. 2010 5(8):1-16.

Robbins BA et al. Diagnostic application of two-color flow cytometry in 161 cases of hairy cell leukemia. Blood 82:1277-87 (1993).

Robinson MK et al. Targeting ErbB2 and ErbB3 with a bispecific single-chain Fv enhances targeting selectivity and induces a therapeutic effect in vitro. British Journal of Cancer 99:1415-1425 (2008).

Roguska MA et al. Humanization of murine monoclonal antibodies through variable domain resurfacing. Proc Natl Acad Sci 91(3):969-73 (1994).

Roland J et al. Role of the intracellular domains of CXCR4 in SDF-1-mediated signaling. Blood. 101:399-406 (2003).

Roy DC et al. Anti-MY9-blocked-ricin: an immunotoxin for selective targeting of acute myeloid leukemia cells. Blood 77(11):2404-2412 (1991).

Russell MR et al. Targeting the {alpha} receptor for platelet-derived growth factor as a primary or combination therapy in a preclinical model of prostate cancer skeletal metastasis. Clin Cancer Res. 16(20):5002-10 (2010).

Sato S et al. Altered blood B lymphocyte homeostasis in systemic sclerosis: expanded naive B cells and diminished but activated memory B cell. Arthritis Rheum 50:1918-1927 (2004) (abstract).

Scartozzi M et al. The role of HER-3 expression in the prediction of clinical outcome for advanced colorectal cancer patients receiving irinotecan and cetuximab. Oncologist. 16(1):53-60 (Epub Jan. 6, 2011).

Schlapschy M et al. Functional humanization of an anti-CD30 Fab fragment for the immunotherapy of Hodgkin's lymphoma using an in vitro evolution approach. Protein Eng Des Sel 17(12):847-860 (2004).

Schoeberl B et al. An ErbB3 antibody, MM-121, is active in cancers with ligand dependent activation. Cancer Res. 70(6): 2485-2494 (2010).

International Search Report and Written Opinion issued in International Application No. PCT/US2019/066542, dated Jun. 23, 2020, 21 pages.

* cited by examiner

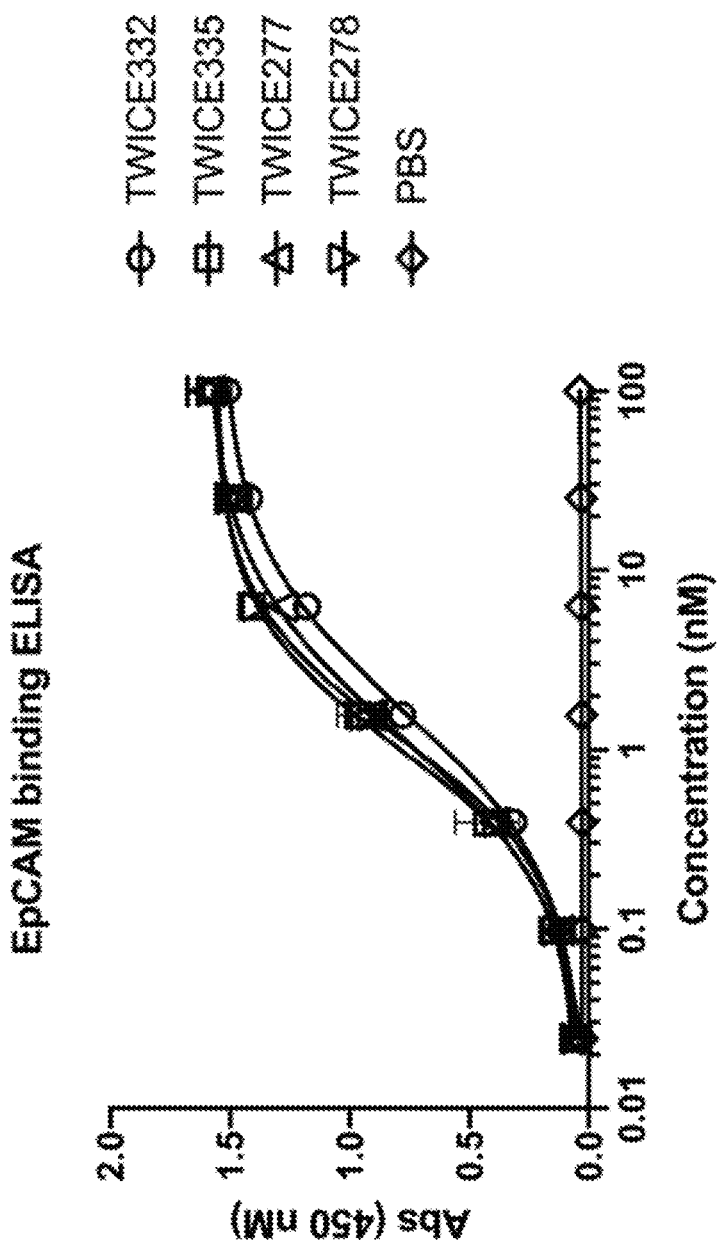

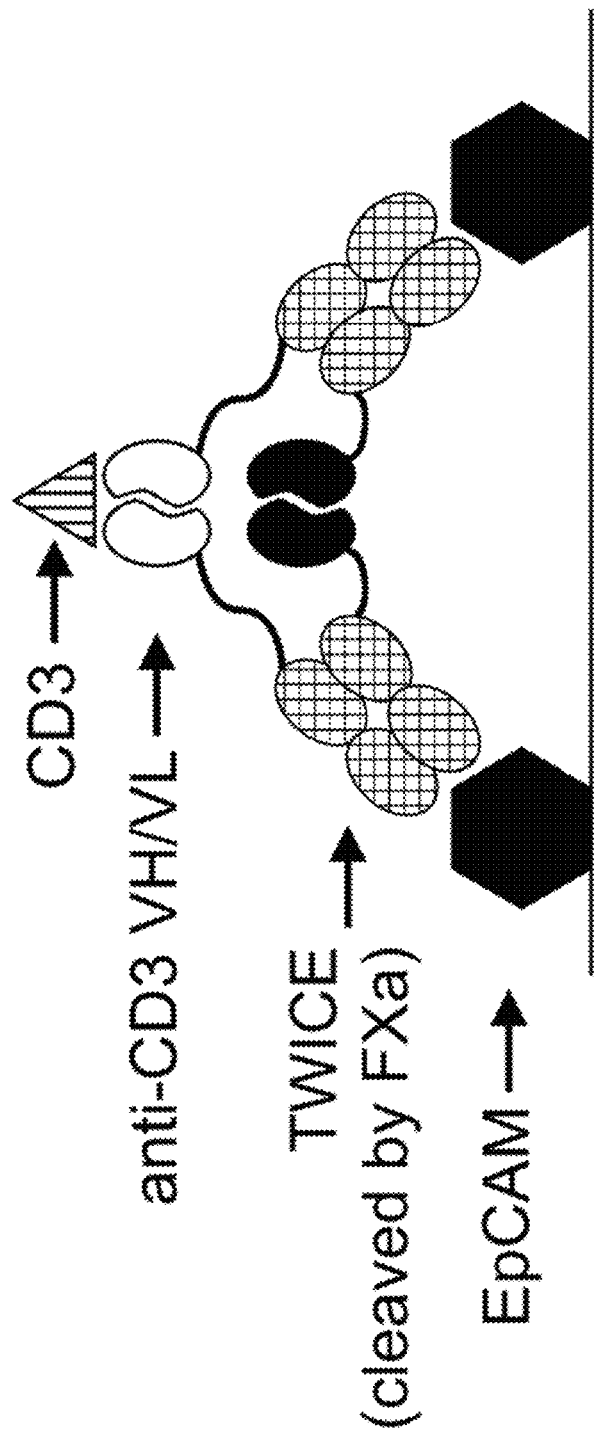

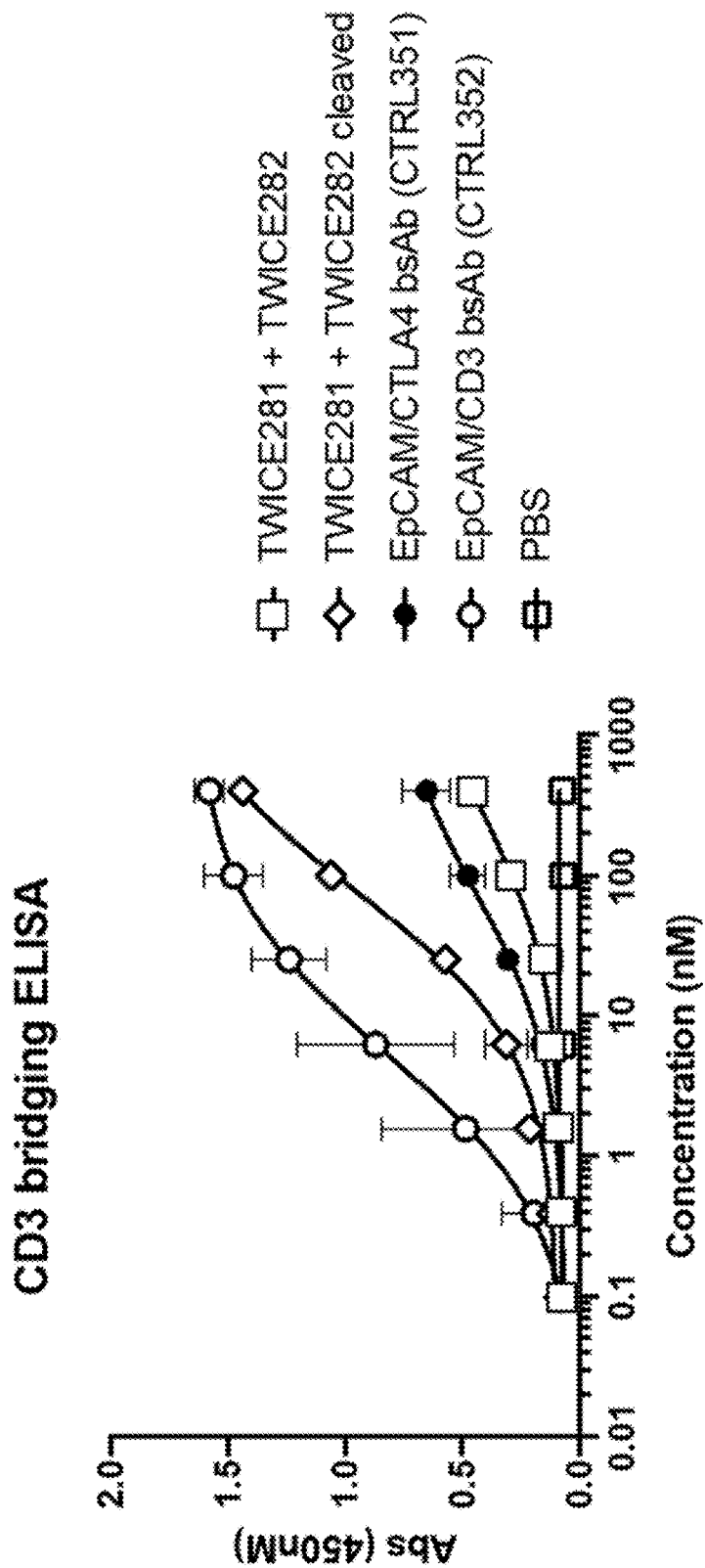

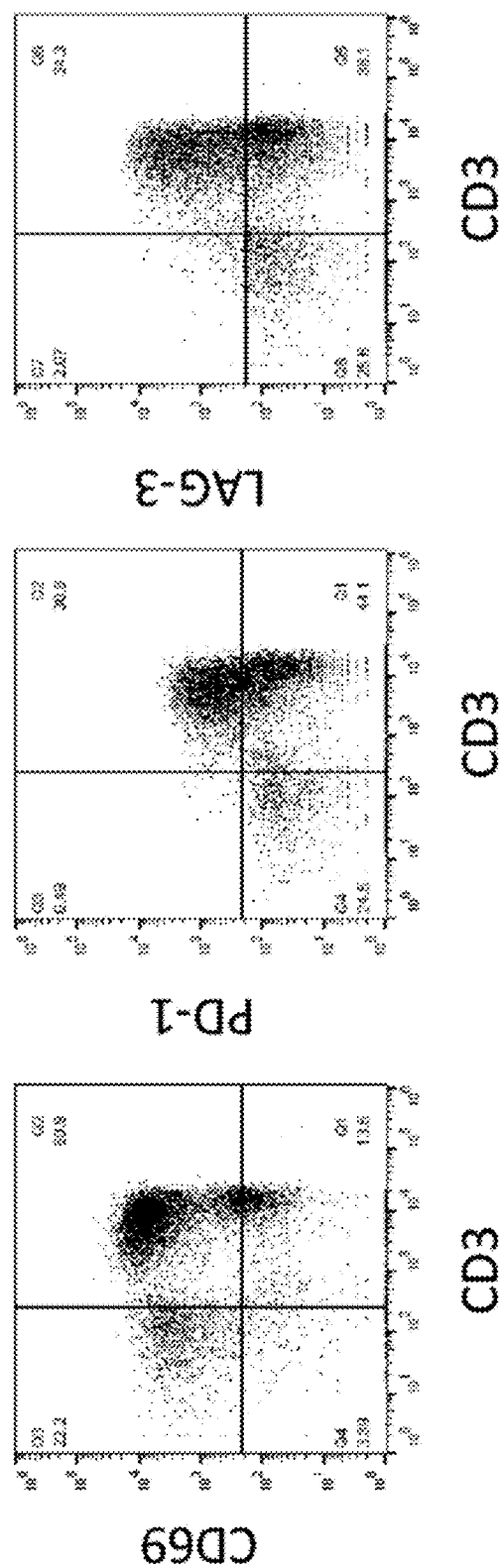

TWIN IMMUNE CELL ENGAGER

CROSS-REFERENCE TO RELATED APPLICATIONS

This application claims the benefit of priority of U.S. Provisional Application No. 62/780,770, filed Dec. 17, 2018, which is incorporated by reference herein in its entirety for any purpose.

SEQUENCE LISTING

The present application is filed with a Sequence Listing in electronic format. The Sequence Listing is provided as a file entitled "2019-12-12_01131-0023-00PCT_ST25.txt" created on Dec. 12, 2019, which is 212,992 bytes in size. The information in the electronic format of the sequence listing is incorporated herein by reference in its entirety.

FIELD

This application relates to improved targeted immune cell engaging antibody complexes for treating a condition characterized by the presence of cancer cells. In particular, it relates to agents that can be used to treat a condition characterized by the presence of cancer cells.

BACKGROUND

Cancer creates significant loss of life, suffering, and economic impact. Immunotherapeutic strategies for targeting cancer have been an active area of translational clinical research.

Various immunooncology approaches have been developed to address cancer and other diseases caused by the presence of unwanted cells. In one context, targeted T-cell engaging antibody complexes have shown promising data. See U.S. Pat. No. 10,035,856. These masked compositions comprise a first component and a second component that both bind the unwanted cell and that each become available to bind to the other after the release of an inert binding partner from each component in the tumor microenvironment. After the first component and second component bind to each other, they form an active T-cell binding domain.

Other developments have shown that other immune interventions (in addition to activating T cells) have benefited patients with cancer and other diseases. For example, PD-L1 pathway inhibition can block immune evasion and reverse T-cell exhaustion of some tumors (see Chen D S et al. *Clin Cancer Res.* 18:6580-6587 (2012)). Simultaneous activation of T cells and binding of tumor-associated antigens, such as checkpoint molecules, has been proposed as a more robust and selective approach to activate T cells against cancer cells (see Harris et. al *Cancer Biol Med* 13(2):171-193 (2016) and Kobold et al. *Front Oncol* 8:285 (2018)). No single therapeutic approach, however, has encompassed all of these features in a way that the various functions only become active at the desired site of treatment.

Thus, depending on the disease and patient, further immunooncology or other biological interventions could also benefit the patient. Some prior constructs had the ability to activate T cells in the tumor microenvironment but did not have any other attributes. Specifically, the prior constructs that restricted activity to the desired site of treatment did not have any way to incorporate additional functional domains. Therefore, additional developments in this field of re-directed immunotherapy are required.

SUMMARY

The present TWICE complexes offer a unique ability to combine multiple functions into a two-component complex that becomes activated in the tumor microenvironment. The present complexes, thus, provide meaningful advantages in having a single approach to administering a two-component complex that is localized to the tumor microenvironment and has the ability to effect two different signals to benefit patients. This unique construct offers benefits that were not present in prior art constructs.

In accordance with the description, this application describes a kit or composition for treating cancer in a patient comprising a first component comprising a targeted immune cell binding agent comprising a first targeting moiety that binds a tumor antigen expressed by the cancer; a first immune cell binding domain capable of immune cell binding activity when binding a second immune cell binding domain, wherein the second immune cell binding domain is not part of the first component, and wherein the first immune cell binding domain is either a VH domain or VL domain; and a first complementary binding domain capable of binding to a complementary antigen when binding a second complementary binding domain, wherein the second complementary binding domain is not part of the first component, when the first immune cell binding domain is a VH domain the first complementary binding domain is a VL domain, when the first immune cell binding domain is a VL domain, the first complementary binding domain is a VH domain, and wherein the first complementary binding domain is a binding partner for the first immune cell binding domain, such that the first immune cell binding domain does not bind to the second immune cell binding domain unless the first immune cell binding domain is not bound to the first complementary domain; and a second component comprising a targeted immune cell binding agent comprising a second targeting moiety; a second immune cell binding domain capable of immune cell binding activity when binding a first immune cell binding domain, wherein the second immune cell binding domain is a VH if the first immune cell binding domain is a VL and wherein the second immune cell binding domain is a VL if the first immune cell binding domain is a VH; and a second complementary binding domain capable of binding to a complementary antigen when binding the first complementary binding domain, wherein when the second immune cell binding domain is a VH domain the second complementary binding domain is a VL domain, when the second immune cell binding domain is a VL domain, the second complementary binding domain is a VH domain, and wherein the second complementary binding domain is a binding partner for the second immune cell binding domain, such that the second immune cell binding domain does not bind to the first immune cell binding domain unless the second immune cell binding domain is not bound to the second complementary domain.

In some embodiments, the first immune cell binding domain is bound to the first complementary binding domain by a first dimerization domain and a second dimerization domain, wherein the first dimerization domain is attached to the first immune cell binding domain by a first linker; the second dimerization domain is attached to the first complementary binding domain by a second linker; and the first and/or second linker is a cleavable linker. In some embodiments, the first and second linkers are cleavable linkers.

In some embodiments, the second T-cell binding domain is bound to the second complementary binding domain by a first dimerization domain and a second dimerization domain, wherein the first dimerization domain is attached to the second T-cell binding domain by a first linker; the second dimerization domain is attached to the second complementary binding domain by a second linker; and the first and/or second linker is a cleavable linker.

In some embodiments, the first and second linkers are cleavable linkers. In some embodiments, the first and second linkers are the same. In some embodiments, the first and second linkers are different. In some embodiments, the first and second linkers are from 5 to 30 amino acids in length. In some embodiments, the first and second linkers are from 8 to 16 amino acids in length. In some embodiments, the protease cleavage sites of the first and/or second cleavable linkers are cleaved by a protease expressed by the cancer or tumor microenvironment cell. In some embodiments, the protease cleavage sites of the first and/or second cleavable linkers are cleaved by a protease that is colocalized to the cancer by a targeting moiety that is an antibody or antigen binding fragment thereof that binds a tumor antigen expressed by the cancer and that is the same or different from the targeting moiety in at least one of the first components or the second component.

In some embodiments, the first and second dimerization domains are both leucine zippers; immunoglobulin domains; or T-cell receptor (TCR) domains. In some embodiments, the immunoglobulin domains comprise immunoglobulin variable domains or immunoglobulin constant domains. In some embodiments, the immunoglobulin constant domains comprise CH1/CL, CH2, CH3, or CH4. In some embodiments, the TCR domains comprise TCR constant domains. In some embodiments, the dimerization domains in the first component are the same as the dimerization domains in the second component. In some embodiments, the dimerization domains in the first component are different than the dimerization domains in the second component.

In some embodiments, the first complementary binding domain and the second complementary binding domain are, when bound to each other, capable of binding the cancer. In some embodiments, the first complementary binding domain and the second complementary binding domain are, when bound to each other, capable of binding an immune checkpoint molecule, RANK or RANKL, or a cell-death-inducing antigen.

In some embodiments, the first complementary binding domain and the second complementary binding domain are, when bound to each other, capable of binding an immune checkpoint molecule. In some embodiments, the first complementary binding domain and the second complementary binding domain are, when bound to each other, capable of binding PD-L1. In some embodiments, the first and second complementary binding domains comprise all or part of a VH and/or VL of atezolizumab, durvalumab, or avelumab.

In some embodiments, the first complementary binding domain and the second complementary binding domain are, when bound to each other, capable of binding RANK. In some embodiments, the first complementary binding domain and the second complementary binding domain are, when bound to each other, capable of binding RANKL. In some embodiments, the first and second complementary binding domains comprise all or part of a VH and/or VL of denosumab.

In some embodiments, the first complementary binding domain and the second complementary binding domain are, when bound to each other, capable of binding a cell-death-inducing antigen. In some embodiments, the first complementary binding domain and the second complementary binding domain are, when bound to each other, capable of binding Fas/CD95/Apo1, TNFR1/p55/CD120a, DR3/Apo3/WSL-1/TRAMP/LARD, TRAIL-R1/DR4, DR5/Apo2/TRAIL-R2/TRICK2/KILLER, DR6, or CAR1. In some embodiments, the first complementary binding domain and the second complementary binding domain are, when bound to each other, capable of binding TRAIL-R1/DR4. In some embodiments, the first and second complementary binding domains comprise all or part of a VH and/or VL of mapatumumab. In some embodiments, the first complementary binding domain and the second complementary binding domain are, when bound to each other, capable of binding DR5/Apo2/TRAIL-R2/TRICK2/KILLER. In some embodiments, the first and second complementary binding domains comprise all or part of a VH and/or VL of conatumumab (AMG655), lexatumumab, tigatuzumab (CS1008), or drozitumab (PRO95780).

In some embodiments, the first complementary binding domain and the second complementary binding domain are, when bound to each other, capable of binding a molecule associated with the extracellular matrix.

In some embodiments, the first complementary binding domain and the second complementary binding domain are, when bound to each other, capable of binding a T cell, a macrophage, or a natural killer cell.

In some embodiments, the first complementary binding domain and the second complementary binding domain are, when bound to each other, capable of binding a T cell. In some embodiments, the first complementary binding domain and the second complementary binding domain are, when bound to each other, capable of binding CD3, programmed cell death protein 1 (PD-1), cytotoxic T-lymphocyte-associated protein 4 (CTLA-4), T-cell immunoglobulin and mucin-domain 3 (TIM-3), lymphocyte-activation gene 3 (LAG-3), killer-cell immunoglobulin-like receptor (KIR), CD28, CD137, OX40, CD27, glucocorticoid induced TNF receptor (GITR or TNFRSF18), T cell immune receptor with Ig and ITIM domains (TIGIT), or inducible T-cell costimulatory (ICOS).

In some embodiments, the first and second complementary binding domains are, when bound together, capable of binding CD3. In some embodiments, the first and second complementary binding domains comprise all or part of a VH and/or VL of muromonab, otelixizumab, teplizumab, visilizumab, foralumab, SP34, or blinatumomab.

In some embodiments, the first and second complementary binding domains are, when bound together, capable of binding PD-1. In some embodiments, the first and second complementary binding domains comprise all or part of a VH and/or VL of pembrolizumab or nivolumab.

In some embodiments, the first and second complementary binding domains are, when bound together, capable of binding CTLA-4. In some embodiments, the first and second complementary binding domains comprise all or part of a VH and/or VL of ipilimumab.

In some embodiments, the first and second complementary binding domains are, when bound together, capable of binding TIM-3. In some embodiments, the first and second complementary binding domains comprise all or part of a VH and/or VL of TSR-022 or Sym023.

In some embodiments, the first and second complementary binding domains are, when bound together, capable of binding LAG-3. In some embodiments, wherein the first and second complementary binding domains comprise all or part of a VH and/or VL of BMS-986016.

In some embodiments, the first and second complementary binding domains are, when bound together, capable of binding KIR. In some embodiments, the first and second complementary binding domains comprise all or part of a VH and/or VL of lirilumab.

In some embodiments, the first and second complementary binding domains are, when bound together, capable of binding CD28. In some embodiments, the first and second complementary binding domains comprise all or part of a VH and/or VL of theralizumab.

In some embodiments, the first and second complementary binding domains are, when bound together, capable of binding CD137. In some embodiments, the first and second complementary binding domains comprise all or part of a VH and/or VL of utomilumab or urelumab.

In some embodiments, the first and second complementary binding domains are, when bound together, capable of binding OX40. In some embodiments, the first and second complementary binding domains comprise all or part of a VH and/or VL of PF-04518600 or BMS 986178.

In some embodiments, the first and second complementary binding domains are, when bound together, capable of binding CD27. In some embodiments, the first and second complementary binding domains comprise all or part of a VH and/or VL of varlilumab.

In some embodiments, the first and second complementary binding domains are, when bound together, capable of binding GITR (TNFRSF18). In some embodiments, the first and second complementary binding domains comprise all or part of a VH and/or VL of GWN323 or BMS-986156.

In some embodiments, the first and second complementary binding domains are, when bound together, capable of binding TIGIT. In some embodiments, the first and second complementary binding domains comprise all or part of a VH and/or VL of OMP-313M32, MTIG7192A, BMS-986207, or MK-7684.

In some embodiments, the first and second complementary binding domains are, when bound together, capable of binding ICOS. In some embodiments, the first and second complementary binding domains comprise all or part of a VH and/or VL of JTX-2011.

In some embodiments, the first complementary binding domain and the second complementary binding domain are, when bound to each other, capable of binding a macrophage.

In some embodiments, the first complementary binding domain and the second complementary binding domain are, when bound to each other, capable of binding CSF1R. In some embodiments, the first and second complementary binding domains comprise all or part of a VH and/or VL of emactuzumab or IMC-CS4.

In some embodiments, the first complementary binding domain and the second complementary binding domain are, when bound to each other, capable of binding CD40. In some embodiments, the first and second complementary binding domains comprise all or part of a VH and/or VL of CP-870,893.

In some embodiments, the first complementary binding domain and the second complementary binding domain are, when bound to each other, capable of binding a natural killer cell.

In some embodiments, the first complementary binding domain and the second complementary binding domain are, when bound to each other, capable of binding CD16A. In some embodiments, the first and second complementary binding domains comprise all or part of a VH and/or VL of NTM-1633 or AFM13.

In some embodiments, the first complementary binding domain and the second complementary binding domain, when bound to each other, and the first immune cell binding domain and the second immune cell binding domain, when bound to each other, are capable of binding the same antigen.

In some embodiments, the first complementary binding domain and the second complementary binding domain, when bound to each other, and the first immune cell binding domain and the second immune cell binding domain, when bound to each other, are capable of binding different antigens on the same cell.

In some embodiments, the first complementary binding domain and the second complementary binding domain, when bound to each other, and the first immune cell binding domain and the second immune cell binding domain, when bound to each other, are capable of binding different cells.

In some embodiments, the first and second immune cell binding domains are capable of forming a Fv when not bound to the first and second complementary binding domains. In some embodiments, the first and second complementary binding domains are capable of forming a Fv when not bound to the first and second immune cell binding domains.

This application also describes a kit or composition for treating cancer in a patient comprising a first component comprising a targeted immune cell binding agent comprising a first targeting moiety that binds a tumor antigen expressed by the cancer; a first immune cell binding domain capable of immune cell binding activity when binding a second immune cell binding domain, wherein the second immune cell binding domain is not part of the first component, and wherein the first immune cell binding domain is either a VH domain or VL domain; a first inert binding partner for the first immune cell binding domain, wherein the first inert binding partner binds to the first immune cell binding domain such that the first immune cell binding domain does not bind to the second immune cell binding domain unless the inert binding partner is removed, wherein if the first immune cell binding domain is a VH domain, the inert binding partner is a VL domain and if the first immune cell binding domain is a VL domain, the inert binding partner is a VH domain; a protease cleavage site separating the first immune cell binding domain and the first inert binding partner, wherein the protease cleavage site is capable of releasing the inert binding partner from the immune cell binding domain in the presence of a protease expressed by the cancer or a tumor microenvironment cell; or colocalized to the cancer by a targeting moiety that is an antibody or antigen binding fragment thereof that binds (a) a tumor antigen expressed by the cancer and that is the same or different from the first and/or second targeting moiety in the agent or (b) an antigen expressed by a cell in the tumor microenvironment; and a first complementary functional domain capable of immune cell binding, and a second component comprising a targeted immune cell binding agent comprising a second targeting moiety; a second immune cell binding domain; and optionally a second complementary functional domain capable of immune cell binding.

In some embodiments, the second component comprises a complementary functional domain. In some embodiments, the complementary functional domain of the first and/or second component comprises a ligand for a receptor. In some embodiments, the complementary functional domain is a latent form of a member of the TGF-beta family. In some embodiments, the complementary functional domain of the first and/or second component comprises a cytokine. In some embodiments, the cytokine is IL-2, IL-7, IL-12, IL-15, GM-CSF, IFN-α, IFN-γ, or a member of the TNF-superfamily.

In some embodiments, the complementary functional domain of the first and/or second component comprises an attenuated cytokine. In some embodiments, the attenuated cytokine is a variant of IL-2, IL-7, IL-12, IL-15, GM-CSF, IFN-α, IFN-γ, or a member of the TNF-superfamily.

In some embodiments, the second component further comprises a second inert binding partner for the second immune cell binding domain, wherein the second inert binding partner binds to the second immune cell binding domain such that the second immune cell binding domain does not bind to the first immune cell binding domain unless the inert binding partner is removed, wherein if the second immune cell binding domain is a VH domain, the inert binding partner is a VL domain and if the second immune cell binding domain is a VL domain, the inert binding partner is a VH domain; and further wherein a protease cleavage site separating the second immune cell binding domain and the second inert binding partner, wherein the protease cleavage site is capable of releasing the inert binding partner from the immune cell binding domain in the presence of a protease expressed by the cancer; or colocalized to the cancer by a targeting moiety that is an antibody or antigen binding fragment thereof that binds (a) a tumor antigen expressed by the cancer and that is the same or different from the first and/or second targeting moiety in the agent or (b) an antigen expressed by a cell in the tumor microenvironment.

In some embodiments, the first component is not covalently bound to the second component. In some embodiments, the first component is covalently bound to the second component. In some embodiments, the first component is covalently bound to the second component via a cleavable linker.

In some embodiments, the first immune cell binding domain and the second immune cell binding domain are, when bound to each other, capable of binding a T cell, a macrophage, or a natural killer cell.

In some embodiments, the first immune cell binding domain and the second immune cell binding domain are, when bound to each other, capable of binding a T cell. In some embodiments, the first immune cell binding domain and the second immune cell binding domain are, when bound to each other, capable of binding CD3, the T-cell receptor, programmed cell death protein 1 (PD-1), cytotoxic T-lymphocyte-associated protein 4 (CTLA-4), T-cell immunoglobulin and mucin-domain 3 (TIM-3), lymphocyte-activation gene 3 (LAG-3), killer-cell immunoglobulin-like receptor (KIR), CD28, CD137, OX40, CD27, GITR (TNFRSF18), TIGIT, or inducible T-cell costimulatory (ICOS).

In some embodiments, the first immune cell binding domain and the second immune cell binding domain are, when bound to each other, capable of binding CD3. In some embodiments, the first and second immune cell binding domains comprise all or part of a VH and/or VL of muromonab, otelixizumab, teplizumab, visilizumab, foralumab, SP34, or blinatumomab.

In some embodiments, the first immune cell binding domain and the second immune cell binding domain are, when bound to each other, capable of binding the T-cell receptor.

In some embodiments, the first and second immune cell binding domains are, when bound together, capable of binding PD-1. In some embodiments, the first and second immune cell binding domains comprise all or part of a VH and/or VL of pembrolizumab or nivolumab.

In some embodiments, the first and second immune cell binding domains are, when bound together, capable of binding CTLA-4. In some embodiments, the first and second immune cell binding domains comprise all or part of a VH and/or VL of ipilimumab.

In some embodiments, the first and second immune cell binding domains are, when bound together, capable of binding TIM-3. In some embodiments, the first and second immune cell binding domains comprise all or part of a VH and/or VL of TSR-022 or Sym023.

In some embodiments, the first and second immune cell binding domains are, when bound together, capable of binding LAG-3. In some embodiments, the first and second immune cell binding domains comprise all or part of a VH and/or VL of BMS-986016.

In some embodiments, the first and second immune cell binding domains are, when bound together, capable of binding KIR. In some embodiments, the first and second immune cell binding domains comprise all or part of a VH and/or VL of lirilumab.

In some embodiments, the first and second immune cell binding domains are, when bound together, capable of binding CD28. In some embodiments, the first and second immune cell binding domains comprise all or part of a VH and/or VL of theralizumab.

In some embodiments, the first and second immune cell binding domains are, when bound together, capable of binding CD137. In some embodiments, the first and second immune cell binding domains comprise all or part of a VH and/or VL of utomilumab or urelumab.

In some embodiments, the first and second immune cell binding domains are, when bound together, capable of binding OX40. In some embodiments, the first and second immune cell binding domains comprise all or part of a VH and/or VL of PF-04518600 or BMS 986178.

In some embodiments, the first and second immune cell binding domains are, when bound together, capable of binding CD27. In some embodiments, the first and second immune cell binding domains comprise all or part of a VH and/or VL of varlilumab.

In some embodiments, the first and second immune cell binding domains are, when bound together, capable of binding GITR (TNFRSF18). In some embodiments, the first and second complementary binding domains comprise all or part of a VH and/or VL of GWN323 or BMS-986156.

In some embodiments, the first and second immune cell binding domains are, when bound together, capable of binding TIGIT. In some embodiments, the first and second immune cell binding domains comprise all or part of a VH and/or VL of OMP-313M32, MTIG7192A, BMS-986207, or MK-7684.

In some embodiments, the first and second immune cell binding domains are, when bound together, capable of binding ICOS. In some embodiments, the first and second immune cell binding domains comprise all or part of a VH and/or VL of JTX-2011.

In some embodiments, the first immune cell binding domain and the second immune cell binding domain are, when bound to each other, capable of binding a macrophage.

In some embodiments, the first immune cell binding domain and the second immune cell binding domain are, when bound to each other, capable of binding CSF1R. In some embodiments, the first and second immune cell binding domains comprise all or part of a VH and/or VL of emactuzumab or IMC-CS4.

In some embodiments, the first immune cell binding domain and the second immune cell binding domain are, when bound to each other, capable of binding CD40. In some embodiments, the first and second immune cell binding domains comprise all or part of a VH and/or VL of CP-870,893.

In some embodiments, the first immune cell binding domain and the second immune cell binding domain are, when bound to each other, capable of binding a natural killer cell. In some embodiments, the first immune cell binding domain and the second immune binding domain are, when bound to each other, capable of binding CD16A.

In some embodiments, the first and second immune cell binding domains comprise all or part of a VH and/or VL of NTM-1633 or AFM13. In some embodiments, the first and the second targeting moieties are different.

In some embodiments, the first and the second targeting moieties are the same.

In some embodiments, the first and/or second targeting moiety comprises an antibody or antigen binding fragment thereof. In some embodiments, the first and/or second targeting moiety comprises a DNA aptamer, RNA aptamer, albumin, lipocalin, fibronectin, ankyrin, fynomer, Obody, DARPin, knotin, avimer, atrimer, anti-callin, affilin, affibody, bicyclic peptide, cys-knot, FN3 (adnectins, centryrins, pronectins, or TN3), or Kunitz domain.

In some embodiments, the second targeting moiety binds a tumor antigen expressed by the cancer. In some embodiments, the first and/or second targeting moiety comprises an antibody or antigen binding fragment thereof that binds α4-integrin; A33; ACVRL 1/ALK1; ADAM17; ALK; APRIL; BCMA; C242; CA125; Cadherin-19; CAIX; CanAg; Carbonic Anhydrase IX; CCN1; CCR4; CD123; CD133; CD137 (4-1BB); CD138/Syndecan1; CD19; CD2; CD20; CD22; CD30; CD33; CD37; CD38; CD4; CD40; CD44; CD45; CD48; CD5; CD52; CD56; CD59; CD70; CD70b; CD71; CD74; CD79b; CD80; CD86; CD98; CEA; CEACAM; CEACAM1; CK8; c-Kit; Claudin-1 (CLDN1); CLDN18 (including CLDN18.2); CLDN6; c-met/HGFR; c-RET; Cripto; CTLA-4; CXCR4; DKK-1; DLL3; DLL4; TRAIL-R2/DR5; DRS; EGFL7; EGFR; EGFRvIII; endoglin; ENPP3; EpCAM; EphA2; Episialin; FAP; FGFR1; FGFR2; FGFR3; FGFR4; fibronectin extra-domain B; FLT-3; flt4; folate receptor 1; Guanylyl Cyclase C (GCC); GD2; GD3; Glypican-3; Glypicans; GM3; GPNMB; GPR49; GRP78; Her2/Neu; HER3/ERBB3; HLA-DR; ICAM-1; IGF-1R; IGFR; IL-3Ra; Integrin α5β1; Integrin α6β4; Integrin αV; Integrin αVβ3; Lewis Y; Lewis y/b antigen; LFL2; LIV-1; Ly6E; MCP-1; Mesothelin; MMP-9; MUC1; MUC18; MUC5A; MUC5AC; Myostatin; NaPi2b; Neuropilin 1; NGcGM3; NRP1; P-cadherin; PCLA; PD-1; PDGFRa; PD-L1; PD-L2; Phosphatidylserine; PIVKA-II; PLVAP; PRLR; Progastrin; PSCA; PSMA; RANKL; RG1; Siglec-15; SLAMF6; SLAMF7; SLC44A4; STEAP-1; TACSTD-2; Tenascin C; TPBG; TRAIL-R1/DR4; TROP-2; TWEAKR; TYRP1; VANGL2; VEGF; VEGF-C; VEGFR-2; or VEGF-R2.

In some embodiments, the first and/or second targeting moiety comprises an antibody or antigen binding fragment thereof is an anti α4-integrin antibody; an anti-CD137 antibody; an anti-CCR4 antibody; an anti-CD123 antibody; an anti-CD133 antibody; an anti-CD138 antibody; an anti-CD19 antibody; an anti-CD20 antibody; an anti-CD22 antibody; an anti-CD33 antibody; an anti-CD38 antibody; an anti-CD40 antibody; an anti-CD49d antibody; an anti-CD52 antibody; an anti-CD70 antibody; an anti-CD74 antibody; an anti-CD79b antibody; an anti-CD80 antibody; an anti-CEA antibody; an anti-cMet antibody; an anti-Cripto antibody; an anti-CTLA-4 antibody; an anti-DLL3 antibody; an anti-TRAIL-2/DR5 antibody; an anti-E-cadherin antibody; an anti-endoglin antibody; an anti-EpCAM antibody; an anti-epidermal growth factor receptor antibody; an anti-FGFR3 antibody; an anti-fibronectin extra-domain B antibody; an anti-folate receptor 1 antibody; an anti-glypican 3 antibody; an anti-gp95/97 antibody; an anti-Her2 antibody; an anti-IGF-1R antibody; an anti-IL-13R antibody; an anti-IL-4 antibody; an anti-IL-6 antibody; an anti-MMP-9 antibody; an anti-MUC1 antibody; an anti-mucin core protein antibody; an anti-NGcGM3 antibody; an anti-P-cadherin antibody; an anti-PD-L1 antibody; an anti-p-glycoprotein antibody; an anti-PSCA antibody; an anti-PSMA antibody; an anti-SLAMF7 antibody; an anti-TRAIL-R1/DR4 antibody; an anti-transferrin antibody; an anti-TROP-2 antibody; or an anti-VEGF antibody.

In some embodiments, the first and/or second targeting moiety comprises Alemtuzumab, Andecaliximab, Atezolizumab, Avelumab, BCD-100, Bevacizumab, BGB-A317, Blinatumomab, Brentuximab, BU59, Camrelizumab, Carotuximab, Catumaxomab, Cemiplimab, Cetuximab, Daratumumab, Depatuxizumab, Dinutuximab, DS-8201, Durvalumab, Edrecolomab, Elotuzumab, G544, Gemtuzumab, Glembatumumab, GP1.4, hp67.6, IBI308, Ibritumomab, Inotuzumab, Ipilimumab, Isatuximab, L19IL2, L19TNF, Margetuximab, Mirvetuximab, Mogamuizumab, Moxetumomab, Natalizumab, Necitumumab, Nivolumab, Obinutuzumab, Ofatumumab, Olaratumab, Oportuzumab, Panitumumab, PDR001, Pembrolizumab, Pertuzumab, Polatuzumab, Racotumomab, Ramucirumab, Rituximab, Rovalpituzumab, Sacituzumab, SM3, TAK-164, Tositumomab, Trastuzumab, Tremelimumab, Ublituximab, Urelumab, Utomilumab, XMAB-5574, or Zolbetuximab.

In some embodiments, the first and/or second targeting moiety comprises IL-2, IL-4, IL-6, α-MSH, transferrin, folic acid, EGF, TGF, PD-1, IL-13, stem cell factor, insulin-like growth factor (IGF), or CD40. In some embodiments, the first and/or second targeting moiety comprises a full-length sequence of IL-2, IL-4, IL-6, α-MSH, transferrin, folic acid, EGF, TGF, PD-1, IL-13, stem cell factor, insulin-like growth factor (IGF), or CD40. In some embodiments, the first and/or second targeting moiety comprises a truncated form, analog, variant, or derivative of IL-2, IL-4, IL-6, α-MSH, transferrin, folic acid, EGF, TGF, PD-1, IL-13, stem cell factor, insulin-like growth factor (IGF), or CD40.

In some embodiments, the first and/or second targeting moiety binds the IL-2 receptor, IL-4, IL-6, melanocyte stimulating hormone receptor (MSH receptor), transferrin receptor (TR), folate receptor 1 (FOLR), folate hydroxylase (FOLH1), EGF receptor, PD-L1, PD-L2, IL-13R, CXCR4, IGFR, or CD40L.

In some embodiments, the second targeting moiety binds an antigen expressed by a tumor microenvironment cell. In some embodiments, the tumor microenvironment cell is a fibroblast or macrophage. In some embodiments, the antigen expressed by a fibroblast is fibroblast activation protein. In some embodiments, the antigen expressed by a macrophage is MAC-1/CD11b or sideroflexin 3.

This application also describes a method of treating cancer expressing a tumor antigen that binds the first targeting moiety and/or second targeting moiety in a patient comprising administering a composition to the patient. In some embodiments, the cancer is evaluated for the presence of infiltrating immune cells before administering the composition. In some embodiments, the cancer is evaluated for the presence of tumor antigens before administering the composition. In some embodiments, the first targeting moiety and second targeting moiety bind the same antigen. In some embodiments, the first targeting moiety and second targeting moiety bind different antigens.

In some embodiments, the cancer expressing a tumor antigen that binds the first and/or second targeting moiety is any one of breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, nonHodgkin lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease or premalignant disease.

In some embodiments, a method of targeting immune cells to cancer expressing a tumor antigen that binds both the first and/or second targeting moiety in a patient comprises administering a composition to the patient. In some embodiments, a method of targeting immune cells to cancer expressing two tumor antigens, wherein one tumor antigen binds the first targeting moiety and one tumor antigen binds the second targeting moiety, in a patient comprises administering a composition to the patient.

In some embodiments, a method of delivering a cytokine to an immune cell of a patient comprises administering a composition to the patient, wherein the first and/or second complementary functional domain of the composition comprise IL-2, IL-7, IL-12, IL-15, GM-CSF, IFN-α, IFN-γ, or a member of the TNF-superfamily.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 1A shows the two constructs before administration to a patient. FIG. 1B shows the TWICE binding and engaging two signaling molecules on one effector (immune) cell after targeting of both components of the TWICE to a cancer cell. The hexagon and diamond represent two different antigens on a cancer cell bound by the targeting moieties (two sets each of four striped ovals) of the first and second components. Each component comprises an immune cell binding domain (black domains of each component) and a complementary binding domain (white domains of each component). Linkers between the targeting moiety and the immune cell binding domain and the complementary binding domain are also shown. When the two components are in close proximity, domain swapping can occur such the two immune cell binding domains (one from each component) and the two complementary binding domains (one from each component) can pair with each other. The triangle and circle represent different antigens on the effector cell that can be bound by either the paired immune cell binding domains (binding to the antigen represented by the triangle) or the paired complementary binding domains (binding to the antigen represented by the circle). In the absence of domain swapping and pairing, the immune cell binding domains and the complementary binding domains of the two components do not modulate the effector cell.

When the two components are in close proximity and the inert binding partners have been released, domain swapping can occur such the two immune cell binding domains (one from each component) can pair with each other. In addition, the complementary functional domain can bind and engage a target cell based on the targeting moiety localizing it to a target cell (such as a cancer cell or an effector cell). Activity of the complementary functional domain occurs without the need for pairing with another domain, but is enhanced when the complementary functional domain is localized to a target cell by the targeting moiety. In the absence of domain swapping and pairing, the immune cell binding domains of the two components do not modulate the target cell. In some embodiments, both components may comprise a complementary functional domain. In some embodiments, only one component comprises an inert binding partner.

Figure 6:
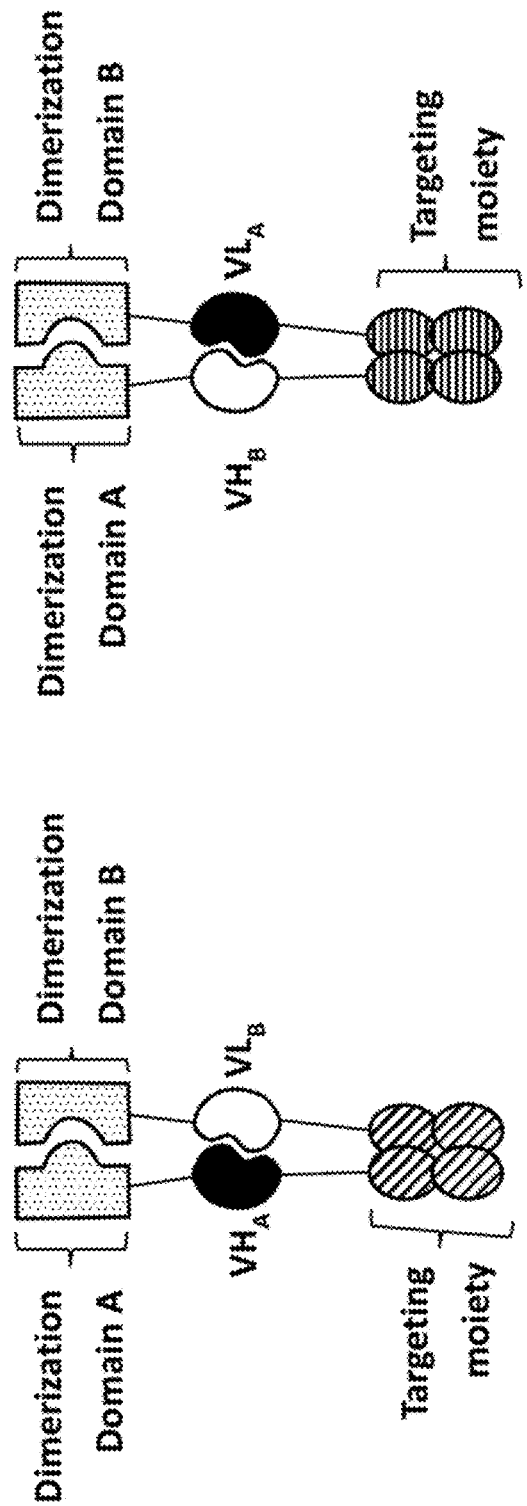

FIG. 6 shows a TWICE comprising dimerization domains before administration to a patient. The targeting moieties (two sets each of four striped ovals) of the first and second components are shown. Each component comprises an immune cell binding domain (black domains of each component) and a complementary binding domain (white domains of each component). Linkers between the targeting moiety and the immune cell binding domain and the complementary binding domain are also shown. A dimerization domain is attached to the immune cell binding domain and to the complementary binding domain of each component via a linker (such that each component has a dimerization domain A and dimerization domain B that can associate). Association of a pair of dimerization domains (pairing of dimerization domain A and dimerization domain B) enhances association of the VH and VL domains of each component. The dimerization domain linker may be cleavable, such that the linker is cleaved and the dimerization domain is lost following cleavage in the tumor microenvironment. After removal of the dimerization domains and when the two components are in close proximity, domain swapping can occur such the two immune cell binding domains (one from each component) and the two complementary binding domains (one from each component) can pair with each other. In the absence of domain swapping and pairing, the immune cell binding domains and complementary binding domains of the two components do not modulate the target cell. In the absence of cleavage of the dimerization domain linker, the VH and VL domains of each component remain associated together without a domain swap. In some embodiments, only one component comprises a pair of dimerization domains, and the other component does not comprise dimerization domains.

Figure 7A:
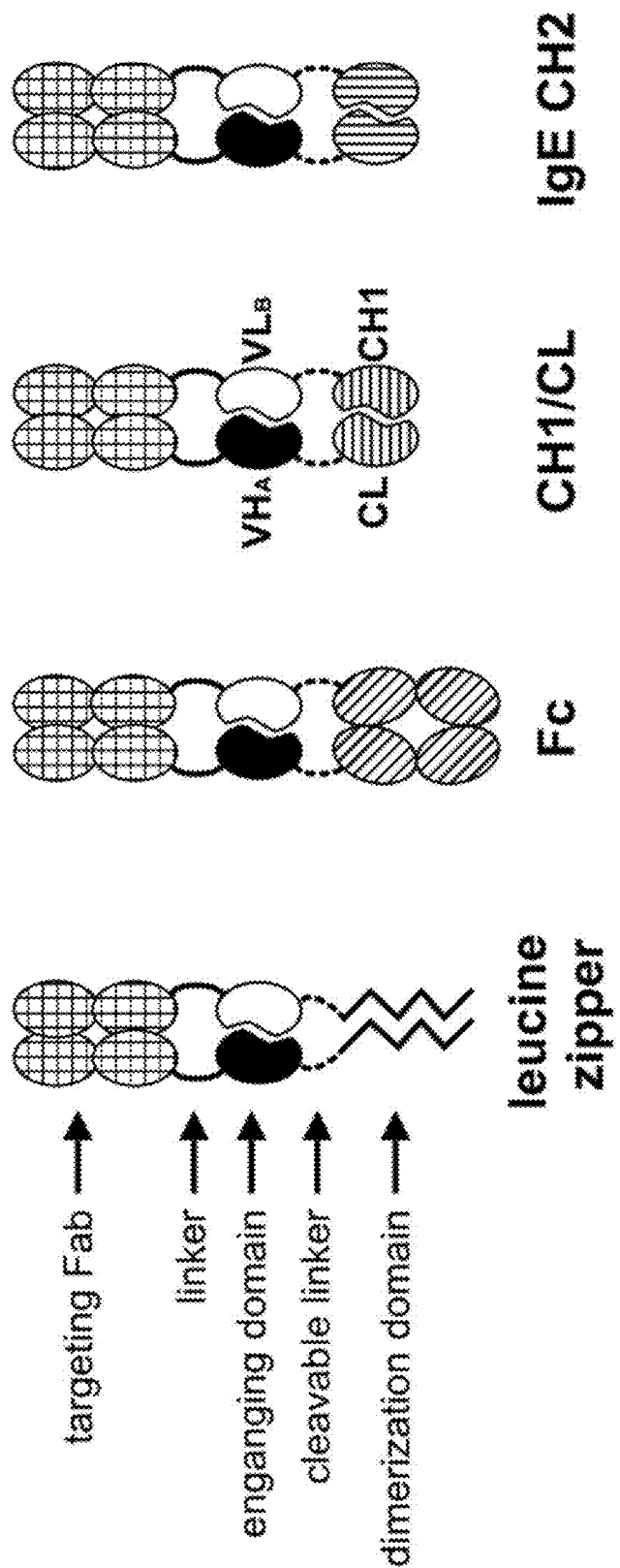
Figure 7B:
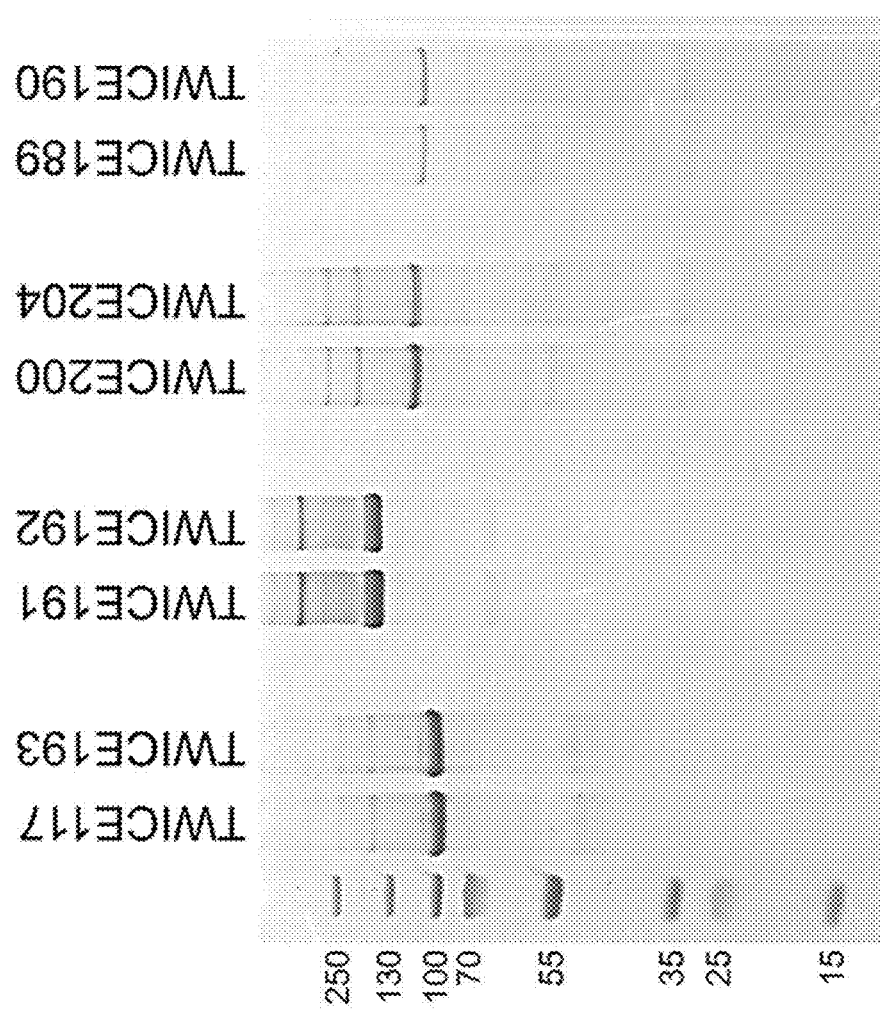
Figure 7C:
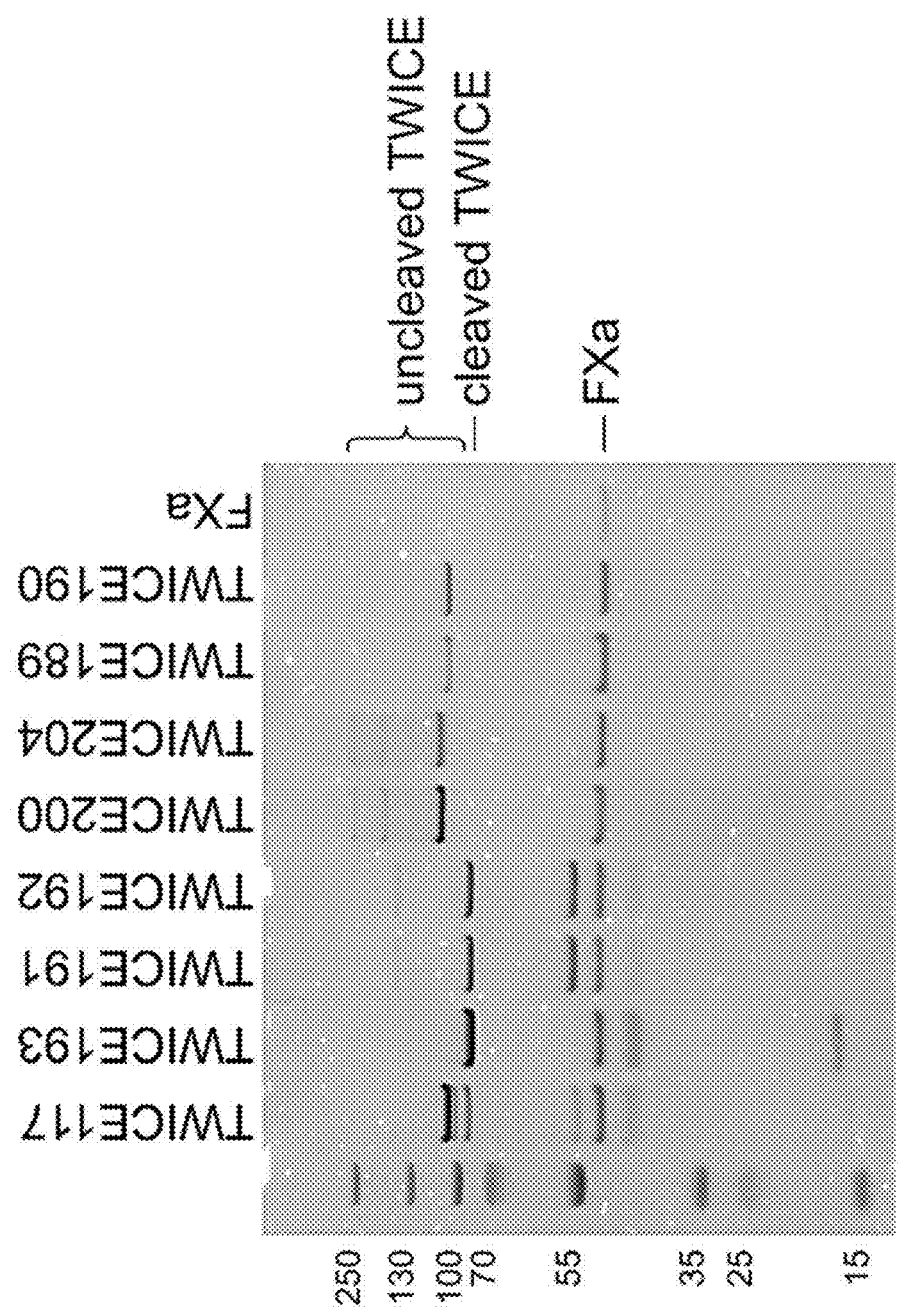

FIGS. 7A-7C show expression and cleavage of TWICE molecules listed in Table 12 with various dimerization domain linkers and dimerization domains. FIG. 7A shows TWICE with various dimerization domain linkers and dimerization domains. TWICE were analysed by SDS-PAGE (FIG. 7B) and cleavage products were also analysed (FIG. 7C).

FIGS. 8A-8B show target binding by TWICE containing Fab or dsFv binding moieties over a range of concentrations (FIG. 8A) or with an EC50 measurement (FIG. 8B).

Figure 9B:
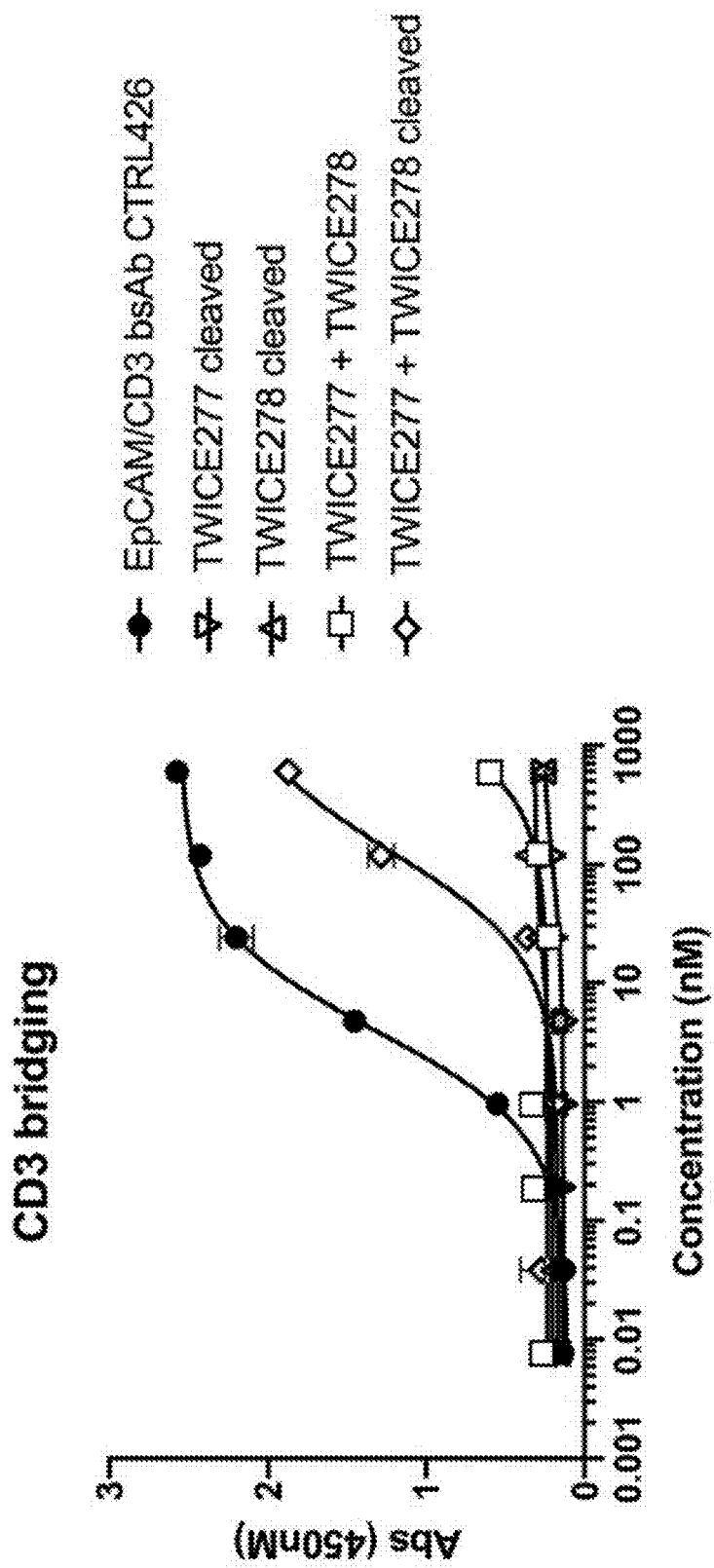
Figure 9C:
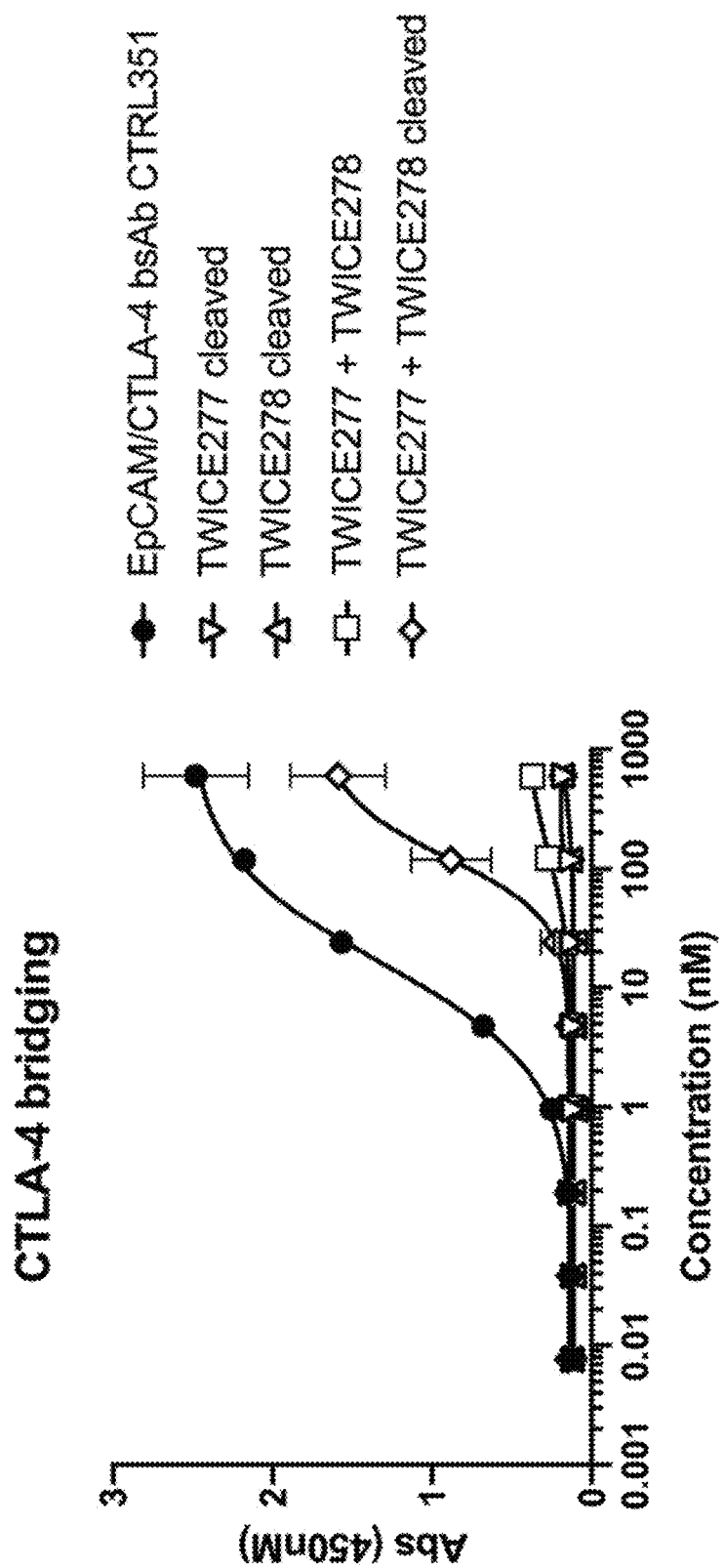

FIGS. 9A-9C show bridging ELISA of CD3/CTLA4 TWICE with hetero-Fc dimerization domain. FIG. 9A shows the assay design, while FIG. 9B shows results with CD3 bridging and FIG. 9C shows results with CTLA-4 bridging.

Figure 10B:
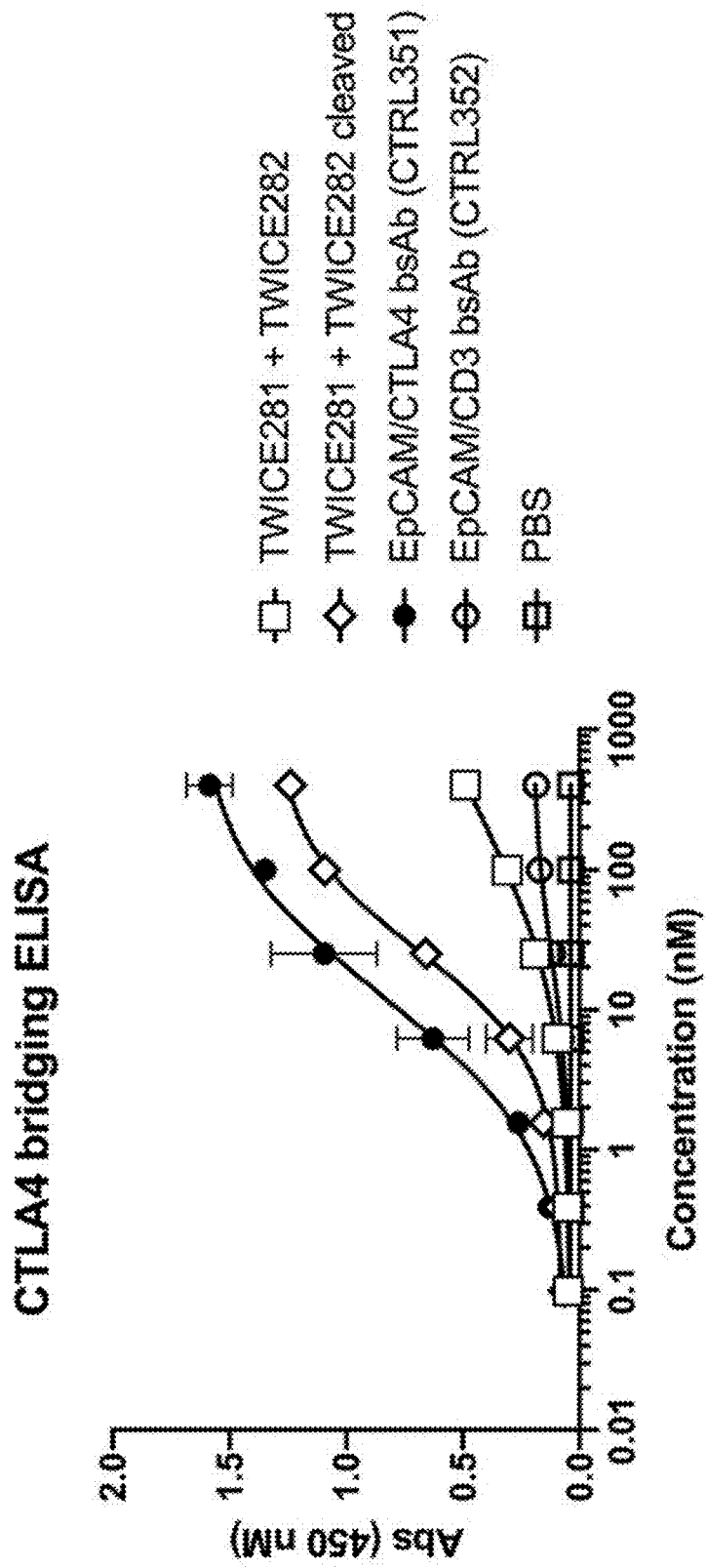

FIGS. 10A-10B shows results for CD3/CTLA4 TWICE with coiled-coil dimerization domain with CD3 bridging ELISA (FIG. 10A) or CTLA4 bridging ELISA (FIG. 10B).

Figure 11A:
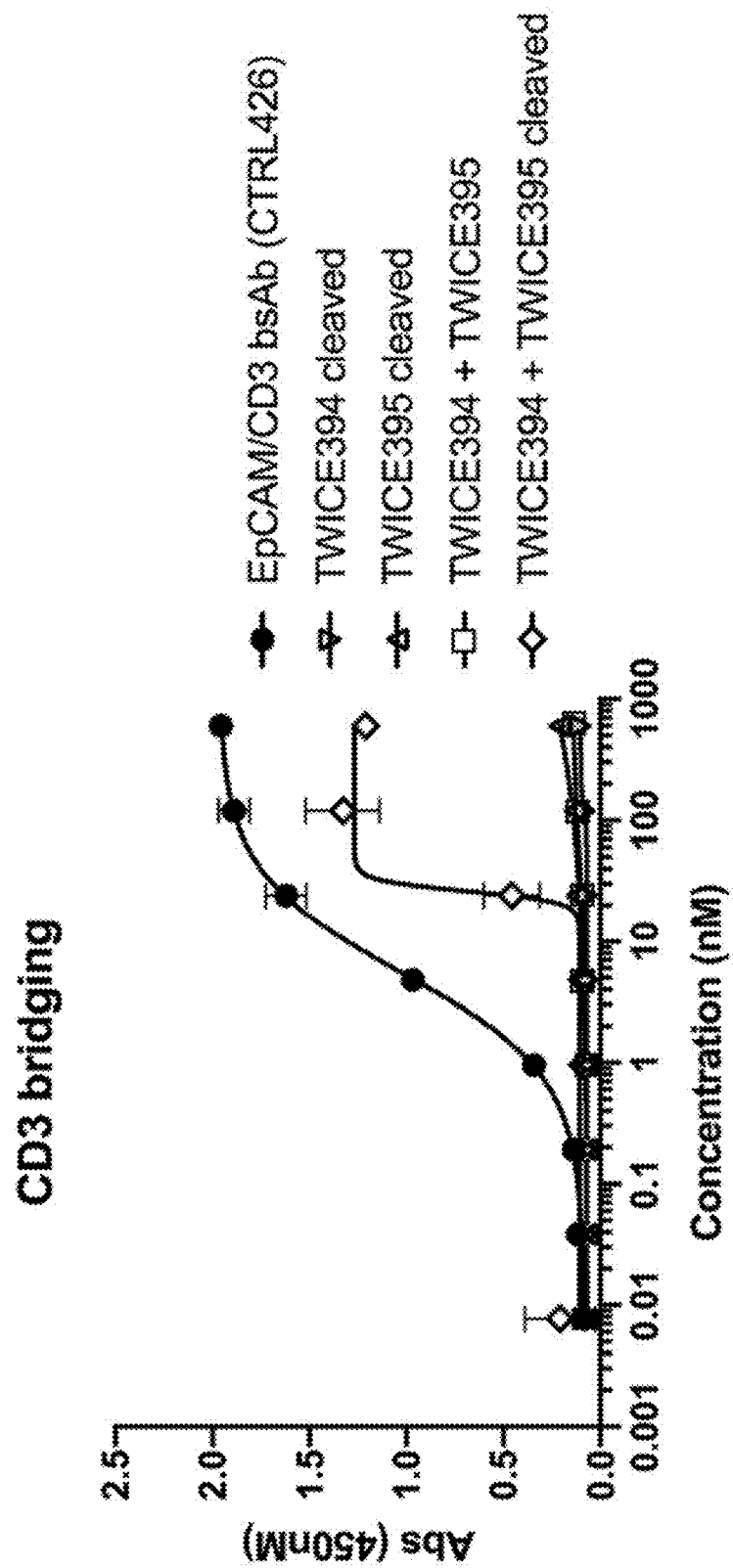
Figure 11B:
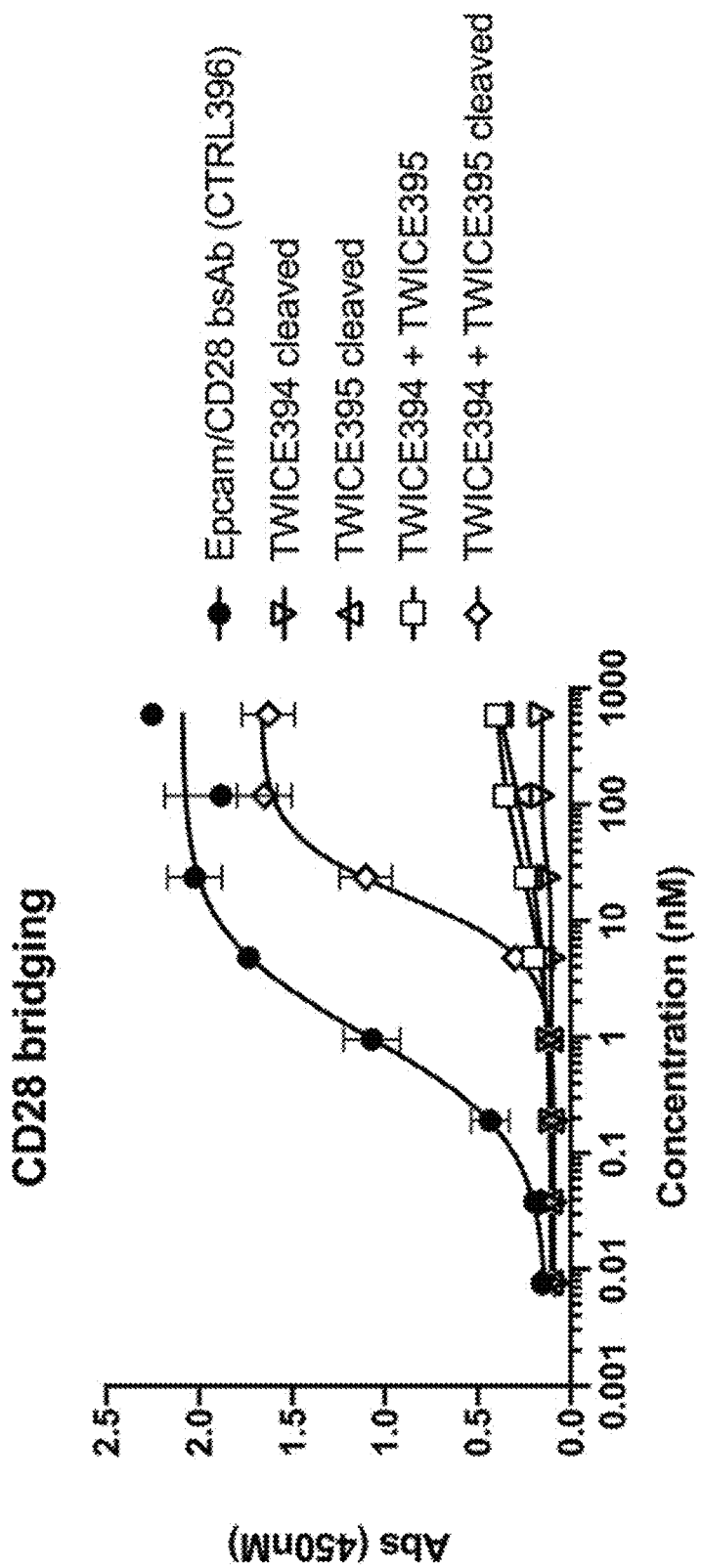

FIGS. 11A-11B show results with a CD28/CD3 TWICE in a CD3 bridging ELISA (FIG. 11A) or a CD28 bridging ELISA (FIG. 11B).

Figure 12A:
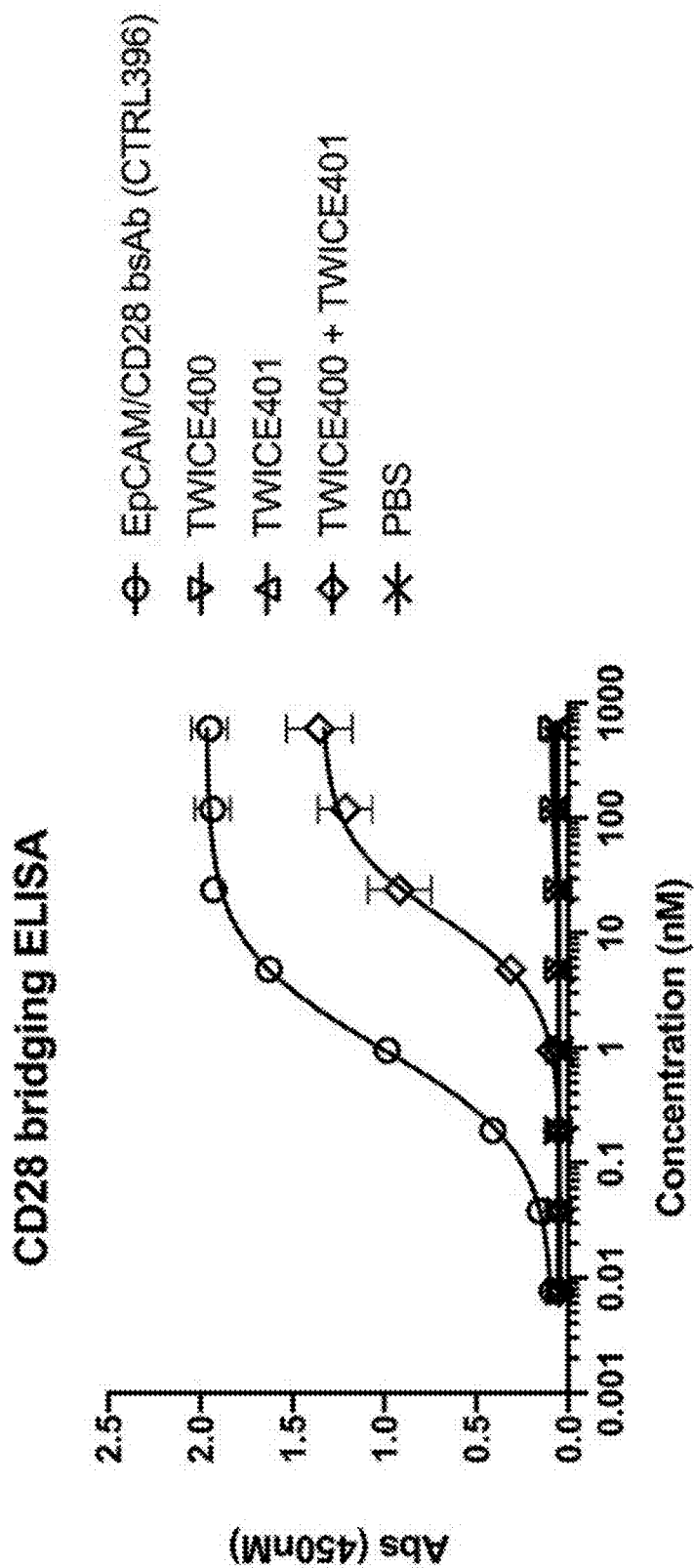
Figure 12B:
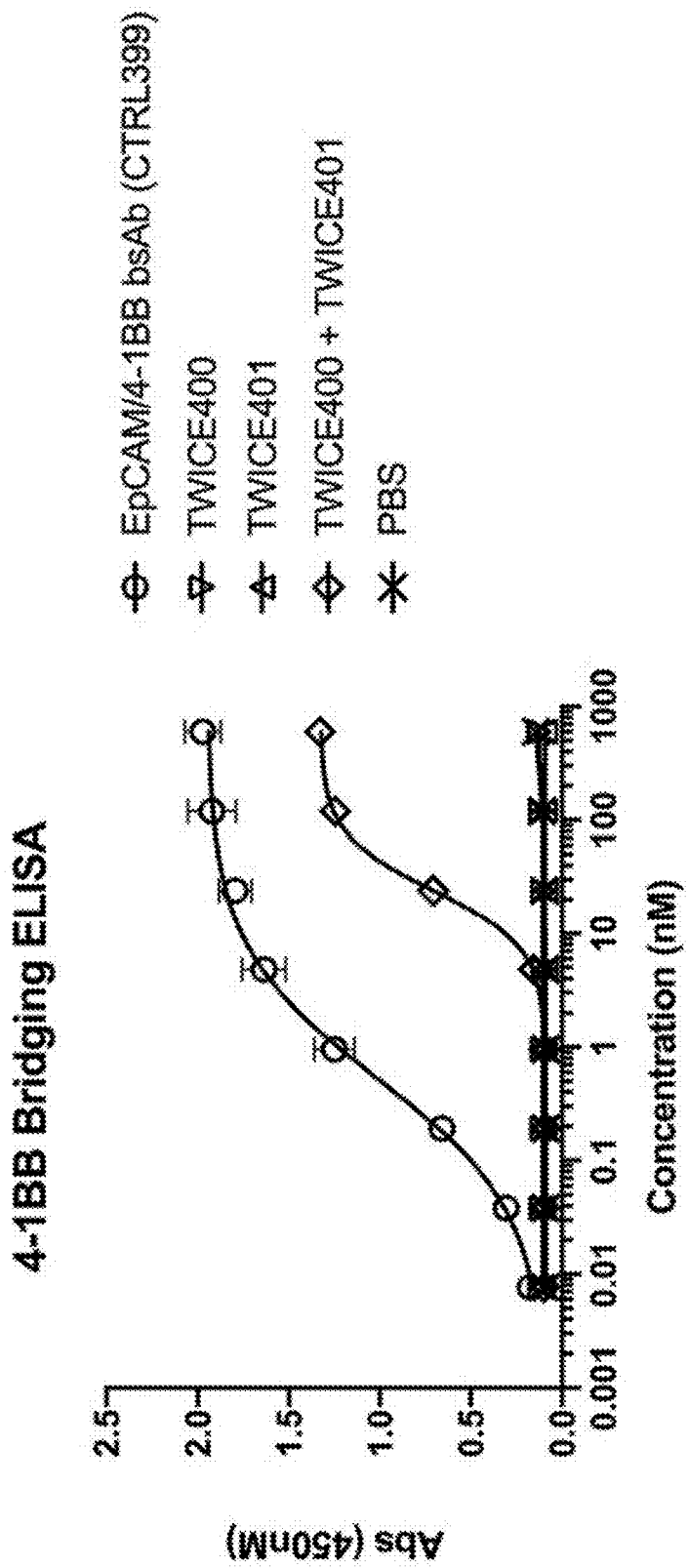

FIGS. 12A-12B show a bridging ELISA with Theralizumab (anti-CD28) and Urelumab (anti-4-IBB) TWICE. Specifically, this shows results with a CD28/4-1BB (CD137) TWICE in a CD28 bridging ELISA (FIG. 12A) or a 4-1BB bridging ELISA (FIG. 12B).

Figure 13:
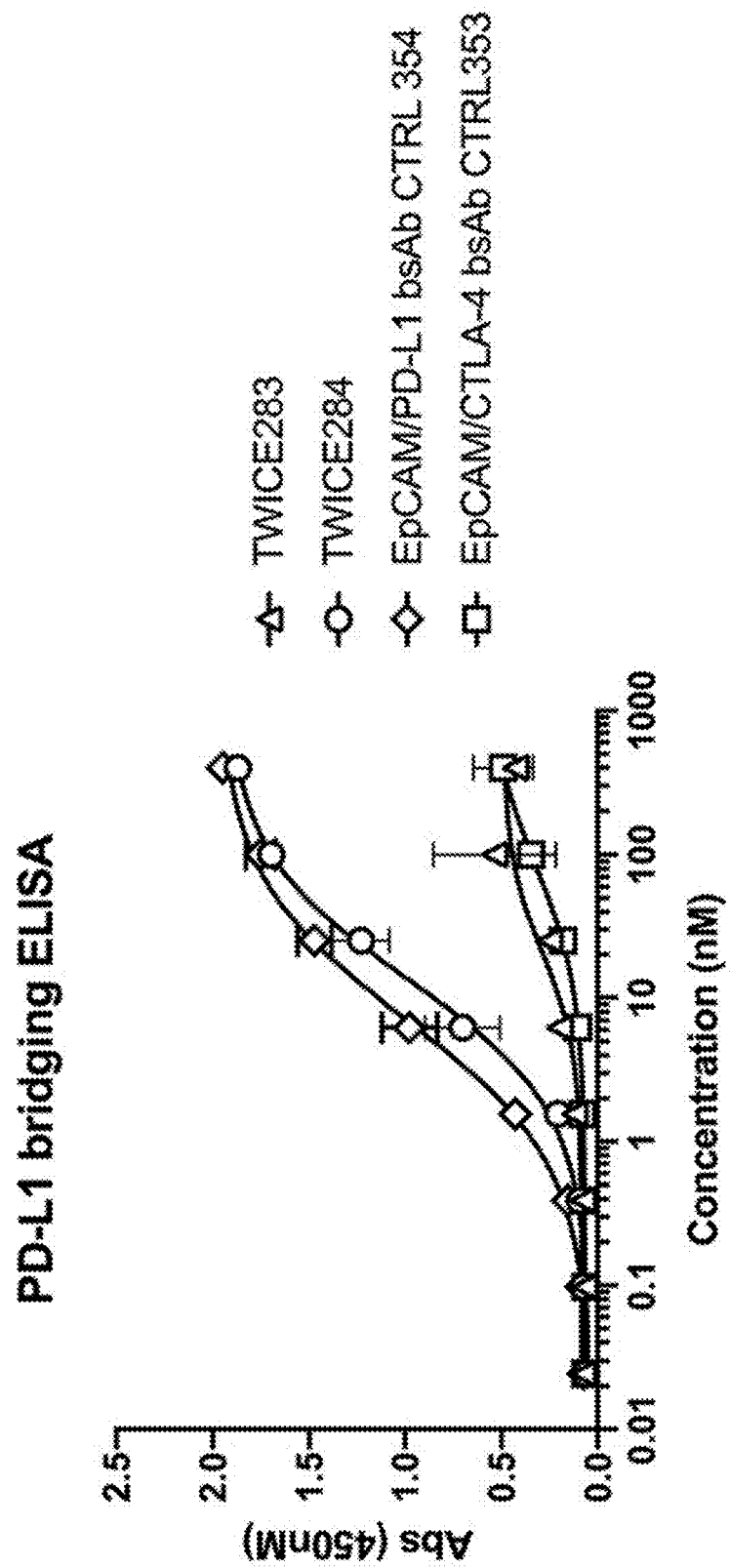

FIG. 13 shows PD-L1 binding of Atezolizumab/Ipilimumab TWICE. Specifically, this shows results with a PD-L1/CTLA-4 TWICE in a PD-L1 bridging ELISA.

Figure 14A:
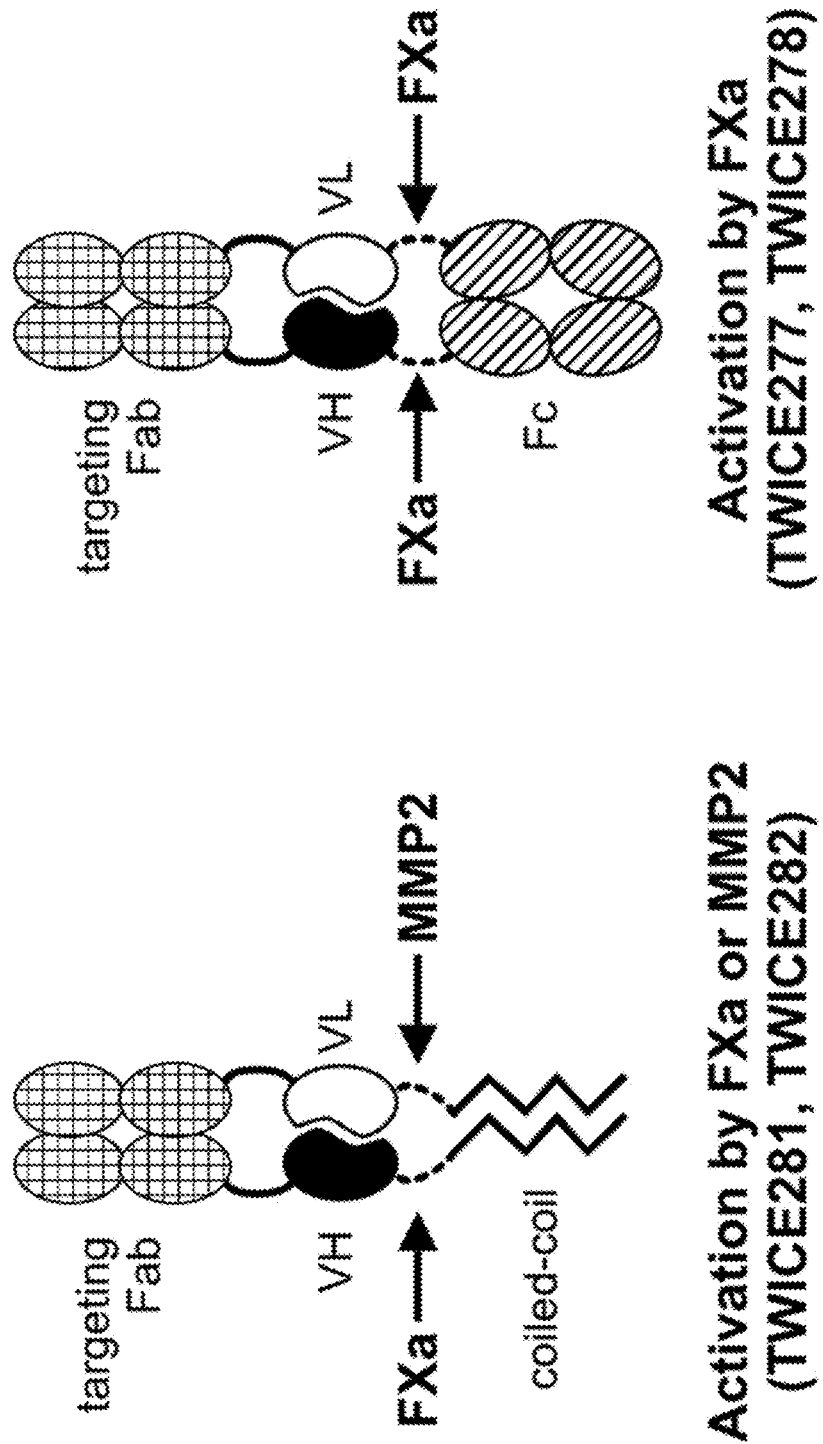
Figure 14B:
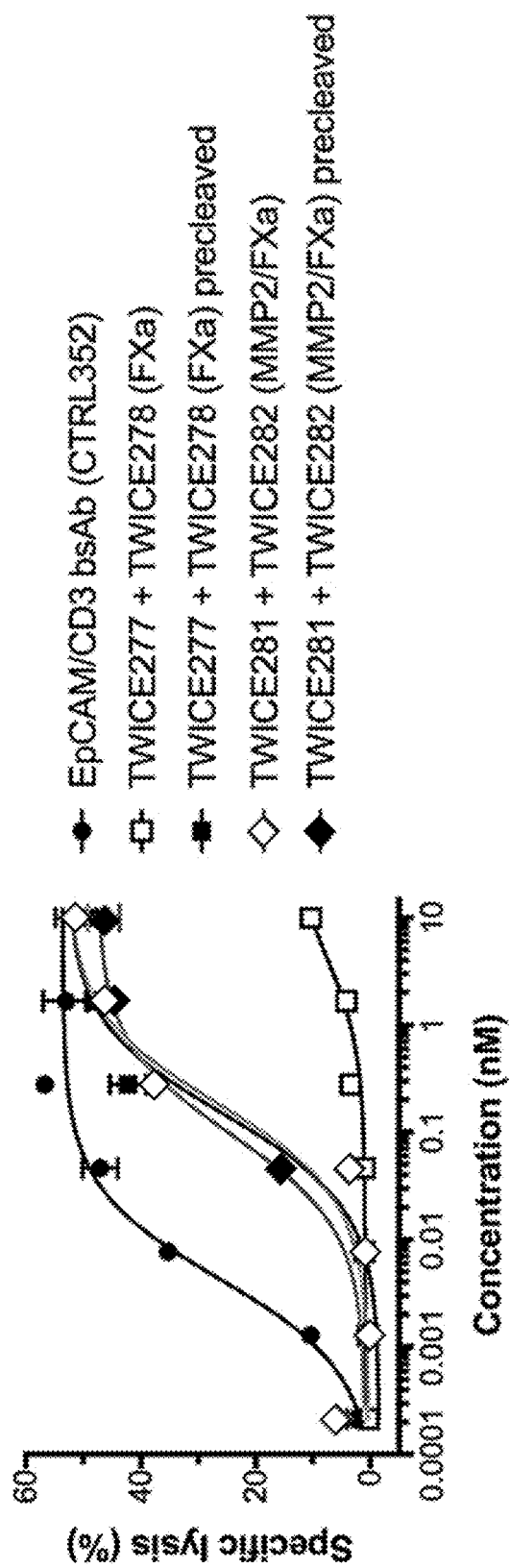

FIGS. 14A-14B show T-cell redirection by a CD3/CTLA4 TWICE with or without pre-cleavage on HCT-15 cells. FIG. 14A shows activation by pre-cleavage. FIG. 14B shows experimental results with and without pre-cleavage.

Figure 15A:
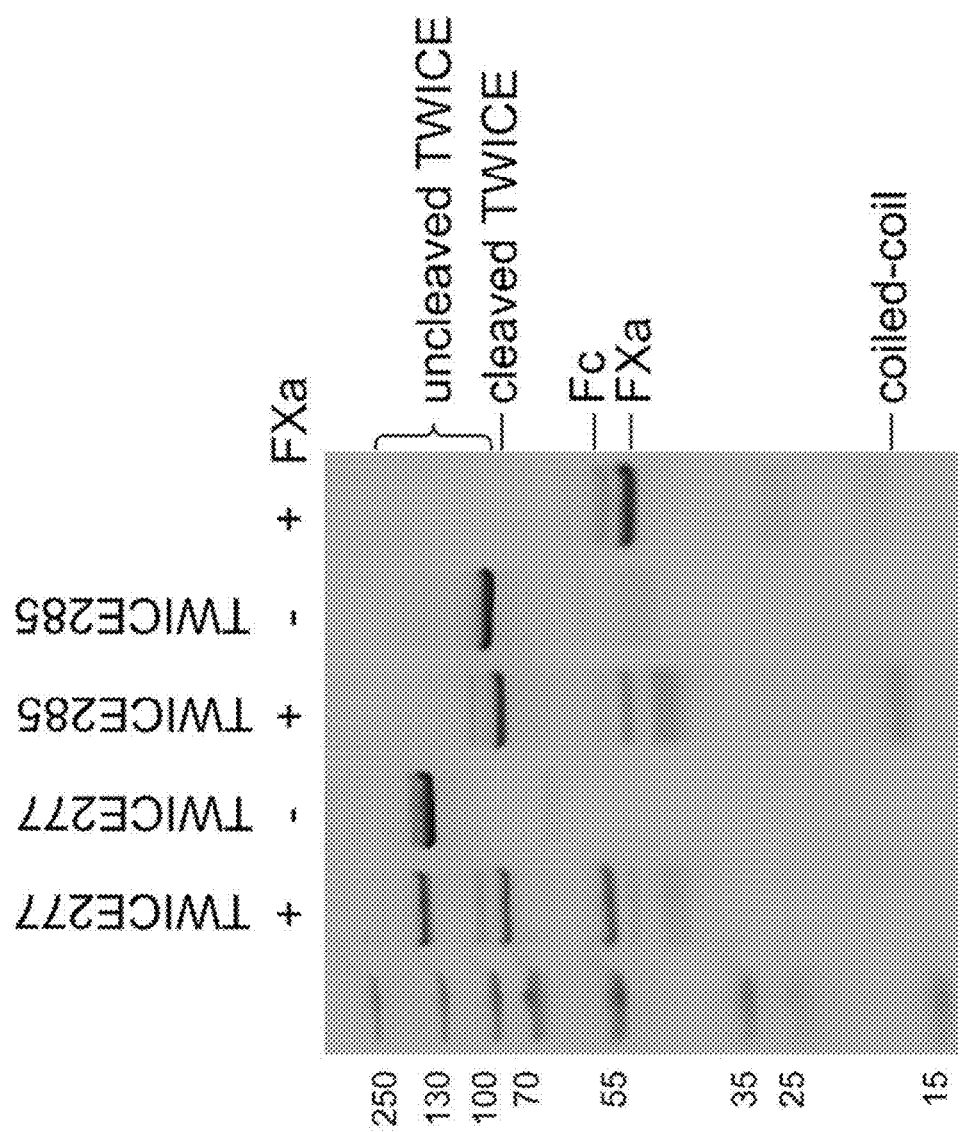
Figure 15B:
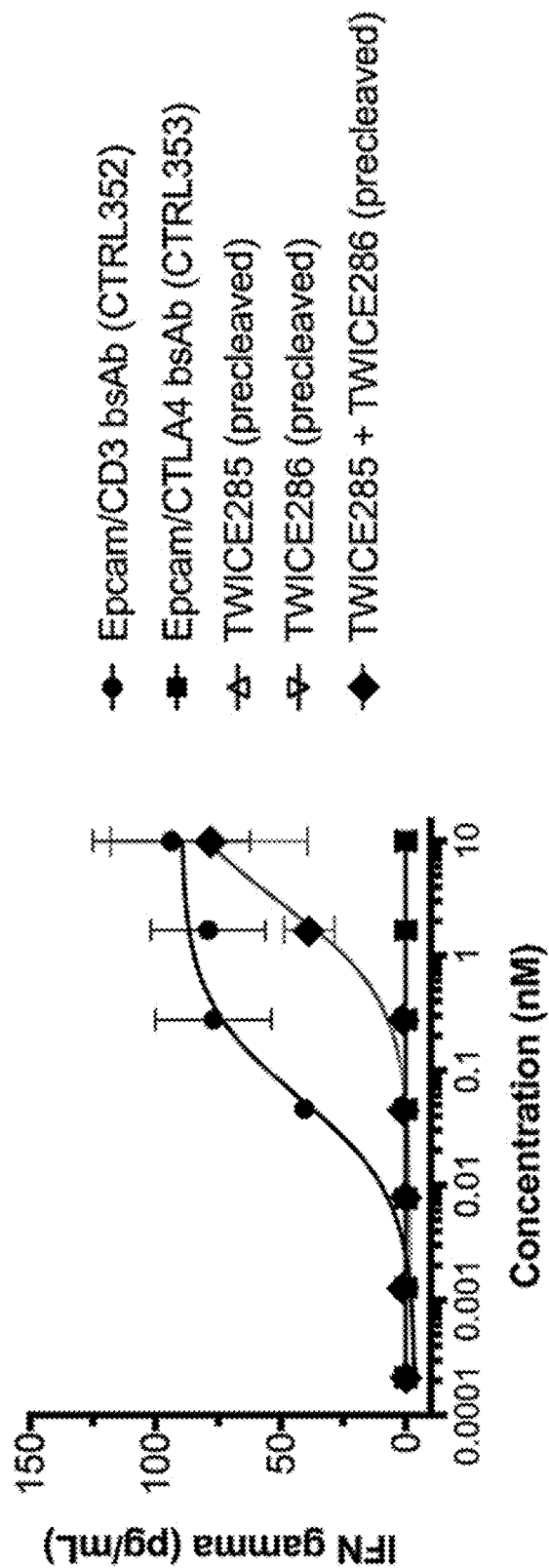
Figure 15C:
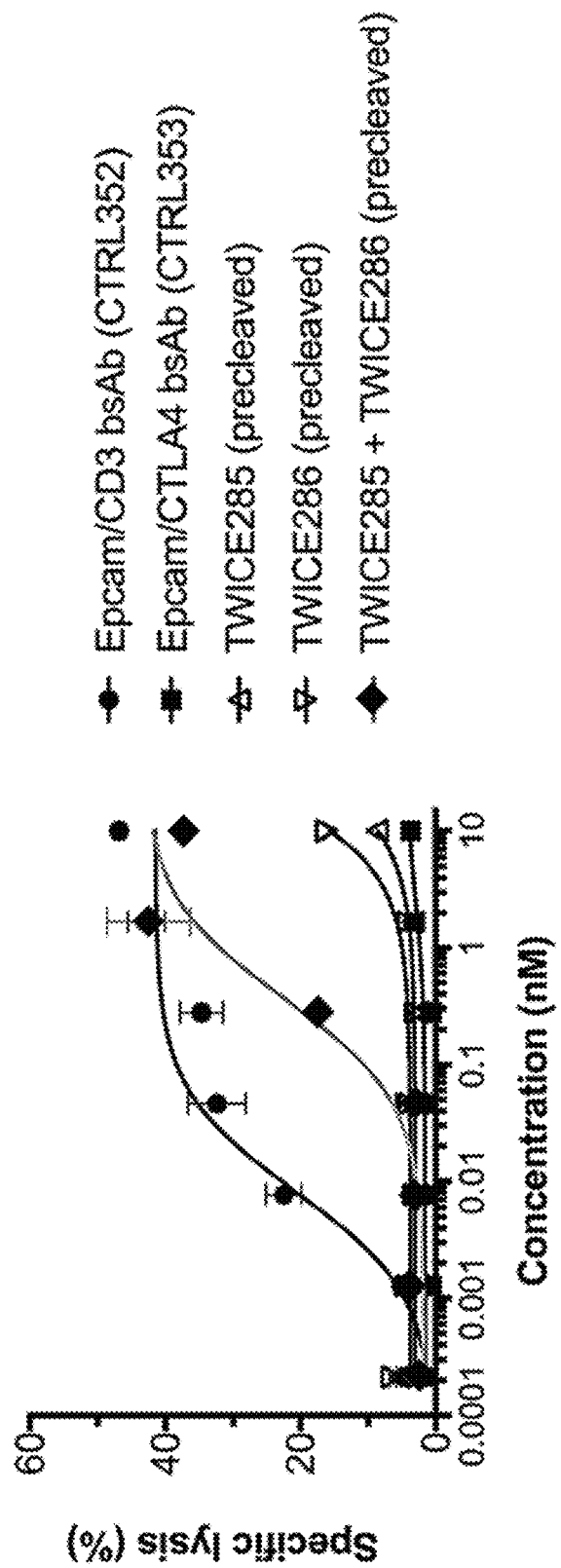
Figure 15D:
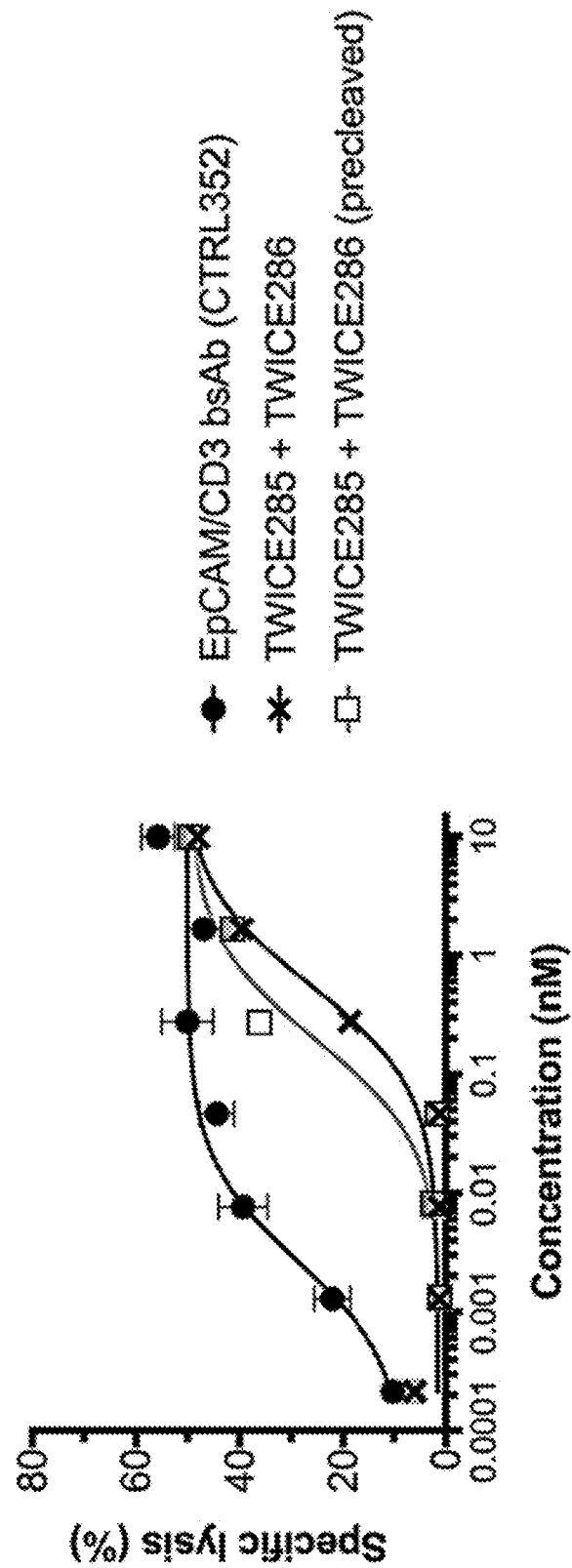

FIGS. 15A-15D show T cell redirection and killing of HCT15 cells by a CD3/CTLA-4 TWICE. FIG. 15A shows results of cleavage analysis. FIG. 15B shows interferon gamma release. FIGS. 15C and 15D show results for LDH release measuring specific lysis of HCT15 cells under different conditions.

Figure 16:
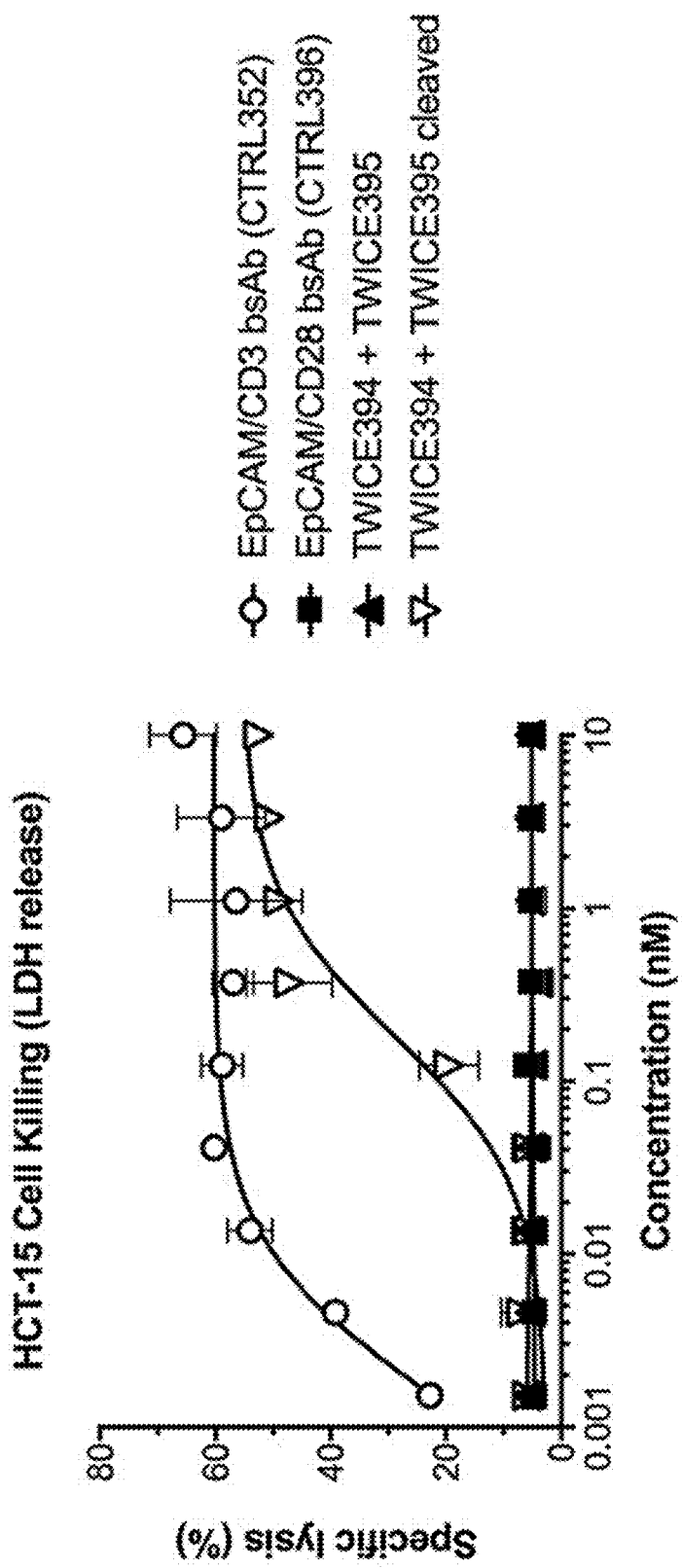

FIG. 16 shows T-cell redirection by CD3/CD28 TWICE on HCT-15. This figure shows HCT-15 cell killing as measured by LDH release with a CD3/CD28 TWICE.

Figure 17B:
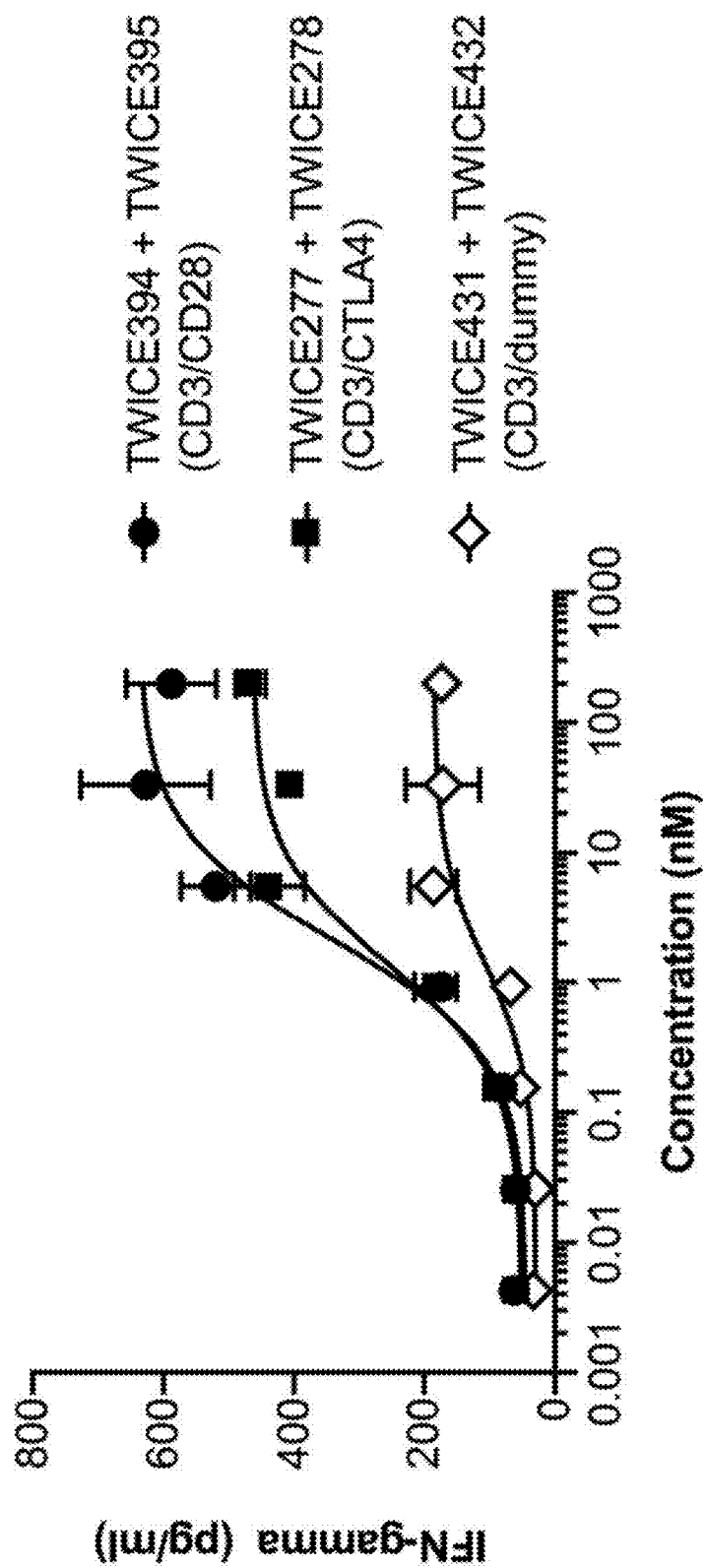

FIGS. 17A-17B show redirection of pre-activated/exhausted peripheral blood mononuclear cells (PMBCs) against HCT15 cells as measured by flow cytometry (FIG. 17A) or interferon gamma release (FIG. 17B).

Figure 18A:
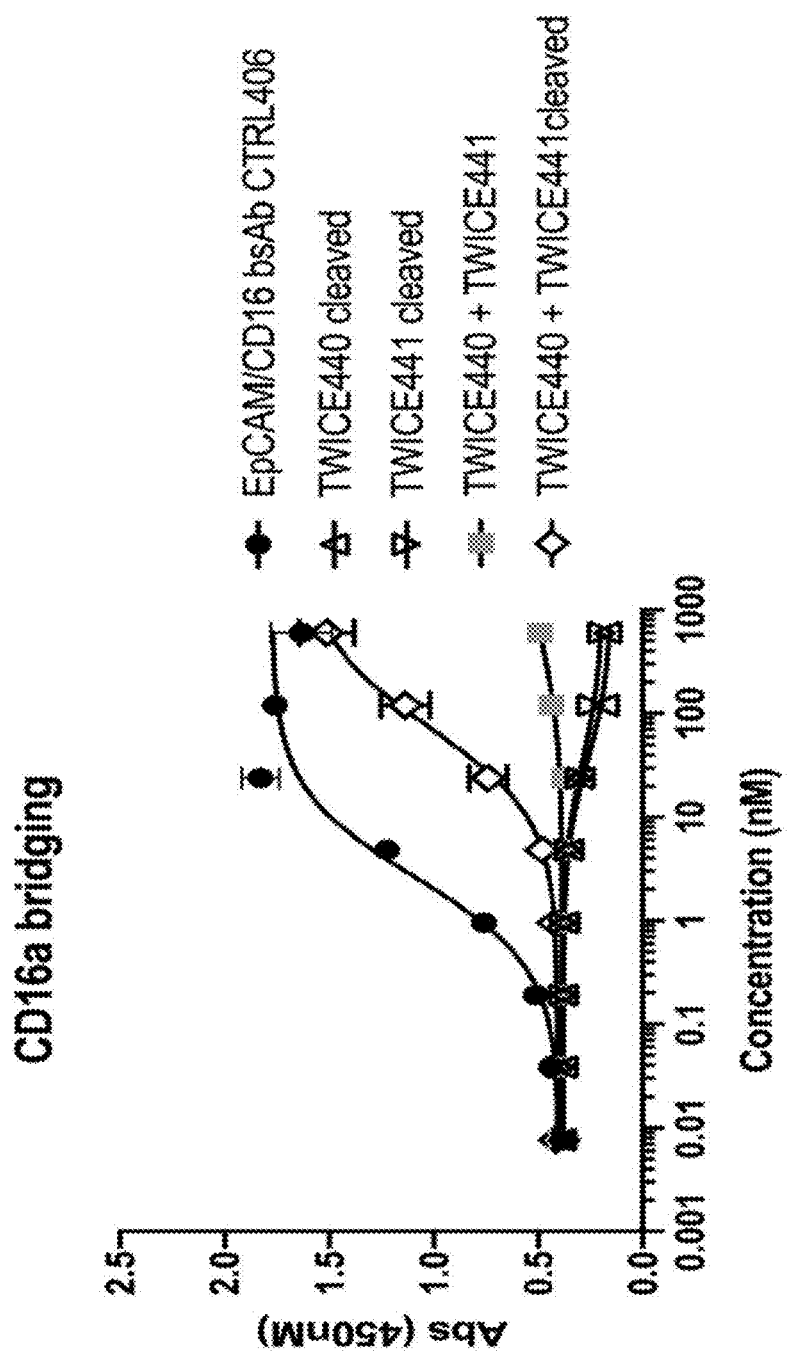
Figure 18B:
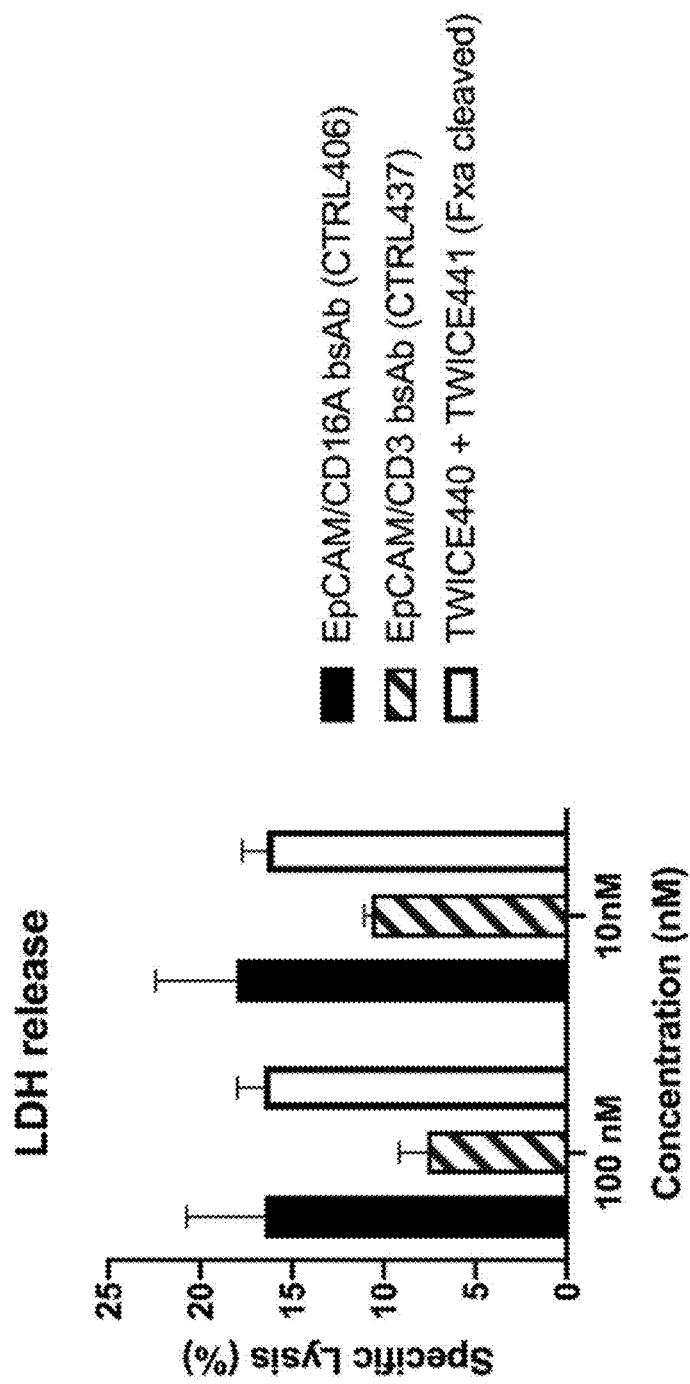

FIGS. 18A-18B show redirection of NK cells against HCT15 cells as measured by a CD16a bridging ELISA (FIG. 18A) or LDH release (FIG. 18B).

DESCRIPTION OF THE SEQUENCES

Table 1 provides a listing of certain sequences referenced herein.

TABLE 1

Description of the Sequences and SEQ ID NOs

| Description | Sequence | # |
|---|---|---|
| ADAM28 cleavage site | KPAKFFRL | 1 |
| ADAM28 cleavage site | DPAKFFRL | 2 |
| ADAM28 cleavage site | KPMKFFRL | 3 |
| ADAM28 cleavage site | LPAKFFRL | 4 |
| ADAM28 cleavage site | LPMKFFRL | 5 |
| ADAM28 cleavage site | KPAMFFRL | 6 |
| ADAM28 cleavage site | YPAKFFRL | 7 |
| ADAM28 cleavage site | KWAKFFRL | 8 |
| ADAM28 cleavage site | DPMKFFRL | 9 |
| ADAM28 cleavage site | DPAMFFRL | 10 |
| ADAM28 cleavage site | DPMMFFRL | 11 |
| ADAM28 cleavage site | KMAMFFRL | 12 |
| ADAM28 cleavage site | KMAMFFIM | 13 |
| ADAM28 cleavage site | KPAMFFIM | 14 |
| ADAM28 cleavage site | LPAMFFRL | 15 |
| ADAM28 cleavage site | LPMMFFRL | 16 |
| ADAM28 cleavage site | LMAMFFRL | 17 |
| ADAM28 cleavage site | LMAMFFIM | 18 |
| ADAM28 cleavage site | LPAMFFIM | 19 |
| ADAM28 cleavage site | LPAMFFYM | 20 |
| ADAM28 cleavage site | KPMMFFRL | 21 |
| ADAM28 cleavage site | KPAKFFYM | 22 |
| ADAM28 cleavage site | KPAKFFIM | 23 |
| ADAM28 cleavage site | IPMKFFRL | 24 |
| ADAM28 cleavage site | IPAMFFRL | 25 |
| ADAM28 cleavage site | IPMMFFRL | 26 |
| ADAM28 cleavage site | IMAMFFRL | 27 |
| ADAM28 cleavage site | IMAMFFIM | 28 |
| ADAM28 cleavage site | IPAMFFIM | 29 |
| ADAM28 cleavage site | IPAMFFYM | 30 |
| cathepsin B cleavage site | FR | 31 |
| cathepsin B cleavage site | FK | 32 |
| cathepsin B cleavage site | VA | 33 |
| cathepsin B cleavage site | VR | 34 |
| cathepsin B cleavage site {Cit} = citrulline | V{Cit} | 35 |

TABLE 1-continued

Description of the Sequences and SEQ ID NOs

| Description | Sequence | # |
| --- | --- | --- |
| cathepsin B cleavage site | HLVEALYL | 36 |
| cathepsin B cleavage site | SLLKSRMVPNFN | 37 |
| cathepsin B cleavage site | SLLIARRMPNFN | 38 |
| cathepsin B cleavage site | KKFA | 39 |
| cathepsin B cleavage site | AFKK | 40 |
| cathepsin B cleavage site | QQQ | 41 |
| cathepsin D cleavage site | PRSFFRLGK | 42 |
| cathepsin D cleavage site | SGVVIATVIVIT | 43 |
| cathepsin K cleavage site | GGP | 44 |
| MMP1 cleavage site | SLGPQGIWGQFN | 45 |
| MMP2 cleavage site | AIPVSLR | 46 |
| MMP2 cleavage site | SLPLGLWAPNFN | 47 |
| MMP2 cleavage site | HPVGLLAR | 48 |
| MMP2 cleavage site | GPLGVRGK | 49 |
| MMP2 cleavage site | GPLGLWAQ | 50 |
| MMP3 cleavage site | STAVIVSA | 51 |
| MMP7 cleavage site | GPLGLARK | 52 |
| MMP7 cleavage site | RPLALWRS | 53 |
| MMP7 cleavage site | SLRPLALWRSFN | 54 |
| MMP2/9 cleavage site | GILGVP | 55 |
| MMP2/9 cleavage site | GPLGIAGQ | 56 |
| MMP9 cleavage site | AVRWLLTA | 57 |
| MMP9 cleavage site | PLGLYAL | 58 |
| MMP9 cleavage site | GPQGIAGQR | 59 |
| MMP9 cleavage site | KPVSLSYR | 60 |
| MMP11 cleavage site | AAATSIAM | 61 |
| MMP11 cleavage site | AAGAMFLE | 62 |
| MMP13 cleavage site | GPQGLAGQRGIV | 63 |
| MMP14 cleavage site | PRHLR | 64 |
| MMP14 cleavage site | PQGLLGAPGILG | 65 |
| MMP14 cleavage site | PRSAKELR | 66 |
| PSA/KLK3 | HSSKLQ | 67 |
| PSA/KLK3 | SSKLQ | 68 |
| KLK4 | RQQR | 69 |
| TMPRSS2 | GGR | 70 |
| Legumain | AAN | 71 |
| ST14 (Matriptase) | QAR | 72 |
| C1s cleavage site | YLGRSYKV | 73 |

TABLE 1-continued

Description of the Sequences and SEQ ID NOs

| Description | Sequence | # |
|---|---|---|
| C1s cleavage site | MQLGRX | 74 |
| MASP2 cleavage site | SLGRKIQI | 75 |
| C2a and Bb cleavage site | GLARSNLDE | 76 |
| uPa cleavage site | TYSRSRYL | 77 |
| uPa cleavage site | KKSPGRVVGGSV | 78 |
| uPa cleavage site | NSGRAVTY | 79 |
| uPa cleavage site | AFK | 80 |
| tissue-type plasminogen activator (tPA) | GGSGQRGRKALE | 81 |
| ADAM10 | PRYEAYKMGK | 82 |
| ADAM12 | LAQAF | 83 |
| ADAM17 | EHADLLAVVAK | 84 |
| flexible amino acid linker (may be presented in repeating fashion) | GGGGS | 85 |
| flexible amino acid linker (may be presented in repeating fashion) | GGGS | 86 |
| flexible amino acid linker (may be presented in repeating fashion) | GS | 87 |
| flexible amino acid linker (may be presented in repeating fashion) | GSGGS | 88 |
| flexible amino acid linker (may be presented in repeating fashion) | GGSG | 89 |
| flexible amino acid linker (may be presented in repeating fashion) | GGSGG | 90 |
| flexible amino acid linker (may be presented in repeating fashion) | GSGSG | 91 |
| flexible amino acid linker (may be presented in repeating fashion) | GSGGG | 92 |
| flexible amino acid linker (may be presented in repeating fashion) | GGGSG | 93 |
| flexible amino acid linker (may be presented in repeating fashion) | GSSSG | 94 |
| Anti-EGFR aptamer (tight binder with $K_d$ = 2.4 nM) | UGCCGCUAUAAUGCACGGAUUUAAUCGCCGUAGAAAAGCAUGUCAAAGCCG | 95 |
| Anti-EGFR aptamer | UGGCGCUAAAUAGCACGGAAAUAAUCGCCGUAGAAAAGCAUGUCAAAGCCG | 96 |
| Anti-EGFR aptamer | UGCUAGUAUAUCGCACGGAUUUAAUCGCCGUAGAAAAGCAUGUCAAAGCCG | 97 |
| Anti-EGFR aptamer | UGCCGCCAUAUCACACGGAUUUAAUCGCCGUAGAAAAGCAUGUCAAAGCCG | 98 |

TABLE 1-continued

Description of the Sequences and SEQ ID NOs

| Description | Sequence | # |
|---|---|---|
| Anti-EGFR aptamer | UUCCGCUGUAUAACACGGACUUAAUCGCCGU AGUAAAGCAUGUCAAAGCCG | 99 |
| Anti-EGFR aptamer | UGUCGCUCUAUUGCACGGAUUUAAUCGCCGU AGAAAAGCAUGUCAAAGCCG | 100 |
| Anti-EGFR aptamer | UGCUGCUUUAUCCCACAUAUUUUUCCCCUC AUAACAAUAUUUCUCCCCCC | 101 |
| Anti-EGFR aptamer | UGCNGCUAUAUCGCNCGUAUUUAAUCGCCGU AGAAAAGCAUGUCNANGCCG | 102 |
| Anti-EGFR aptamer | UGCAAAGAAAACGCACGUAUUUAAUCGCCGU AGUAAAGCAUGUCAAAGCCG | 103 |
| Anti-EGFR aptamer | UGCAUCACUAUCGAACCUAUUUAAUCCACCA AAAUAAUUGCAAGUCCAUACUC | 104 |
| Anti-EGFR aptamer | UGCCNNAAUAACACACNUAUAUAAUCGCCGU ACAAAAUCAUGUCAAANCCG | 105 |
| Anti-EGFR aptamer | UGCAGCUGUAUUGCACGUAUUUAAUCGCCGU AGAAAAGCAUGUCAAAGCCG | 106 |
| Anti-EGFR aptamer | UUCCGAUAAUCCCGCGUACUAAAUCACCAUA GUCAACAAUUUCCAACCUC | 107 |
| Anti-EGFR aptamer | UCCACUAUAUCACACGUAUUUAAUCGCCGUA GAAAAGCAUGUCAAAGCCG | 108 |
| Anti-EGFR aptamer | UCCCUCAACCUCGCUACUAUUUAAUCGCCGU AGAAAAGCAUGUCAAAGCCU | 109 |
| Anti-EGFR aptamer | UGCCGCUAUAUCACACGAAUUUAAUCGCCGU AGAAAAGCAUGUCAAAGCCG | 110 |
| Anti-EGFR aptamer | AGCCCCUAGAACACACGGAUUUAAUCGCCGU AGAAAAGCAUGUCAAAGCCG | 111 |
| Anti-EGFR aptamer | UGCCAAUAUAUAACACGGAAUUUAAUCGCCGU AGAAAAGCAUGUCAAAGCCG | 112 |
| Anti-EGFR aptamer | UGCCGCUAUAGCGCACGGAUUUAAUCGCCGU AGAAAAGCAUGUCAAAGCCG | 113 |
| Anti-EGFR aptamer | UGCAGAUAUAUGUCACUCAUUAAUCCCCGUA UAAAAACAUAACUAAGCUC | 114 |
| Anti-EGFR aptamer | UGUAGCUGUAUUGCACACAUUAAAUCGCCGU AGUAAAGCAUGUCAAAGCCG | 115 |
| Anti-EGFR aptamer | UACCAAUAUAUCGCCACACAUAAUCGCCGUA GAAAAGCAUGUCAAAGCCG | 116 |
| Anti-EGFR aptamer | UGCCGCUAUGCCCACGGAAUUUAAUCGCCGU AGAAAAACAUGUCAAAGUCG | 117 |
| Anti-EGFR aptamer | UGCCGCUAUUUAGCACGGAUUAAAUCGCCGU AGAAAAGCAUGUCAAAGCCG | 118 |
| Anti-EGFR aptamer | UGCCGCUAUUUAGCACGGAUUAAAUCGCCGU AGAAAAGCAUGUCNAAGCCG | 119 |
| Anti-EGFR aptamer | UGUAGUAAUAUGACACGGAUUUAAUCGCCGU AGAAAAGCANGUCAAAGCCU | 120 |
| Anti-EGFR aptamer | UGUCGCCAUUACGCACGGAUUUAAUCGCCGU AGAAAAGCAUGUCAAAGCCG | 121 |
| Anti-EGFR aptamer | UGCCCCCAAACUACACAAAUUUAAUCGCCGU AUAAAAGCAUGUCAAAGCCG | 122 |
| Anti-EGFR aptamer | UGCACUAUCUCACACGUACUAAUCGCCGUAU AAAGCAUGUCAAAGCCG | 123 |

TABLE 1-continued

Description of the Sequences and SEQ ID NOs

| Description | Sequence | # |
|---|---|---|
| Anti-EGFR aptamer | UGUCGCAAUAAUACACUAAUUUAAUCGCCGU AGAAAAGCAUGUCAAAGCCG | 124 |
| Anti-EGFR aptamer | UGCAACAAUAUAGCACGUAUUUAAUCGCCGU AGUAAAGCAUGUCAAAGG | 125 |
| Anti-EGFR aptamer | CUACCACAAAUCCCACAUAUUUAAUCUCCCA AUCAAAUCUUGUCCAUUCCC | 126 |
| Anti-EGFR aptamer | UGCCCUAAACUCACACGGAUAUAAUCGCCGU AGAAAAGCAUGUCAAAGCCG | 127 |
| Anti-EGFR aptamer | UUGUCGUAUGUCACACGUAUUUAAAUCGCCGU AUAAAAGCAUGUCAAAGCCG | 128 |
| Anti-EGFR aptamer | UUCCGCUAUAACACACGGAGAAAAUCGCCGU AGUAAAGCAUGUCAAAGCCG | 129 |
| Anti-EGFR aptamer | UGCCGAUAUAACGCACGGAUAUAAUCGCCGU AGAAAAGCAUGUCAAAGCCG | 130 |
| Anti-EGFR aptamer | UGCCAUUAUACAGCACGGAUUUAAUCGCCGU AGAAAAGCAUGUCAAAGCCG | 131 |
| Anti-EGFR aptamer | UCCAGAAAUAUGCACACAUUUAAUCGCCGUA GAAAAGCAUGUCAAAGCCG | 132 |
| Anti-EGFR aptamer | UCCGCUAAACAACACGGAUACAAUCGCCGUA GAAAAGCAUGUCCAAGCCG | 133 |
| Anti-EGFR aptamer | UGCACUAUCUCACACGUACUAAUCGCCGUAU AAAAGCAUGUCAAANNNG | 134 |
| Anti-EGFR aptamer | AUNGCNANNNUACACGUAUUNAAUCGCCGUA GAAAAGCAUGUCANAGCCG | 135 |
| Anti-EGFR aptamer | UGCUGCUAUAUUGCAAUUUUUUAAACUAAGU AGAAAACCAUGUACAAGUCG | 136 |
| Anti-EGFR aptamer | UGUCGCCAUAUUGCACGGAUUUAAUCGCCGU AGAAAAGCAUGUCCAAGCCG | 137 |
| Anti-EGFR aptamer | UGCCGUUAUAACCCACGGAAUUUAACCUCCG UAGAAAAGCAUGUCAAAGCCG | 138 |
| Anti-EGFR aptamer | UGUGAAUAUAUAUCACGGAUUUAAUCGCCGU AUAAAAGCNAUGUCAAAGCCG | 139 |
| Anti-EGFR aptamer | UGCCGAUAUNNANCACGGAUUUAAUCGCCGU AGAAAAGCAUGUCCAAGCCG | 140 |
| Anti-EGFR aptamer | UGUCACUAAAUUGCACGUAUAUAAUCGCCGU AGUAAGCAUGUCAAAGCCG | 141 |
| Anti-EGFR aptamer | UGCAACCAUAAAGCACGUAUAAAUCGCCGU AUAUAAGCAUGUCaAAGCCG | 142 |
| Anti-EGFR aptamer | UGCCGCUAUAUAGCACGUAUUAAUCGCCGUA GUAAAGCAUGUCaAAGCCG | 143 |
| Anti-EGFR aptamer | UGCCGCUAUAGCACACGGAAUUUAAUCGCCG UAGUAAAGCAUGUCAAAGCCG | 144 |
| Anti-EGFR aptamer | UGCAGGUAUAUAACNCGGAUUUAAUCGCCGU AGAAAAGCAUGUCNAAGCCG | 145 |
| Anti-EGFR aptamer | UGCUCCUAUAACACACGGAUUUAAUCGCCGU AGAAAAGCAUGUCCAAGCCG | 146 |
| Anti-EGFR aptamer | UGCCCGUAAUUGCACGGAUUUAAUCGCCGUA GAAAAGCAUGUCCAAGCCGG | 147 |
| Anti-EGFR aptamer | ACUCCCUAUAUNGCAACUACAUAAUCGCCGU AAAUAAGCAUGUNCAAGCCG | 148 |

TABLE 1-continued

Description of the Sequences and SEQ ID NOs

| Description | Sequence | # |
|---|---|---|
| Anti-EGFR aptamer | UGAAGCUAGAUCACACUAAAUUAAUCGCCGU AGAAAAGCAUGUCAAAAAGCCG | 149 |
| Anti-EGFR aptamer | UGACUCUUUAUCCCCCGUACAUUAUUcACCGA ACCAAAGCAUUACCAUCCCC | 150 |
| Anti-EGFR aptamer | UGACGCCCUAACACACGUAUAUAAUCGCCGU AGAAAAGCAUGUCAAAGCCG | 151 |
| Anti-EGFR aptamer | UGUCGCAAAAUAGCACGUAUUUAAUCGCCGU AGAAAAGCAUGUCCAAGCCG | 152 |
| Anti-EGFR aptamer | UGAGUGUAUAAUUCACGUAUUUAAUCGCCGU AGAAAAGCAUGUCAAAGCCG | 153 |
| Anti-EGFR aptamer | UGCUACUAUAUCGUAGGUAACUAAUCGCCCU ACAAACUCACUCUAAAACCG | 154 |
| Anti-EGFR aptamer | UUACGCUAUAUCACACGGAAUUUUAAUCGCC GUAGAAAAGCAUGUCCAAGCCG | 155 |
| Anti-EGFR aptamer | CCCAUCUGUACUACAGGAAUUUAAUCGCCGU AGAAAAGCAUGUCCAAGCCG | 156 |
| Anti-EGFR aptamer | UGCCCAUAAAUAGCACGGAUUUUAAUCGCCGU AGAAAAGCAUGUCCAAGCCG | 157 |
| Anti-EGFR aptamer | UGCCGCAAUAACAUACACAUAUAAUCGCCGU AGAAAAGCAUGUCAAAGCCG | 158 |
| Anti-EGFR aptamer | UGCAACUAUAUCGCACGUAUGUAAUCGCCGU AGAAAAAGCAUGUCAAAGCC | 159 |
| Anti-EGFR aptamer | UUCCGCUAUAUAGCACGGAAUUAAUCGCCGU AGAAAAGCAUGUCCAAGCCG | 160 |
| Anti-EGFR aptamer | UUCCGCUAAGUCACACGAAAUUAAUCGCCGU AGAAAAGCAUGUCCAAGCCG | 161 |
| Anti-EGFR aptamer | UGUAGCAAUAUCACACGUAAUUAAUCGCCGU AUAUAAGCAUGUCAAAGCCG | 162 |
| Anti-EGFR aptamer | UGCCGUUAUAUAUCACGGAUUUAAUCGCCGU AGAAAAGCAUGUCCAAGCCG | 163 |
| Anti-EGFR aptamer | UAACACAUAUAUCAAGUAACUUAUCUCCUUA GUAACCAUCUCCAAGCCG | 164 |
| Anti-EpCAM VH-CH1, SP34 VH, FXa, basic coil | EVQLLEQSGAELVRPGTSVKISCKASGYAFTNYW LGWVKQRPGHGLEWIGDIFPGSGNIHYNEKPFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVKPGGSLRLSCAASGFTFNT YAMNWVRQAPGKGLEWVARIRSKYNNYATYY ADSVKGRFTISRDDSKNSLYLQMNSLKTEDTAVY YCVRHGNFGNSYVSWFAYWGQGTLVTVSSGGG GSIEGRGGGGSKNAQCKKKLQALKKKNAQLKW KLQALKKKLAQGHHHHHH | 165 |
| Anti-EpCAM VL-CL, Atezolizumab VL, MMP2, acid coil | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKV EIKGGPLGVRGKGGGSENAQCEKELQALEKENA QLEWELQALEKELAQ | 166 |

TABLE 1-continued

Description of the Sequences and SEQ ID NOs

| Description | Sequence | # |
|---|---|---|
| Anti-EpCAM VH-CH1, SP34 VH, FXa, IgE CH2 | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVKPGGSLRLSCAASGFTFNT YAMNWVRQAPGKGLEWVARIRSKYNNYATYY ADSVKGRFTISRDDSKNSLYLQMNSLKTEDTAVY YCVRHGNEGNSYVSWFAYWGQGTLVTVSSGIEG RGPPTVKILQSSCDGGGHFPPTIQLLCLVSGYTPG TIQITWLEDGQVMDVDLSTASTTQEGELASTQSE LTLSQKHWLSDRTYTCQVTYQGHTFEDSTKKCA HHHHHH | 167 |
| Anti-EpCAM VL-CL, Atezolizumab VL, FXa, IgE CH2 | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKV EIKGGGIEGRGPPTVKILQSSCDGGGHFPPTIQLLC LVSGYTPGTIQITWLEDGQVMDVDLSTASTTQEG ELASTQSELTLSQKHWLSDRTYTCQVTYQGHTFE DSTKKCA | 168 |
| Anti-EpCAM VH-CH1, SP34 VH, FXa, IgE CH2 | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVKPGGSLRLSCAASGFTFNT YAMNWVRQAPGKGLEWVARIRSKYNNYATYY ADSVKGRFTISRDDSKNSLYLQMNSLKTEDTAVY YCVRHGNFGNSYVSWFAYWGQGTLVTVSSGGGI EGRGPPTVKILQSSCDGGGHFPPTIQLLCLVSGYT PGTIQITWLEDGQVMDVDLSTASTTQEGELASTQ SELTLSQKHWLSDRTYTCQVTYQGHTFEDSTKK CAHHHHHH | 169 |
| Anti-EpCAM VL-CL, Atezolizumab VL, FXa, IgE CH2 | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKV EIKGGGIEGRGGGDKTHTCPPCPAPELLGGPSVFL FPPKPKDTLMISRTPEVTCVVVDVSHEDPEVKFN WYVDGVEVHNAKTKPREEQYQSTYRVVSVLTV LHQDWLNGKEYKCKVSNKALPAPIEKTISKAKG QPREPQVYTLPPSRDELTKNQVSLTCLVSGFYPS DIAVEWESNGQPENNYKTTPPVLDSDGSFKLYSK LTVDKSRWQQGNVFSCSVMHEALHNHYTQKSLS LSPG | 170 |
| Anti-EpCAM VH-CH1, SP34 VH, FXa, Fc | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVKPGGSLRLSCAASGFTFNT YAMNWVRQAPGKGLEWVARIRSKYNNYATYY | 171 |

TABLE 1-continued

Description of the Sequences and SEQ ID NOs

| Description | Sequence | # |
|---|---|---|
| | ADSVKGRFTISRDDSKNSLYLQMNSLKTEDTAVY YCVRHGNFGNSYVSWFAYWGQGTLVTVSSGGGI EGRGGGDKTHTCPPCPAPELLGGPSVFLFPPKPK DTLMISRTPEVTCVVVDVSHEDPEVKFNWYVDG VEVHNAKTKPREEQYQSTYRVVSVLTVLHQDWL NGKEYKCKVSNKALPAPIEKTISKAKGQPREPQV YTLPPSRDELTKNQVKLTCLVKGFYPSDIAVEWE SNGQPENNYKTTPPVLDSDGSFFLYSLLTVDKSR WQQGNVFSCSVMHEALHNHYTQKSLSLSPG | |
| Anti-EpCAM VL-CL, Atezolizumab VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKV EIKGGGIEGRGGGDKTHTCPPCPAPELLGGPSVFL FPPKPKDTLMISRTPEVTCVVVDVSHEDPEVKFN WYVDGVEVHNAKTKPREEQYQSTYRVVSVLTV LHQDWLNGKEYKCKVSNKALPAPIEKTISKAKG QPREPQVYTLPPSRDELTKNQVSLTCLVSGFYPS DIAVEWESNGQPENNYKTTPPVLDSDGSFKLYSK LTVDKSRWQQGNVFSCSVMHEALHNHYTQKSLS LSPG | 172 |
| Anti-EpCAM VH-CH1, SP34 VH, FXa, Fc | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVKPGGSLRLSCAASGFTFNT YAMNWVRQAPGKGLEWVARIRSKYNNYATYY ADSVKGRFTISRDDSKNSLYLQMNSLKTEDTAVY YCVRHGNFGNSYVSWFAYWGQGTLVTVSSGGG GSIEGRGGGDKTHTCPPCPAPELLGGPSVFLEPPK PKDTLMISRTPEVTCVVVDVSHEDPEVKFNWYV DGVEVHNAKTKPREEQYQSTYRVVSVLTVLHQD WLNGKEYKCKVSNKALPAPIEKTISKAKGQPREP QVYTLPPSRDELTKNQVKLTCLVKGFYPSDIAVE WESNGQPENNYKTTPPVLDSDGSFFLYSLLTVDK SRWQQGNVFSCSVMHEALHNHYTQKSLSLSPG | 173 |
| Anti-EpCAM VL-CL, Atezolizumab VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKV EIKGGGGSIEGRGGGDKTHTCPPCPAPELLGGPSV FLFPPKPKDTLMISRTPEVTCVVVDVSHEDPEVKF NWYVDGVEVHNAKTKPREEQYQSTYRVVSVLT VLHQDWLNGKEYKCKVSNKALPAPIEKTISKAK GQPREPQVYTLPPSRDELTKNQVSLTCLVSGFYP SDIAVEWESNGQPENNYKTTPPVLDSDGSFKLYS KLTVDKSRWQQGNVFSCSVMHEALHNHYTQKS LSLSPG | 174 |
| Anti-EpCAM VH-CH1, SP34 VH, FXa, basic coil | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVKPGGSLRLSCAASGFTFNT YAMNWVRQAPGKGLEWVARIRSKYNNYATYY | 175 |

TABLE 1-continued

Description of the Sequences and SEQ ID NOs

| Description | Sequence | # |
|---|---|---|
| | ADSVKGRFTISRDDSKNSLYLQMNSLKTEDTAVY YCVRHGNFGNSYVSWFAYWGQGTLVTVSSGGG GSIEGRGGSGGGSKNAQCKKKLQALKKKNAQLK WKLQALKKKLAQGHHHHHH | |
| Anti-EpCAM VL-CL, Atezolizumab VL, FXa, acid coil | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCRASQDVSTAVAW YQQKPGKAPKLLIYSASFLYSGVPSRFSGSGSGTD FTLTISSLQPEDFATYYCQQYLYHPATFGQGTKV EIKGGGGSIEGRGGSGGGSENAQCEKELQALEKE NAQLEWELQALEKELAQ | 176 |
| Anti-EpCAM VL-CL, SP34 VH, FXa, Ckappa | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSE VQLVESGGGLVKPGGSLRLSCAASGFTFNTYAM NWVRQAPGKGLEWVARIRSKYNNYATYYADSV KGRFTISRDDSKNSLYLQMNSLKTEDTAVYYCV RHGNFGNSYVSWFAYWGQGTLVTVSSIEGRGPS VFIFPPSDEQLKSGTASVVCLLNNFYPREAKVQW KVDNALQSGNSQESVTEQDSKDSTYSLSSTLTLS KADYEKHKVYACEVTHQGLSSPVTKSFNRGEC | 177 |
| Anti-EpCAM VH-CH1, Atezolizumab VL, FXa, CH1, 6His | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSDIQMTQSPSSLSASVGDRVTITCRASQDVST AVAWYQQKPGKAPKLLIYSASFLYSGVPSRFSGS GSGTDFTLTISSLQPEDFATYYCQQYLYHPATFG QGTKVEIKGGIEGRGPSVFPLAPSSKSTSGGTAAL GCLVKDYFPEPVTVSWNSGALTSGVHTFPAVLQ SSGLYSLSSVVTVPSSSLGTQTYICNVNHKPSNTK VDKKVEPKSCHHHHHH | 178 |
| Anti-EpCAM VL-CL, Atezolizumab VH, FXa, Ckappa | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSE VQLVESGGGLVQPGGSLRLSCAASGFTFSDSWIH WVRQAPGKGLEWVAWISPYGGSTYYADSVKGR FTISADTSKNTAYLQMNSLRAEDTAVYYCARRH WPGGFDYWGQGTLVTVSSIEGRGPSVFIFPPSDE QLKSGTASVVCLLNNFYPREAKVQWKVDNALQS GNSQESVTEQDSKDSTYSLSSTLTLSKADYEKHK VYACEVTHQGLSSPVTKSFNRGEC | 179 |
| Anti-EpCAM VH-CH1, SP34 VL, FXa, CH1, 6His | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSQAVVTQEPSLTVSPGGTVTLTCRSSTGAVTA SNYANWVQQKPGQAPRGLIGGTNKRAPWTPARF SGSLLGGKAALTITGAQAEDEADYYCALWYSNL WVFGGGTKLTVLGGIEGRGPSVFPLAPSSKSTSG | 180 |

TABLE 1-continued

Description of the Sequences and SEQ ID NOs

| Description | Sequence | # |
|---|---|---|
| | GTAALGCLVKDYFPEPVTVSWNSGALTSGVHTF PAVLQSSGLYSLSSVVTVPSSSLGTQTYICNVNHK PSNTKVDKKVEPKSCHHHHHH | |
| Anti-EpCAM VL-CL, Ipilimumab VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSEI VLTQSPGTLSLSPGERATLSCRASQSVGSSYLAW YQQKPGQAPRLLIYGAFSRATGIPDRFSGSGSGTD FTLTISRLEPEDFAVYYCQQYGSSPWTFGQGTKV EIKGGGIEGRGGGDKTHTCPPCPAPELLGGPSVFL FPPKPKDTLMISRTPEVTCVVVDVSHEDPEVKFN WYVDGVEVHNAKTKPREEQYQSTYRVVSVLTV LHQDWLNGKEYKCKVSNKALPAPIEKTISKAKG QPREPQVYTLPPSRDELTKNQVSLTCLVSGFYPS DIAVEWESNGQPENNYKTTPPVLDSDGSFKLYSK LTVDKSRWQQGNVFSCSVMHEALHNHYTQKSLS LSPG | 181 |
| Anti-EpCAM VH-CH1, Ipilimumab VH, FXa, Fc | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSQVQLVESGGGVVQPGRSLRLSCAASGFTFSS YTMHWVRQAPGKGLEWVTFISYDGNNKYYADS VKGRFTISRDNSKNTLYLQMNSLRAEDTAIYYCA RTGWLGPFDYWGQGTLVTVSSGGGIEGRGGGDK THTCPPCPAPELLGGPSVFLFPPKPKDTLMISRTPE VTCVVVDVSHEDPEVKFNWYVDGVEVHNAKTK PREEQYQSTYRVVSVLTVLHQDWLNGKEYKCK VSNKALPAPIEKTISKAKGQPREPQVYTLPPSRDE LTKNQVKLTCLVKGFYPSDIAVEWESNGQPENN YKTTPPVLDSDGSFFLYSLLTVDKSRWQQGNVFS CSVMHEALHNHYTQKSLSLSPG | 182 |
| Anti-EpCAM VL-CL, SP34 VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSQ AVVTQEPSLTVSPGGTVTLTCRSSTGAVTASNYA NWVQQKPGQAPRGLIGGTNKRAPWTPARFSGSL LGGKAALTITGAQAEDEADYYCALWYSNLWVF GGGTKLTVLGGGIEGRGGGDKTHTCPPCPAPELL GGPSVFLFPPKPKDTLMISRTPEVTCVVVDVSHE DPEVKFNWYVDGVEVHNAKTKPREEQYQSTYR VVSVLTVLHQDWLNGKEYKCKVSNKALPAPIEK TISKAKGQPREPQVYTLPPSRDELTKNQVSLTCLV SGFYPSDIAVEWESNGQPENNYKTTPPVLDSDGS FKLYSKLTVDKSRWQQGNVFSCSVMHEALHNH YTQKSLSLSPG | 183 |
| Anti-EpCAM VL-CL, Ipilimumab VL, MMP2, acid coil | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSEI VLTQSPGTLSLSPGERATLSCRASQSVGSSYLAW YQQKPGQAPRLLIYGAFSRATGIPDRFSGSGSGTD FTLTISRLEPEDFAVYYCQQYGSSPWTFGQGTKV EIKGGPLGVRGKGGGSENAQCEKELQALEKENA QLEWELQALEKELAQ | 184 |

TABLE 1-continued

Description of the Sequences and SEQ ID NOs

| Description | Sequence | # |
|---|---|---|
| Anti-EpCAM VH-CH 1, Ipilimuab VH, FXa, basic coil | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSQVQLVESGGGVVQPGRSLRLSCAASGFTFSS YTMHWVRQAPGKGLEWVTFISYDGNNKYYADS VKGRFTISRDNSKNTLYLQMNSLRAEDTAIYYCA RTGWLGPFDYWGQGTLVTVSSGGGGSIEGRGGG GSKNAQCKKKLQALKKKNAQLKWKLQALKKKL AQGHHHHHH | 185 |
| Anti-EpCAM VL-CL, SP34 VL, MNIP2, acid coil | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSQ AVVTQEPSLTVSPGGTVTLTCRSSTGAVTASNYA NWVQQKPGQAPRGLIGGTNKRAPWTPARFSGSL LGGKAALTITGAQAEDEADYYCALWYSNLWVF GGGTKLTVLGGPLGVRGKGGGSENAQCEKELQA LEKENAQLEWELQALEKELAQ | 186 |
| Anti-EpCAM VH-CH1, Atezolizumab VH, FXa, basic coil | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVQPGGSLRLSCAASGFTFSD SWIHWVRQAPGKGLEWVAWISPYGGSTYYADS VKGRFTISADTSKNTAYLQMNSLRAEDTAVYYC ARRHWPGGFDYWGQGTLVTVSSGGGGSIEGRGG GGSKNAQCKKKLQALKKKNAQLKWKLQALKK KLAQGHHHHHH | 187 |
| Anti-EpCAM VL-CL, Ipilimumab VL, FXa, acid coil | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSEI VLTQSPGTLSLSPGERATLSCRASQSVGSSYLAW YQQKPGQAPRLLIYGAFSRATGIPDRFSGSGSGTD FTLTISRLEPEDFAVYYCQQYGSSPWTFGQGTKV EIKGGGGSIEGRGGSGGGSENAQCEKELQALEKE NAQLEWELQALEKELAQ | 188 |
| Anti-EpCAM VH-CH1, Ipilimumab VH, FXa, basic coil | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSQVQLVESGGGVVQPGRSLRLSCAASGFTFSS YTMHWVRQAPGKGLEWVTFISYDGNNKYYADS VKGRFTISRDNSKNTLYLQMNSLRAEDTAIYYCA RTGWLGPFDYWGQGTLVTVSSGGGGSIEGRGGS GGGSKNAQCKKKLQALKKKNAQLKWKLQALK KKLAQGHHHHHH | 189 |
| Anti-EpCAM VL-CL, SP34 VL, FXa, acid coil | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSQ | 190 |

TABLE 1-continued

Description of the Sequences and SEQ ID NOs

| Description | Sequence | # |
|---|---|---|
| | AVVTQEPSLTVSPGGTVTLTCRSSTGAVTASNYA<br>NWVQQKPGQAPRGLIGGTNKRAPWTPARFSGSL<br>LGGKAALTITGAQAEDEADYYCALWYSNLWVF<br>GGGTKLTVLGGGGSIEGRGGSGGGSENAQCEKE<br>LQALEKENAQLEWELQALEKELAQ | |
| Anti-EpCAM VH 44Cys,<br>Sp34 VH, FXa, Fc | EVQLLEQSGAELVRPGTSVKISCKASGYAFTNYW<br>LGWVKQRPGHCLEWIGDIFPGSGNIHYNEKFKGK<br>ATLTADKSSSTAYMQLSSLTFEDSAVYFCARLRN<br>WDEPMDYWGQGTTVTSSGGGSGGGGSEVQLV<br>ESGGGLVKPGGSLRLSCAASGFTFNTYAMNWVR<br>QAPGKGLEWVARIRSKYNNYATYYADSVKGRFT<br>ISRDDSKNSLYLQMNSLKTEDTAVYYCVRHGNF<br>GNSYVSWFAYWGQGTLVTVSSGGGIEGRGGGD<br>KTHTCPPCPAPELLGGPSVFLFPPKPKDTLMISRT<br>PEVTCVVVDVSHEDPEVKFNWYVDGVEVHNAK<br>TKPREEQYQSTYRVVSVLTVLHQDWLNGKEYKC<br>KVSNKALPAPIEKTISKAKGQPREPQVYTLPPSRD<br>ELTKNQVKLTCLVKGFYPSDIAVEWESNGQPEN<br>NYKTTPPVLDSDGSFFLYSLLTVDKSRWQQGNV<br>FSCSVMHEALHNHYTQKSLSLSPG | 191 |
| Anti-EpCAM VL 100<br>Cys, Ipilimumab VL,<br>FXa, Fc | ELVMTQSPSSLTVTAGEKVTMSCKSSQSLLNSGN<br>QKNYLTWYQQKPGQPPKLLIYWASTRESGVPDR<br>FTGSGSGTDFTLTISSVQAEDLAVYYCQNDYSYP<br>LTFGCGTKLEIKGGGGSGGGGSEIVLTQSPGTLSL<br>SPGERATLSCRASQSVGSSYLAWYQQKPGQAPR<br>LLIYGAFSRATGIPDRFSGSGSGTDFTLTISRLEPE<br>DFAVYYCQQYGSSPWTFGQGTKVEIKGGGIEGR<br>GGGDKTHTCPPCPAPELLGGPSVFLFPPKPKDTL<br>MISRTPEVTCVVVDVSHEDPEVKFNWYVDGVEV<br>HNAKTKPREEQYQSTYRVVSVLTVLHQDWLNG<br>KEYKCKVSNKALPAPIEKTISKAKGQPREPQVYT<br>LPPSRDELTKNQVSLTCLVSGFYPSDIAVEWESN<br>GQPENNYKTTPPVLDSDGSFKLYSKLTVDKSRW<br>QQGNVFSCSVMHEALHNHYTQKSLSLSPG | 192 |
| Anti-EpCAM VH 44 Cys,<br>Ipilimumab VH, FXa, Fc | EVQLLEQSGAELVRPGTSVKISCKASGYAFTNYW<br>LGWVKQRPGHCLEWIGDIFPGSGNIHYNEKFKGK<br>ATLTADKSSSTAYMQLSSLTFEDSAVYFCARLRN<br>WDEPMDYWGQGTTVTSSGGGSGGGGSQVQLV<br>ESGGGVVQPGRSLRLSCAASGFTFSSYTMHWVR<br>QAPGKGLEWVTFISYDGNNKYYADSVKGRFTISR<br>DNSKNTLYLQMNSLRAEDTAIYYCARTGWLGPF<br>DYWGQGTLVTVSSGGGIEGRGGGDKTHTCPPCP<br>APELLGGPSVFLFPPKPKDTLMISRTPEVTCVVVD<br>VSHEDPEVKFNWYVDGVEVHNAKTKPREEQYQ<br>STYRVVSVLTVLHQDWLNGKEYKCKVSNKALP<br>APIEKTISKAKGQPREPQVYTLPPSRDELTKNQVK<br>LTCLVKGFYPSDIAVEWESNGQPENNYKTTPPVL<br>DSDGSFFLYSLLTVDKSRWQQGNVFSCSVMHEA<br>LHNHYTQKSLSLSPG | 193 |
| Anti-EpCAM VL 100<br>Cys, SP34 VL, FXa, Fc | ELVMTQSPSSLTVTAGEKVTMSCKSSQSLLNSGN<br>QKNYLTWYQQKPGQPPKLLIYWASTRESGVPDR<br>FTGSGSGTDFTLTISSVQAEDLAVYYCQNDYSYP<br>LTFGCGTKLEIKGGGGSGGGGSQAVVTQEPSLTV<br>SPGGTVTLTCRSSTGAVTASNYANWVQQKPGQA<br>PRGLIGGTNKRAPWTPARFSGSLLGGKAALTITG<br>AQAEDEADYYCALWYSNLWVFGGGTKLTVLGG<br>GIEGRGGGDKTHTCPPCPAPELLGGPSVFLFPPKP<br>KDTLMISRTPEVTCVVVDVSHEDPEVKFNWYVD<br>GVEVHNAKTKPREEQYQSTYRVVSVLTVLHQD<br>WLNGKEYKCKVSNKALPAPIEKTISKAKGQPREP<br>QVYTLPPSRDELTKNQVSLTCLVSGFYPSDIAVE<br>WESNGQPENNYKTTPPVLDSDGSFKLYSKLTVD<br>KSRWQQGNVFSCSVMHEALHNHYTQKSLSLSPG | 194 |
| Anti-EpCAM VH-CH1,<br>Theralizumab VH, FXa,<br>Fc | EVQLLEQSGAELVRPGTSVKISCKASGYAFTNYW<br>LGWVKQRPGHGLEWIGDIFPGSGNIHYNEKFKG<br>KATLTADKSSSTAYMQLSSLTFEDSAVYFCARLR<br>NWDEPMDYWGQGTTVTVSSASTKGPSVFPLAPS<br>SKSTSGGTAALGCLVKDYFPEPVTVSWNSGALTS<br>GVHTFPAVLQSSGLYSLSSVVTVPSSSLGTQTYIC<br>NVNHKPSNTKVDKKVEPKSCDKTHTGGGGSGG<br>GGSEVQLVESGGGLVQPGGSLRLSCAASGFTFSD | 195 |

TABLE 1-continued

Description of the Sequences and SEQ ID NOs

| Description | Sequence | # |
|---|---|---|
| | SWIHWVRQAPGKGLEWVAWISPYGGSTYYADS VKGRFTISADTSKNTAYLQMNSLRAEDTAVYYC ARRHWPGGFDYWGQGTLVTVSSGGGGSIEGRGG SGGGSKNAQCKKKLQALKKKNAQLKWKLQALK KKLAQGHHHHHH | |
| Anti-EpCAM VL-CL, Theralizumab VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCHASQNIYVWLNW YQQKPGKAPKLLIYKASNLHTGVPSRFSGSGSGT DFTLTISSLQPEDFATYYCQQGQTYPYTEGGGTK VEIKGGGIEGRGGGDKTHTCPPCPAPELLGGPSVF LEPPKPKDTLMISRTPEVTCVVVDVSHEDPEVKF NWYVDGVEVHNAKTKPREEQYQSTYRVVSVLT VLHQDWLNGKEYKCKVSNKALPAPIEKTISKAK GQPREPQVYTLPPSRDELTKNQVSLTCLVSGFYP SDIAVEWESNGQPENNYKTTPPVLDSDGSFKLYS KLTVDKSRWQQGNVFSCSVMHEALHNHYTQKS LSLSPG | 196 |
| Anti-EpCAM VH-CH1, Urelumab VH, FXa, Fc | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSQVQLQQWGAGLLKPSETLSLTCAVYGGSFS GYYWSWIRQSPEKGLEWIGEINHGGYVTYNPSLE SRVTISVDTSKNQFSLKLSSVTAADTAVYYCARD YGPGNYDWYFDLWGRGTLVTVSSGGGIEGRGG GDKTHTCPPCPAPELLGGPSVFLEPPKPKDTLMIS RTPEVTCVVVDVSHEDPEVKFNWYVDGVEVHN AKTKPREEQYQSTYRVVSVLTVLHQDWLNGKEY KCKVSNKALPAPIEKTISKAKGQPREPQVYTLPPS RDELTKNQVKLTCLVKGFYPSDIAVEWESNGQPE NNYKTTPPVLDSDGSFFLYSLLTVDKSRWQQGN VFSCSVMHEALHNHYTQKSLSLSPG | 197 |
| Anti-EpCAM VL-CL, Urelumab VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI QMTQSPSSLSASVGDRVTITCHASQNIYVWLNW YQQKPGKAPKLLIYKASNLHTGVPSRFSGSGSGT DFTLTISSLQPEDFATYYCQQGQTYPYTEGGGTK VEIKGGGIEGRGGGDKTHTCPPCPAPELLGGPSVF LEPPKPKDTLMISRTPEVTCVVVDVSHEDPEVKF NWYVDGVEVHNAKTKPREEQYQSTYRVVSVLT VLHQDWLNGKEYKCKVSNKALPAPIEKTISKAK GQPREPQVYTLPPSRDELTKNQVSLTCLVSGFYP SDIAVEWESNGQPENNYKTTPPVLDSDGSFKLYS KLTVDKSRWQQGNVFSCSVMHEALHNHYTQKS LSLSPG | 198 |
| Anti-EpCAM VL-CL, Dummy VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSQ AVVTQEPSLTVSPGGTVTLTCRSSTGAVTTSNYA NWVQQKPGQAPRGLIGGTNKRAPWTPARFSGSL LGGKAALTITGAQAEDEADYYCALWYSNLAVFG GGTKLTVLGGGIEGRGGGDKTHTCPPCPAPELLG GPSVFLFPPKPKDTLMISRTPEVTCVVVDVSHEDP EVKFNWYVDGVEVHNAKTKPREEQYQSTYRVV | 199 |

TABLE 1-continued

Description of the Sequences and SEQ ID NOs

| Description | Sequence | # |
|---|---|---|
| | SVLTVLHQDWLNGKEYKCKVSNKALPAPIEKTIS KAKGQPREPQVYTLPPSRDELTKNQVSLTCLVSG FYPSDIAVEWESNGQPENNYKTTPPVLDSDGSFK LYSKLTVDKSRWQQGNVFSCSVMHEALHNHYT QKSLSLSPG | |
| Anti-EpCAM VH-CH1, Dummy VH, FXa, Fc | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSEVQLVESGGGLVQPGGSLRLSCAASGFTFSS YAMNWVRQAPGKGLEWVARISGSGGSTYYADS VKDRFTISRDDSKNSLYLQMNSLKTEDTAVYYC VRGKGNTHKPYGYVRYFDVWGQGTLVTVSSGG GIEGRGGGDKTHTCPPCPAPELLGGPSVFLFPPKP KDTLMISRTPEVTCVVVDVSHEDPEVKFNWYVD GVEVHNAKTKPREEQYQSTYRVVSVLTVLHQD WLNGKEYKCKVSNKALPAPIEKTISKAKGQPREP QVYTLPPSRDELTKNQVKLTCLVKGFYPSDIAVE WESNGQPENNYKTTPPVLDSDGSFFLYSLLTVDK SRWQQGNVFSCSVMHEALHNHYTQKSLSLSPG | 200 |
| Basic coil | KNAQCKKKLQALKKKNAQLKWKLQALKKKLA Q | 201 |
| Acid coil | ENAQCEKELQALEKENAQLEWELQALEKELAQ | 202 |
| Leucine zipper sequence | GGGGSIEGRGGGGS | 203 |
| Leucine zipper sequence | GGPLGVRGKGGGS | 204 |
| Leucine zipper sequence | GGGGSIEGRGGSGGGS | 205 |
| Hetero Fc sequence | GGGIEGRGGG | 206 |
| Hetero Fc sequence | GGGGSIEGRGGG | 207 |
| CH1 sequence | IEGRG | 208 |
| CL sequence | GGIEGRG | 209 |
| IgE CH2 sequence | GIEGRG | 210 |
| IgE CH2 sequence | GGGIEGRG | 211 |
| Anti-EpCAM VH-CH1, OKT3 VH, FXa, Fc | EVQLLEQSGAELVRPGTSVKISCKASGYAFTNYW LGWVKQRPGHGLEWIGDIFPGSGNIHYNEKFKG KATLTADKSSSTAYMQLSSLTFEDSAVYFCARLR NWDEPMDYWGQGTTVTVSSASTKGPSVFPLAPS SKSTSGGTAALGCLVKDYFPEPVTVSWNSGALTS GVHTFPAVLQSSGLYSLSSVVTVPSSSLGTQTYIC NVNHKPSNTKVDKKVEPKSCDKTHTGGGGSGG GGSDVQLVQSGAEVKKPGASVKVSCKASGYTFT RYTMHWVRQAPGQGLEWIGYINPSRGYTNYADS VKGRFTITTDKSTSTAYMELSSLRSEDTATYYCA RYYDDHYCLDYWGQGTTVTVSSGGGIEGRGGG DKTHTCPPCPAPELLGGPSVFLFPPKPKDTLMISR TPEVTCVVVDVSHEDPEVKFNWYVDGVEVHNA KTKPREEQYQSTYRVVSVLTVLHQDWLNGKEYK CKVSNKALPAPIEKTISKAKGQPREPQVYTLPPSR DELTKNQVKLTCLVKGFYPSDIAVEWESNGQPE NNYKTTPPVLDSDGSFFLYSLLTVDKSRWQQGN VFSCSVMHEALHNHYTQKSLSLSPG | 212 |
| Anti-EpCAM VL-CL, OKT3 VL, FXa, Fc | ELVMTQSPSSLTVTAGEKVTMSCKSSQSLLNSGN QKNYLTWYQQKPGQPPKLLIYWASTRESGVPDR FTGSGSGTDFTLTISSVQAEDLAVYYCQNDYSYP LTFGAGTKLEIKRTVAAPSVFIFPPSDEQLKSGTA SVVCLLNNFYPREAKVQWKVDNALQSGNSQESV TEQDSKDSTYSLSSTLTLSKADYEKHKVYACEVT HQGLSSPVTKSFNRGECGGGGSGGGGSGGGGSDI VLTQSPATLSLSPGERATLSCRASQSVSYMNWYQ QKPGKAPKRWIYDTSKVASGVPARFSGSGSGTD YSLTINSLEAEDAATYYCQQWSSNPLTFGGGTKV | 213 |

TABLE 1-continued

Description of the Sequences and SEQ ID NOs

| Description | Sequence | # |
|---|---|---|
| | EIKGGGIEGRGGGDKTHTCPPCPAPELLGGPSVFL<br>FPPKPKDTLMISRTPEVTCVVVDVSHEDPEVKFN<br>WYVDGVEVHNAKTKPREEQYQSTYRVVSVLTV<br>LHQDWLNGKEYKCKVSNKALPAPIEKTISKAKG<br>QPREPQVYTLPPSRDELTKNQVSLTCLVSGFYPS<br>DIAVEWESNGQPENNYKTTPPVLDSDGSFKLYSK<br>LTVDKSRWQQGNVFSCSVMHEALHNHYTQKSLS<br>LSPG | |
| Anti-EpCAM VH-CH1,<br>anti-CD16A VH, FXa, Fc | EVQLLEQSGAELVRPGTSVKISCKASGYAFTNYW<br>LGWVKQRPGHGLEWIGDIFPGSGNIHYNEKFKG<br>KATLTADKSSSTAYMQLSSLTFEDSAVYFCARLR<br>NWDEPMDYWGQGTTVTVSSASTKGPSVFPLAPS<br>SKSTSGGTAALGCLVKDYFPEPVTVSWNSGALTS<br>GVHTFPAVLQSSGLYSLSSVVTVPSSSLGTQTYIC<br>NVNHKPSNTKVDKKVEPKSCDKTHTGGGGSGG<br>GGSQVQLVQSGAEVKKPGESLKVSCKASGYTFT<br>SYYMHWVRQAPGQGLEWMGIINPSGGSTSYAQK<br>FQGRVTMTRDTSTSTVYMELSSLRSEDTAVYYC<br>ARGSAYYYDFADYWGQGTLVTVSSGGGIEGRGG<br>GDKTHTCPPCPAPELLGGPSVFLFPPKPKDTLMIS<br>RTPEVTCVVVDVSHEDPEVKFNWYVDGVEVHN<br>AKTKPREEQYQSTYRVVSVLTVLHQDWLNGKEY<br>KCKVSNKALPAPIEKTISKAKGQPREPQVYTLPPS<br>RDELTKNQVKLTCLVKGFYPSDIAVEWESNGQPE<br>NNYKTTPPVLDSDGSFFLYSLLTVDKSRWQQGN<br>VFSCSVMHEALHNHYTQKSLSLSPG | 214 |
| Anti-EpCAM VL-CL,<br>anti-CD16A VL, FXa, Fc | ELVMTQSPSSLTVTAGEKVTMSCKSSQSLLNSGN<br>QKNYLTWYQQKPGQPPKLLIYWASTRESGVPDR<br>FTGSGSGTDFTLTISSVQAEDLAVYYCQNDYSYP<br>LTFGAGTKLEIKRTVAAPSVFIFPPSDEQLKSGTA<br>SVVCLLNNFYPREAKVQWKVDNALQSGNSQESV<br>TEQDSKDSTYSLSSTLTLSKADYEKHKVYACEVT<br>HQGLSSPVTKSFNRGECGGGGSGGGGSGGGGSS<br>YVLTQPSSVSVAPGQTATISCGGHNIGSKNVHWY<br>QQRPGQSPVLVIYQDNKRPSGIPERFSGSNSGNTA<br>TLTISGTQAMDEADYYCQVWDNYSVLFGGGTKL<br>TVLGGGIEGRGGGDKTHTCPPCPAPELLGGPSVF<br>LFPPKPKDTLMISRTPEVTCVVVDVSHEDPEVKF<br>NWYVDGVEVHNAKTKPREEQYQSTYRVVSVLT<br>VLHQDWLNGKEYKCKVSNKALPAPIEKTISKAK<br>GQPREPQVYTLPPSRDELTKNQVSLTCLVSGFYP<br>SDIAVEWESNGQPENNYKTTPPVLDSDGSFKLYS<br>KLTVDKSRWQQGNVFSCSVMHEALHNHYTQKS<br>LSLSPG | 215 |

DESCRIPTION OF THE EMBODIMENTS

I. Twin Immune Cell Engager

A Twin Immune Cell Engager ("TWICE") refers to a two-component complexes wherein domains of the two components can pair and bind and engage immune cells. As such, a single TWICE comprises two components, which may be present in two separate polypeptides or in a single polypeptide. Thus, a TWICE may be a single construct or it may be a kit of two components. The use of the term TWICE throughout the application and claims encompasses both embodiments, unless specifically discussed otherwise. This application describes a range of TWICE. TWICE can activate different pathways to mediate a variety of anti-cancer effects.

As this application will describe, a TWICE can comprise a first and second component that each comprise a targeting moiety, an immune cell binding domain, and a complementary binding domain. The targeting moieties of the first and second component function to target the TWICE to cancer cells or cells in the tumor microenvironment. When the immune cell binding domain from both components pair together and/or the complementary binding domain from both components pair together, these paired domains can function to modulate immune cell activity or serve other (i.e., complementary) functions. For example, paired complementary binding domains may block immune checkpoints or induce death cell death of cancer cells.

The presence of complementary binding domains in a TWICE is expected to improve their efficacy in treating cancer compared to complexes not comprising complementary domains (i.e., compared to complexes that only bind a single antigen on immune cells).

As this application will also describe, the first component and optionally the second component can comprise a complementary functional domain capable of immune cell binding. In some embodiments with complementary functional domains, the immune cell binding domain is masked. The complementary functional domain of a TWICE can modulate immune function without needing to pair with a different domain.

A major advantage of the present TWICE complexes described herein is that the immune cell binding domains, and in some embodiments the complementary binding domains, will only be paired when both the first and second components of the TWICE are in close proximity (here when in the tumor microenvironment because they are both targeted to a cancer). The pairing of domains between different components of the TWICE at the cancer site may improve specificity and reduce off-target effects, because the immune cell binding domains and optionally the complementary binding domains only function after pairing of domains from both components at the cancer cell or its microenvironment.

After describing some representative types of TWICE, the application will then describe components that comprise different types of TWICE. The TWICE is not limited to the representative descriptions herein, as a TWICE could modulate many pathways related to cancer survival and the anti-cancer immune responses.

The present TWICE complexes offer a unique ability to combine multiple functions into a two-component complex that becomes activated in the tumor microenvironment. The present complexes, thus, provide meaningful advantages in having a single approach to administering a two-component complex that is localized to the tumor microenvironment and has the ability to effect two different signals to benefit patients. In some embodiments, one of those signals (from the paired immune cell binding domains) is activated only when the two-component complex comes together. In some embodiments, both of those signals (from the paired immune cell binding domains and from the paired complementary binding domains) are activated only when the two-component complex comes together. This unique construct offers many benefits that were not present in prior art constructs.

1. TWICE that Activates Two Signaling Pathways on One Type of Immune Cell

In some embodiments, the immune cell binding domains, when paired together, and the complementary binding domains, when paired together, bind to the same type of immune cell.

As used herein, immune cells may also be termed "effector cells." The term "effector cell" mean an immune cell that mediates activity against the cancer.

In some embodiments, the immune cell binding domains, when paired together, and the complementary binding domains, when paired together, bind to T cells.

In some embodiments, the immune cell binding domains, when paired together, and the complementary binding domains, when paired together, bind to the same antigen on an immune cell. In this embodiment, the two signaling pathways are the same and the impact is amplified. In some embodiments, the immune cell binding domains, when paired together, and the complementary binding domains, when paired together, bind to different antigens on an immune cell. In this embodiment, the two signaling pathways are different and two different signals are transmitted to the immune cell.

In general, the process of T-cell activation involves multiple signals. The primary signal comes from the binding of the T-cell receptor (TCR) to the major histocompatibility complex (MHC) molecule presented by an antigen presenting cell (APC). A costimulatory signal may arise from one of several distinct T-cell and APC interactions (see Buchbinder E I, Desai A *Am J Clin Oncol.* 39(1):98-106 (2016)). The activation of T cells is enhanced by several co-stimulatory receptors, such as CD28, CD137 (4-1BB), OX40, CD27, GITR (TNFRSF18), and ICOS. The interactions between T cell and APC or cancer cells can also involve several inhibitory/checkpoint molecules that reduce T cell activation, such as PD-1, CTLA-4, TIM-3, LAG-3, and KIR (Torphy R J et al. *Int J Mol Sci.* 18:2642 (2017)). Thus, combining the effects of two antibodies against costimulatory or coinhibitory receptors can enhance an anti-tumor T-cell response.

Figure 1A:
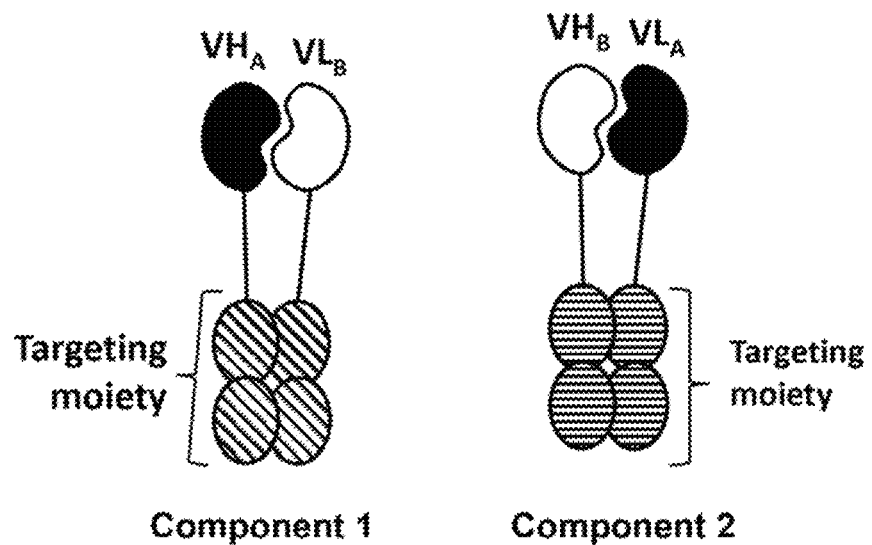
FIGS. 1A-1B shows a Twin Immune Cell Engager ("TWICE").
Figure 1B:
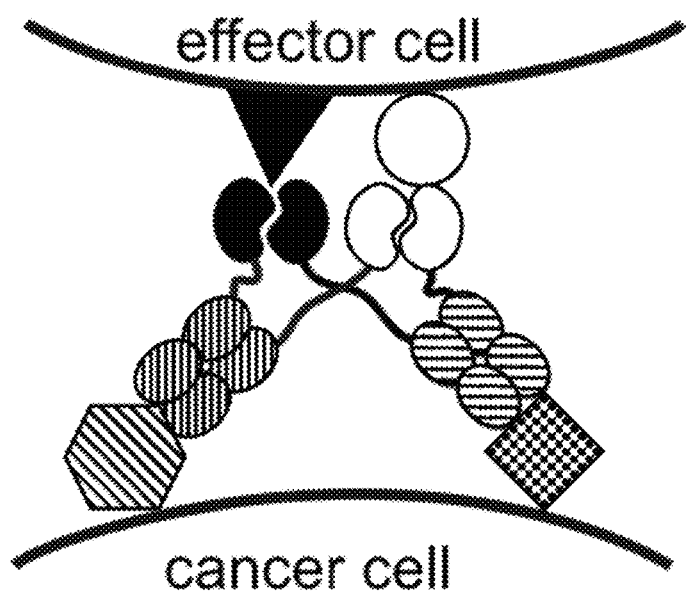

The TWICE can comprise (after pairing) two functional antibodies against co-stimulatory or checkpoint molecules on T cells, leading to robust T-cell activation (FIG. 1B, showing pairing of the black immune cell binding domains of the two components and pairing of the white complementary binding domains of the two components). Robust T-cell activation may be useful in patients when T cells are present in the tumor but are inactive due to immunosuppressive signals from the cancer cells (Wu A A et al. *OncoImmunology* 4:7 (2015)).

In some embodiments, the immune cell binding domains, when paired together, and the complementary binding domains, when paired together, can engage an immune cell through agonistic or antagonistic binding to T cells.

By "agonistic," it is meant that binding of paired immune cell binding or paired complementary binding domains to an antigen activates a signaling pathway. Agonistic binding may be of interest when binding to an antigen leads to immune cell activation.

By "antagonistic," it is meant that binding of paired immune cell binding or paired complementary binding domains to an antigen blocks or inhibits a signaling pathway. Antagonistic binding may be of interest when binding of natural ligands to an antigen normally leads to immune cell deactivation. In this manner, binding of an "antagonistic" set of paired domains of the present TWICE can activate immune cells by blocking or inhibiting a pathway that normally mediates immune cell anergy or deactivation.

Antibodies known to have antagonist or agonist effects on immune cells can be used for generating paired binding domains of the present TWICE. If a signaling pathway promotes T-cell activation, an agonistic approach will increase T-cell activation. If a signaling pathway inhibits T-cell activation, an antagonistic approach will increase T-cell activation. Thus, many different types of pathways can be employed in this approach.

One example of an agonistic antibody is a CD3 epsilon antibody that stimulates the TCR complex (e.g. SP34, OKT3). In another example, agonistic antibodies against GITR may activate CD8+ T effector cells, while inhibiting regulatory T cell function (see Knee et al., *European Journal of Cancer* 67:1e10 (2016). Examples of antagonistic antibodies that lead to the stimulation of immune cells are PD-1 antibodies (e.g., Pembrolizumab or Nivolumab). PD-1 inhibits the immune cell and thus these antibodies block the interaction of PD-1 with its ligands and thereby antagonize an inhibitory signal.

In some embodiments, the immune cell binding domains, when paired together, and the complementary binding domains, when paired together, can generate two agonistic antibodies and provide two positive stimuli to the immune system (e.g., an anti-CD3 epsilon with an anti-CD137 antibody). Both CD3 and CD137 promote T-cell activation.

In some embodiments, the immune cell binding domains, when paired together, and the complementary binding domains, when paired together, can generate one agonist antibody and one antagonist antibody (e.g., an anti-CD3 epsilon antibody and an anti-CTLA4 antibody). CD3, as discussed above, stimulates the TCR complex, while CTLA4 provides an inhibitory signal. Antagonizing the inhibitory signal of CTLA4 will promote T-cell activation.

In some embodiments, the immune cell binding domains, when paired together, and the complementary binding domains, when paired together, can generate two antagonistic antibodies that block two inhibitory signals (e.g. anti-CTLA4 antibody and anti-PD-1 antibody). As discussed above, both of these signals inhibit T-cell activation and antagonizing them will promote T-cell activation.

Another exemplary TWICE combines a CD3 epsilon (CD3e) antibody with another antibody that promotes T-cell activation. Current evidence suggests that CD3 bispecific antibodies are further regulated through diverse checkpoint molecules (see Kobold S et al. *Front Oncol.* 8: 285 (2018)). In addition, the therapeutic effect of T-cell-activating bispecific antibodies may, in some patients or settings, also be restricted by induced T-cell anergy (the absence of normal immune response to a particular antigen). Thus, combining an anti-CD3 epsilon antibody that activates T cells with an antibody that potentiates T-cell activation and prevents anergy may generate an enhanced and/or more durable anti-tumor T-cell response.

2. TWICE that Modulates Two Immune Cells

Figure 2:
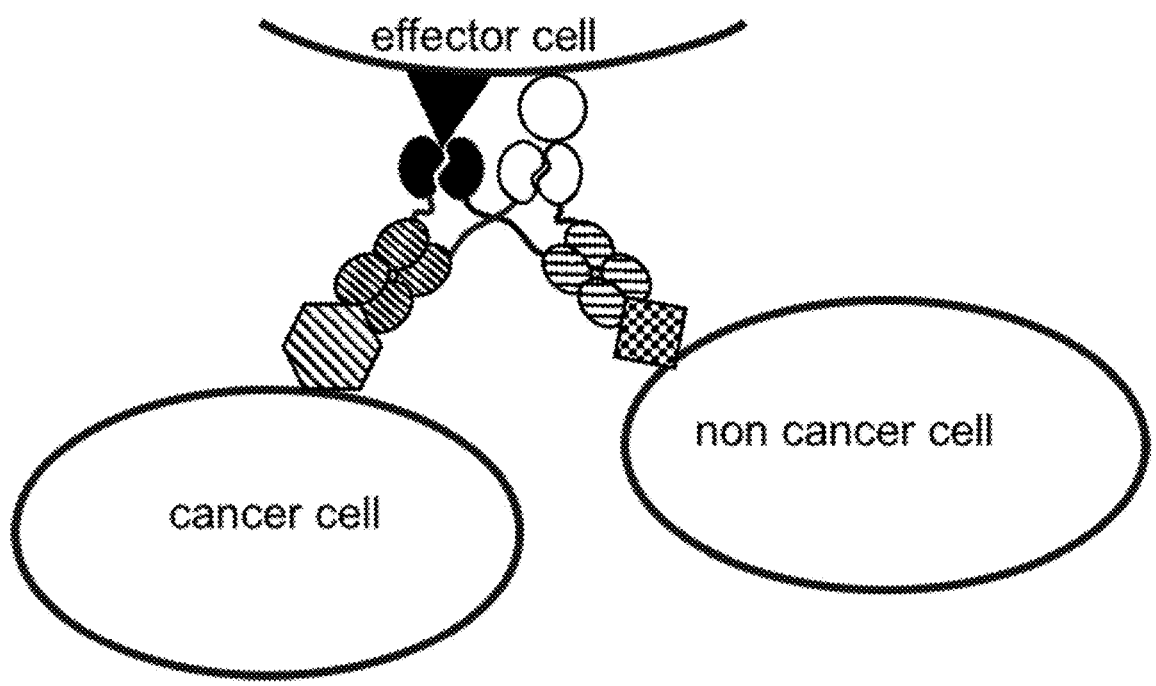
FIG. 2 shows a TWICE that engages two signaling molecules on one effector (immune) cell after targeting of the first component to a cancer cell and targeting of the second component to a non-cancer cell. The hexagon represents an antigen on a cancer cell bound by the targeting moiety (four striped ovals) of the first component. The square represents an antigen on a non-cancer cell in the tumor micro-environment (such as a tumor-associated macrophage or fibroblast) bound by the targeting moiety (four striped ovals) of the second component. Each component comprises an immune cell binding domain (black domains of each component) and a complementary binding domain (white domains of each component). When the two components are in close proximity, domain swapping can occur such the two immune cell binding domains (one from each component) and the two complementary binding domains (one from each component) can pair with each other. The triangle and circle represent different antigens on the effector cell that can be bound by the paired immune cell binding domains (antigen represented by the triangle) and the paired complementary binding domains (antigen represented by the circle). In the absence of domain swapping and pairing, the immune cell binding domains and the complementary binding domains of the two components do not modulate the effector cell.

In some embodiments, the immune cell binding domains, when paired together, and the complementary binding domains, when paired together, bind to two different immune cells. In this way, a TWICE may modulate two different types of immune cells. A wide range of different immune cells could be modulated by a TWICE, including the following representative examples. FIG. 2 shows a representative model of activation of two immune cells (effector cell #1 and effector cell #2) via a TWICE.

a) TWICE that Stimulates T Cells and Inhibit Tumor-Associated Macrophages

Binding of two different immune cells may be useful in a tumor microenvironment, where T cells are excluded from the tumor and tumor-associated macrophages (TAM) can be present. TAMs represent a class of alternatively activated macrophages that facilitate tumor growth by promoting angiogenesis, immunosuppression, and inflammation (Poh and Ernst, *Front Oncol.* 12(8):49 (2018)). In some embodiments, the TWICE, when the complementary binding domain and the immune cell binding domains are paired, combines activities by blocking TAM activity and activating T cells.

In some embodiments, the TWICE comprises immune cell binding domains, where paired together, that mediate T-cell activation and complementary binding domains, when paired together, that inhibit TAMs.

For example, targeting TAMs with an anti-CSF1R blocking antibody reduces TAM infiltration and promotes CD8+ T-cell expansion (Ries C H et al. *Cancer Cell.* 25(6):846-59 (2014)). Activation of the CD40 pathway can also interfere with the immunosuppressive effect of TAMs. A CD40 agonistic antibody can lead to the reprogramming or recruitment of classically activated macrophages, which may be used trigger effective immune responses against tumors. Representative TWICE that combine a T-cell activating antibody and a CD40 agonistic antibody or an anti-CSF1R blocking antibody, after pairing of the immune binding domains and the complementary binding domains, could provide additive efficacy compared to any of these antibodies alone.

b) TWICE that Stimulates T Cells and NK Cells

A TWICE may be used to activate both T cells and NK cells to kill cancer cells. The coactivation of T cells and NK cells may lead to a more robust immune response to the cancer than activation of either cell alone.

In some embodiments, the TWICE comprises immune cell binding domains, where paired together, that mediate T-cell activation and complementary binding domains, when paired together, that mediate NK-cell activation such as with an anti-CD16A antibody. For example, in a TWICE comprising TWICE440 and TWICE441, the anti-CD16A antibody was combined with the anti-CD3 antibody OKT3 (See SEQ ID NOs: 212-215 and FIGS. 18A-18B).

3. TWICE that Stimulates Immune Cells and Mediate Effects on Cancer Cells

A TWICE can also bind an immune cell with the paired immune cell binding domains and bind the cancer cell with the paired complementary binding domains. This therapeutic strategy can induce a biological function directly on the targeted cancer cell, as well as mediating anti-cancer immune cell activation. The biological function induced in the cancer cell could be, for example, the induction of cell death via a death receptor or the inhibition of an immunosuppressive signal.

Paired immune cell binding domains that can activate immune cells have already been described, and TWICE components can also comprise complementary binding domains that bind cancer.

a) TWICE that Stimulates Immune Cells and Block Immune Cell Deactivation by the Cancer The present TWICE may be used to both activate immune cells and block inhibitory signals from cancer cells to immune cells. In some embodiments, the complementary binding domains, when paired together, may block a signal from the cancer cell that inhibits immune cell activation.

For example, some cancers express PD-L1, which can bind PD-1 or B7.1 on T cells and lead to T-cell inactivation. In some embodiments, the complementary binding domains, when paired together, bind to PD-L1 on cancer cells. In some embodiments, binding to PD-L1 blocks interaction with PD-1 on T cells. Blocking the interaction of PD-1 and PD-L1 has been shown to improve anti-tumor responses. PD-L1 antibodies (such as Atezolizumab, Durvalumab, and Avelumab) are approved to treat several malignant diseases, including non-small cell lung cancer and melanoma.

In another example, some cancers can express tumor necrosis factor Receptor (TNFR) family members, which downregulate anti-tumor immune response. An example of such a molecule is receptor activator of nuclear factor kappa-B (RANK), which binds to its ligand, RANKL, on regulatory T cells to generate an immunosuppressive environment (see Wu et al. *Oncoimmunology.* 4(7) (2015)). In some embodiments, the complementary binding domains, when paired together, bind to RANK on cancer cells. In some embodiments, binding to RANK blocks interaction with RANKL on T cells. Blockade of RANK signaling by an antagonistic antibody against RANKL enhances the anti-tumor effect of an anti-CTLA4 antibody, which can activate T cells, in a preclinical mouse model of cancer (Ahern et al *Clin Cancer Res.* 23(19):5789-5801 (2017)).

b) TWICE that Stimulates Immune Cells and Trigger Cell Death of Cancer Cells

The present TWICE may also be used to both activate immune cells and trigger cell death of cancer cells. In some embodiments, the complementary binding domains, when paired together, may trigger death of cancer cells by binding to receptors expressed by cancer cells.

Examples of receptors that can be stimulated to trigger cell death include members of the TNFR family, such as Fas/CD95/Apo1, TNFR1/p55/CD120a, DR3/Apo3/WSL-1/TRAMP/LARD, TRAIL-R1/DR4, DR5/Apo2/TRAIL-R2/TRICK2/KILLER, or CAR1. A TNFR family agonist antibody in clinical development that induces cell death in cancer cells is mapatumumab (NCT01258608). A TWICE that combines activity to directly kill cancer cells and activate an anti-cancer immune response could have additive efficacy.

4. TWICE Comprising Complementary Functional Domains

Figure 5:
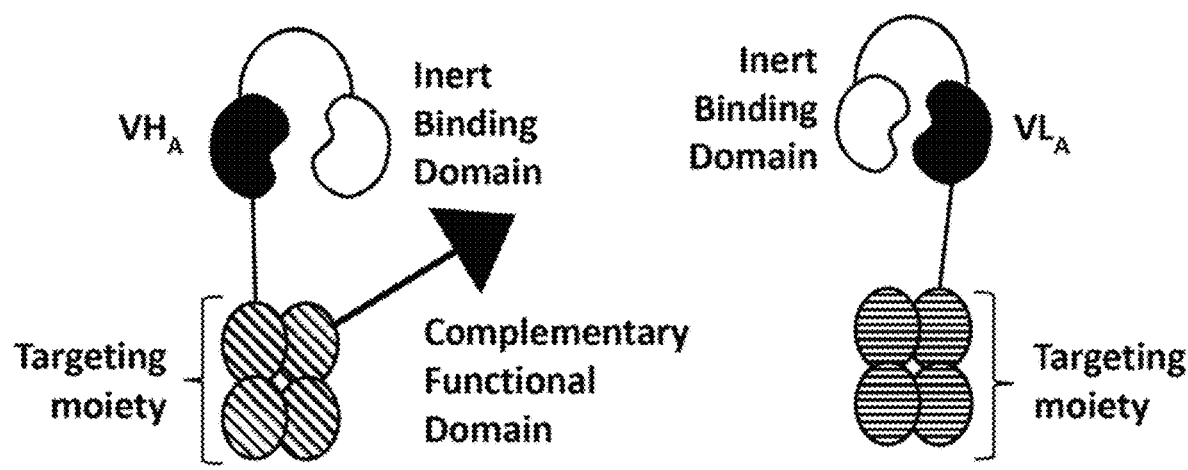
FIG. 5 shows a TWICE comprising a functional domain before administration to a patient. The targeting moieties (two sets each of four striped ovals) of the first and second components are shown. Each component comprises an immune cell binding domain (black curved domains of each component). Each component also comprises an inert binding domain (white curved domains of each component, also known as an inert binding partner) attached to the immune cell binding domains. One component also comprises a complementary functional domain (black triangle). Linkers between the targeting moiety and the immune cell binding domain or the complementary functional domain are also shown. In addition, a linker is shown between the immune cell binding domains and the inert binding partners of each component. The linker attaching the inert binding partner may be a cleavable linker that is cleaved in the tumor microenvironment. This cleavage releases the inert binding partners.

The first and/or second component of a TWICE can also comprise complementary functional domains. "Complementary functional domains," as used herein, refers to molecules that modulate immune function when targeted to the appropriate immune cell, without needing to pair with another domain. Thus, a TWICE can target complementary functional domains to immune cells and facilitate activity of complementary functional domains that lack activity without targeting or may be too toxic to deliver systemically. Exemplary complementary functional domains are attenuated cytokines that must be targeted to appropriate immune cells to have activity. This embodiment is shown in FIG. 5. Attenuated cytokines can preferentially activate target cells, as shown by data with bempegaldesleukin (NKTR-214), a CD-122-preferential IL-2 pathway agonist.

In this way, a TWICE can mediate additive anti-cancer immune responses by the activity of paired immune cell binding domains, as well activity from complementary functional domains—in effect delivering a "care-package" for effector cells that is only activated in the effector cell/cancer cell engagement synapse.

B. Single Polypeptide Chain or Two Components

A TWICE may comprise a single polypeptide chain or two separate components.

In some embodiments, the first component is not covalently bound to the second component. In some embodiments, the first component is covalently bound to the second component.

In some embodiments, the TWICE is comprised of two separate components. In other words, the TWICE can be comprised of a first and second component that are separate polypeptides.

In some components, the TWICE is comprised of a single polypeptide chain. In some embodiments, the first and second components are contained within a single amino acid sequence.

When the TWICE is comprised of a single polypeptide chain, the first and second components may be separated by a linker. In some embodiments, this linker covalently binds the first and second components. In some embodiments, this linker comprises a cleavable linker. In some embodiments, the cleavable linker between the first and second components comprises a protease cleavage site.

In some embodiments, a cleavage site comprised within a linker covalently binding a first component and the second component is a protease cleavage site. SEQ ID NOs: 1-84 list some exemplary protease cleavage sites that may be used, but the TWICE is not limited to this set of proteases cleavage sites and other protease cleavage sites may be employed.

In some embodiments, a cleavage site comprised within a linker covalently binding a first component and the second component is a tumor-associated protease cleavage site. A tumor associated-protease is one that is associated with a tumor. In some embodiments, a tumor-associated protease has higher expression in the tumor versus other regions of the body. Table 2 (show in Section IV below) provides examples of tumor-associated proteases, although any protease with expression in a tumor may be used to select a tumor-associated protease cleavage site for the TWICE. In some embodiments, the protease is expressed by a non-cancer cell in the tumor microenvironment, such as a tumor-associated macrophage of fibroblast.

In some embodiments, a cleavage site comprised within a linker covalently binding a first component and the second component is a cleavage site for a protease found in the blood. Exemplary proteases found in the blood include thrombin, neutrophil elastase, and furin.

C. Targeting Moieties

The targeting moieties of the first components functions by delivering the agent to the local environment of the cancer cells, enabling a localized treatment strategy. In some embodiments, the first targeting moiety targets the cancer cells by specifically binding to the cancer cells.

In some embodiments, both the first and second targeting moieties binds a tumor antigen expressed by the cancer.

In some embodiments, the first targeting moiety binds a tumor antigen expressed by the cancer and the second targeting moiety binds an antigen expressed by a tumor microenvironment cell.

In some embodiments, a targeting moiety is an antibody or antigen-binding fragment thereof. By antigen-binding fragment, we mean any antibody fragment that retains its binding activity to the target, such as an scFv or other functional fragment including an immunoglobulin devoid of light chains, VHH, VNAR, Fab, Fab', F(ab')2, Fv, antibody fragment, diabody, scAB, single-domain heavy chain antibody, single-domain light chain antibody, Fd, CDR regions, or any portion or peptide sequence of the antibody that is capable of binding antigen or epitope. VHH and VNAR are alternatives to classical antibodies and even though they are produced in different species (camelids and sharks, respectively), we will also include them in antigen-binding fragments of antibodies. In some embodiments, an Fv domain is a disulfide-stabilized Fv (dsFv). Unless specifically noted as "full length antibody," when the application refers to antibody it inherently includes a reference to an antigen-binding fragment thereof.

In some embodiments, a targeting moiety is not an antibody, but is another type of targeting moiety. A wide range of targeting moieties capable of targeting cancer are known, including DNA aptamers, RNA aptamers, albumins, lipocalins, fibronectins, ankyrins, fynomers, Obodies, DARPins, knotins, avimers, atrimers, anticallins, affilins, affibodies, bicyclic peptides, cys-knots, FN3 (adnectins, centryrins, pronectins, TN3), and Kunitz domains. These and other non-antibody scaffold structures may be used for targeting to a cancer cell. Smaller non-antibody scaffolds are rapidly removed from the bloodstream and have a shorter half-life than monocolonal antibodies. They also show faster tissue penetration owing to fast extravasation from the capillary lumen through the vascular endothelium and basement membrane. See Vazquez-Lombardi et al., Drug Discovery Today 20(1):1271-1283 (2015). A number of non-antibody scaffolds targeting cancer are already under clinical development, with other candidates in the preclinical stage. See Vazquez-Lombardi, Table 1.

1. Targeting Moiety Capable of Targeting the Cancer

In some embodiments, only the first targeting moiety binds an antigen expressed by the cancer, and the second targeting moiety does not. In some embodiments, both the first and second targeting moieties bind an antigen expressed by the cancer.

In some embodiments, the first and second targeting moieties are the same and bind the same antigen. In some embodiments, the first and second targeting moieties bind the same antigen expressed by the cancer. In some embodiments, the first and second targeting moieties bind different epitopes on the same antigen expressed by the cancer. In some embodiments, the first and second targeting moieties bind different antigens expressed by the cancer.

Certain tumor antigens that may be used for targeting (with examples of cancer cell types in parentheses) include: Her2/Neu (epithelial malignancies); CD22 (B cell malignancies); EpCAM (CD326) (epithelial malignancies); EGFR (epithelial malignancies); PSMA (prostate carcinoma); CD30 (B cell malignancies); CD20 (B cell malignancies); CD33 (myeloid malignancies); CD80 (B cell malignancies); CD86 (B cell malignancies); CD2 (T-cell or NK-cell lymphomas); CA125 (multiple cancers including ovarian carcinoma); Carbonic Anhydrase IX (multiple cancers including renal cell carcinoma); CD70 (B-cell malignancies); CD74 (B-cell malignancies); CD56 (T-cell or NK-cell lymphomas); CD40 (B-cell malignancies); CD19 (B-cell malignancies); c-met/HGFR (gastrointestinal tract and hepatic malignancies; TRAIL-R1/DR4 (multiple malignancies including ovarian and colorectal carcinoma); DR5 (multiple malignancies including ovarian and colorectal carcinoma); PD-1 (B-cell malignancies); PD-L1 (multiple malignancies including epithelial adenocarcinoma); IGF-1R (most malignancies including epithelial adenocarcinoma); VEGF-R2 (the vasculature associated with the majority of malignancies including epithelial adenocarcinomas; prostate stem cell antigen (PSCA) (prostate adenocarcinoma); MUC1 (epithelial malignancies); CanAg (tumors such as carcinomas of the colon and pancreas); Mesothelin (many tumors including mesothelioma and ovarian and pancreatic adenocarcinoma); P-cadherin (epithelial malignancies, including breast adenocarcinoma); Myostatin (GDF8) (many tumors including sarcoma and ovarian and pancreatic adenocarcinoma); Cripto (TDGF1) (epithelial malignancies including colon, breast, lung, ovarian, and pancreatic cancers); ACVRL 1/ALK1 (multiple malignancies including leukemias and lymphomas); MUC5AC (epithelial malignancies, including breast adenocarcinoma); CEACAM (epithelial malignancies, including breast adenocarcinoma); CD137 (B-cell or T-cell malignancies); CXCR4 (B-cell or T-cell malignancies); Neuropilin 1 (epithelial malignancies, including lung cancer); Glypicans (multiple cancers including liver, brain and breast cancers); HER3/ERBB3 (epithelial malignancies); PDGFRa (epithelial malignancies); EphA2 (multiple cancers including neuroblastoma, melanoma, breast cancer, and small cell lung carcinoma); CD38 (myeloma); CD138 (myeloma); α4-integrin (AML, myeloma, CLL, and most lymphomas); CCR4 antibody (lymphoma); CD52 (leukemia); CD79b (lymphoma); CTLA-4 (multiple cancers including non-small cell lung, head and neck, urothelial cancer, and hepatocellular carcinoma); DLL3 (lung cancer); endoglin (multiple cancers including soft tissue sarcoma, angiosarcoma, and renal cell carcinoma); fibronectin extra-domain B (melanoma); folate receptor 1 (multiple cancers including epithelial ovarian cancer, peritoneal carcinoma, and fallopian tube cancer); MMP-9 (gastric cancer or gastroesophageal junction adenocarcinoma); NGcGM3 (lung cancer); SLAMF7 (multiple myeloma); TROP-2 (breast cancer); or VEGF (colorectal cancer).

In some embodiments, the targeting moiety binds α4-integrin; A33; ACVRL 1/ALK1; ADAM17; ALK; APRIL; BCMA; C242; CA125; Cadherin-19; CAIX; CanAg; Carbonic Anhydrase IX; CCN1; CCR4; CD123; CD133; CD137 (4-1BB); CD138/Syndecan1; CD19; CD2; CD20; CD22; CD30; CD33; CD37; CD38; CD4; CD40; CD44; CD45; CD48; CD5; CD52; CD56; CD59; CD70; CD70b; CD71; CD74; CD79b; CD80; CD86; CD98; CEA; CEACAM; CEACAM1; CK8; c-Kit; CLDN1; CLDN18; CLDN18.2; CLDN6; c-met/HGFR; c-RET; Cripto; CTLA-4; CXCR4; DKK-1; DLL3; DLL4; TRAIL-R2/DR5; DR5; EGFL7; EGFR; EGFRvIII; endoglin; ENPP3; EpCAM; EphA2; Episialin; FAP; FGFR1; FGFR2; FGFR3; FGFR4; fibronectin extra-domain B; FLT-3; flt4; folate receptor 1; GCC; GD2; GD3; Glypican-3; Glypicans; GM3; GPNMB; GPR49; GRP78; Her2/Neu; HER3/ERBB3; HLA-DR; ICAM-1; IGF-1R; IGFR; IL-3Ra; Integrin α5β1; Integrin α6β4; Integrin αV; Integrin αVβ3; Lewis Y; Lewis y/b antigen; LFL2; LIV-1; Ly6E; MCP-1; Mesothelin; MMP-9; MUC1; MUC18; MUC5A; MUC5AC; Myostatin; NaPi2b; Neuropilin 1; NGcGM3; NRP1; P-cadherin; PCLA; PD-1; PDGFRa; PD-L1; PD-L2; Phosphatidylserine; PIVKA-II; PLVAP; PRLR; Progastrin; PSCA; PSMA; RANKL; RG1; Siglec-15; SLAMF6; SLAMF7; SLC44A4, STEAP-1; TACSTD-2; Tenascin C; TPBG; TRAIL-R1/DR4; TROP-2; TWEAKR; TYRP1; VANGL2; VEGF; VEGF-C; VEGFR-2; or VEGF-R2.

Table 2 (shown in Section IV below) provides nonlimiting examples of cancer types, possible targets for targeting moieties, and proteases that are expressed by those cancer types. A protease associated with a cancer may be termed a tumor-associated protease. In order to prepare a TWICE that needs cleavage at the site of the tumor, the cancer may be identified and a target chosen for the targeting moiety (as desired), and one or two proteases chosen for the cancer type or the desired tumor microenvironment cell (such as a TAM or TAF). Not every TWICE requires protease cleavage, but protease cleavage may be beneficial for a TWICE that is generated as single molecules with a cleavage site or for a TWICE comprising inert binding partners.

Table 3 (shown in Section IV below) provides additional information about cancers that may be targeting with different targeting moieties, including the fact that some targeting moieties may be able to target a number of different types of cancer. In a TWICE, both the first component and the second component may comprise a targeting moiety capable of targeting a cancer. The targeting moiety of the first component and the second component may bind to the same antigen or to different antigens.

Antibodies that bind tumor antigens and that have specificity for tumor cells are well-known in the art.

The FDA maintains listings of approved antibody drugs for treating cancer, many of which bind to cancer antigens and can be employed in this context. See The Orange Book Online or Drugs@FDA on the FDA website. The FDA also maintains listings of clinical trials in progress in the clinicaltrials.gov database, which may be searched by disease names. Table 4 (shown in Section IV below) provides a representative list of approved antibodies with specificity for tumor cells. Table 5 (shown in Section IV below) provides a representative list of antibodies in development with specificity for tumor cells.

Table 6 (shown in Section IV below) summarizes selected publications on exemplary antibodies that bind tumor antigens and that could be used as targeting moieties in the TWICE. These publications show that targeting moieties capable of binding tumor antigens were well within both the skill in the art and the possession of the inventors at the time of filing of the present application.

Other antibodies well-known in the art may be used as targeting moieties to target to a given cancer. The antibodies and their respective antigens include nivolumab (anti-PD-1 Ab), TA99 (anti-gp75), 3F8 (anti-GD2), 8H9 (anti-B7-H3), abagovomab (anti-CA-125 (imitation)), adecatumumab (anti-EpCAM), afutuzumab (anti-CD20), alacizumab pegol (anti-VEGFR2), altumomab pentetate (anti-CEA), amatuximab (anti-mesothelin), AME-133 (anti-CD20), anatumomab mafenatox (anti-TAG-72), apolizumab (anti-HLA-DR), arcitumomab (anti-CEA), bavituximab (anti-phosphatidylserine), bectumomab (anti-CD22), belimumab (anti-BAFF), besilesomab (anti-CEA-related antigen), bevacizumab (anti-VEGF-A), bivatuzumab mertansine (anti-CD44 v6), blinatumomab (anti-CD19), BMS-663513 (anti-CD137), brentuximab vedotin (anti-CD30 (TNFRSF8)), cantuzumab mertansine (anti-mucin CanAg), cantuzumab ravtansine (anti-MUC1), capromab pendetide (anti-prostatic carcinoma cells), carlumab (anti-MCP-1), catumaxomab (anti-EpCAM, CD3), cBR96-doxorubicin immunoconjugate (anti-Lewis-Y antigen), CC49 (anti-TAG-72), cedelizumab (anti-CD4), Ch.14.18 (anti-GD2), ch-TNT (anti-DNA associated antigens), citatuzumab bogatox (anti-EpCAM), cixutumumab (anti-IGF-1 receptor), clivatuzumab tetraxetan (anti-MUC1), conatumumab (anti-TRAIL-R2), CP-870893 (anti-CD40), dacetuzumab (anti-CD40), daclizumab (anti-CD25), dalotuzumab (anti-insulin-like growth factor I receptor), daratumumab (anti-CD38 (cyclic ADP ribose hydrolase)), demcizumab (anti-DLL4), detumomab (anti-B-lymphoma cell), drozitumab (anti-DR5), duligotumab (anti-HER3), dusigitumab (anti-ILGF2), ecromeximab (anti-GD3 ganglioside), edrecolomab (anti-EpCAM), elotuzumab (anti-SLAMF7), elsilimomab (anti-IL-6), enavatuzumab (anti-TWEAK receptor), enoticumab (anti-DLL4), ensituximab (anti-SAC), epitumomab cituxetan (anti-episialin), epratuzumab (anti-CD22), ertumaxomab (anti-HER2/neu, CD3), etaracizumab (anti-integrin $\alpha v\beta 3$), faralimomab (anti-Interferon receptor), farletuzumab (anti-folate receptor 1), FBTA05 (anti-CD20), ficlatuzumab (anti-HGF), figitumumab (anti-IGF-1 receptor), flanvotumab (anti-TYRP1 (glycoprotein 75)), fresolimumab (anti-TGF $\beta$), futuximab (anti-EGFR), galiximab (anti-CD80), ganitumab (anti-IGF-I), gemtuzumab ozogamicin (anti-CD33), girentuximab (anti-carbonic anhydrase 9 (CA-IX)), glembatumumab vedotin (anti-GPNMB), guselkumab (anti-IL13), ibalizumab (anti-CD4), ibritumomab tiuxetan (anti-CD20), icrucumab (anti-VEGFR-1), igovomab (anti-CA-125), Zolbetuximab (IMAB362, an anti-CLDN18.2), IMC-CS4 (anti-CSF1R), IMC-TR1 (TGF$\beta$RII), imgatuzumab (anti-EGFR), inclacumab (anti-selectin P), indatuximab ravtansine (anti-SDC1), inotuzumab ozogamicin (anti-CD22), intetumumab (anti-CD51), ipilimumab (anti-CD152), iratumumab (anti-CD30 (TNFRSF8)), KM3065 (anti-CD20), KW-0761 (anti-CD194), LY2875358 (anti-MET) labetuzumab (anti-CEA), lambrolizumab (anti-PDCD1), lexatumumab (anti-TRAIL-R2), lintuzumab (anti-CD33), lirilumab (anti-KIR2D), lorvotuzumab mertansine (anti-CD56), lucatumumab (anti-CD40), lumiliximab (anti-CD23 (IgE receptor)), mapatumumab (anti-TRAIL-R1), margetuximab (anti-ch4D5), matuzumab (anti-EGFR), mavrilimumab (anti-GMCSF receptor a-chain), milatuzumab (anti-CD74), minretumomab (anti-TAG-72), mitumomab (anti-GD3 ganglioside), mogamulizumab (anti-CCR4), moxetumomab pasudotox (anti-CD22), nacolomab tafenatox (anti-C242 antigen), naptumomab estafenatox (anti-5T4), narnatumab (anti-RON), necitumumab (anti-EGFR), nesvacumab (anti-angiopoietin 2), nimotuzumab (anti-EGFR), nivolumab (anti-IgG4), nofetumomab merpentan, ocrelizumab (anti-CD20), ocaratuzumab (anti-CD20), olaratumab (anti-PDGF-R $\alpha$), onartuzumab (anti-c-MET), ontuxizumab (anti-TEM1), oportuzumab monatox (anti-EpCAM), oregovomab (anti-CA-125), otlertuzumab (anti-CD37), pankomab (anti-tumor specific glycosylation of MUC1), parsatuzumab (anti-EGFL7), pascolizumab (anti-IL-4), patritumab (anti-HER3), pemtumomab (anti-MUC1), pertuzumab (anti-HER2/neu), pidilizumab (anti-PD-1), pinatuzumab vedotin (anti-CD22), pintumomab (anti-adenocarcinoma antigen), polatuzumab vedotin (anti-CD79B), pritumumab (anti-vimentin), PRO131921 (anti-CD20), quilizumab (anti-IGHE), racotumomab (anti-N-glycolylneuraminic acid), radretumab (anti-fibronectin extra domain-B), ramucirumab (anti-VEGFR2), rilotumumab (anti-HGF), robatumumab (anti-IGF-1 receptor), roledumab (anti-RHD), rovelizumab (anti-CD11 & CD18), samalizumab (anti-CD200), satumomab pendetide (anti-TAG-72), seribantumab (anti-ERBB3), SGN-CD19A (anti-CD19), SGN-CD33A (anti-CD33), sibrotuzumab (anti-FAP), siltuximab (anti-IL-6), solitomab (anti-EpCAM), sontuzumab (anti-episialin), tabalumab (anti-BAFF), tacatuzumab tetraxetan (anti-alpha-fetoprotein), taplitumomab paptox (anti-CD19), telimomab aritox, tenatumomab (anti-tenascin C), teneliximab (anti-CD40), teprotumumab (anti-CD221), TGN1412 (anti-CD28), ticilimumab (anti-CTLA-4), tigatuzumab (anti-TRAIL-R2), TNX-650 (anti-IL-13), tositumomab (anti-CS20), tovetumab (anti-CD140a), TRBS07 (anti-GD2), tregalizumab (anti-CD4), tremelimumab (anti-CTLA-4), TRU-016 (anti-CD37), tucotuzumab celmoleukin (anti-EpCAM), ublituximab (anti-CD20), urelumab (anti-4-1BB), vantictumab (anti-Frizzled receptor), vapaliximab (anti-AOC3 (VAP-1)), vatelizumab (anti-ITGA2), veltuzumab (anti-CD20), vesencumab (anti-NRP1), visilizumab (anti-CD3), volociximab (anti-integrin $\alpha 5\beta 1$), vorsetuzumab mafodotin (anti-CD70), votumumab (anti-tumor antigen CTAA16.88), zalutumumab (anti-EGFR), zanolimumab (anti-CD4), zatuximab (anti-HER1), ziralimumab (anti-CD147 (basigin)), RG7636 (anti-ETBR), RG7458 (anti-MUC16), RG7599 (anti-NaPi2b), MPDL3280A (anti-PD-L1), RG7450 (anti-STEAP1), TAK-164 (anti-GCC), and GDC-0199 (anti-Bc1-2).

Antibodies that bind these antigens may also be used in the TWICE, especially for the types of cancers noted: aminopeptidase N (CD13), annexin A1, B7-H3 (CD276, various cancers), CA125 (ovarian cancers), CA15-3 (carcinomas), CA19-9 (carcinomas), L6 (carcinomas), Lewis Y (carcinomas), Lewis X (carcinomas), alpha fetoprotein (carcinomas), CA242 (colorectal cancers), placental alkaline phosphatase (carcinomas), prostate specific antigen (prostate), prostatic acid phosphatase (prostate), epidermal growth factor (carcinomas), CD2 (Hodgkin's disease, NHL lymphoma, multiple myeloma), CD3 epsilon (T-cell lymphoma, lung, breast, gastric, ovarian cancers, autoimmune diseases, malignant ascites), CD19 (B cell malignancies), CD20 (non-Hodgkin's lymphoma, B-cell neoplasmas, autoimmune diseases), CD21 (B-cell lymphoma), CD22 (leukemia, lymphoma, multiple myeloma, SLE), CD30 (Hodgkin's lymphoma), CD33 (leukemia, autoimmune diseases), CD38 (multiple myeloma), CD40 (lymphoma, multiple myeloma, leukemia (CLL)), CD51 (metastatic melanoma, sarcoma), CD52 (leukemia), CD56 (small cell lung cancers, ovarian cancer, Merkel cell carcinoma, and the liquid tumor, multiple myeloma), CD66e (carcinomas), CD70 (metastatic renal cell carcinoma and non-Hodgkin lymphoma), CD74 (multiple myeloma), CD80 (lymphoma), CD98 (carcinomas), CD123 (leukemia), mucin (carcinomas), CD221 (solid tumors), CD22 (breast, ovarian cancers), CD262 (NSCLC and other cancers), CD309 (ovarian cancers), CD326 (solid tumors), CEACAM3 (colorectal, gastric cancers), CEACAM5 (CEA, CD66e) (breast, colorectal and lung cancers), DLL4 (A-like-4), EGFR (various cancers), CTLA4 (melanoma), CXCR4 (CD 184, heme-oncology, solid tumors), Endoglin (CD 105, solid tumors), EPCAM (epithelial cell adhesion molecule, bladder, head, neck, colon, NHL prostate, and ovarian cancers), ERBB2 (lung, breast, prostate cancers), FCGR1 (autoimmune diseases), FOLR (folate receptor, ovarian cancers), FGFR (carcinomas), GD2 ganglioside (carcinomas), G-28 (a cell surface antigen glycolipid, melanoma), GD3 idiotype (carcinomas), heat shock proteins (carcinomas), HER1 (lung, stomach cancers), HER2 (breast, lung and ovarian cancers), HLA-DR10 (NHL), HLA-DRB (NHL, B cell leukemia), human chorionic gonadotropin (carcinomas), IGF1R (solid tumors, blood cancers), IL-2 receptor (T-cell leukemia and lymphomas), IL-6R (multiple myeloma, RA, Castleman's disease, IL6 dependent tumors), integrins ($\alpha v\beta 3$, $\alpha 5\beta 1$, $\alpha 6\beta 4$, $\alpha 11\beta 3$, $\alpha 5\beta 5$, $\alpha v\beta 5$, for various cancers), MAGE-1 (carcinomas), MAGE-2 (carcinomas), MAGE-3 (carcinomas), MAGE 4 (carcinomas), anti-transferrin receptor (carcinomas), p97 (melanoma), MS4A1 (membrane-spanning 4-domains subfamily A member 1, Non-Hodgkin's B cell lymphoma, leukemia), MUC1 (breast, ovarian, cervix, bronchus and gastrointestinal cancer), MUC16 (CA125) (ovarian cancers), CEA (colorectal cancer), gp100 (melanoma), MARTI (melanoma), MPG (melanoma), MS4A1 (membrane-spanning 4-domains subfamily A, small cell lung cancers, NHL), nucleolin, Neu oncogene product (carcinomas), P21 (carcinomas), nectin-4 (carcinomas), paratope of anti-(N-glycolylneuraminic acid, breast, melanoma cancers), PLAP-like testicular alkaline phosphatase (ovarian, testicular cancers), PSMA (prostate tumors), PSA (prostate), ROB04, TAG 72 (tumour associated glycoprotein 72, AML, gastric, colorectal, ovarian cancers), T-cell transmembrane protein (cancers), Tie (CD202b), tissue factor, TNFRSF10B (tumor necrosis factor receptor superfamily member 10B, carcinomas), TNFRSF13B (tumor necrosis factor receptor superfamily member 13B, multiple myeloma, NHL, other cancers, RA and SLE), TPBG (trophoblast glycoprotein, renal cell carcinoma), TRAIL-R1 (tumor necrosis apoptosis inducing ligand receptor 1, lymphoma, NHL, colorectal, lung cancers), VCAM-1 (CD106, Melanoma), VEGF, VEGF-A, VEGF-2 (CD309) (various cancers). Some other tumor associated antigen targets have been reviewed (Gerber, et al, mAbs 2009 1:247-253; Novellino et al, Cancer Immunol Immunother. 2005 54:187-207, Franke, et al, Cancer Biother Radiopharm. 2000, 15:459-76, Guo, et al., Adv Cancer Res. 2013; 119: 421-475, Parmiani et al. J Immunol. 2007 178:1975-9). Examples of these antigens include Cluster of Differentiations (CD4, CDS5, CD6, CD7, CD8, CD9, CD10, CD11a, CD11b, CD11c, CD12w, CD14, CD15, CD16, CDw17, CD18, CD21, CD23, CD24, CD25, CD26, CD27, CD28, CD29, CD31, CD32, CD34, CD35, CD36, CD37, CD41, CD42, CD43, CD44, CD45, CD46, CD47, CD48, CD49b, CD49c, CD53, CD54, CD55, CD58, CD59, CD61, CD62E, CD62L, CD62P, CD63, CD68, CD69, CD71, CD72, CD79, CD81, CD82, CD83, CD86, CD87, CD88, CD89, CD90, CD91, CD95, CD96, CD100, CD103, CD105, CD106, CD109, CD117, CD120, CD127, CD133, CD134, CD135, CD138, CD141, CD142, CD143, CD144, CD147, CD151, CD152, CD154, CD156, CD158, CD163, CD166, CD168, CD184, CDw186, CD195, CD202 (a, b), CD209, CD235a, CD271, CD303, CD304), annexin A1, nucleolin, endoglin (CD105), ROB04, amino-peptidase N, -like-4 (DLL4), VEGFR-2 (CD309), CXCR4 (CD184), Tie2, B7-H3, WT1, MUC1, LMP2, HPV E6 E7, EGFRvIII, HER-2/neu, idiotype, MAGE A3, p53 nonmutant, NY-ESO-1, GD2, CEA, MelanA/MART1, Ras mutant, gp100, p53 mutant, proteinase3 (PR1), bcr-abl, tyrosinase, survivin, hTERT, sarcoma translocation breakpoints, EphA2, PAP, ML-IAP, AFP, EpCAM, ERG (TMPRSS2 ETS fusion gene), NA17, PAX3, ALK, androgen receptor, cyclin B 1, polysialic acid, MYCN, RhoC, TRP-2, GD3, fucosyl GM1, mesothelin, PSCA, MAGE A1, sLe(a), CYPIB I, PLAC1, GM3, BORIS, Tn, GloboH, ETV6-AML, NY-BR-1, RGSS, SART3, STn, carbonic anhydrase IX, PAXS, OY-TES1, sperm protein 17, LCK, HMWMAA, AKAP-4, SSX2, XAGE 1, B7H3, legumain, Tie 2, Page4, VEGFR2, MAD-CT-1, FAP, PDGFR-$\beta$, MAD-CT-2, and Fos-related antigen 1.

In some embodiments, the targeting moiety capable of targeting a cancer is not an antibody, but is another type of targeting moiety. Table 7 (shown in Section IV below) presents some representative non-antibody targeting moieties and their corresponding targets.

In another embodiment, a targeting moiety may be a binding partner for a protein known to be expressed on the cancer cell. Such expression levels may include overexpression. For example, the binding partners described in Table 8 (shown in Section IV below) may bind to the following targets on a cancer cell.

The binding partner need not comprise the full length or wildtype sequence for the binding partners listed in Table 8. All that is required is that the binding partner bind to the target on the cancer cell and can thus include truncated forms, analogs, variants, and derivatives that are well known in the art.

Additionally, in some embodiments, the binding partner may be an aptamer that is capable of binding to a protein known to be expressed on the cancer cell. Aptamers that bind cancer cells are well known and methods for designing them are known.

Cell-based SELEX systems may be used to select a panel of target cell-specific aptamers from a random candidate library. A ssDNA or ssRNA pool may be dissolved in binding buffer and denatured and then incubated with target cells. After washing the bound DNAs or RNAs may be eluted by heating and then incubated with negative cells (if desired), centrifuged, and the supernatant removed. The supernatant may be amplified by PCR with biotin labeled primers. The selected sense ssDNA or ssRNA may be separated from the antisense biotinylated strand using streptavidin coated beads. To increase affinity, washing strength may be increased through increasing washing time, volume of buffer, and number of washes. After the desired rounds of selection, the selected ssDNA or ssRNA pool may be PCR amplified and cloned into *E. coli* and sequenced. See Shangguan et al., Aptamers evolved from live cells as effective molecular probes for cancer study, *PNAS* 103(32): 11838-11843 (2006); Lyu et al, Generating Cell Targeting Aptamers for Nanotherapeutics Using Cell-SELEX, *Theranostics* 6(9):1440-1452 (2016); see also Li et al., Inhibition of Cell Proliferation by an Anti-EGFR Aptamer, *PLoS One* 6(6):e20229 (2011). The specific approaches for designing aptamers and specific aptamers binding to cancer cells in these references are hereby incorporated by reference.

For example, an aptamer may comprise SEQ ID NO: 94 to 164. In some embodiments, an aptamer may comprise SEQ ID NO: 95. These aptamers are directed to EGFR and are provided only as representative of the aptamers that can bind to targets presented on cancer cells. Other aptamers against other targets on cancer cells are equally part of the description herein and incorporated by reference as described in Zhu et al., *Theranostics* 4(9):931-944 (2014).

In some embodiments, aptamers for use herein bind to the target on the cancer cell with a $K_d$ in the nanomolar to picomolar range (such as 1 picomolar to 500 nanomolar or 1 picomolar to 100 nanomolar).

2. Targeting Moiety Capable of Targeting a Tumor Microenvironment Cell

Current cancer immunotherapeutic antibodies require effector cells to be present within the tumor. However, tumors can generate an immunosuppressive environment that excludes effector cells, rendering immunotherapy less effective (see Herbst et al *Nature.* 515(7528):563-7 (2014)). Tumors devoid of effector cells may be termed "cold tumors" (see Whiteside T L et al. *Clin Cancer Res.* 22(8): 1845-55 (2016)).

Effector cells may be excluded from the tumors by the tumor stroma, in particular by non-cancer cells in the tumor microenvironment, such as tumor-associated fibroblasts (TAFs) (see Ziani et al, *Front Immunol.* 9:414 (2018)). A non-cancer cell in the tumor microenvironment may be termed a "tumor microenvironment cell." Since T cells in cold tumors can be restricted to the stroma, immunotherapeutics targeted to the interface of malignant cells and the stroma could potentially overcome immune exclusion. Targeting the tumor microenvironment cell with the second target moiety may therefore provide additional specificity for the present kit or composition.

In some embodiments, the first targeting moiety binds an antigen expressed by the cancer, and the second targeting moiety binds an antigen expressed by a tumor microenvironment cell. In some embodiments, the tumor microenvironment cell is a fibroblast or macrophage. These cells may be termed tumor-associated fibroblasts or cancer-associated fibroblasts (TAFs or CAFs) or tumor-associated macrophages or cancer-associated macrophages (TAMs or CAMs). As used herein, a "tumor-associated fibroblast" refers to a fibroblast found in close proximity to or within a tumor mass. As used herein, a "tumor-associated macrophage" refers to a macrophage found in close proximity to or with a tumor mass.

FIG. 2 shows targeting of one component of a TWICE to a cancer cell and targeting of the other component to a non-cancer cell in the tumor microenvironment. With this type of TWICE, the immune binding domains of the two components and/or the complementary binding domains of the two components would only pair when the cancer cells and the non-cancer tumor microenvironment cell were in close proximity.

TAFs are characterized by the expression of activation markers such as fibroblast activation protein alpha (FAP) and alpha-smooth muscle actin (see Barnett and Vilar, *J Natl Cancer Inst* 110(1):11-13 (2018)) and may create an immunosuppressive environment by direct or indirect mechanisms. Direct immunosuppressive effects may be mediated by growth factors such as TGF-beta or cytokines such as CXCL12, and the indirect immunosuppressives effects may be mediated by remodeling of the extracellular matrix in the tumor microenvironment (see Ziani et al, 2018).

In some embodiments, the targeting moiety of the second component binds to an antigen expressed by TAFs. In some embodiments, the targeting moiety targeting to TAFs comprises an antibody that binds FAP such as sibrotuzumab (see US20120258119A1). FAP is expressed mostly expressed on tumor stroma and not on normal fibroblasts (Brennen et al. *Mol Cancer Ther.* 11(2): 257-266 (2012)).

In some embodiments, the targeting moiety of the second component binds to an antigen expressed by TAMs. In some embodiments, the targeting moiety targeting to TAMs comprises an antibody that binds MAC-1/CD11b (see EP0488061A2) or sideroflexin 3 (see WO2018020000).

D. Immune Cell Binding Domains

The first immune cell binding domain and the second immune cell binding domain are, when bound to each other, capable of binding an antigen on an immune cell. As used herein, an "immune cell" can be any cell comprised in the immune system. The immune cell may be a cell involved in the innate or adaptive immune response.

In some embodiments, the immune cell is a natural killer cell (NK), macrophage, or T cell. In some embodiments, the T cell is a γδ T cell or a natural killer T cell (NKT cells).

1. T-Cell Binding Domains

In some embodiments, the first T-cell binding domain and the second T-cell binding domain are, when bound to each other, capable of binding a T cell. In some embodiments, the first T-cell binding domain and the second T-cell binding domain are, when bound to each other, capable of binding CD3 or the T-cell receptor (TCR).

CD3 is present on all T cells and consists of subunits designated γ, δ, ε, ζ and η. TCR is another molecule present on T cells that consists of different subunits designated α, β, γ, and δ. The cytoplasmic tail of CD3 is sufficient to transduce the signals necessary for T-cell activation in the absence of the other components of the TCR receptor complex. Normally, activation of T-cell cytotoxicity depends first on binding of the TCR with a major histocompatibility complex (MHC) protein, itself bound to a foreign antigen, located on a separate cell. Without outside intervention, only when this initial TCR-MHC binding has taken place can the CD3 dependent signally cascade responsible for T-cell clonal expansion and, ultimately, T-cell cytotoxicity ensue. In some of the present embodiments, however, when the first T-cell binding domain and the second T-cell binding domain bind to CD3 and/or the TCR, activation of cytotoxic T cells in the absence of independent TCR-MHC can take place by virtue of the crosslinking of the CD3 and/or TCR molecules mimicking an immune synapse formation. This means that T cells may be cytotoxically activated in a clonally independent fashion, i.e. in a manner that is independent of the specific TCR clone carried by the T cell. This allows for activation of the entire T-cell compartment rather than only specific T cells of a certain clonal identity.

In some embodiments, the first T-cell binding domain is a VH domain and the second T-cell binding domain is a VL domain. In some embodiments, the first T-cell binding domain is a VL domain and the second T-cell binding domain is a VH domain. In some embodiments, the first and second T-cell binding domains when paired together may comprise an Fv. As used herein, an "Fv" refers to a VH and VL associated together. In other words, when paired together the first and second T-cell binding domains may comprise an "scFv," except for the fact that the VH and VL are not in a single-chain configuration with a linker between the VH and VL.

If the first and second T-cell binding domains are a pair of VH and VL domains, the VH and VL domains may be specific for an antigen expressed on the surface of a T cell, such as CD3 or TCR. In some embodiments, the anti-CD3 or anti-TCR antibody binds to a subunit of CD3 or TCR. If the antigen is CD3, one potential T-cell binding domain may be derived from muromonab (muromonab-CD3 or OKT3), otelixizumab, teplizumab, visilizumab, foralumab, SP34, or blinatumomab. One skilled in the art would be aware of a wide range of anti-CD3 antibodies, some of which are approved therapies or have been clinically tested in human patients (see Kuhn and Weiner *Immunotherapy* 8(8):889-906 (2016)). Table 9 (shown in Section IV below) presents selected publications on exemplary anti-CD3 antibodies.

Antibodies with specificity to the TCR, including the αβ and γδ TCRs, are also well-known. Table 10 (shown in Section IV below) presents selected publications on exemplary anti-TCR antibodies.

T-cell binding domains can also include any antibodies listed as potential complementary binding domains, such as programmed cell death protein 1 (PD-1), cytotoxic T-lymphocyte-associated protein 4 (CTLA-4), T-cell immunoglobulin and mucin-domain 3 (TIM-3), lymphocyte-activation gene 3 (LAG-3), killer-cell immunoglobulin-like receptor (KIR), CD28, CD137, OX40, CD27, GITR (TNFRSF18), TIGIT, or inducible T-cell costimulatory (ICOS).

2. Natural Killer Cell Binding Domains

In some embodiments, the first and second immune cell binding domains, when paired together, are capable of activating natural killer (NK) cells. In some embodiments, the first and second immune cell binding domains, when paired together, are capable of binding CD16A. In some embodiments, binding of paired immune cell binding domains to CD16A on NK cells activates NK cells against CD33-positive leukemia cells. In some embodiments, the first and second immune cell binding domains comprise all or part of a VH and/or VL of NTM-1633 (see NCT03603665) or AFM13 (see NCT01221571).

3. Macrophage Binding Domains

In some embodiments, the first and second immune cell binding domains, when paired together, are capable of binding macrophages. In some embodiments, the macrophages are activated macrophages.

In some embodiments, the first and second immune cell binding domains, when paired together, are capable of binding CSF1R. In some embodiments, the first and second immune cell binding domains comprise all or part of a VH and/or VL of Emactuzumab/RG7155 (NCT01494688) or IMC-CS4 (NCT01346358).

In some embodiments, the first and second immune cell binding domains, when paired together, are capable of binding CD40. In some embodiments, the first and second immune cell binding domains comprise all or part of a VH and/or VL of CP-870,893.

E. Complementary Binding Domains

In some embodiments, the first and second components comprise complementary binding domains. When the complementary binding domains of the two components are paired, this leads to an additional function. This additional function may be, for example, to induce death of cancer cells or increase the anti-tumor immune response. The additional function may also serve to make the tumor microenvironment more hospitable to immune cells.

Because the two components of the TWICE are targeted to the cancer or to the tumor microenvironment, the additional function mediated by pairing of the complementary binding domains would happen in the tumor or its microenvironment. In some embodiments, the additional function mediated by the paired complementary binding domains is limited to the tumor and its microenvironment, thereby reducing off-targets effects. For example, this ability to limit activity to the tumor and its microenvironment may be an advantage for activating or inhibiting a target molecule with widespread expression and/or a range of physiologic functions, such as TGF-beta.

In some embodiments, the first complementary binding domain and the second complementary binding domain, when bound to each other, and the first immune cell binding domain and the second immune cell binding domain, when bound to each other, are capable of binding the same antigen. For example, the first complementary binding domain and the second complementary binding domain, when bound to each other, and the first immune cell binding domain and the second immune cell binding domain, when bound to each other, may bind CD3 on T cells. Binding of both the paired complementary binding domains and the paired immune cell binding domains to CD3 may lead to more robust activation of an anti-cancer immune response.

In some embodiments, the first complementary binding domain and the second complementary binding domain, when bound to each other, and the first immune cell binding domain and the second immune cell binding domain, when bound to each other, are capable of binding different antigens on the same cell. For example, the first complementary binding domain and the second complementary binding domain, when bound to each other, and the first immune cell binding domain and the second immune cell binding domain, when bound to each other, may bind different antigens on T cells. Binding of both the paired complementary binding domains and the paired immune cell binding domains to two different antigens on T cells may lead to robust activation of an anti-cancer immune response.

In some embodiments, the first complementary binding domain and the second complementary binding domain, when bound to each other, and the first immune cell binding domain and the second immune cell binding domain, when bound to each other, are capable of binding different cells. For example, the first complementary binding domain and the second complementary binding domain, when bound to each other, may bind a cancer cell to lead to cell death and the first immune cell binding domain and the second immune cell binding domain, when bound to each other, may bind a T cell to mediate an anti-cancer immune response. Activation of a cell death pathways in the tumor cell and activation of an anti-cancer immune response may increase tumor regression.

In some embodiments, the first complementary binding domain and the second complementary binding domain are, when bound to each other, capable of modulating T-cell, macrophage, or NK-cell activity. In some embodiments, the first complementary binding domain and the second complementary binding domain are, when bound to each other, capable of binding a costimulatory antigen or a coinhibitory antigen on T cells.

In some embodiments, the first complementary binding domain and the second complementary binding domain are, when bound to each other, capable of cell-death-inducing activity directed towards the cancer. In some embodiments, the first complementary binding domain and the second complementary binding domain are, when bound to each other, capable of binding a cell-death-inducing antigen.

In some embodiments, the first complementary binding domain is a VH domain and the second complementary binding domain is a VL domain. In some embodiments, the first complementary binding domain is a VL domain and the second complementary binding domain is a VH domain. In some embodiments, the first and second complementary binding domains when paired together may comprise an Fv. In other words, when paired together the first and second complementary binding domains may comprise an "scFv," except for the fact that the VH and VL are not in a single-chain configuration.

In some embodiments, the VH domain of a known antibody can be used as the first complementary binding domain, while the VL domain can be used as the second complementary binding domain.

In some embodiments, the VL domain of a known antibody can be used as the first complementary binding domain, while the VH domain can be used as the second complementary binding domain.

1. Complementary Binding Domains that Modulate T-Cell Activity

In some embodiments, the first complementary binding domain and the second complementary binding domain are, when bound to each other, capable of modulating TCR activity. In some embodiments, the first complementary binding domain and the second complementary binding domain are, when bound to each other, capable of binding a T-cell co-signaling molecule. T-cell co-signaling molecules have been well characterized in the literature (see Chen L and Flies D B *Nat Rev Immunol* 13(4): 227-242 (2013)) and include costimulatory and coinhibitory antigens. In some embodiments, the co-signaling molecules are members of the immunoglobulin superfamily (IgSF) or tumor necrosis factor receptor superfamily (TNFRSF). A coinhibitory antigen may also be termed an immune checkpoint molecule.

Table 11 (shown in Section IV below) provides examples of clinically studied antibodies that can induce anti-tumor responses by modulating T-cell function.

In some embodiments, the first and second complementary binding domains, when paired together, are capable of binding CD3e. In some embodiments, the first and second complementary binding domains comprise all or part of a VH and/or VL of muromonab, otelixizumab, teplizumab, visilizumab, foralumab, SP34, or blinatumomab.

In some embodiments, the first and second complementary binding domains, when paired together, are capable of binding programmed cell death protein 1 (PD-1). In some embodiments, the first and second complementary binding domains comprise all or part of a VH and/or VL of pembrolizumab or nivolumab.

In some embodiments, the first and second complementary binding domains, when paired together, are capable of binding cytotoxic T-lymphocyte-associated protein 4 (CTLA-4). In some embodiments, the first and second complementary binding domains comprise all or part of a VH and/or VL of ipilimumab.

In some embodiments, the first and second complementary binding domains, when paired together, are capable of binding T-cell immunoglobulin and mucin-domain 3 (TIM-3). In some embodiments, the first and second complementary binding domains comprise all or part of a VH and/or VL of TSR-022 or Sym023.

In some embodiments, the first and second complementary binding domains, when paired together, are capable of binding lymphocyte-activation gene 3 (LAG-3). In some embodiments, the first and second complementary binding domains comprise all or part of a VH and/or VL of BMS-986016.

In some embodiments, the first and second complementary binding domains, when paired together, are capable of binding killer-cell immunoglobulin-like receptor (KIR). In some embodiments, the first and second complementary binding domains comprise all or part of a VH and/or VL of lirilumab.

In some embodiments, the first and second complementary binding domains, when paired together, are capable of binding CD28. In some embodiments, the first and second complementary binding domains comprise all or part of a VH and/or VL of theralizumab.

In some embodiments, the first and second complementary binding domains, when paired together, are capable of binding CD137. In some embodiments, the first and second complementary binding domains comprise all or part of a VH and/or VL of utomilumab or urelumab.

In some embodiments, the first and second complementary binding domains, when paired together, are capable of binding OX40. In some embodiments, the first and second complementary binding domains comprise all or part of a VH and/or VL of PF-04518600 or BMS 986178.

In some embodiments, the first and second complementary binding domains, when paired together, are capable of binding CD27. In some embodiments, the first and second complementary binding domains comprise all or part of a VH and/or VL of varlilumab.

In some embodiments, the first and second complementary binding domains, when paired together, are capable of binding GITR. In some embodiments, the first and second complementary binding domains comprise all or part of a VH and/or VL of GWN323 or BMS-986156.

In some embodiments, the first and second complementary binding domains, when paired together, are capable of binding T cell immunoreceptor with Ig and ITIM domains (TIGIT). In some embodiments, the first and second complementary binding domains comprise all or part of a VH and/or VL of OMP-313M32, MTIG7192A, BMS-986207, or MK-7684.

In some embodiments, the first and second complementary binding domains, when paired together, are capable of binding inducible T-cell costimulatory (ICOS). In some embodiments, the first and second complementary binding domains comprise all or part of a VH and/or VL of JTX-2011 (an anti-ICOS antibody in clinical development).

2. Complementary Binding Domains that Target Tumor-Associated Macrophages (TAMs)

In some embodiments, binding of the first and second complementary binding domains to antigens on TAMs mediates increased immune responses to tumors. For example, an anti-CSF1R blocking antibody reduces TAM infiltration and promotes CD8+ T-cell expansion (Ries C H et al. *Cancer Cell.* 25(6):846-59 (2014)).

In some embodiments, the first and second complementary binding domains, when paired together, are capable of inhibiting TAMs. In some embodiments, the first and second complementary binding domains, when paired together, are capable of reprogramming or recruitment of active macrophages.

In some embodiments, the first and second complementary binding domains, when paired together, are capable of binding CSF1R. In some embodiments, the first and second complementary binding domains comprise all or part of a VH and/or VL of emactuzumab/RG7155 (NCT01494688) or IMC-CS4 (NCT01346358).

In some embodiments, the first and second complementary binding domains, when paired together, are capable of binding CD40. In some embodiments, the first and second complementary binding domains comprise all or part of a VH and/or VL of CP-870,893.

3. Complementary Binding Domains that Stimulate NK Cells

In some embodiments, the first and second complementary binding domains, when paired together, are capable of activating NK cells. In some embodiments, the first and second complementary binding domains, when paired together, are capable of binding CD16A. In some embodiments, binding of paired complementary binding domains to CD16A on NK cells activates NK cells against CD33-positive leukemia cells. In some embodiments, the first and second complementary binding domains comprise all or part of a VH and/or VL of NTM-1633 (see NCT03603665) or AFM13 (see NCT01221571).

4. Complementary Binding Domains that Inhibit Checkpoint Molecules Expressed by Cancer Cells In some embodiments, the first and second complementary binding domains, when paired together, are capable of inhibiting a checkpoint molecule expressed by cancer cells. In some embodiments, the first and second complementary binding domains, when paired together, are capable of blocking a signal from the cancer cell that inhibits immune cell activation. A number of different immune checkpoint molecules have been described in the literature (see Park et al., *Experimental & Molecular Medicine* 50:109 (2018), which is incorporated by reference in its entirety for the disclosure of different immune checkpoint molecules).

In some embodiments, the first and second complementary binding domains, when paired together, are capable of binding PD-L1. In some embodiments, the first and second complementary binding domains comprise all or part of a VH and/or VL of Atezolizumab, Durvalumab, or Avelumab.

In some embodiments, the first and second complementary binding domains, when paired together, are capable of binding CD73.

In some embodiments, the first and second complementary binding domains comprise all or part of a VH and/or VL of CPI-006 or MEDI9447.

5. Complementary Binding Domains that Bind RANK

In some embodiments, the first and second complementary binding domains, when paired together, are capable of inhibiting activation of regulatory T cells.

In some embodiments, the complementary binding domains, when paired together, bind to RANK or RANKL. RANK is expressed on cancer cells and can bind to RANKL on regulatory T cells to generate an immunosuppressive environment (see de Groot et al., *Cancer Treatment Reviews* 62:18-28 (2018)). In some embodiments, binding to RANK or RANKL on cancer cells blocks regulatory T-cell activation and stimulates an immune response.

In some embodiments, the first and second complementary binding domains, when paired together, are capable of binding RANK.

In some embodiments, the first and second complementary binding domains, when paired together, are capable of binding RANKL.

In some embodiments, the first and second complementary binding domains comprise all or part of a VH and/or VL of denosumab.

6. Complementary Binding Domains that Bind Cell-Death-Inducing Antigens

As used herein, a "cell-death-inducing" antigen is an antigen that stimulates cell death after being bound by a ligand. All types of cell death are encompassed. The cell death may be programmed (e.g., apoptosis) or non-programmed (e.g., necrosis). In some embodiments, the cell death is necrosis, apoptosis, or necroptosis.

In some embodiments, the cell-death-inducing antigen comprises a death receptor. Death receptors are members of the tumor necrosis factor receptor superfamily characterized by the presence of an intracellular "death domain." In some embodiments, the death receptor is Fas/CD95/Apo1, TNFR1/p55/CD120a, DR3/Apo3/WSL-1/TRAMP/LARD, TRAIL-R1/DR4, DR5/Apo2/TRAIL-R2/TRICK2/KILLER, DR6, or CAR1.

In some embodiments, the first and second complementary binding domains, when paired together, are capable of binding TRAIL-R1/DR4. In some embodiments, the first and second complementary binding domains comprise all or part of a VH and/or VL of mapatumumab (anti-TRAIL-R1/DR4 death receptor antibody). In one embodiment, an anti-DR5/Apo2/TRAIL-R2/TRICK2/KILLER antibody comprises conatumumab (AMG655), lexatumumab, tigatuzumab (CS1008), or drozitumab (PRO95780).

F. Dimerization Domains

In some embodiments, the first and second components further comprise dimerization domains, as shown in FIG. 6. As used herein, "dimerization domains" refer to amino acid sequences that allow two protein monomers (i.e., single proteins) to bind together. As such, dimerization domains can comprise any sequences that cause two protein monomers to form a dimer. In some embodiments, this binding is covalent. In some embodiments, this binding is non-covalent.

A dimerization domain may be attached to a complementary binding domain or to an immune cell binding domain.

In some embodiments, dimerization domains promote association of the first complementary binding domain with the first immune cell binding domain and/or the second complementary binding domain with the second immune cell binding domain. In this way, dimerization can reduce the potential for the complementary binding domain to dissociate from the immune cell binding domain outside of the tumor site.

In some embodiments, a cleavable linker (i.e., a linker comprising a cleavage site) mediates dissociation of the first immune cell binding domain from the first complementary binding domain of the first component and/or the second immune cell binding domain from the second complementary binding domain. In some embodiments, the first immune cell binding domain binds to the first complementary binding domain until at least one cleavable linker is cleaved so that either (or both) the first immune cell binding domain and the first complementary binding domain is released from its respective dimerization domain. In some embodiments, the second immune cell binding domain binds to the second complementary binding domain until at least one cleavable linker is cleaved so that either (or both) the second immune cell binding domain and the second complementary binding domain is released from its respective dimerization domain.

In some embodiments, the first immune cell binding domain is bound to the first complementary binding domain by a first dimerization domain and a second dimerization domain, wherein the first dimerization domain is attached to the first immune cell binding domain by a first linker; the second dimerization domain is attached to the first complementary binding domain by a second linker; and the first and/or second linker is a cleavable linker.

In some embodiments, the second immune cell binding domain is bound to the second complementary binding domain by a first dimerization domain and a second dimerization domain, wherein the first dimerization domain is attached to the second immune cell binding domain by a first linker; the second dimerization domain is attached to the second complementary binding domain by a second linker; and the first and/or second linker is a cleavable linker.

Dimerization domains may comprise all or part of known dimerization domain amino acid sequences. Dimerization domains may comprise sequences with homology to known dimerization amino acid sequences, but not match a known sequence. In some embodiments, dimerization domains may comprise amino acids that are optimized to improve binding.

In some embodiments, the dimerization domains comprise amino acid sequences from transcription factors or receptor/ligand pairs. Non-limiting examples of dimerization domains include sequences from receptor tyrosine kinases, transcription factors, 14-3-3 proteins, and G-protein coupled receptors.

In some embodiments, dimerization domains comprise leucine zippers (also known as coiled coils). As used herein, a "leucine zipper" refers to any amino acid sequence comprising periodic repetition of a leucine residue. A wide variety of leucine zippers have been described for use in dimerization, such as U.S. Pat. No. 9,994,646.

In some embodiments, dimerization domains comprise immunoglobulin domains.

In some embodiments, dimerization domains comprise immunoglobulin variable domains. In some embodiments, the immunoglobulin variable domains are VH or VL domains.

In some embodiments, dimerization domains comprise immunoglobulin constant domains. In some embodiments, the immunoglobulin constant domains are Fc domains. In some embodiments, the immunoglobulin constant domains are CH1/CL, CH2, CH3, or CH4.

In some embodiments, dimerization domains comprise IgE CH2 domains.

In some embodiments, dimerization domains comprise TCR constant domains. The TCR constant domains may be from any chain (e.g., α, β, γ, or δ).

In some embodiments, the dimerization domains in the first component are the same as the dimerization domains in the second component. For example, the dimerization domains in the first component and the second component may be leucine zippers. When the dimerization domains in the first and second component are the same, this may be termed "homodimerization."

In some embodiments, the dimerization domains in the first component are different than the dimerization domains in the second component. For example, the dimerization domains in the first component and the second component may comprise a receptor/ligand pair. When the dimerization domains in the first and second component are different, this may be termed "heterodimerization."

Dimerization domains may also be engineered to create a "knob" or a "hole" to dimerize two proteins. Such knob-into-hole dimerization sequences can include knobs-into-holes Fc or knobs-into-holes $C_H3$ domains. A wide range of knobs-into-holes examples have been described for production of bispecific antibodies (see Xu et al., mAbs 7(1):231-242 (2015)).

In some embodiments, dimerization domains are engineered. By "engineered," it is meant that a mutation is made to the amino acid sequence to change one or more properties of a protein. In some embodiments, engineering makes association of two protein domains electrostatically favorable, when these two domains do not generally associate in the absence of the engineering. In some embodiments, two immunoglobulin constant domains are engineered and may be referred to as "engineered immunoglobulin constant domains." In some embodiments, engineering of Fc regions leads to heterodimerization of Fc regions, such as CH domains.

In some embodiments, two Fc regions are engineered to comprise opposite charges and associate together (see WO2009089004). In some embodiments, two Fc regions are engineered to comprise two leucine zippers and associate together (see U.S. Pat. No. 9,994,646). In some embodiments, two Fc regions are engineered by lysine repositioning (see WO2017106462).

The domains may be engineered so that each component of the TWICE is sufficiently stable during manufacturing, transport, and administration, but that when the two components of a TWICE were in close proximity, binding kinetics would still favor pairing of the immune binding domains to each other and, when applicable, the complementary functional domains to each other.

Several ways of generating a heterodimeric Fc may be employed to make the constructs described herein. In an effort to generate bispecific antibodies in the form of an asymmetric IgG, i.e. an IgG that is formed by two different heavy chains paired into a heterodimer, Ridgway et al. have engineered the CH3 domains of IgG1 by mutations such that one chain contains a "knob" and the other chain contains a corresponding "hole" (J. B. Ridgway, et al. *Protein Eng.* 9:617-621 (1196)). The two engineered heavy chains of this "knobs-into-holes" approach would preferentially form heterodimers when co-expressed from the same cells due to a steric clash in the homodimer. Several other mutations have since been published using similar strategies of steric clashes or repelling charges in engineered Fc domains to facilitate the formation of heterodimers between two different chains (Atwell et al. *Journal of Molecular Biology* 270:26-35 (1997); Gunasekaran et al., *Journal of Biological Chemistry* 285:19637-46 (2010); Moore et al. mAbs 3, 546-557 (2011); Strop P et al. *J. Mol. Biol.* 420, 204-219 (2012), Von Kreudenstein et al. 2013, *mAbs;* 5:646-54 (2013)) The combination of steric clashes and repelling charges has also been employed to engineer IgG heavy chains to efficiently form heterodimers (WO2017106462A1). Using a different approach, Davis et al. (Davis et al., *Protein Engineering, Design & Selection* 23(4):195-202 (2010)) have developed strand-exchange engineered domains (SEED) using IgG and IgA sequences to engineer an asymmetric CH3 domain that enables Fc heterodimerization.

G. Complementary Functional Domains

In some embodiments, the first or second component comprise a complementary functional domain. As used herein, "a complementary functional domain" refers to a domain that has function when binding a specific cell type. Complementary functional domains are different from complementary binding domains, in that complementary functional domains do not need to pair with another domain to have function.

In some embodiments, both the first and the second component comprise a complementary functional domain. In some embodiments, only the first component comprises a complementary functional domain.

In general, any extracellular domain of a cell surface protein that act as a ligand for a receptor may be used as a complementary functional domain. In some embodiments, the complementary functional domain is a costimulatory molecule for T cell activation. In some embodiments, the complementary functional domain is a ligand for binding to an integrin.

In some embodiments, the complementary functional domain is a latent form of a member of the TGF-beta family. In some embodiments, the latent form is activated in the tumor microenvironment to act locally at a tumor cell.

In some embodiments, the complementary functional domain is a cytokine. A wide range of cytokines have been tested clinically in cancer (see Vazquez-Lombardi et al, *Antibodies* 2:426-451 (2013)). Further, incorporating a cytokine as a complementary functional domain of a TWICE allows local delivery of a cytokine and thus may improve upon systemic administration of cytokines. In some embodiments, the cytokine is IL-2, IL-7, IL-12, IL-15, GM-CSF, IFN-α, IFN-γ, or a member of the TNF-superfamily.

In some embodiments, the complementary functional domain is an attenuated cytokine.

As used herein, "an attenuated cytokine" is one with a mutation that decreases its activity compared to the wild-type cytokine or a cytokine that is "masked" with the mask linked to the cytokine by a linker that may be cleavable in the tumor or tumor stromal microenvironment. The attenuated cytokine may thus be a variant form of a naturally-occurring cytokine. In some embodiments, the attenuated cytokine lacks activity unless it is targeted to the target cell. Attenuated cytokines that are targeted to tumors may have robust anti-tumor effects with limited systemic toxicity (see Pogue et al., *PLoS ONE* 11(9):e0162472 (2016) and Pogue et al., *Cytokine* 1:66 (2015)).

Attenuated cytokines have also been proposed to activate the immune system and induce proliferation of effector T cells, when the same cytokine without attenuation may lead to depression of the immune system and proliferation of regulatory T cells.

In some embodiments, an attenuated cytokine is a variant form of IL-2, IL-7, IL-12, IL-15, GM-CSF, IFN-α, IFN-γ, or a member of the TNF-superfamily. In some embodiments, the attenuated cytokine must be targeted to a cancer or its microenvironment to have function.

H. Linkers

By linker, we include any chemical moiety that attaches parts of the TWICE together.

In some embodiments, linkers used in a TWICE may be flexible linkers. Linkers include peptides, polymers, nucleotides, nucleic acids, polysaccharides, and lipid organic species (such as polyethylene glycol). In some embodiments, the linker is a peptide linker. Peptide linkers may be from about 2-100, 10-50, or 15-30 amino acids long. In some embodiments, peptide linkers may be at least 10, at least 15, or at least 20 amino acids long and no more than 80, no more than 90, or no more than 100 amino acids long. In some embodiments, the linker is a peptide linker that has a single or repeating GGGGS (SEQ ID NO: 85), GGGS (SEQ ID NO: 86), GS (SEQ ID NO: 87), GSGGS (SEQ ID NO: 88), GGSG (SEQ ID NO: 89), GGSGG (SEQ ID NO: 90), GSGSG (SEQ ID NO: 91), GSGGG (SEQ ID NO: 92), GGGSG (SEQ ID NO: 93), and/or GSSSG (SEQ ID NO: 94) sequence(s).

In some embodiments, the linker does not comprise a cleavage site (i.e., non-cleavable linkers). Exemplary linkers not comprising a cleavage site include maleimide (MPA) or SMCC linkers.

In some embodiments, the linker comprises a cleavage site (i.e., a cleavable linker).

In some embodiments, linkers attach targeting moieties to immune cell binding domains, complementary binding domains, or complementary functional domains. In some embodiments, linkers attach dimerization domains to immune cell binding domains or complementary binding domains.

1. Linkers to Attach Targeting Moieties

In some embodiments, a linker attaches a targeting moiety to the immune cell binding domain. In some embodiments, a linker attaches a targeting moiety to a complementary binding domain or complementary functional domain. In some embodiments, linkers attaching targeting moieties to complementary binding domains or to complementary functional domains are non-cleavable linkers. In some embodiments, linkers attaching targeting moieties to complementary binding domains or to complementary functional domains are flexible linkers.

2. Linkers to Attach Dimerization Domains

In some embodiments, a linker attaches a dimerization domain to an immune cell binding domain. In some embodiments, a linker attaches a dimerization domain to a complementary binding domain.

A linker used to attach a dimerization domain to an immune cell binding domain or a complementary binding domain may be referred to as a "dimerization domain linker." In some embodiments, the dimerization domain linker is a cleavable linker.

In some embodiments, a dimerization domain linker may comprise a cleavage site. In some embodiments, the dimerization domain linker comprises a protease cleavage site. In some embodiments, the dimerization domain linker comprises a protease cleavage site that can be cleaved in the tumor microenvironment. In some embodiments, the dimerization domain linker comprises a cleavage site for one or more matrix metalloproteases.

Depending on the dimerization domain employed, a range of dimerization domain linker lengths may be used in the TWICE. The length of a dimerization domain linker may need to be long enough to allow flexibility for protease cleavage. However, a dimerization domain linker that is too long could allow the two dimerization domains to be too spatially far apart to ensure dimerization.

In some embodiments, the first dimerization domain linker and the second dimerization domain linker are the same or similar lengths. In some embodiments, the first dimerization domain linker and second dimerization domain linker are different lengths.

In some embodiments, the dimerization domain linker length helps promote association of the two dimerization domains.

In some embodiments, the first and second dimerization domain linkers are from 5-30 amino acids in length. In some embodiments, the first and second dimerization domain linkers are from 8-16 amino acids in length.

In some embodiments, the first and second dimerization domain linkers are from 5-15 amino acids in length. For example, linkers of this length may be appropriate when the dimerization domains are CH1/CL.

In some embodiments, the first and second dimerization domain linkers are from 12-30 amino acids in length. For example, linkers of this length may be appropriate when the dimerization domains are leucine zippers (coiled coils). In some embodiments, the first and second dimerization domain linkers are from 15-20 amino acids in length. For example, linkers of this length may be appropriate for certain leucine zipper dimerization domains.

Examples of representative dimerization domain linkers include SEQ ID NOs: 203-211.

I. Cleavage Sites and Cleavable Linkers

In some embodiments, cleavage sites allow specific cleavage of constructs at certain locations. A linker comprising a cleavage site may be referred to as a cleavable linker.

For example, a TWICE that is a single polypeptide construct may comprise a cleavable linker between the first and second components. Other embodiments of this TWICE may also employ cleavable linkers, such as dimerization domain linkers.

In some embodiments, cleavage can occur outside the unwanted cell, without first being internalized into a cell and being engaged in the classical antigen-processing pathways.

In certain embodiments, at least one cleavage site may be cleaved by an enzyme expressed by the cancer cells. Cancer cells, for instance, are known to express certain enzymes, such as proteases. By way of nonlimiting example, cathepsin B cleaves FR, FK, VA and VR amongst others; cathepsin D cleaves PRSFFRLGK (SEQ ID NO: 45), ADAM28 cleaves KPAKFFRL (SEQ ID NO: 1), DPAKFFRL (SEQ ID NO: 2), KPMKFFRL (SEQ ID NO: 3) and LPAKFFRL (SEQ ID NO: 4); and MMP2 cleaves AIPVSLR (SEQ ID NO: 46), SLPLGLWAPNFN (SEQ ID NO: 47), HPVGLLAR (SEQ ID NO: 48), GPLGVRGK (SEQ ID NO: 49), and GPLGLWAQ (SEQ ID NO: 50), for example. Other cleavage sites listed in Table 1 or 2 may also be employed. Protease cleavage sites and proteases associated with cancer are well known in the art. Oncomine (www.oncomine.org) is an online cancer gene expression database, so when the agent of the TWICE is for treating cancer, the skilled person may search the Oncomine database to identify a particular protease cleavage site (or two protease cleavage sites) that will be appropriate for treating a given cancer type. Alternative databases include the European Bioinformatic Institute (www.ebi.ac.uk), in particular (www.ebi.ac.uk/gxa). Protease databases include ExPASy Peptide Cutter (www.ca.expasy.org/tools/peptidecutter).

In some embodiments, the protease is expressed by a non-cancer cell in the tumor microenvironment, such as a tumor-associated macrophage of fibroblast.

In some embodiments, the protease cleavage sites of one or more cleavable linkers are cleaved by a protease that is colocalized. In some embodiments, the protease is colocalized to the cancer by a targeting moiety that binds a tumor antigen expressed by the cancer and that is the same or different from the targeting moiety in the first component or the second component. In some embodiments, the protease is colocalized to the cancer by a targeting moiety that binds an antigen expressed by a cell in the tumor microenvironment.

Cleavage sites in a cleavable linker can function to release the dimerization domain from the complementary binding domain and/or immune cell binding domain. The cleavage sites can function to release the complementary binding domain and/or immune cell binding domain from the first and/or immune cell engaging domain in the microenvironment of the unwanted cells.

In some embodiments, the protease cleavage sites in the first and/or second cleavable linkers that attach dimerization domains to immune cell binding domains or complementary binding domains are cleaved by a protease expressed by the cancer or colocalized to the cancer by a targeting moiety that binds a tumor antigen expressed by the cancer.

J. Binding of a Complementary Binding Domain to an Immune Cell Binding Domain

In some embodiments, the first complementary binding domain is a binding partner for the first immune cell binding domain, such that the first immune cell binding domain does not bind to the second immune cell binding domain unless the first immune cell binding domain is not bound to the first complementary domain.

In some embodiments, the second complementary binding domain is a binding partner for the second immune cell binding domain, such that the second immune cell binding domain does not bind to the first immune cell binding domain unless the second immune cell binding domain is not bound to the second complementary domain.

When a complementary binding domain dissociates from an immune cell binding domain and associates with a paired complementary domain or when an immune cell binding domain dissociates from a complementary binding domain and associates with a paired immune cell binding domain, this can be referred to as a domain swap. In this domain swap event, the domains move from a mismatched configuration to an active and paired configuration.

In some embodiments, the first and second immune cell binding domains are capable of forming a Fv when not bound to the first and second complementary binding domains. In some embodiments, the first and second complementary binding domains are capable of forming a Fv when not bound to the first and second immune cell binding domains.

In some embodiments, the first and second components comprise dimerization domains to promote association of the immune cell binding domain and the complementary binding domain of a single component. In some embodiments, cleavage of a cleavable linker in a dimerization domain linker allows dissociation of the immune cell binding domain and the complementary binding domain of a single component at the cancer cell or its microenvironment. In some embodiments, the first and second components do not comprise dimerization domains.

K. Masking by Inert Binding Partners

In some embodiments, the TWICE comprises an inert binding partner to mask the first and/or second immune cell binding domain. In some embodiments, only the first immune cell binding domain is masked. In some embodiments, both the first and second immune cell binding domain are masked.

For example, In some embodiments, inert binding partners are a component of those TWICE that comprise complementary functional domains, as those described in FIG. 5 and Section Complementary functional domainsG.

In some embodiments, first and/or second components that comprise a complementary functional domain comprise an inert binding partner.

In some embodiments, a first inert binding partner binds to the first immune cell binding domain such that the first immune cell binding domain does not bind to the second immune cell binding domain unless the inert binding partner is removed.

In some embodiments, the first immune cell binding domain is a VH domain, and the inert binding partner is a VL domain. In some embodiments, the first immune cell binding domain is a VL domain, and the inert binding partner is a VH domain.

In some embodiments, a protease cleavage site separates the first immune cell binding domain and the first inert binding partner. In some embodiments, the protease cleavage site is capable of releasing the inert binding partner from the immune cell binding domain in the presence of a protease.

In some embodiments, a second inert binding partner binds to the second immune cell binding domain such that the second immune cell binding domain does not bind to the first immune cell binding domain unless the inert binding partner is removed.

In some embodiments, the second immune cell binding domain is a VH domain, and the inert binding partner is a VL domain. In some embodiments, the second immune cell binding domain is a VL domain, and the inert binding partner is a VH domain.

In some embodiments, a protease cleavage site separates the second immune cell binding domain and the second inert binding partner. In some embodiments, protease cleavage site is capable of releasing the inert binding partner from the immune cell binding domain in the presence of a protease.

In some embodiments, the protease is expressed by the cancer. In some embodiments, the protease is expressed by a cell in the tumor microenvironment, such as a TAF or TAM.

In some embodiments, the protease colocalized to the cancer by a targeting moiety that is an antibody or antigen binding fragment that binds (a) a tumor antigen expressed by the cancer and that is the same or different from the first and/or second targeting moiety in the agent or (b) an antigen expressed by a cell in the tumor microenvironment.

L. Methods of Making

The different TWICE as described herein can be made using genetic engineering techniques. Specifically, one or two nucleic acids may be expressed in a suitable host to produce a TWICE or its components. For example, a vector may be prepared comprising a nucleic acid sequence that encodes the TWICE including all of its component parts and linkers and that vector may be used to transform an appropriate host cell (or individual vectors may be used to individually express each component).

Various regulatory elements may be used in the vector as well, depending on the nature of the host and the manner of introduction of the nucleic acid into the host, and whether episomal maintenance or integration is desired.

Chemical linkage techniques, such as using maleimide or SMCC linkers, may also be employed.

In instances where the targeting moiety is an aptamer, a person of ordinary skill in the art would appreciate how to conjugate an aptamer to a protein, namely the immune cell binding domain or the complementary binding domain. Aptamers may be conjugated using a thiol linkage or other standard conjugation chemistries. A maleimide, succinimide, or SH group may be affixed to the aptamer to attach it to the immune cell binding domain or the complementary binding domain.

II. Pharmaceutical Compositions

The TWICE may be employed as pharmaceutical compositions. As such, they may be prepared along with a pharmaceutically acceptable carrier. If parenteral administration is desired, for instance, the TWICE may be provided in sterile, pyrogen-free water for injection or sterile, pyrogen-free saline or other form that is acceptable for parenteral administration. Alternatively, the TWICE may be provided in lyophilized form for resuspension with the addition of a sterile liquid carrier. If in separate form, the TWICE may be provided in a single pharmaceutical composition or in two pharmaceutical compositions.

III. Methods of Using TWICE

The TWICE described herein may be used in a method of treating cancer comprising administering a TWICE comprising at least a first and a second component to the patient, as each of the components have been described in detail in various embodiments above.

Additionally, the agents described herein may also be used in a method of targeting a patient's own immune response to cancer cells comprising administering a TWICE to the patient.

In some embodiments, the TWICE described herein may be used in a method of targeting immune cells to cancer expressing a tumor antigen that binds both the first targeting moiety and the second targeting moiety. In some embodiments, the immune cells are T cells expressing CD3 or TCR.

In some embodiments, the TWICE described herein may be used in a method of targeting immune cells to cancer expressing two tumor antigens, wherein one tumor antigen binds the first targeting moiety and one tumor antigen binds the second targeting moiety. In some embodiments, the immune cells are T cells expressing CD3 or TCR.

In some embodiments, the TWICE described herein may be used in a method of delivering a cytokine to an immune cell of a patient. In some embodiments, the first and/or second complementary functional domain of the TWICE comprise IL-2, IL-7, IL-12, IL-15, GM-CSF, IFN-α, IFN-γ, or a member of the TNF-superfamily.

In some embodiments, the patient has cancer or a recognized pre-malignant state. In some embodiments, the patient has undetectable cancer, but is at high risk of developing cancer, including having a mutation associated with an increased risk of cancer. In some embodiments, the patient at high risk of developing cancer has a premalignant tumor with a high risk of transformation. In some embodiments, the patient at high risk of developing cancer has a genetic profile associated with high risk. In some embodiments, the presence of cancer or a pre-malignant state in a patient is determined based on the presence of circulating tumor DNA (ctDNA) or circulating tumor cells. In some embodiments, treatment is pre-emptive or prophylactic. In some embodiments, treatment slow or blocks the occurrence or reoccurrence of cancer.

The amount of the agent administered to the patient may be chosen by the patient's physician so as to provide an effective amount to treat the condition in question. The first component and the second component of the TWICE may be administered in the same formulation or two different formulations within a sufficiently close period of time to be active in the patient.

The patient receiving treatment may be a human. The patient may be a primate or any mammal. Alternatively, the patient may be an animal, such as a domesticated animal (for example, a dog or cat), a laboratory animal (for example, a laboratory rodent, such as a mouse, rat, or rabbit), or an animal important in agriculture (such as horses, cattle, sheep, or goats).

The cancer may be a solid or non-solid malignancy. In some embodiments, the cancer may be a solid tumor wherein the solid tumor is not a lymphoma. The cancer may be any cancer such as breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, nonHodgkin lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease, and premalignant disease or any other cancer that is suitable for treatment.

In some embodiments, one skilled in the art may evaluate a tumor prior to initiating treatment.

For example, one skilled in the art may evaluate a tumor for the presence of infiltrating T cells. In some embodiments, a method of treatment comprises confirming the presence of T cells in the tumor before initiating treatment. In some embodiments, the patient will have a solid tumor with T-cell infiltration. A tumor sample may be stained for T-cell markers and demonstrate the presence and optionally concentration of T-cell infiltration in the tumor using imaging techniques.

In some embodiments, a method of treatment comprises confirming the presence of tumor antigens before initiating treatment. In some embodiments, a method of treatment comprises evaluating the concentration of tumor antigens before initiating treatment. For example, one skilled in the art could select tumor antigens or select patients for treatment based on a profile of antigens overexpressed by the tumor. One skilled in the art could also select patients for treatment with a TWICE based on their antigen expression profiles by select patients overexpressing particular antigens. In some embodiments, these tumor antigens are cell-surface tumor antigens. A tumor sample may be stained for antigens of interest to demonstrate the presence and optionally concentration of tumor antigens. The lower limit of expression can also be determined using in vitro T-cell activation assays with a specific TWICE. These methods allow an investigator to confirm that a patient's tumor has appropriate antigens for targeting of the TWICE to the tumor microenvironment.

In some embodiments, a method of treatment comprises (i) confirming the presence of T cells in the tumor; (ii) confirming the presence of tumor antigen(s), and/or (iii) evaluating the concentration of tumor antigens. In some embodiments, the expression of tumor antigen(s) that bind the first and second targeting moieties are expressed at a high enough level to bring the two components of the TWICE into close proximity.

In some embodiments, the presence of a biomarker is used to select patients for receiving the TWICE. A wide variety of tumor markers are known in the art, such as those described at www.cancer.gov/about-cancer/diagnosis-staging/diagnosis/tumor-markers-fact-sheet. In some embodiments, the tumor marker is ALK gene rearrangement or overexpression; alpha-fetoprotein; beta-2-microglobulin; beta-human chorionic gonadotropin; BRCA1 or BRCA2 gene mutations; BCR-ABL fusion genes (Philadelphia chromosome); BRAF V600 mutations; C-kit/CD117; CA15-3/CA27.29; CA19-9; CA-125; calcitonin; carcinoembryonic antigen (CEA); CD20; chromogranin A (CgA); chromosomes 3, 7, 17, or 9p21; circulating tumor cells of epithelial origin (CELL-SEARCH®); cytokeratin fragment 21-1; EGFR gene mutation analysis; estrogen receptor (ER)/progesterone receptor (PR); fibrin/fibrinogen; HE4; HER2/neu gene amplification or protein overexpression; immunoglobulins; KRAS gene mutation analysis; lactate dehydrogenase; neuron-specific enolase (NSE); nuclear matrix protein 22; programmed death ligand 1 (PD-L1); prostate-specific antigen (PSA); thyroglobulin; urokinase plasminogen activator (uPA); plasminogen activator inhibitor (PAI-1); 5-protein signature (OVA1®); 21-gene signature (Oncotype DX®); or 70-gene signature (Mammaprint®).

The TWICE may be administered alone or in conjunction with other forms of therapy, including surgery, radiation, traditional chemotherapy, or other immunotherapy.

In some embodiments, the other immunotherapy may include separate treatment with immune cytokines or cytokine fusions. Cytokines refer to cell-signaling proteins naturally made by the body to activate and regulate the immune system. Cytokine fusions refer to engineered molecules comprising all or part of a cytokine. For example, a cytokine fusion may comprise all or part of a cytokine attached to an antibody that allows targeting to a tumor such as Darleukin (see Zegers et al. (2015) Clin. Cancer Res., 21, 1151-60), Teleukin (see WO2018087172).

In some embodiments, the other immunotherapy is cancer treatment vaccination. In some embodiments, cancer treatment vaccination boosts the body's natural defenses to fight cancer. These can either be against shared tumor antigens (such as E6, E7, NY-ESO, MUC1, or HER2) or against personalized mutational neoantigens.

IV. Embodiments

The following numbered items provide embodiments as described herein, though the embodiments recited here are not limiting.

Item 1. A kit or composition for treating cancer in a patient comprising a first component comprising a targeted immune cell binding agent comprising a first targeting moiety that binds a tumor antigen expressed by the cancer; a first immune cell binding domain capable of immune cell binding activity when binding a second immune cell binding domain, wherein the second immune cell binding domain is not part of the first component, and wherein the first immune cell binding domain is either a VH domain or VL domain; and a first complementary binding domain capable of binding to a complementary antigen when binding a second complementary binding domain, wherein the second complementary binding domain is not part of the first component, when the first immune cell binding domain is a VH domain the first complementary binding domain is a VL domain, when the first immune cell binding domain is a VL domain, the first complementary binding domain is a VH domain, and wherein the first complementary binding domain is a binding partner for the first immune cell binding domain, such that the first immune cell binding domain does not bind to the second immune cell binding domain unless the first immune cell binding domain is not bound to the first complementary domain; and a second component comprising a targeted immune cell binding agent comprising a second targeting moiety; a second immune cell binding domain capable of immune cell binding activity when binding a first immune cell binding domain, wherein the second immune cell binding domain is a VH if the first immune cell binding domain is a VL and wherein the second immune cell binding domain is a VL if the first immune cell binding domain is a VH; and a second complementary binding domain capable of binding to a complementary antigen when binding the first complementary binding domain, wherein when the second immune cell binding domain is a VH domain the second complementary binding domain is a VL domain, when the second immune cell binding domain is a VL domain, the second complementary binding domain is a VH domain, and wherein the second complementary binding domain is a binding partner for the second immune cell binding domain, such that the second immune cell binding domain does not bind to the first immune cell binding domain unless the second immune cell binding domain is not bound to the second complementary domain.

Item 2. The kit or composition of item 1, wherein the first immune cell binding domain is bound to the first complementary binding domain by a first dimerization domain and a second dimerization domain, wherein the first dimerization domain is attached to the first immune cell binding domain by a first linker; the second dimerization domain is attached to the first complementary binding domain by a second linker; and the first and/or second linker is a cleavable linker.

Item 3. The kit or composition of any one of items 1-2, wherein the second T-cell binding domain is bound to the second complementary binding domain by a first dimerization domain and a second dimerization domain, wherein the first dimerization domain is attached to the second T-cell binding domain by a first linker; the second dimerization domain is attached to the second complementary binding domain by a second linker; and the first and/or second linker is a cleavable linker.

Item 4. The kit or composition of any one of items 2-3, wherein the first and second linkers are cleavable linkers.

Item 5. The kit or composition of any one of items 2-4, wherein the first and second linkers are the same.

Item 6. The kit or composition of any one of items 2-4, wherein the first and second linkers are different.

Item 7. The kit or composition of any one of items 2-6, wherein the first and second linkers are from 5 to 30 amino acids in length.

Item 8. The kit or composition of any one of items 2-6, wherein the first and second linkers are from 8 to 16 amino acids in length.

Item 9. The kit or composition of any one of items 2-8, wherein the protease cleavage sites of the first and/or second cleavable linkers are cleaved by a protease expressed by the cancer or tumor microenvironment cell.

Item 10. The kit or composition of any one of items 2-9, wherein the protease cleavage sites of the first and/or second cleavable linkers are cleaved by a protease that is colocalized to the cancer by a targeting moiety that is an antibody or antigen binding fragment thereof that binds a tumor antigen expressed by the cancer and that is the same or different from the targeting moiety in at least one of the first components or the second component.

Item 11. The kit or composition of any one of items 1-10, wherein the first and second dimerization domains are both leucine zippers; immunoglobulin domains; or T-cell receptor (TCR) domains.

Item 12. The kit or composition of item 11, wherein the immunoglobulin domains comprise immunoglobulin variable domains or immunoglobulin constant domains.

Item 13. The kit or composition of item 12, wherein the immunoglobulin constant domains comprise CH1/CL, CH2, CH3, or CH4.

Item 14. The kit or composition of item 11, wherein the TCR domains comprise TCR constant domains.

Item 15. The kit or composition of any one of items 1-14, wherein the dimerization domains in the first component are the same as the dimerization domains in the second component.

Item 16. The kit or composition of any one of items 1-14, wherein the dimerization domains in the first component are different than the dimerization domains in the second component.

Item 17. The kit or composition of any one of items 1-16, wherein the first complementary binding domain and the second complementary binding domain are, when bound to each other, capable of binding the cancer.

Item 18. The kit or composition of item 17, wherein the first complementary binding domain and the second complementary binding domain are, when bound to each other, capable of binding an immune checkpoint molecule, RANK or RANKL, or a cell-death-inducing antigen.

Item 19. The kit or composition of item 18, wherein the first complementary binding domain and the second complementary binding domain are, when bound to each other, capable of binding an immune checkpoint molecule.

Item 20. The kit or composition of item 19, wherein the first complementary binding domain and the second complementary binding domain are, when bound to each other, capable of binding PD-L1.

Item 21. The kit or composition of item 20, wherein the first and second complementary binding domains comprise all or part of a VH and/or VL of atezolizumab, durvalumab, or avelumab.

Item 22. The kit or composition of item 19, wherein the first complementary binding domain and the second complementary binding domain are, when bound to each other, capable of binding CD73.

Item 23. The kit or composition of item 22, wherein the first and second complementary binding domains comprise all or part of a VH and/or VL of CPI-006 or MEDI9447.

Item 24. The kit or composition of item 18, wherein the first complementary binding domain and the second complementary binding domain are, when bound to each other, capable of binding RANK.

Item 25. The kit or composition of item 18, wherein the first complementary binding domain and the second complementary binding domain are, when bound to each other, capable of binding RANKL.

Item 26. The kit or composition of item 25, wherein the first and second complementary binding domains comprise all or part of a VH and/or VL of denosumab.

Item 27. The kit or composition of item 18, wherein the first complementary binding domain and the second complementary binding domain are, when bound to each other, capable of binding a cell-death-inducing antigen.

Item 28. The kit or composition of item 27, wherein the first complementary binding domain and the second complementary binding domain are, when bound to each other, capable of binding Fas/CD95/Apo1, TNFR1/p55/CD120a, DR3/Apo3/WSL-1/TRAMP/LARD, TRAIL-R1/DR4, DR5/Apo2/TRAIL-R2/TRICK2/KILLER, DR6, or CAR1.

Item 29. The kit or composition of item 28, wherein the first complementary binding domain and the second complementary binding domain are, when bound to each other, capable of binding TRAIL-R1/DR4.

Item 30. The kit or composition of item 29, wherein the first and second complementary binding domains comprise all or part of a VH and/or VL of mapatumumab.

Item 31. The kit or composition of item 28, wherein the first complementary binding domain and the second complementary binding domain are, when bound to each other, capable of binding DR5/Apo2/TRAIL-R2/TRICK2/KILLER.

Item 32. The kit or composition of item 31, wherein the first and second complementary binding domains comprise all or part of a VH and/or VL of conatumumab (AMG655), lexatumumab, tigatuzumab (CS1008), or drozitumab (PRO95780).

Item 33. The kit or composition of any one of items 1-16, wherein the first complementary binding domain and the second complementary binding domain are, when bound to each other, capable of binding a molecule associated with the extracellular matrix.

Item 34. The kit or composition of any one of items 1-16, wherein the first complementary binding domain and the second complementary binding domain are, when bound to each other, capable of binding a T cell, a macrophage, or a natural killer cell.

Item 35. The kit or composition of item 34, wherein the first complementary binding domain and the second complementary binding domain are, when bound to each other, capable of binding a T cell.

Item 36. The kit or composition of item 35, wherein the first complementary binding domain and the second complementary binding domain are, when bound to each other, capable of binding CD3, programmed cell death protein 1 (PD-1), cytotoxic T-lymphocyte-associated protein 4 (CTLA-4), T-cell immunoglobulin and mucin-domain 3 (TIM-3), lymphocyte-activation gene 3 (LAG-3), killer-cell immunoglobulin-like receptor (KIR), CD28, CD137, OX40, CD27, GITR (TNFRSF18), TIGIT, or inducible T-cell costimulatory (ICOS).

Item 37. The kit or composition of item 36, wherein the first and second complementary binding domains are, when bound together, capable of binding CD3.

Item 38. The kit or composition of item 37, wherein the first and second complementary binding domains comprise all or part of a VH and/or VL of muromonab, otelixizumab, teplizumab, visilizumab, foralumab, SP34, or blinatumomab.

Item 39. The kit or composition of item 36, wherein the first and second complementary binding domains are, when bound together, capable of binding PD-1.

Item 40. The kit or composition of item 39, wherein the first and second complementary binding domains comprise all or part of a VH and/or VL of pembrolizumab or nivolumab.

Item 41. The kit or composition of item 36, wherein the first and second complementary binding domains are, when bound together, capable of binding CTLA-4.

Item 42. The kit or composition of item 41, wherein the first and second complementary binding domains comprise all or part of a VH and/or VL of ipilimumab.

Item 43. The kit or composition of item 36, wherein the first and second complementary binding domains are, when bound together, capable of binding TIM-3.

Item 44. The kit or composition of item 43, wherein the first and second complementary binding domains comprise all or part of a VH and/or VL of TSR-022 or Sym023.

Item 45. The kit or composition of item 36, wherein the first and second complementary binding domains are, when bound together, capable of binding LAG-3.

Item 46. The kit or composition of item 45, wherein the first and second complementary binding domains comprise all or part of a VH and/or VL of BMS-986016.

Item 47. The kit or composition of item 36, wherein the first and second complementary binding domains are, when bound together, capable of binding KIR.

Item 48. The kit or composition of item 47, wherein the first and second complementary binding domains comprise all or part of a VH and/or VL of lirilumab.

Item 49. The kit or composition of item 36, wherein the first and second complementary binding domains are, when bound together, capable of binding CD28.

Item 50. The kit or composition of item 49, wherein the first and second complementary binding domains comprise all or part of a VH and/or VL of theralizumab.

Item 51. The kit or composition of item 36, wherein the first and second complementary binding domains are, when bound together, capable of binding CD137.

Item 52. The kit or composition of item 51, wherein the first and second complementary binding domains comprise all or part of a VH and/or VL of utomilumab or urelumab.

Item 53. The kit or composition of item 36, wherein the first and second complementary binding domains are, when bound together, capable of binding OX40.

Item 54. The kit or composition of item 53, wherein the first and second complementary binding domains comprise all or part of a VH and/or VL of PF-04518600 or BMS 986178.

Item 55. The kit or composition of item 36, wherein the first and second complementary binding domains are, when bound together, capable of binding CD27.

Item 56. The kit or composition of item 55, wherein the first and second complementary binding domains comprise all or part of a VH and/or VL of varlilumab.

Item 57. The kit or composition of item 36, wherein the first and second complementary binding domains are, when bound together, capable of binding GITR (TNFRSF18).

Item 58. The kit or composition of item 57, wherein the first and second complementary binding domains comprise all or part of a VH and/or VL of GWN323 or BMS-986156.

Item 59. The kit or composition of item 36, wherein the first and second complementary binding domains, when paired together, are capable of binding TIGIT.

Item 60. The kit or composition of item 59, wherein first and second complementary binding domains comprise all or part of a VH and/or VL of OMP-313M32, MTIG7192A, BMS-986207, or MK-7684.

Item 61. The kit or composition of item 36, wherein the first and second complementary binding domains are, when bound together, capable of binding ICOS.

Item 62. The kit or composition of item 61, wherein the first and second complementary binding domains comprise all or part of a VH and/or VL of JTX-2011.

Item 63. The kit or composition of item 34, wherein the first complementary binding domain and the second complementary binding domain are, when bound to each other, capable of binding a macrophage.

Item 64. The kit or composition of item 63, wherein the first complementary binding domain and the second complementary binding domain are, when bound to each other, capable of binding CSF1R.

Item 65. The kit or composition of item 65, wherein the first and second complementary binding domains comprise all or part of a VH and/or VL of emactuzumab or IMC-CS4.

Item 66. The kit or composition of item 63, wherein the first complementary binding domain and the second complementary binding domain are, when bound to each other, capable of binding CD40.

Item 67. The kit or composition of item 66, wherein the first and second complementary binding domains comprise all or part of a VH and/or VL of CP-870,893.

Item 68. The kit or composition of item 34, wherein the first complementary binding domain and the second complementary binding domain are, when bound to each other, capable of binding a natural killer cell.

Item 69. The kit or composition of item 68, wherein the first complementary binding domain and the second complementary binding domain are, when bound to each other, capable of binding CD16A.

Item 70. The kit or composition of item 69, wherein the first and second complementary binding domains comprise all or part of a VH and/or VL of NTM-1633 or AFM13.

Item 71. The kit or composition of any one of items 1-70, wherein the first complementary binding domain and the second complementary binding domain, when bound to each other, and the first immune cell binding domain and the second immune cell binding domain, when bound to each other, are capable of binding the same antigen.

Item 72. The kit or composition of any one of items 1-70, wherein the first complementary binding domain and the second complementary binding domain, when bound to each other, and the first immune cell binding domain and the second immune cell binding domain, when bound to each other, are capable of binding different antigens on the same cell.

Item 73. The kit or composition of any one of items 1-70, wherein the first complementary binding domain and the second complementary binding domain, when bound to each other, and the first immune cell binding domain and the second immune cell binding domain, when bound to each other, are capable of binding different cells.

Item 74. The kit or composition of any one of items 1-73, wherein the first and second immune cell binding domains are capable of forming a Fv when not bound to the first and second complementary binding domains.

Item 75. The kit or composition of any one of items 1-74, wherein the first and second complementary binding domains are capable of forming a Fv when not bound to the first and second immune cell binding domains.

Item 76. A kit or composition for treating cancer in a patient comprising a first component comprising a targeted immune cell binding agent comprising a first targeting moiety that binds a tumor antigen expressed by the cancer; a first immune cell binding domain capable of immune cell binding activity when binding a second immune cell binding domain, wherein the second immune cell binding domain is not part of the first component, and wherein the first immune cell binding domain is either a VH domain or VL domain; a first inert binding partner for the first immune cell binding domain, wherein the first inert binding partner binds to the first immune cell binding domain such that the first immune cell binding domain does not bind to the second immune cell binding domain unless the inert binding partner is removed, wherein if the first immune cell binding domain is a VH domain, the inert binding partner is a VL domain and if the first immune cell binding domain is a VL domain, the inert binding partner is a VH domain; a protease cleavage site separating the first immune cell binding domain and the first inert binding partner, wherein the protease cleavage site is capable of releasing the inert binding partner from the immune cell binding domain in the presence of a protease expressed by the cancer or a tumor microenvironment cell; or colocalized to the cancer by a targeting moiety that is an antibody or antigen binding fragment thereof that binds (a) a tumor antigen expressed by the cancer and that is the same or different from the first and/or second targeting moiety in the agent or (b) an antigen expressed by a cell in the tumor microenvironment; and a first complementary functional domain capable of immune cell binding, and a second component comprising a targeted immune cell binding agent comprising a second targeting moiety; a second immune cell binding domain; and optionally a second complementary functional domain capable of immune cell binding.

Item 77. The kit or composition of item 76, wherein the second component comprises a complementary functional domain.

Item 78. The kit or composition of any one of items 76-77, wherein the complementary functional domain of the first and/or second component comprises a ligand for a receptor.

Item 79. The kit or composition of item 78, wherein the complementary functional domain is a latent form of a member of the TGF-beta family.

Item 80. The kit or composition of item 78, wherein the complementary functional domain of the first and/or second component comprises a cytokine.

Item 81. The kit or composition of item 78, wherein the cytokine is IL-2, IL-7, IL-12, IL-15, GM-CSF, IFN-α, IFN-γ, or a member of the TNF-superfamily.

Item 82. The kit or composition of item 80, wherein the complementary functional domain of the first and/or second component comprises an attenuated cytokine.

Item 83. The kit or composition of item 82, wherein the attenuated cytokine is a variant of IL-2, IL-7, IL-12, IL-15, GM-CSF, IFN-α, IFN-γ, or a member of the TNF-superfamily.

Item 84. The kit or composition of any one of items 76-83, wherein the second component further comprises a second inert binding partner for the second immune cell binding domain, wherein the second inert binding partner binds to the second immune cell binding domain such that the second immune cell binding domain does not bind to the first immune cell binding domain unless the inert binding partner is removed, wherein if the second immune cell binding domain is a VH domain, the inert binding partner is a VL domain and if the second immune cell binding domain is a VL domain, the inert binding partner is a VH domain; and further wherein a protease cleavage site separating the second immune cell binding domain and the second inert binding partner, wherein the protease cleavage site is capable of releasing the inert binding partner from the immune cell binding domain in the presence of a protease expressed by the cancer; or colocalized to the cancer by a targeting moiety that is an antibody or antigen binding fragment thereof that binds (a) a tumor antigen expressed by the cancer and that is the same or different from the first and/or second targeting moiety in the agent or (b) an antigen expressed by a cell in the tumor microenvironment.

Item 85. The kit or composition of any one of items 1-84, wherein the first component is not covalently bound to the second component.

Item 86. A molecule comprising the kit or composition of any one of items 1-85, wherein the first component is covalently bound to the second component.

Item 87. The single molecule of item 86, wherein the first component is covalently bound to the second component via a cleavable linker.

Item 88. The kit or composition of any one of items 1-87, wherein the first immune cell binding domain and the second immune cell binding domain are, when bound to each other, capable of binding a T cell, a macrophage, or a natural killer cell.

Item 89. The kit or composition of item 88, wherein the first immune cell binding domain and the second immune cell binding domain are, when bound to each other, capable of binding a T cell.

Item 90. The kit or composition of item 89, wherein the first immune cell binding domain and the second immune cell binding domain are, when bound to each other, capable of binding CD3, the T-cell receptor, programmed cell death protein 1 (PD-1), cytotoxic T-lymphocyte-associated protein 4 (CTLA-4), T-cell immunoglobulin and mucin-domain 3 (TIM-3), lymphocyte-activation gene 3 (LAG-3), killer-cell immunoglobulin-like receptor (KIR), CD28, CD137, OX40, CD27, GITR (TNFRSF18), TIGIT, or inducible T-cell costimulatory (ICOS).

Item 91. The kit or composition of item 90, wherein the first immune cell binding domain and the second immune cell binding domain are, when bound to each other, capable of binding CD3.

Item 92. The kit or composition of item 91, wherein the first and second immune cell binding domains comprise all or part of a VH and/or VL of muromonab, otelixizumab, teplizumab, visilizumab, foralumab, SP34, or blinatumomab.

Item 93. The kit or composition of item 90, wherein the first immune cell binding domain and the second immune cell binding domain are, when bound to each other, capable of binding the T-cell receptor.

Item 94. The kit or composition of item 90, wherein the first and second immune cell binding domains are, when bound together, capable of binding PD-1.

Item 95. The kit or composition of item 94, wherein the first and second immune cell binding domains comprise all or part of a VH and/or VL of pembrolizumab or nivolumab.

Item 96. The kit or composition of item 90, wherein the first and second immune cell binding domains are, when bound together, capable of binding CTLA-4.

Item 97. The kit or composition of item 96, wherein the first and second immune cell binding domains comprise all or part of a VH and/or VL of ipilimumab.

Item 98. The kit or composition of item 90, wherein the first and second immune cell binding domains are, when bound together, capable of binding TIM-3.

Item 99. The kit or composition of item 98, wherein the first and second immune cell binding domains comprise all or part of a VH and/or VL of TSR-022 or Sym023.

Item 100. The kit or composition of item 90, wherein the first and second immune cell binding domains are, when bound together, capable of binding LAG-3.

Item 101. The kit or composition of item 100, wherein the first and second immune cell binding domains comprise all or part of a VH and/or VL of BMS-986016.

Item 102. The kit or composition of item 90, wherein the first and second immune cell binding domains are, when bound together, capable of binding KIR.

Item 103. The kit or composition of item 102, wherein the first and second immune cell binding domains comprise all or part of a VH and/or VL of lirilumab.

Item 104. The kit or composition of item 90, wherein the first and second immune cell binding domains are, when bound together, capable of binding CD28.

Item 105. The kit or composition of item 104, wherein the first and second immune cell binding domains comprise all or part of a VH and/or VL of theralizumab.

Item 106. The kit or composition of item 90, wherein the first and second immune cell binding domains are, when bound together, capable of binding CD137.

Item 107. The kit or composition of item 106, wherein the first and second immune cell binding domains comprise all or part of a VH and/or VL of utomilumab or urelumab.

Item 108. The kit or composition of item 90, wherein the first and second immune cell binding domains are, when bound together, capable of binding OX40.

Item 109. The kit or composition of item 108, wherein the first and second immune cell binding domains comprise all or part of a VH and/or VL of PF-04518600 or BMS 986178.

Item 110. The kit or composition of item 90, wherein the first and second immune cell binding domains are, when bound together, capable of binding CD27.

Item 111. The kit or composition of item 110, wherein the first and second immune cell binding domains comprise all or part of a VH and/or VL of varlilumab.

Item 112. The kit or composition of item 90, wherein the first and second immune cell binding domains are, when bound together, capable of binding GITR (TNFRSF18).

Item 113. The kit or composition of item 112, wherein the first and second immune cell binding domains comprise all or part of a VH and/or VL of GWN323 or BMS-986156.

Item 114. The kit or composition of item 90, wherein the first and second immune cell binding domains are, when bound together, capable of binding TIGIT.

Item 115. The kit or composition of item 114, wherein the first and second immune cell binding domains comprise all or part of a VH and/or VL of OMP-313M32, MTIG7192A, BMS-986207, or MK-7684.

Item 116. The kit or composition of item 90, wherein the first and second immune cell binding domains are, when bound together, capable of binding ICOS.

Item 117. The kit or composition of item 116, wherein the first and second immune cell binding domains comprise all or part of a VH and/or VL of JTX-2011.

Item 118. The kit or composition of item 88, wherein the first immune cell binding domain and the second immune cell binding domain are, when bound to each other, capable of binding a macrophage.

Item 119. The kit or composition of item 118, wherein the first immune cell binding domain and the second immune cell binding domain are, when bound to each other, capable of binding CSF1R.

Item 120. The kit or composition of item 119, wherein the first and second immune cell binding domains comprise all or part of a VH and/or VL of emactuzumab or IMC-CS4.

Item 121. The kit or composition of item 120, wherein the first immune cell binding domain and the second immune cell binding domain are, when bound to each other, capable of binding CD40.

Item 122. The kit or composition of item 121, wherein the first and second immune cell binding domains comprise all or part of a VH and/or VL of CP-870,893.

Item 123. The kit or composition of item 88, wherein the first immune cell binding domain and the second immune cell binding domain are, when bound to each other, capable of binding a natural killer cell.

Item 124. The kit or composition of item 123, wherein the first immune cell binding domain and the second immune binding domain are, when bound to each other, capable of binding CD16A.

Item 125. The kit or composition of item 124, wherein the first and second immune cell binding domains comprise all or part of a VH and/or VL of NTM-1633 or AFM13.

Item 126. The kit or composition of any one of items 1-125, wherein the first and the second targeting moieties are different.

Item 127. The kit or composition of any one of items 1-125, wherein the first and the second targeting moieties are the same.

Item 128. The kit or composition of any one of items 1-127, wherein the first and/or second targeting moiety comprises an antibody or antigen binding fragment thereof.

Item 129. The kit or composition of any one of items 1-128, wherein the first and/or second targeting moiety comprises a DNA aptamer, RNA aptamer, albumin, lipocalin, fibronectin, ankyrin, fynomer, Obody, DARPin, knotin, avimer, atrimer, anti-calin, affilin, affibody, bicyclic peptide, cys-knot, FN3 (adnectins, centryrins, pronectins, or TN3), or Kunitz domain.

Item 130. The kit of composition of any one of items 1-129, wherein the second targeting moiety binds a tumor antigen expressed by the cancer.

Item 131. The kit of composition of item 128, wherein the first and/or second targeting moiety comprises an antibody or antigen binding fragment thereof that binds α4-integrin; A33; ACVRL 1/ALK1; ADAM17; ALK; APRIL; BCMA; C242; CA125; Cadherin-19; CAIX; CanAg; Carbonic Anhydrase IX; CCN1; CCR4; CD123; CD133; CD137 (4-1BB); CD138/Syndecan1; CD19; CD2; CD20; CD22; CD30; CD33; CD37; CD38; CD4; CD40; CD44; CD45; CD48; CD5; CD52; CD56; CD59; CD70; CD70b; CD71; CD74; CD79b; CD80; CD86; CD98; CEA; CEACAM; CEACAM1; CK8; c-Kit; CLDN1; CLDN18; CLDN18.2; CLDN6; c-met/HGFR; c-RET; Cripto; CTLA-4; CXCR4; DKK-1; DLL3; DLL4; TRAIL-R2/DRS; DRS; EGFL7; EGFR; EGFRvIII; endoglin; ENPP3; EpCAM; EphA2; Episialin; FAP; FGFR1; FGFR2; FGFR3; FGFR4; fibronectin extra-domain B; FLT-3; flt4; folate receptor 1; GCC; GD2; GD3; Glypican-3; Glypicans; GM3; GPNMB; GPR49; GRP78; Her2/Neu; HER3/ERBB3; HLA-DR; ICAM-1; IGF-1R; IGFR; IL-3Ra; Integrin α5β1; Integrin α6β4; Integrin αV; Integrin αVβ3; Lewis Y; Lewis y/b antigen; LFL2; LIV-1; Ly6E; MCP-1; Mesothelin; MMP-9; MUC1; MUC18; MUC5A; MUC5AC; Myostatin; NaPi2b; Neuropilin 1; NGcGM3; NRP1; P-cadherin; PCLA; PD-1; PDGFRa; PD-L1; PD-L2; Phosphatidylserine; PIVKA-II; PLVAP; PRLR; Progastrin; PSCA; PSMA; RANKL; RG1; Siglec-15; SLAMF6; SLAMF7; SLC44A4, STEAP-1; TACSTD-2; Tenascin C; TPBG; TRAIL-R1/DR4; TROP-2; TWEAKR; TYRP1; VANGL2; VEGF; VEGF-C; VEGFR-2; or VEGF-R2.

Item 132. The kit or composition of item 128, wherein the first and/or second targeting moiety comprises an antibody or antigen binding fragment thereof is an anti α4-integrin antibody; an anti-CD137 antibody; an anti-CCR4 antibody; an anti-CD123 antibody; an anti-CD133 antibody; an anti-CD138 antibody; an anti-CD19 antibody; an anti-CD20 antibody; an anti-CD22 antibody; an anti-CD33 antibody; an anti-CD38 antibody; an anti-CD40 antibody; an anti-CD49d antibody; an anti-CD52 antibody; an anti-CD70 antibody; an anti-CD74 antibody; an anti-CD79b antibody; an anti-CD80 antibody; an anti-CEA antibody; an anti-cMet antibody; an anti-Cripto antibody; an anti-CTLA-4 antibody; an anti-DLL3 antibody; an anti-TRAIL-2/DR5 antibody; an anti-E-cadherin antibody; an anti-endoglin antibody; an anti-EpCAM antibody; an anti-epidermal growth factor receptor antibody; an anti-FGFR3 antibody; an anti-fibronectin extra-domain B antibody; an anti-folate receptor 1 antibody; an anti-glypican 3 antibody; an anti-gp95/97 antibody; an anti-Her2 antibody; an anti-IGF-1R antibody; an anti-IL-13R antibody; an anti-IL-4 antibody; an anti-IL-6 antibody; an anti-MMP-9 antibody; an anti-MUC1 antibody; an anti-mucin core protein antibody; an anti-NGcGM3 antibody; an anti-P-cadherin antibody; an anti-PD-L1 antibody; an anti-p-glycoprotein antibody; an anti-PSCA antibody; an anti-PSMA antibody; an anti-SLAMF7 antibody; an anti-TRAIL-R1/DR4 antibody; an anti-transferrin antibody; an anti-TROP-2 antibody; or an anti-VEGF antibody.

Item 133. The kit or composition of item 128, wherein the first and/or second targeting moiety comprises Alemtuzumab, Andecaliximab, Atezolizumab, Avelumab, BCD-100, Bevacizumab, BGB-A317, Blinatumomab, Brentuximab, BU59, Camrelizumab, Carotuximab, Catumaxomab, Cemiplimab, Cetuximab, Daratumumab, Depatuxizumab, Dinutuximab, DS-8201, Durvalumab, Edrecolomab, Elotuzumab, G544, Gemtuzumab, Glembatumumab, GP1.4, hp67.6, IBI308, Ibritumomab, Inotuzumab, Ipilimumab, Isatuximab, L19IL2, L19TNF, Margetuximab, Mirvetuximab, Mogamuizumab, Moxetumomab, Natalizumab, Necitumumab, Nivolumab, Obinutuzumab, Ofatumumab, Olaratumab, Oportuzumab, Panitumumab, PDR001, Pembrolizumab, Pertuzumab, Polatuzumab, Racotumomab, Ramucirumab, Rituximab, Rovalpituzumab, Sacituzumab, SM3, TAK-164, Tositumomab, Trastuzumab, Tremelimumab, Ublituximab, Urelumab, Utomilumab, XMAB-5574, or Zolbetuximab.

Item 134. The kit or composition of any one of items 1-127, wherein the first and/or second targeting moiety comprises IL-2, IL-4, IL-6, α-MSH, transferrin, folic acid, EGF, TGF, PD-1, IL-13, stem cell factor, insulin-like growth factor (IGF), or CD40.

Item 135. The kit or composition of item 134, wherein the first and/or second targeting moiety comprises a full-length sequence of IL-2, IL-4, IL-6, α-MSH, transferrin, folic acid, EGF, TGF, PD-1, IL-13, stem cell factor, insulin-like growth factor (IGF), or CD40.

Item 136. The kit or composition of item 134, wherein the first and/or second targeting moiety comprises a truncated form, analog, variant, or derivative of IL-2, IL-4, IL-6, α-MSH, transferrin, folic acid, EGF, TGF, PD-1, IL-13, stem cell factor, insulin-like growth factor (IGF), or CD40.

Item 137. The kit or composition of any one of items 1-134, wherein the first and/or second targeting moiety binds the IL-2 receptor, IL-4, IL-6, melanocyte stimulating hormone receptor (MSH receptor), transferrin receptor (TR), folate receptor 1 (FOLR), folate hydroxylase (FOLH1), EGF receptor, PD-L1, PD-L2, IL-13R, CXCR4, IGFR, or CD40L.

Item 138. The kit or composition of any one of items 1-129, wherein the second targeting moiety binds an antigen expressed by a tumor microenvironment cell.

Item 139. The kit or composition of item 138, wherein the tumor microenvironment cell is a fibroblast or macrophage.

Item 140. The kit or composition of item 139, wherein the antigen expressed by a fibroblast is fibroblast activation protein.

Item 141. The kit or composition of item 139, wherein the antigen expressed by a macrophage is MAC-1/CD11b or sideroflexin 3.

Item 142. A method of treating cancer expressing a tumor antigen that binds the first targeting moiety and/or second targeting moiety in a patient comprising administering the composition of any one of items 1-141 to the patient.

Item 143. The method of item 142, wherein the cancer is evaluated for the presence of infiltrating immune cells before administering the composition.

Item 144. The method of any one of items 142-143, wherein the cancer is evaluated for the presence of tumor antigens before administering the composition.

Item 145. The method of any one of items 142-144, wherein the first targeting moiety and second targeting moiety bind the same antigen.

Item 146. The method of any one of items 142-144, wherein the first targeting moiety and second targeting moiety bind different antigens.

Item 147. The method of any one of items 142-146, wherein the cancer expressing a tumor antigen that binds the first and/or second targeting moiety is any one of breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, nonHodgkin lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease or premalignant disease.

Item 148. A method of targeting immune cells to cancer expressing a tumor antigen that binds both the first and/or second targeting moiety in a patient comprising administering the composition of any one of items 1-141 to the patient.

Item 149. A method of targeting immune cells to cancer expressing two tumor antigens, wherein one tumor antigen binds the first targeting moiety and one tumor antigen binds the second targeting moiety, in a patient comprising administering the composition of any one of items 1-141 to the patient.

Item 150. A method of delivering a cytokine to an immune cell of a patient comprising administering the composition of any one of items 76-147 to the patient, wherein the first and/or second complementary functional domain of the TWICE comprise IL-2, IL-7, IL-12, IL-15, GM-CSF, IFN-α, IFN-γ, or a member of the TNF-superfamily.

V. Supporting Tables

The following supporting tables have been referred to in the application above.

TABLE 2

Coordination of Cancer Type, Targets for Targeting Moiety, and Optional Proteases that Can Cleave Cleavage Sites

| Cancer | Targets for Targeting Moiety | Optional Proteases that can Cleave Cleavage Site if TWICE Presented as a Cleavable Single Polypeptide Chain or if TWICE comprises an inert binding partner |
|---|---|---|
| Prostate Cancer | ADAM17, CD59, EpCAM, HER2, Integrin αV, Integrin αVβ3, MCP-1, PCLA, PSCA, PSMA, RANKL, RG1, SLC44A4 STEAP-1, VEGF-C | KLK2, KLK3 (PSA), KLK4, ADAM17, Cathepsin B, uPA, uPAR, HPN, ST14, TMPRSS2 |
| Breast Cancer | CA125, CCN1, CD44, CD98, c-RET, DLL4, EpCAM, Episialin, GPNMB, HER2/neu, HER3, IGF-1R, Integrin α6β4, LFL2, LIV-1, Ly6E, MUC1, MUC18, NRP1, Phosphatidylserine, PRLR, TAC STD-2, Tenascin C, TWEAKR, VANGL2, PD-L1, PD-L2 | MMP2, MMP9, Cathepsin L, Cathepsin K, Cathepsin B, MMP11, HPN, STM, ADAM28 |
| Myeloma | BCMA, IGF-1R, DKK-1, ICAM-1, CD138/Syndecan1, CD38, GRP78, FGFR3, SLAMF6, CD48, TfR(CD71) APRIL, CD40, CD19, TRAIL-R2/DR5, CXCR4 | MMP2, MMP9, MMP1, MMP7, TMPRSS2, PRSS22, KLK11 |
| B-cell Lymphoma | CD20, CD22, CD19, CD37, CD70, HLA-DR, CD70b | ADAM28, Cathepsin B, MMP9 |
| Renal Cell carcinoma | PD-L1, PD-L2, CAIX, TPBG, CD70, ENPP3, FGFR1 | STM, MMP9 |
| Gastric Carcinoma | VEGFR-2, CLDN18, GCC, C242, HER2/neu, FGFR2, EpCAM, GPR49, HER3, IGFR | MMP2, MMP9, Cathepsin B, uPA, uPAR |
| Glioblastoma | HER2/neu, EGFR, ALK, EphA2, GD2, EGFRvIII, ALK | MMP2, MMP9, |
| T-cell lymphoma | CD2, CD4, CD5, CD71, CD30 | Cathepsin B, Cathepsin D, MMP9 |
| Hodgkin Lymphoma | CD30, CD40, IL-3Ra, CD30 | Cathepsin B |
| Lung Cancer | EGFR, IGF-1R, HER3, Integrin α5β1, Lewis y/b antigen, EGFL7, TPBG, DKK-1, NaPi2b, flt4, cMet, CD71 | Cathepsin B, MMP2, MMP9, STM, ADAM17 |
| Pancreatic Carcinoma | SLC44A4, uPAR, MUC1, MUCH16, TACSTD-2, CEA, EphhA4, mesothelin, EGFR, MUC13, MU5AC, AGF-1R, HER3, CD71 | Cathepsin B, ST14, ADAM28 |
| Head and Neck cancer | EGFR, EpCAM, HER2 | Cathepsin B, ST14, ADAM17 |
| Acute myeloid leukemia | CD33, CD133, CD123, CD45, CD98, c-Kit, Lewis Y, Siglec-15, FLT-3 | ADAM17, Cathepsin B, uPA, uPAR |
| Melanoma | MUC18, CD40, GD2, CEACAM1, Cadherin-19, GM3, Integrin α5β1, TYRP1, GD3, Integrin αV | Cathepsin B, MMP9 |
| Ovarian Cancer | HER2/neu, EpCAM, CA125, DLL4, Integrin αVβ3, MUC5A, NaPi2B, Mesothelin, CLDN6 | Cathepsin B, MMP2, MMP9 |
| Liver Cancer | Glypican-3, FGFR4, ENPP3, PIVKA-II, PLVAP, cMet, EpCAM | Cathepsin B, MMP9 |
| Colorectal Carcinoma | EGFR, Lewis y/b, Progastrin, GPR49, CEA, CLDN1, A33, CK8, Integrin αV, EpCAM, DLL4, EGFL7, FAP, | Cathepsin S, Cathepsin L, Cathepsin B, uPA, uPAR, MMP2, MMP9, ST14 |

TABLE 3

Potential Targeting Moieties

| Targeting Moiety | Cancer Type |
| --- | --- |
| Antibody against CD20 (such as Rituximab) | Lymphoma |
| Antibody against CD80 | Lymphoma |
| Antibody against CD22 (such as Inotuzumab) | Lymphoma |
| Antibody against CD70 | Lymphoma |
| Antibody against CD30 | Lymphoma (Hodgkin, T-cell, and B-cell) |
| Antibody against CD19 | Lymphoma |
| Antibody against CD74 | Lymphoma |
| Antibody against CD40 | Lymphoma |
| Antibody against HER2 | Epithelial malignancies, breast cancer, sarcoma |
| Antibody against EpCAM | Epithelial malignancies, hepatocellular carcinoma, lung cancer, pancreatic cancer, colorectal carcinoma |
| Antibody against EGFR (such as Cetuximab) | Breast cancer, epithelial malignancies, gliomas, lung cancer, colorectal carcinoma, ovarian carcinoma, brain cancer |
| Antibody against mucin protein core | Breast cancer |
| Antibody against transferrin receptor | Gliomas |
| Antibody against gp95/gp97 | Drug-resistant melanomas |
| Antibody against p-glycoprotein | Drug-resistant melanomas |
| Antibody against TRAIL-R1/DR4 | Multiple malignancies, including ovarian and colorectal carcinoma |
| Antibody against TRAIL-R2/DR5 | Multiple malignancies, including ovarian and colorectal carcinoma |
| Antibody against IL-4 | Lymphomas and leukemias |
| Antibody against IL-6 | Lymphomas and leukemias |
| Antibody against PSMA | Prostate carcinoma |
| Antibody against PSCA | Prostate carcinoma |
| Antibody against P-cadherin (CDH3) | Epithelial malignancies |
| Antibody against LI-cadherin (CDH17) | Gastrointestinal malignancies |
| Antibody against CEACAM5 | Epithelial malignancies |
| Antibody against CEACAM6 | Epithelial malignancies |
| Antibody against CEACAM7 | Epithelial malignancies |
| Antibody against TMPRSS4 | Epithelial malignancies |
| Antibody against CA9 | Epithelial malignancies |
| Antibody against GPA33 | Epithelial malignancies |
| Antibody against STEAP1 | Epithelial malignancies, particularly prostate |
| Antibody against CLDN6 | Epithelial malignancies, particularly ovarian |
| Antibody against CLDN16 | Epithelial malignancies, particularly ovarian |
| Antibody against LRRC15 | Epithelial malignancies |
| Antibody against TREM2 | Epithelial malignancies |
| Antibody against CLDN18 | Epithelial malignancies, particularly pancreatic |
| Antibody against Cripto (TDGF1) | Epithelial malignancies |
| Antibody against PD-L1 | Epithelial adenocarcinoma |
| Antibody against IGF-1R | Epithelial adenocarcinoma |
| Antibody against CD38 | Myeloma |
| Antibody against BCMA | Myeloma |
| Antibody against CD138 | Myeloma |
| Antibody against CD33 | Myeloid malignancies, such as AML |
| Antibody against CD37 | B-cell malignancies |
| Antibody against CD123 | Myeloid malignancies such as AML |
| Antibody against CD133 | Myeloid malignancies such as AML |
| Antibody against CD49d | Myeloid malignancies such as AML |
| Antibody against Glypican 3 | Hepatocellular carcinoma |
| Antibody against TM4SF5 | Hepatocellular carcinoma, pancreatic cancer |
| Antibody against cMet | Hepatocellular carcinoma |
| Antibody against MUC1 | Pancreatic cancer, ovarian carcinoma |
| Antibodies against mesothelin (MSLN) | Pancreatic, ovarian and epithelial cancers and mesothelioma |
| Antibody against GD2 | Sarcoma, brain cancers |
| Antibody against HER3 | Breast cancer |
| Antibody against IL-13R | Brain cancer |
| Antibody against DLL3 | Small-cell carcinoma, brain cancer |
| Antibody against MUC16 | Ovarian cancer |

TABLE 3-continued

Potential Targeting Moieties

| Targeting Moiety | Cancer Type |
| --- | --- |
| Antibodies against TFR2 | Liver cancer |
| Antibodies against TCR B1 or TCRB2 constant region | T-cell malignancies |
| Antibodies against TSHR | Thyroid malignancies |

TABLE 4

Representative antibodies approved for cancer indications

| International Nonproprietary Name | Target; Format | 1st indication approved/reviewed |
| --- | --- | --- |
| Ado-trastuzumab emtansine | HER2; Humanized IgG1, ADC | Breast cancer |
| Alemtuzumab | CD52; Humanized IgG1 | Chronic myeloid leukemia; multiple sclerosis |
| Atezolizumab | PD-L1; Humanized IgG1 | Bladder cancer |
| Avelumab | PD-L1; Human IgG1 | Merkel cell carcinoma |
| Bevacizumab | VEGF; Humanized IgG1 | Colorectal cancer |
| Blinatumomab | CD19, CD3; Murine bispecific tandem scFv | Acute lymphoblastic leukemia |
| Brentuximab vedotin | CD30; Chimeric IgG1, ADC | Hodgkin lymphoma, systemic anaplastic large cell lymphoma |
| Catumaxomab | EPCAM/CD3; Rat/mouse bispecific mAb | Malignant ascites |
| Cemiplimab | PD-1; Human mAb | Cutaneous squamous cell carcinoma |
| Cetuximab | EGFR; Chimeric IgG1 | Colorectal cancer |
| Daratumumab | CD38; Human IgG1 | Multiple myeloma |
| Dinutuximab | GD2; Chimeric IgG1 | Neuroblastoma |
| Durvalumab | PD-L1; Human IgG1 | Bladder cancer |
| Edrecolomab | EpCAM; Murine IgG2a | Colorectal cancer |
| Elotuzumab | SLAMF7; Humanized IgG1 | Multiple myeloma |
| Gemtuzumab | CD33; Humanized IgG4, ADC | Acute myeloid leukemia |
| Ibritumomab tiuxetan | CD20; Murine IgG1 | Non-Hodgkin lymphoma |
| Inotuzumab | CD22; Humanized IgG4, ADC | Hematological malignancy |
| Ipilimumab | CTLA-4; Human IgG1 | Metastatic melanoma |
| Mogamuizumab | CCR4; Humanized IgG1 | Cutaneous T-cell lymphoma |
| Moxetumomab pasudotox | CD22; Murine IgG1 dsFv immunotoxin | Hairy cell leukemia |
| Necitumumab | EGFR; Human IgG1 | Non-small cell lung cancer |
| Nivolumab | PD-1; Human IgG4 | Melanoma, non-small cell lung cancer |
| Obinutuzumab | CD20; Humanized IgG1; Glycoengineered | Chronic lymphocytic leukemia |
| Ofatumumab | CD20; Human IgG1 | Chronic lymphocytic leukemia |
| Olaratumab | PDGRFα; Human IgG1 | Soft tissue sarcoma |
| Panitumumab | EGFR; Human IgG2 | Colorectal cancer |
| Pembrolizumab | PD-1; Humanized IgG4 | Melanoma |
| Pertuzumab | HER2; Humanized IgG1 | Breast Cancer |
| Ramucirumab | VEGFR2; Human IgG1 | Gastric cancer |
| Rituximab | CD20; Chimeric IgG1 | Non-Hodgkin lymphoma |
| Sacituzumab govitecan | TROP-2; Humanized IgG1 ADC | Triple-negative breast cancer |
| Tositumomab-I131 | CD20; Murine IgG2a | Non-Hodgkin lymphoma |
| Trastuzumab | HER2; Humanized IgG1 | Breast cancer |

TABLE 5

Antibodies in development for cancer indications

| INN or code name | Molecular format | Target | Late-stage study indication(s) |
| --- | --- | --- | --- |
| Utomilumab | Human IgG2 | CD137 (4-1BB) | Diffuse large B-cell lymphoma |

TABLE 5-continued

Antibodies in development for cancer indications

| INN or code name | Molecular format | Target | Late-stage study indication(s) |
|---|---|---|---|
| XMAB-5574, MOR208 | Humanized IgG1 | CD19 | Diffuse large B-cell lymphoma |
| Ublituximab | Chimeric IgG1 | CD20 | Chronic lymphocytic Leukemia, non-Hodgkin lymphoma, multiple sclerosis |
| Moxetumomab pasudotox | Murine IgG1 dsFv immunotoxin | CD22 | Hairy cell leukemia |
| Isatuximab | Humanized IgG1 | CD38 | Multiple myeloma |
| Polatuzumab vedotin | Humanized IgG1 ADC | CD79b | Diffuse large B-cell lymphoma |
| Tremelimumab | Human IgG2 | CTLA-4 | Non-small cell lung, head & neck, urothelial cancer, hepatocellular carcinoma |
| Rovalpituzumab tesirine | Humanized IgG1 ADC | DLL3 | Small cell lung cancer |
| Depatuxizumab mafodotin | IgG1 ADC | EGFR | Glioblastoma |
| Carotuximab | Chimeric IgG1 | Endoglin | Soft tissue sarcoma, angiosarcoma, renal cell carcinoma, wet age-related macular degeneration |
| Oportuzumab monatox | Humanized scFv immunotoxin | EpCAM | Bladder cancer |
| L19IL2/L19TNF | scFv immuno-conjugates | Fibronectin extra-domain B | Melanoma |
| Mirvetuximab soravtansine | IgG1 ADC | Folate receptor 1 | Epithelial ovarian cancer, peritoneal carcinoma, fallopian tube cancer |
| Glembatumumab vedotin | Human IgG2 ADC | gpNMB | gpNMB+ breast cancer, melanoma |
| Margetuximab | Chimeric IgG1 | HER2 | Breast cancer |
| (vic-)trastuzumab duocarmazine | Humanized IgG1 ADC | HER2 | Breast cancer |
| DS-8201 | Humanized ADC | HER2 | HER2+ gastric or gastroesophageal junction adenocarcinoma |
| Andecaliximab | Humanized IgG4 | MMP-9 | Gastric cancer or gastroesophageal junction adenocarcinoma |
| Racotumomab | Murine IgG1 | NGcGM3 | Non-small cell lung cancer |
| Camrelizumab | Humanized IgG4 | PD-1 | Hepatocellular carcinoma, esophageal carcinoma |
| Cemiplimab | Human mAb | PD-1 | Cutaneous squamous cell carcinoma; non-small cell lung cancer, cervical cancer |
| IBI308 | Human mAb | PD-1 | Squamous cell non-small cell lung cancer |
| BGB-A317 | Humanized mAb | PD-1 | Non-small cell lung cancer |
| BCD-100 | Human mAb | PD-1 | Melanoma |
| PDR001 | Humanized IgG4 | PD-1 | Melanoma |
| Sacituzumab govitecan | IgG1 ADC | TROP-2 (epithelial glyco-protein-1) | Triple-neg. breast cancer |

TABLE 6

Selected publications on antibodies that bind tumor antigens

| Antigen | Publications |
|---|---|
| Her2/Neu | Carter P et al., Humanization of an anti-p185HER2 antibody for human cancer therapy, Proc Natl Acad Sci USA 89(10): 4285-9 (1992). This paper discloses the heavy and light chain sequences in its FIG. 1B.<br>US20090202546 (Composition comprising antibody that binds to domain II of her 2 and acidic variants thereof). This application discloses the variable light and variable heavy chain sequences in its claim 8.<br>Olafsen T et al., Characterization of engineered anti-p185HER-2 (scFv-CH3)2 antibody fragments (minibodies) for tumor targeting, Protein Eng Des Sel (4): 315-23 (2004). This paper discloses light and heavy chain variable region sequences in its FIG. 1. |
| EpCAM/CD326 | WO2008122551 (Anti-epcam antibody and uses thereof). This application discloses CDR sequences in claims 1-7.<br>WO2010142990 A1 (Anti-EpCAM Antibodies). This application |

TABLE 6-continued

Selected publications on antibodies that bind tumor antigens

| Antigen | Publications |
| --- | --- |
| | discloses CDR sequences in its claims 1-5 and 7.<br>U.S. Pat. No. 6,969,517 (Recombinant tumor specific antibody and use thereof. This application discloses light and heavy chain sequences in its claims 1-4. |
| EGFR | Garrett J et al., Antibodies specifically targeting a locally misfolded region of tumor associated EGFR, Proc Natl Acad Sci USA 106(13): 5082-5087 and pages 1-7 of Supporting Information including FIGS. S1-S5 (2009). This paper discloses CDR sequences in its Supplemental Information FIG. S1. (A).<br>U.S. Pat. No. 5,844,093 Anti-egfr single-chain fws and anti egfr antibodies). This patent discloses CDR sequences in its FIG. 1. |
| PSMA | US20110028696 A1 (Monoclonal antibodies against prostate specific membrane antigen (psma) lacking in fucosyl residues). This application discloses CDR sequences in claims 3-4.<br>WO2003064606 (Human monoclonal antibodies to prostate specific membrane antigen (psma)). This application discloses CDR sequences in its claim 1. |
| CA125 | WO2011119979 A2 (Antibodies to muc16 and methods of use thereof). This application discloses VH and VL sequences in its claim 6.<br>US20080311134 A1 (Cysteine engineered anti-muc16 antibodies and antibody drug conjugates). FIGS. 1-4 of this application show heavy and light chain sequences. |
| Carbonic Anhydrase IX | WO2007065027 A2 (Carbonic anhydrase ix (g250) antibodies and methods of use thereof). This application discloses CDR sequences in its claims 4-10.<br>U.S. Pat. No. 7,378,091B2 (Antibodies against carbonic anhydrase IX (CA IX) tumor antigen). This application discloses CDR sequences in its FIGS. 26-29. |
| c-met/HGFR | US20050054019 A1 (Antibodies to c-met). This application discloses heavy and light chain sequences in its claim 6 and CDR sequences in its claim 7.<br>US 20090175860 A1 (Compositions and methods of use for antibodies of c-Met). This application discloses CDRs in its FIGS. 1-3 and heavy and light chain sequences in its claims 12-13. |
| TRAIL-R1/DR4 | US20040214235 A1 (Anti-trail-r antibodies). This application discloses heavy and light chain sequences in its claims 54-55.<br>US20060062786 A1 (Antibodies that immunospecifically bind to TRAIL receptors). This application discloses VH and VL sequences in its claims 1-2. |
| TRAIL-R2/DR5 | US20070031414A1 (DR5 antibodies and uses thereof). This application discloses heavy and light chain sequences in its claim 1.<br>U.S. Pat. No. 7,790,165B2 (Antibody selective for a tumor necrosis factor-related apoptosis-inducing ligand receptor and uses thereof). This application discloses heavy and light chains sequences in its claims 1-5. |
| IGF-1R | US 20040086503 A1 (Antibodies to insulin-like growth factor receptor). This application discloses light and heavy chain variable region sequences and CDR sequences in its claims 11-14.<br>US 20070196376 A1 (Binding proteins specific for insulin-like growth factors and uses thereof. This application discloses CDR sequence data in its claims 46-47.<br>WHO Drug Information Vol. 24, No. 2, 2010 INN_PL103. This document discloses the sequence of ganitumab on pages 144-145. |
| VEGF-R2 | Rinderknecht M et al., Phage-Derived Fully Human Monoclonal Antibody Fragments to Human Vascular Endothelial Growth Factor-C Block Its Interaction with VEGF Receptor-2 and 3, PLoS One 5(8): e11941 (2010). This paper discloses CDR sequences in its Table 2.<br>WO1998045331 A2 (Anti-VEGF antibodies). This application discloses CDR sequences in its claims 6, 8, and 9. |
| Prostate stem cell antigen (PSCA) | US20090181034 A1 (Antibodies and related molecules that bind to psca proteins). This application discloses VH and VL sequences in its claim 17.<br>U.S. Pat. No. 6,790,939 B2 (Anti-PSCA antibodies). This application discloses CDR sequences in its FIG. 61.<br>WO2009032949 A2 (High affinity anti-prostate stem cell antigen (psca) antibodies for cancer targeting and detection). This application discloses CDR sequences in its FIG. 2. |

TABLE 6-continued

Selected publications on antibodies that bind tumor antigens

| Antigen | Publications |
|---|---|
| MUC1 | Thie H et al., Rise and Fall of an Anti-MUC1 Specific Antibody, PLoS One Jan 14; 6(1): e15921 (2011). This paper discloses CDR sequences in its FIG. 1.<br>Henderikx H et al., Human Single-Chain Fv Antibodies to MUC1 Core Peptide Selected from Phage Display Libraries Recognize Unique Epitopes and Predominantly Bind Adenocarcinoma, Cancer Res. 58(19): 4324-32 (1998). This paper discloses CDR sequences in its Table 2. |
| CanAg | US20080138898 A1 (Methods for improving antibody production). This application discloses CDR sequences in its FIG. 5. |
| Mesothelin | WO2009068204 A1 (Anti-mesothelin antibodies and uses therefor). This application discloses CDR sequences in its Table 7. |
| P-cadherin | WO2010001585 A1 (Anti-CDH3 antibodies labeled with radioisotope label and uses thereof). This application discloses VH and VL variable region sequences disclosed in its paragraph [0033] and CDR sequences in claim 2-7. |
| Myostatin/GDF8 | U.S. Pat. No. 7,632,499 B2 (Anti-myostatin antibodies). This application discloses CDR sequences in its claim 1.<br>US 20090148436 A1 (Antibody to GDF8 and uses thereof). This application discloses CDR, VH, and VL sequences in its claims 2-8. |
| Cripto/TDGF1 | US20100008906 A1 (Cripto binding molecules). This application discloses light and heavy chain sequences in its paragraph [0491] and CDR sequences in its paragraph [0492].<br>U.S. Pat. No. 7,531,174 B2 (Cripto blocking antibodies and uses thereof). This application discloses a list of hybridomas that secrete anti-Cripto antibodies in its Tables 1 and 2. These hybridomas were available for purchase from the ATCC. |
| MUC5AC | Chung WC et al., CREB mediates prostaglandin F2alpha-induced MUC5AC over expression, J Immunol 182(4): 2349-56 (2009) at page 3, second paragraph discloses that clone 45M1 was an anti-MUC5AC antibody available for purchase. |
| CEACAM | Pavoni E. et al., Selection, affinity maturation, and characterization of a human scFv antibody against CEA protein, BMC Cancer 6: 41 (2006). This paper discloses CDR sequences of clone E8 in its FIG. 3. Reactivity of E8 with CEACAM is shown in its FIG. 6. |
| SLC44A4 (formerly known as protein 24P4C12 which was renamed SLC44A4 by the Hugo Convention (see U.S. Pat. No. 8,039,497 at 114: 56-62)) | US20090175796 A1 (Antibodies and related molecules that bind to 24p4c12 Proteins). This application discloses light and heavy chain variable domain sequences in its FIGS. 2 and 3.<br>U.S. Pat. No. 8,039,597 B2 (Antibodies and related molecules that bind to 24p4c12 Proteins). This application discloses light and heavy chain variable domain sequences in its claim 1 and in its FIGS. 2 and 3.<br>U.S. Pat. No. 8,309,093 B2 (Antibody drug conjugates (ADC) that bind to 24P4C12 proteins). This application discloses light and heavy chain variable domain sequences in its claim 1 and in its FIGS. 2 and 3.<br>US20100330107A1 (Antibody drug conjugates (ADC) that bind to 24P4C12 proteins). This application discloses light and heavy chain variable domain sequences in its claims 1 and 2, and in its FIGS. 2 and 3.<br>WO2010111018 A1 (Antibody drug conjugates (ADC) that bind to 24P4C12 proteins). This application discloses light and heavy chain variable domain sequences in its claims 1 and 2, and in its FIGS. 2 and 3. |
| Neuropilin 1 | U.S. Pat. No. 8,318,163 B2 (Anti-pan neuropilin antibody and binding fragments thereof). This application discloses light and heavy chain variable domain sequences in its claim 1 and in its FIGS. 7 and 8.<br>WO 2008/143666 (Crystal structures of neuropilin fragments and neuropilin-antibody complexes). This application discloses light and heavy chain variable domain sequences in its claim 8 and in its FIGS. 7 and 8. |
| Glypican | U.S. Pat. No. 7,867,734 B2 (Anti-glypican 3 antibody having modified sugar chain). This application discloses the heavy chain variable region in its claim 1. CDR sequences are disclosed in Table 1 of this application.<br>U.S. Pat. No. 7,871,613 B2 (Adjuvant therapy with the use of anti-glypican 3 antibody). This application discloses the heavy chain sequence in its claim 6 and the light chain sequence in its claim 7. |
| EphA2 | US20100298545 A1. (Epha2 agonistic monoclonal antibodies and methods of use thereof). This application discloses CDR sequences in its claim 50. |

TABLE 6-continued

Selected publications on antibodies that bind tumor antigens

| Antigen | Publications |
|---|---|
|  | US20100278838 A1. (Epha2 monoclonal antibodies and methods of use thereof). This application discloses VH/VL and CDR sequences in its claim 101.<br>US20100183618 A1 (knti-epha2 antibody). This application discloses CDR sequences in its claim 11. |
| E-cadherin | U.S. Pat. No. 5,610,281 (Antibodies for modulating heterotypic E-cadherin interactions with human T lymphocytes). This application discloses that anti- E-cadherin clone E4.6 is available for the ATCC (HB 11996) in its claim 4. |
| CEA | WO2004032962 A1 (Combination therapy with class iii anti-cea monoclonal antibodies and therapeutic agents). This application discloses CDR sequences in its claim 6 and its claim 14.<br>U.S. Pat. No. 5,877,293 (CDR grafted anti-CEA antibodies and their production). This application discloses antibody sequences in its claims 1-5.<br>US20080069816 A1 (Humanized anti-cea t84.66 antibody and uses thereof). This application discloses antibody sequence in its claims 22-23. |
| FGFR3 | US20080044419 A1 (Treatment of T Cell Mediated Diseases by Inhibition of Fgfr3). This application discloses scFv sequences in claim 6 and VH/VL sequences in its claims 7-10.<br>US20090175866 A1 (Treatment of B-cell malignancies). This application discloses Vh, Vl and CDR sequences in its claims 11-12.<br>Martinez-Torrecuadrada J et al. Targeting the extracellular domain of fibroblast growth factor receptor 3 with human single-chain Fv antibodies inhibits bladder carcinoma cell line proliferation. *Clin Cancer Res* 11(17): 6280-90 (2005). This publication shows VH and VL sequences of a scFv in its FIG. 2. |
| HER3 | Lee-Hoeflich S T et al. A Central Role for HER3 in HER2-Amplified Breast Cancer: Implications for Targeted Therapy. *Cancer Res*. 68(14): 5878-5887 (2008).<br>Scartozzi M et al. The role of HER-3 expression in the prediction of clinical outcome for advanced colorectal cancer patients receiving irinotecan and cetuximab. *Oncologist*. 16(1): 53-60 (Epub Jan. 6, 2011).<br>Sheng Q et al. An activated ErbB3/NRG1 autocrine loop supports in vivo proliferation in ovarian cancer cells. *Cancer Cell*. 17(3): 298-310 (2010).<br>Schoeberl B et al. An ErbB3 antibody, MM-121, is active in cancers with ligand dependent activation. *Cancer Res*. 70(6): 2485-2494 (2010).<br>Khan I H et al. Microbead arrays for the analysis of ErbB receptor tyrosine kinase activation and dimerization in breast cancer cells. *Assay Drug Dev Technol*. 8(1): 27-36. (2010).<br>Robinson M K et al. Targeting ErbB2 and ErbB3 with a bispecific single-chain Fv enhances targeting selectivity and induces a therapeutic effect in vitro. *British Journal of Cancer* 99: 1415-1425 (2008).<br>Reschke M et al. HER3 is a determinant for poor prognosis in melanoma. *Clin Cancer Res*. 14(16): 5188-97 (2008). |
| PDGFRa | Martinhoe, O. et al. Expression, mutation and copy number analysis of platelet-derived growth factor receptor A (PDGFRA) and its ligand PDGFA in gliomas. *Br J Cancer* 101: 973-982 (2009).<br>Loizos N et al. Targeting the platelet-derived growth factor receptor alpha with a neutralizing human monoclonal antibody inhibits the growth of tumor xenografts: implications as a potential therapeutic target. *Mol Cancer Ther*. 4(3): 369-79 (2005).<br>Russell M R et al. Targeting the {alpha} receptor for platelet-derived growth factor as a primary or combination therapy in a preclinical model of prostate cancer skeletal metastasis. *Clin Cancer Res*. 16(20): 5002-10 (2010).<br>Shah G D et al. Rationale for the development of IMC-3G3, a fully human immunoglobulin G subclass 1 monoclonal antibody targeting the platelet-derived growth factor receptor alpha. *Cancer*. 116(4 Suppl): 1018-26 (2010).<br>Dolloff N G et al. Human bone marrow activates the Akt pathway in metastatic prostate cells through transactivation of the alpha-platelet-derived growth factor receptor. *Cancer Res*. 67(2): 555-62 (2007). |

TABLE 6-continued

Selected publications on antibodies that bind tumor antigens

| Antigen | Publications |
| --- | --- |
| CS1 | Tai-Y T et al. Anti-CS1 humanized monoclonal antibody HuLuc63 inhibits myeloma cell adhesion and induces antibody-dependent cellular cytotoxicity in the bone marrow milieu. *Blood* 112(4): 1329-1337 (2008).<br>Van Rhee F et al. Combinatorial efficacy of anti-CS1 monoclonal antibody elotuzumab (HuLuc63) and bortezomib against multiple myeloma. *Mol Cancer Ther.* 8(9): 2616-2624 (2009).<br>Hsi E D et al. CS1, a potential new therapeutic antibody target for the treatment of multiple myeloma. *Clin Cancer Res.* 14(9): 2775-2784 (2008).<br>Lee J K et al. CS1 (CRACC, CD319) induces proliferation and autocrine cytokine expression on human B lymphocytes. *J Immunol* 179: 4672-4678 (2007). |
| CD137 (4-1BB) | Broll K et al. CD137 Expression in Tumor Vessel Walls: High Correlation with Malignant Tumors. *Am J Clin Pathol* 115(4)543-549 (2001).<br>Melero I et al. Monoclonal antibodies against the 4-1BB T-cell activation molecule eradicate established tumors. *Nat Med* 3: 682-5 (1997) (abstract).<br>Niu L et al. Cytokine-mediated disruption of lymphocyte trafficking, hemopoiesis, and induction of lymphopenia, anemia, and thrombocytopenia in anti-CD137-treated mice. *J Immunol.* 178(7): 4194-4213 (2007).<br>Palazon A et al. Agonist anti-CD137 mAb act on tumor endothelial cells to enhance recruitment of activated T lymphocytes. *Cancer Res.* 71(3): 801-11 (February 2011). |
| CXCR4 | Akashi-T et al. Chemokine receptor CXCR4 expression and prognosis in patients with metastatic prostate cancer. *Cancer Sci* 99(3): 539-542 (2008).<br>Mirisola-V. et al. CXCL12/SDF1 expression by breast cancers is an independent prognostic marker of disease-free and overall surviva., *Eur J Cancer* 45(14): 2579-87 (2009) (abstract).<br>Gassmann P et al. CXCR4 regulates the early extravasation of metastatic tumor cells in vivo. *Neoplasia.* 11(7): 651-61. (2009).<br>Roland J et al. Role of the intracellular domains of CXCR4 in SDF-1-mediated signaling. *Blood.* 101: 399-406 (2003).<br>Fischer T et al. Reassessment of CXCR4 chemokine receptor expression in human normal and neoplastic tissues using the novel rabbit monoclonal antibody UMB-2. *PLoS One.* 3(12): e4069 (2008).<br>Otsuka S and Bebb G. The CXCR4/SDF-1 Chemokine Receptor Axis. *J Thorac Oncol.* 3: 1379-1383 (2008).<br>Xu C et al. Human anti-CXCR4 antibodies undergo VH replacement, exhibit functional V-region sulfation, and define CXCR4 antigenic heterogeneity. *J Immunol* 179(4): 2408-2418 (2007). |
| ACVRL1/ALK1 | Goff L et al. Phase I study of pf-03446962, a fully human mab against alk 1, a TGFbeta receptor involved in tumor angiogenesis *J Clin Oncol* 28(15 suppl): 3034 (2010) (abstract).<br>Hu-Lowe D D et al. Targeting activin receptor-like kinase 1 inhibits angiogenesis and tumorigenesis through a mechanism of action complementary to anti-VEGF therapies. *Cancer Res*; 71: 1362-73 (2011).<br>Mancuso P, et al. Validation of a standardized method for enumerating circulating endothelial cells and progenitors: flow cytometry and molecular and ultrastructural analyses *Clin Cancer Res* 15: 267-73 (2009).<br>Naeem S et al. Bone marrow involvement in systemic ALK+ anaplastic large cell lymphoma: morphological resemblance with Hodgkin's lymphoma. *J Coll Physicians Surg Pak* 16(2): 148-9 (2006) (abstract). |
| PD-1 | Iwai Y et al. Involvement of PD-L1 on tumor cells in the escape from host immune system and tumor immunotherapy by PD-L1 blockade. *Proc Natl Acad Sci* 19(19): 12293-12297 (2002).<br>Toshiro I et al. Analysis of the Role of Negative T Cell Costimulatory Pathways in CD4 and CD8 T Cell-Mediated Alloimmune Responses In Vivo. *JImmunol*, 174: 6648-6656 (2005).<br>Brahmer J R et al. Phase I study of single-agent anti-programmed death-1 (MDX-1106) in refractory solid tumors: safety, clinical activity, pharmacodynamics, and immunologic correlates. *J Clin Oncol* 28: 3167-3175 (2010).<br>Tsushima F et al. Interaction between B7-H1 and PD-1 Determines Initiation and Reversal of T-Cell Anergy. *Blood* 110(10): 180-185 (2007). |

TABLE 6-continued

Selected publications on antibodies that bind tumor antigens

| Antigen | Publications |
|---|---|
| PD-L1 | Blank C et al. Blockade of PD-L1 (B7-H1) augments human tumor-specific T cell responses in vitro. *Int J Cancer* 119: 317-327 (2006) (abstract).<br>Ishida M et al. Differential expression of PD-L1 and PD-L2, ligands for an inhibitory receptor PD-1, in the cells of lymphohematopoietic tissues. *Immunol Lett* 84(1): 57-62 (2002) (abstract).<br>Thompson H R et al. Tumor B7-H1 Is Associated with Poor Prognosis in Renal Cell Carcinoma Patients with Long-term Follow-up. *Cancer Res* 66(7): 3381-3385 (2006).<br>Latchman Y E et al. PD-L1-deficient mice show that PD-L1 on T cells, antigen-presenting cells, and host tissues negatively regulates T cells. *Proc Natl Acad Sci* 101(29): 10691-10696 (2004).<br>Dong H et al. Costimulating aberrant T cell responses by B7-H1 autoantibodies in rheumatoid arthritis. *J Clin Invest* 111: 363-370 (2003),<br>Brahmer J R et al. Phase I study of single-agent anti-programmed death-1 (MDX-1106) in refractory solid tumors: safety, clinical activity, pharmacodynamics, and immunologic correlates. *J Clin Oncol* 28: 3167-3175 (2010).<br>Hamanishi J et al. Programmed cell death 1 ligand 1 and tumor infiltrating CD8 T lymphocytes are prognostic factors of human ovarian cancer. *Proc Natl Acad Sci* 105(9): 3360-65 (2007). |
| CD70 | Israel B F et al. Anti-CD70 antibodies: a potential treatment for EBV+ CD70-expressing lymphoma., *Mol Cancer Ther* 4(12): 2037-2044 (2005).<br>Lens S M et al. Aberrant expression and reverse signalling of CD70 on malignant B cells. *Br J Haematol* 106: 491-503 (1999).<br>Ranheim E A et al, Expression of CD27 and its ligand, CD70, on chronic lymphocytic leukemia B cells. *Blood* 85: 3556-65 (1995).<br>Zambello R et al. Analysis of TNF-receptor and ligand superfamily molecules in patients with lymphoproliferative disease of granular lymphocytes. *Blood* 96: 647-54 (2000).<br>Bullock T N et al. Induction of CD70 on dendritic cells through CD40 or TLR stimulation contributes to the development of CD8+ T cell responses in the absence of CD4+ T cells. *J Immunol* 174: 710-7 (2005). |
| CD74 | Stein R et al. CD74: A New Candidate Target for the Immunotherapy of B-Cell Neoplasms *Clin Cancer Res* 13(18): 5556s-5563s (2007).<br>Starlets D et al. Cell surface CD74 initiates a signaling cascade leading to cell proliferation and survival. *Blood* 107: 4807-16 (2006).<br>Stein R et al. Anti-proliferative activity of a humanized anti-CD74 monoclonal antibody, hLL1, on B-cell malignancies. *Blood* 104: 3705-11 (2004).<br>Chang C H et al. Effective therapy of human lymphoma xenografts with a novel recombinant ribonuclease/anti-CD74 humanized IgG4 antibody immunotoxin. *Blood* 106: 4308-14 (2005).<br>Burton J D et al. CD74 Is Expressed by Multiple Myeloma and Is a Promising Target for Therapy. *Clin Cancer Res* 10(19): 6606-6611 (2004). |
| CD56 | Fossella V et al. Phase II trial of BB-10901 (huN901-DM1) given weekly for four consecutive weeks every 6 weeks in patients with relapsed SCLC and CD56-positive small cell carcinoma. *J Clin Oncol* 23(16_suppl): 7159-7159 (2005) (abstract).<br>Roguska M A et al. Humanization of murine monoclonal antibodies through variable domain resurfacing. *Proc Natl Acad Sci* 91(3): 969-73 (1994).<br>Cooper M A et al. Human natural killer cells: a unique innate immunoregulatory role for the CD56(bright) subset. *Blood* 97(10): 3146-51 (2001).<br>Campbell J J et al. Unique subpopulations of CD56+ NK and NK-T peripheral blood lymphocytes identified by chemokine receptor expression repertoire. *J Immunol* 166(11): 6477-82 (2001).<br>De Maria A et al. Revisiting human natural killer cell subset function revealed cytolytic CD56(dim)CD16+ NK cells as rapid producers of abundant IFN-gamma on activation. *Proc Natl Acad Sci* 108: 728-32 (2011). |

TABLE 6-continued

Selected publications on antibodies that bind tumor antigens

| Antigen | Publications |
|---|---|
| | Cho E Y et al. Immunohistochemical study of the expression of adhesion molecules in ovarian serous neoplasms. *Pathol Int* 56(2): 62-70 (2006) (abstract). |
| CD40 | Luqman M et al. The antileukemia activity of a human anti-CD40 antagonist antibody, HCD122, on human chronic lymphocytic leukemia cells *Blood* 112(3): 711-720 (2008). Uckum F M et al. Temporal association of CD40 antigen expression with discrete stages of human B-cell ontogeny and the efficacy of anti-CD40 immunotoxins against clonogenic B-lineage acute lymphoblastic leukemia as well as B- lineage non-Hodgkin's lymphoma cells *Blood* 76 (12) 2449-2456 (1990). Vyth-Dreese F A et al. Localization in situ of costimulatory molecules and cytokines in B-cell non-Hodgkin's lymphoma. *Immunology* 94: 580-586 (1998). Hulkkonen J et al. Surface antigen expression in chronic lymphocytic leukemia: clustering analysis, interrelationships and effects of chromosomal abnormalities. *Leukemia* 16: 178-185 (2002). Kater A P et al. CD40 stimulation of B-cell chronic lymphocytic leukaemia cells enhances the anti-apoptotic profile, but also Bid expression and cells remain susceptible to autologous cytotoxic T-lymphocyte attack. *Br J Haematol* 127: 404-415 (2004) (abstract). Melter M et al. Ligation of CD40 induces the expression of vascular endothelial growth factor by endothelial cells and monocytes and promotes angiogenesis in vivo. *Blood* 96: 3801-3808 (2000). |
| CD19 | Blanc V et al. SAR3419: An Anti-CD19-Maytansinoid Immunoconjugate for the Treatment of B-Cell Malignancies. *Clin Cancer Res* 17(20): 6448-6458 (2011). Herbst R et al. B-cell depletion in vitro and in vivo with an afucosylated anti-CD 19 antibody. *J Pharmacol Exp Ther* 335: 213-22 (2010). D' Arena G et al. Quantitative flow cytometry for the differential diagnosis of leukemic B-cell chronic lymphoproliferative disorders. *Am J Hemat* 64: 275-281 (2000) (abstract). Johnson N A et al. Diffuse large B-cell lymphoma: reduced CD20 expression is associated with an inferior survival. *Blood* 113: 3773-3780 (2009). Sato S et al. Altered blood B lymphocyte homeostasis in systemic sclerosis: expanded naive B cells and diminished but activated memory B cell. *Arthritis Rheum* 50: 1918-1927 (2004) (abstract). Kansas G S et al. Transmembrane signals generated through MHC class II, CD19, CD20, CD39, and CD40 antigens induce LFA-1-dependent and independent adhesion in human B cells through a tyrosine kinase-dependent pathway. *J Immunol* 147: 4094-4102 (1991) (abstract). |
| CD80 | Leonard J W et al. A phase I/II study of galiximab (an anti-CD80 monoclonal antibody) in combination with rituximab for relapsed or refractory, follicular lymphoma. *Ann Oncol* 18(7): 1216-1223 (2007). Vyth-Dreese F A et al. Localization in situ of costimulatory molecules and cytokines in B-cell non-Hodgkin's lymphoma. *Immunology* 94: 580-586 (1998). Dorfman D M et al. In vivo expression of B7-1 and B7-2 by follicular lymphoma cells can prevent induction of T-cell anergy but is insufficient to induce significant T-cell proliferation. *Blood* 90: 4297-4306 (1997). Dogan A et al. Follicular lymphomas contain a clonally linked but phenotypically distinct neoplastic B-cell population in the interfollicular zone *Blood* 91: 4708-4714 (1998). Suvas S et al. Distinct role of CD80 and CD86 in the regulation of the activation of B cell and B cell lymphoma. *J Biol Chem* 277: 7766-7775 (2002). |
| CD86 | Vincenti, F. What's in the pipeline? New immunosuppressive drugs in transplantation. *Am J Transplant* 2: 898-903 (2002) (abstract). Vyth-Dreese F A et al. Localization in situ of costimulatory molecules and cytokines in B-cell non-Hodgkin's lymphoma. *Immunology* 94: 580-586 (1998). Dorfman D M et al. In vivo expression of B7-1 and B7-2 by follicular lymphoma cells can prevent induction of T-cell anergy but is insufficient to induce significant T-cell proliferation. *Blood* 90: 4297-4306 (1997). |

TABLE 6-continued

Selected publications on antibodies that bind tumor antigens

| Antigen | Publications |
|---|---|
|  | Dogan A et al. Follicular lymphomas contain a clonally linked but phenotypically distinct neoplastic B-cell population in the interfollicular zone. *Blood* 91: 4708-4714 (1998).<br>Suvas S et al. Distinct role of CD80 and CD86 in the regulation of the activation of B cell and B cell lymphoma. *J Biol Chem* 277: 7766-7775 (2002). |
| CD2 | Matthews J B et al. Clinical Trials of Transplant Tolerance: Slow But Steady Progress. *Am J Transplant* 3: 794-803 (2003).<br>Przepiorka D et al. A phase II study of BTI-322, a monoclonal anti-CD2 antibody, for treatment of steroid-resistant acute graft-versus-host disease. *Blood* 92: 4066-4071 (1998).<br>Latinne D et al. An anti-CD2 mAb induces immunosuppression and hyporesponsiveness of CD2+ human T cells in vitro. *Int Immunol* 8: 1113 (1996) (abstract).<br>Guckel B et. Anti-CD2 antibodies induce T cell unresponsiveness in vivo. *J Exp Med* 174: 957, (1991).<br>Bromberg J S et al. Anti-CD2 monoclonal antibodies alter cell-mediated immunity in vivo. *Transplantation* 51: 219 (1991) (abstract). |
| CD30 | Maeda-N. Susceptibility of human T-cell leukemia virus type I-infected cells to humanized anti-CD30 monoclonal antibodies in vitro and in vivo. *Cancer Sci* 101(1): 224-30 (2010) (epub 2009 Sep 8) (abstract).<br>Schlapschy M et al. Functional humanization of an anti-CD30 Fab fragment for the immunotherapy of Hodgkin's lymphoma using an in vitro evolution approach. *Protein Eng Des Sel* 17(12): 847-860 (2004).<br>da Costa L et al. Immunoscintigraphy in Hodgkin's disease and anaplastic large cell lymphomas: results in 18 patients using the iodine radiolabeled monoclonal antibody HRS-3. *Ann Oncol.* Sep; 3 Suppl 4: 53-7 (1992) (abstract).<br>Su C C et al. CD30 Is Involved in Inhibition of T-Cell Proliferation by Hodgkin's Reed-Sternberg Cells, *Cancer Res* 64(6): 2148-2152 (2004).<br>Pinto A et al. Human eosinophils express functional CD30 ligand and stimulate proliferation of a Hodgkin's disease cell line. *Blood* 88 (9) 3299-3305 (1996).<br>Barth-S et al. Ki-4(scFv)-ETA', a new recombinant anti-CD30 immunotoxin with highly specific cytotoxic activity against disseminated Hodgkin tumors in SCID mice. *Blood* 95 (12): 3909-3914 (2000). |
| CD20 | McLaughlin P et al. Rituximab chimeric anti-CD20 monoclonal antibody therapy for relapsed indolent lymphoma: half of patients respond to a four-dose treatment program. *J Clin Oncol* 16: 2825-33 (1998) (abstract).<br>Kaminski M S et al. Radioimmunotherapy with iodine (131)I tositumomab for relapsed or refractory B-cell non-Hodgkin lymphoma: updated results and long-term follow-up of the University of Michigan experience. *Blood* 96: 1259-66 (2000).<br>Coiffier B et al. Rituximab in combination with CHOP improves survival in elderly patients with aggressive non-Hodgkin's lymphoma. *Semin Oncol* 29(2 Suppl 6): 18-22 (2002) (abstract).<br>Witzig T E et al. Randomized controlled trial of yttrium-90-labeled ibritumomab tiuxetan radioimmunotherapy versus rituximab immunotherapy for patients with relapsed or refractory low-grade, follicular, or transformed B-cell non-Hodgkin's lymphoma. *J Clin Oncol* 20: 2453-6 (2003) (abstract).<br>Maddipatla-S et al. Augmented Antitumor Activity against B-Cell Lymphoma by a Combination of Monoclonal Antibodies Targeting TRAIL-R1 and CD20. *Clin Cancer Res* 13(15): 4556-4564 (2007). |
| CD33 | Sievers E L et al. Selective ablation of acute myeloid leukemia using antibody-targeted chemotherapy: a phase I study of an anti-CD33 calicheamicin immunoconjugate. *Blood* 93: 3678-84 (1999).<br>Hauswirth A W et al. The Target Receptor Siglec-3 (CD33) Is Expressed on AML Stem Cells in a Majority of All Patients with AML *Blood* 106 (11): 4324 (2005) (abstract).<br>Caron P C et al. Biological and Immunological Features of Humanized M195 (Anti-CD33) Monoclonal Antibodies. *Cancer Res* 52(24): 6761-6767 (1992).<br>Stiff P J et al. Anti-CD33 monoclonal antibody and etoposide/cytosine arabinoside combinations for the ex vivo purification of bone marrow in acute nonlymphocytic leukemia. |

TABLE 6-continued

Selected publications on antibodies that bind tumor antigens

| Antigen | Publications |
|---|---|
| CD22 | *Blood* 77 (2): 355-362 (1991).<br>Roy D C et al. Anti-MY9-blocked-ricin: an immunotoxin for selective targeting of acute myeloid leukemia cells. *Blood* 77 (11): 2404-2412 (1991).<br>Carnahan J et al. Epratuzumab, a humanized monoclonal antibody targeting CD22: characterization of in vitro properties. *Clin Cancer Res* 9(10 Pt 2): 3982S-90S (2003) (abstract).<br>Kreitman R J et al. Efficacy of the anti-CD22 recombinant immunotoxin BL22 in chemotherapy-resistant hairy-cell leukemia. N Engl J Med 345: 241-47 (2001).<br>Robbins B A et al. Diagnostic application of two-color flow cytometry in 161 cases of hairy cell leukemia. *Blood* 82: 1277-87 (1993).<br>Cordone I et al. Diagnostic relevance of peripheral blood Immunocytochemistry in hairy cell leukemia. *J Clin Pathol* 48: 955-960 (1995).<br>Amlot P L et al. A phase I study of an anti-CD22-deglycosylated ricin A chain immunotoxin in the treatment of B-cell lymphomas resistant to conventional therapy. *Blood* 82: 2624-2633 (1993). |

TABLE 7

Non-Antibody Scaffolds and Corresponding Targets

| Scaffold | Demonstrated Targets |
|---|---|
| Adnectin | EGFR, IGF-1R |
| Affibodies | HER2, EGFR, IGF-1R, HER3 |
| Affinlins | CTLA-4 |
| Anticalins | CD137/HER2 (a bispecific) |
| Atrimers | TRAIL-R1/DR4 |
| Avimers | IL6 (could be used in oncology to block growth) |
| Bicyclic peptides | HER2 |
| Cys-knots | NaV1.7 (proof of concept) |
| DARPins | VEGF-a, HER2, VEGF/HGF (bispecific) |
| Fynomers | HER2 |
| Pronectins | VEGFR2 |
| TN3 | TRAIL-R2 |

TABLE 8

Non-Antibody Binding Partners and Corresponding Targets

| Binding Partner | Target on Cancer Cell |
|---|---|
| IL-2 | IL-2 receptor |
| IL-4 | IL-4 receptor |
| IL-6 | IL-6 receptor |
| α-MSH | MSH receptor (melanocyte stimulating hormone receptor) |
| Transferrin | TR (transferrin receptor) |
| Folic acid | FOLR (folate receptor 1) and/or FOLH1 (folate hydroxylase) |
| EGF and/or TGFα | EGFR (EGF receptor) |
| PD-1 | PD-L1 and/or PD-L2 |
| IL13 | IL-13R (Glioblastoma) |
| Stem cell factor | CXCR4 |
| Insulin-like growth factor (IGF) | IGFR |
| CD40 | CD40L |

TABLE 9

Selected References Showing Specificity of Exemplary Anti-CD3 Antibodies

| | |
|---|---|
| Muromonab/<br>OKT3 | Herold K C et al. A single course of anti-CD3 monoclonal antibody hOKT3gamma1(Ala-Ala) results in improvement in C-peptide responses and clinical parameters for at least 2 years after onset of type 1 diabetes. *Diabetes.* 54(6): 1763-9 (2005).<br>Richards J et al. Phase I evaluation of humanized OKT3: toxicity and immunomodulatory effects of hOKT3gamma4. *Cancer Res.* 59(9): 2096-10 (1999).<br>Kuhn C and Weiner H L. Therapeutic anti-CD3 monoclonal antibodies: from bench to bedside. *Immunotherapy* 8(8): 889-906 (2016). |
| Otelixizumab | Kuhn C et al. Human CD3 transgenic mice: preclinical testing of antibodies promoting immune tolerance. *Sci Transl Med.* 3(68): 68ra10 (2011).<br>Kuhn C and Weiner H L. Therapeutic anti-CD3 monoclonal antibodies: from bench to bedside. *Immunotherapy* 8(8): 889-906 (2016).<br>Dean Y et al. Combination therapies in the context of anti-CD3 antibodies for the treatment of autoimmune diseases. *Swiss Med Wkly.* 142: w13711 (2012).<br>Daifotis A G et al. Anti-CD3 clinical trials in type 1 diabetes mellitus. *Clin Immunol.* 149(3): 268-78 (2013) (abstract).<br>Chatenoud L and Waldmann H. CD3 monoclonal antibodies: a first step towards operational immune tolerance in the clinic. *Rev Diabet Stud.* 9(4): 372-81. (2012). |

TABLE 9-continued

Selected References Showing Specificity of Exemplary Anti-CD3 Antibodies

| | |
|---|---|
| Teplizumab | Masharani U B and Becker J. Teplizumab therapy for type 1 diabetes. *Expert Opin Biol Ther*. 10(3): 459-65 (2010).<br>Herold K C et al. Treatment of patients with new onset Type 1 diabetes with a single course of anti-CD3 mAb Teplizumab preserves insulin production for up to 5 years. *Clin Immunol*. 132(2): 166-73 (2009).<br>Kuhn C and Weiner H L. Therapeutic anti-CD3 monoclonal antibodies: from bench to bedside. *Immunotherapy* 8(8): 889-906 (2016).<br>Dean Y et al. Combination therapies in the context of anti-CD3 antibodies for the treatment of autoimmune diseases. *Swiss Med Wkly*. 142: w13711 (2012).<br>Daifotis A G et al. Anti-CD3 clinical trials in type 1 diabetes mellitus. *Clin Immunol*. 149(3): 268-78 (2013) (abstract).<br>Chatenoud L and Waldmann H. CD3 monoclonal antibodies: a first step towards operational immune tolerance in the clinic. *Rev Diabet Stud*. 9(4): 372-81 (2012). |
| Visilizumab | Kuhn C and Weiner H L. Therapeutic anti-CD3 monoclonal antibodies: from bench to bedside. *Immunotherapy* 8(8): 889-906 (2016).<br>Shan L. $^{99m}$Tc-Labeled succinimidyl-6-hydrazinonicotinate hydrochloride (SHNH)-conjugated visilizumab. Molecular Imaging and Contrast Agent Database (MICAD) [Internet]. Created: Dec. 7, 2009; Last Update: Jan. 12, 2010; Downloaded May 3, 2018.<br>Dean Y et al. Combination therapies in the context of anti-CD3 antibodies for the treatment of autoimmune diseases. *Swiss Med Wkly*. 142: w13711 (2012). |
| Foralumab | Kuhn C and Weiner H L. Therapeutic anti-CD3 monoclonal antibodies: from bench to bedside. *Immunotherapy* 8(8): 889-906 (2016).<br>Dean Y et al. Combination therapies in the context of anti-CD3 antibodies for the treatment of autoimmune diseases. *Swiss Med Wkly*. 142: w13711 (2012). |
| SP34 | Pessano S et al. The T3/T cell receptor complex: antigenic distinction between the two 20-kd T3 (T3-6 and T3-E) subunits. *EMBO Journal* 4(2): 337-344 (1985). |

TABLE 10

Selected References Showing Specificity of Exemplary Anti-TCR Antibodies

Verma-B. et al. TCR Mimic Monoclonal Antibody Targets a Specific Peptide/HLA Class I Complex and Significantly Impedes Tumor Growth In Vivo Using Breast Cancer Models *J Immunol*. 184: 2156-2165 (2010).
Conrad M L et al. TCR and CD3 antibody cross-reactivity in 44 species. *Cytometry A*. 71(11): 925-33 (2007).
Koenecke C et al. In vivo application of mAb directed against the gammadelta TCR does not deplete but generates "invisible" gammadelta T cells. *Eur J Immunol*. 39(2): 372-9 (2009).
Exley M A et al. Selective activation, expansion, and monitoring of human iNKT cells with a monoclonal antibody specific for the TCR alpha-chain CDR3 loop. *Eur J Immunol*. 38(6): 1756-66 (2008).
Deetz C O et al. Gamma interferon secretion by human Vgamma2Vdelta2 T cells after stimulation with antibody against the T-cell receptor plus the Toll-Like receptor 2 agonist Pam3Cys. *Infection and Immunity*. 74(8): 4505-4511 (2006).
Tang X et al. Anti-TCR antibody treatment activates a novel population of nonintestinal CD8 alpha alpha+ TCR alpha beta+ regulatory T cells and prevents experimental autoimmune encephalomyelitis. *J Immunol*. 178(10): 6043-50 (2007).
Lavasani S et al. Monoclonal antibody against T-cell receptor alphabeta induces self-tolerance in chronic experimental autoimmune encephalomyelitis. *Scand J Immunol*. 65(1): 39-47 (2007).
Nasreen M et al. In vivo treatment of class II MHC-deficient mice with anti-TCR antibody restores the generation of circulating CD4 T cells and optimal architecture of thymic medulla. *J Immunol*. 171(7): 3394-400 (2003).

TABLE 11

Antibodies that modulate T-cell function

| Antigen | Antibody Examples | Function |
| --- | --- | --- |
| CD3e | Blinatumomab (Blincyto ®) | co-stimulatory |
| PD-1 | Pembrolizumab (Keytruda ®), Nivolumab (Opdivo ®) | antagonist |
| CTLA-4 | Ipilimumab (Yervoy ®) | antagonist |
| TIM-3 | TSR-022 (NCT02817633), Sym023 (NCT03489343) | antagonist |
| LAG-3 | BMS-986016 (NCT01968109) | antagonist |
| KIR | BMS-986015/Lirilumab (NCT01714739) | antagonist |
| CD28 | Theralizumab/TGN1412 (NCT03006029) | co-stimulatory |
| 41BB/CD137/ TNFRSF9 | Utomilumab/PF-05082566 (NCT03364348) or Urelumab | co-stimulatory |
| OX40/CD134 | PF-04518600 (NCT02315066), BMS 986178 (NCT03410901) | co-stimulatory |
| CD27 | Varlilumab/CDX-1127 (NCT01460134) | co-stimulatory |
| ICOS | JTX-2011 (NCT02904226) | co-stimulatory |

EXAMPLES

Example 1. TWICE that Block Two Inhibitory Pathways in an Immune Cell

A TWICE can be developed to act on a range of cancer and immune cells. These examples serve to show how one skilled in the art could generate a TWICE with a particular function.

For example, a TWICE may be generated with a synergistic combination of two checkpoint inhibitory antibodies.

As a first step, one skilled in the art would first choose targeting moieties appropriate for the given cancer. The targeting moieties may be chosen based on literature on a given type of cancer and the prevalence of certain antigens. Alternatively, one could evaluate antigens that are expressed by the cancer in a specific patient. For example, rituximab (anti-CD20 antibody) can be used to target to CD20-positive lymphomas, and cetuximab (anti-EGFR antibody) can be used to target certain solid tumors.

A TWICE may allow use of two targeting moieties. One skilled in the art could choose two targeting moieties to target both the first component and the second component to a given cancer. Ovarian cancer may be targeted using CA125 for targeting one component and using EpCAM to target the other component.

After choosing appropriate targeting moieties, one skilled in the art could determine what type of immune cell binding domains and complementary binding domains, when paired, might have the greatest therapeutic efficacy.

FIG. 1 shows how a TWICE could employ two targeting domains to a cancer cell to allow activation through two signaling pathways on an immune cell.

To enhance an anti-tumor immune response, one may want to generate a TWICE that inhibits two checkpoint molecules, and therefore boost an anti-cancer immune response compared to inhibition of either checkpoint molecule alone.

For example, a TWICE could be generated where the first component comprises the VH of ipilimumab (anti-CTLA4 antibody) as the immune cell binding domain and the VL of nivolumab (an anti-PD-1 antibody) as the complementary binding domain. Then, the second component of this TWICE could comprise the VL of ipilimumab (anti-CTLA4 antibody) as the immune cell binding domain and the VH of nivolumab (an anti-PD-1 antibody) as the complementary binding domain. The function of the TWICE is not impacted by which component has the VH or VL of the given antibody, as long as one component has a VH and the other component has a VL.

By generating a TWICE in this manner, both the first and second components of the TWICE could be targeted to the cancer. At the cancer site, the VH and VL of ipilimumab and the VH and VL of nivolumab could pair based on the close proximity of the first and second components. This would allow the TWICE, after domain pairing, to block two immune checkpoints and lead to robust immune cell activation.

Example 2. TWICE that Stimulates Two Pathways in an Immune Cell

A TWICE may be developed that (when the immune cell binding domains and the complementary binding domains are paired) stimulates two pathways in an immune cell to mediate a robust anticancer effect. For example, the cancer might be breast cancer that expresses EGFR.

For any of these Examples, the second targeting moiety may be selected to target to tumor microenvironment cells. In this Example, the second targeting moiety may be chosen to target to tumor-associated macrophages (TAMs). Thus, while the first targeting moiety (in the first component) may bind an antigen expressed by the tumor, the second targeting moiety (in the second component) may bind an antigen expressed by a TAM. For targeting breast cancer expressing EGFR, the first targeting moiety may be Cetuximab and the second targeting moiety may be MAC-1/CD11b.

FIG. 2 outlines a TWICE where the first component is targeted to a cancer cell and the second component is targeted to a non-cancer cell (in this Example a TAM). This type of TWICE will also pairing of domains only when the cancer cell is in close proximity to the TAM. Pairing of the immune cell binding domains and pairing of the complementary binding domains can stimulate 2 pathways on an immune effector cell.

For example, one skilled in the art may choose to activate both the CD3e and CD137 pathways. To do this, he/she could generate a TWICE wherein the first component comprises a VH for SP34 (anti-CD3 antibody) and a VL for utomilumab (anti-CD137 antibody) and the second component comprises a VL for SP34 (anti-CD3 antibody) and a VH for utomilumab (anti-CD137 antibody).

By generating a TWICE in this manner, both the first and second components of the TWICE could be targeted to a cancer cell that is in close proximity to a TAM, for example at the tumor stroma. The VH and VL of SP34 and the VH and VL of utomilumab could then pair based on the close proximity of the first and second components. This would allow the TWICE, after domain pairing, to provide two positive stimuli to T cells.

In a similar fashion to that described in this Example or Example 1, a TWICE could be generated to both block an inhibitory checkpoint molecule (e.g., by paired immune cell binding domains) and to provide a positive stimulus to the immune system (e.g. by paired complementary binding domains). These types of construct may also robustly activate an anti-cancer immune response.

Example 3. TWICE that Activates Two Different Immune Cells at the Cancer Site

A TWICE could combine activity at two different immune effector cells. For example, a TWICE could be generated to mediate T-cell activation and macrophage activation.

Figure 3:
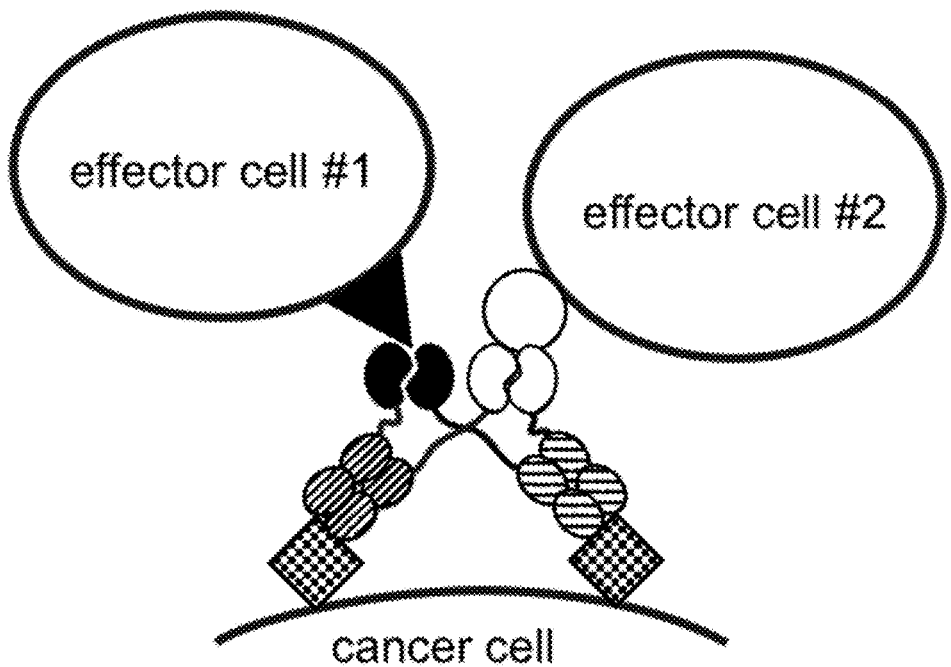
FIG. 3 shows a TWICE that binds and engages signaling molecules on two different effector (immune) cells after targeting of both components of the TWICE to a cancer cell. Various targeting strategies may be employed. If a TWICE has two components that bind a cancer cell, it may employ three different configurations: (a) the two components of a TWICE may either bind the same antigen (single antigen targeting) using two copies of the same targeting moiety; (b) the TWICE may use a single antigen strategy using different targeting moieties that target different epitopes on the same antigen; or (c) the two components of a TWICE may bind two different antigens (dual antigen targeting) when both targeting moieties bind a cancer cell. This Figure represents single antigen targeting using different targeting moieties that target different epitopes on the same antigen. Turning back to the figure, the diamonds represent two molecules of the same antigen on a cancer cell bound by the targeting moieties (two sets of four striped ovals) of the first and second components. Each component comprises an immune cell binding domain (black domains of each component) and a complementary binding domain (white domains of each component). When the two components are in close proximity, domain swapping can occur such the two immune cell binding domains (one from each component) and the two complementary binding domains (one from each component) can pair with each other. The triangle and circle represent antigens on two different effector cells that can be bound by either the paired immune cell binding domains (binding to the antigen represented by the triangle on effector cell #1) or the paired complementary binding domains (binding to the antigen represented by the circle on effector cell #2). In the absence of domain swapping and pairing, the immune cell binding domains and the complementary binding domains of the two components do not modulate the effector cells.

A targeting moiety to an antigen expressed by the cancer cell could be chosen as outlined in Example 1. In this particular example, both targeting moieties can bind HER2 on the breast cancer cell. The two targeting moieties may either be identical or bind to different epitopes on HER2. Then, as shown in FIG. 3, the paired immune cell binding domains of the TWICE could bind to a first effector cell (in this case a T cell) and the paired complementary binding domains could bind to a second effector cell (in this case a macrophage).

One skilled in the art may choose to activate both CD3 in a T cell and the CD40 pathway in a macrophage. To do this, he/she could generate a TWICE wherein the first component comprises a VH for SP34 (anti-CD3 antibody) and a VL for CP-870,893 (anti-CD40 antibody) and the second component comprises a VL for SP34 (anti-CD3 antibody) and a VH for CP-870,893 (anti-CD40 antibody).

By generating a TWICE in this manner, the first and second component would be targeted to the cancer cell. At the cancer cell, the VH and VL of SP34 and the VH and VL of CP-870,893 could pair based on the close proximity of the first and second components. This would allow the TWICE, after domain pairing, to stimulate both T cells and macrophages at the site of the cancer.

In an analogous fashion, a TWICE could be designed to activate combinations of T cells and NK cells at the site of the cancer.

Example 4. TWICE that Modulates Immune Cells and Cancer Cells

A TWICE could also combine activity at both an immune cell and directly at the cancer cell. For example, a TWICE could be generated to mediate T-cell activation and to block an immune checkpoint molecule expressed by the cancer cell.

Figure 4:
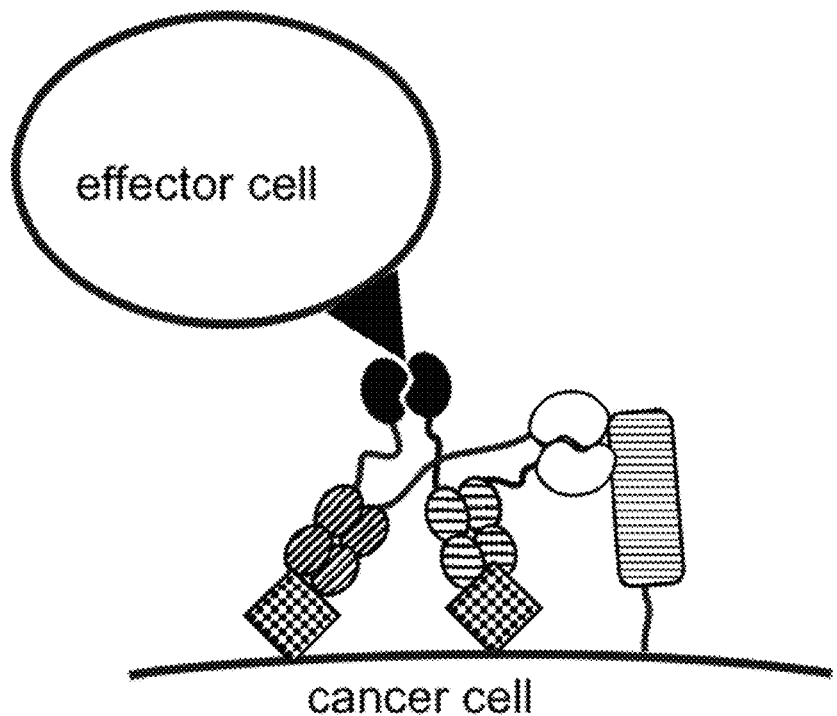
FIG. 4 shows a TWICE that binds and engages a signaling molecule on an effector (immune) cell and binds a signaling molecule on the cancer cell after targeting of both components of the TWICE to a cancer cell. The diamonds represent two molecules of the same antigen on a cancer cell bound by the targeting moieties (two sets of four striped ovals) of the first and second components. Each component comprises an immune cell binding domain (black domains of each component) and a complementary binding domain (white domains of each component). When the two components are in close proximity, domain swapping can occur such the two immune cell binding domains (one from each component) and the two complementary binding domains (one from each component) can pair with each other. The triangle represents an antigen on an effector cell that can be bound by the paired immune cell binding domains. The striped rectangle represents an antigen on the cancer cell that can be bound by the paired complementary binding domains. In the absence of domain swapping and pairing, the immune cell binding domains and the complementary binding domains do not modulate the effector cell or the cancer cell.

Two targeting moieties to a single antigen expressed by the cancer cell could be chosen as outlined in Example 3, such as HER2 on a breast cancer cell. Then, as shown in FIG. 4, the paired immune cell binding domains of the TWICE could bind to an effector cell (in this case a T cell) and the paired complementary binding domains could bind to the cancer.

One skilled in the art may choose to activate CD3 in a T cell and block PD-L1 in the cancer cell. To do this, he/she could generate a TWICE wherein the first component comprises a VH for SP34 (anti-CD3 antibody) and a VL for avelumab (anti-PD-L1 antibody) and the second component comprises a VL for SP34 (anti-CD3 antibody) and a VH for avelumab (anti-PD-L1 antibody).

By generating a TWICE in this manner, both components would be targeted to the cancer cell. At the cancer cell, the VH and VL of SP34 and the VH and VL of avelumab could pair based on the close proximity of the first and second components. This would allow the TWICE, after domain pairing, to stimulate T cells in the tumor microenvironment and block immune inhibition mediated by PD-L1 expressed by the cancer cell.

In an analogous fashion, a TWICE could be designed that bind RANK or cell-death-inducing antigens on the cancer cell.

For example, one skilled in the art may choose to activate CD3 on a T cell and directly induce cancer cell death. To do this, he/she could generate a TWICE wherein the first component comprises a VH for SP34 (anti-CD3 antibody) and a VL for mapatumumab (anti-TRAIL-R1/DR4 death receptor antibody) and the second component comprises a VL for SP34 (anti-CD3 antibody) and a VH for mapatumumab (anti-TRAIL-R1/DR4). This would allow the TWICE, after domain pairing at the cancer cell, to stimulate T cells and directly trigger cancer cell death.

Thus, a TWICE could mediate a direct anti-cancer effect and stimulate an anti-cancer immune response.

Example 5. TWICE Comprising Dimerization Domains

In any of constructs described in Examples 1-4, the TWICE may also comprise a dimerization domain, as shown in FIG. 6. One dimerization domain of a pair could attach to the immune cell binding domain, while the other dimerization domain of the pair could attach to the complementary binding domain. For example, each component may comprise a pair of knob-into-hole dimerization sequences. One or both of the dimerization domains could be attached via a cleavable linker (termed a dimerization domain linker), such as a linker comprising an ADAM28 cleavage site (SEQ ID NO: 1).

In this way, the knob-into-hole dimerization domains of each component force pairing of the immune cell binding domain and the complementary binding domain of an individual component. After targeting to the tumor microenvironment by the targeting moieties, the cleavable linker attaching one or both dimerization domain could be cleaved, and the dimerization domain released. In this way, the immune cell binding domain and/or the complementary binding domain would become available to pair with their corresponding domain in the other component only in the tumor microenvironment.

Thus, dimerization domains could be used to force binding of the immune cell binding domain and complementary binding domain of each component outside of the desired site of action at the tumor microenvironment and to block potential pairing of domains between components outside of the tumor microenvironment. Cleavage of the dimerization domain linker by a protease in the tumor microenvironment, in contrast, could allow domain swapping and activity only at the tumor.

A TWICE could be designed where both components comprise dimerization domains or where only one component comprises dimerization domains.

Example 6. TWICE Comprising a Complementary Functional Domain

Other TWICE may comprise a complementary functional domain that has activity when targeted to a cancer cell, as shown in FIG. 5. In this Example, the first component comprises an attenuated IFN-alpha cytokine (see Pogue et al., *PLoS ONE* 11(9): e0162472 (2016)).

Both the first and second components may comprise an anti-EPCAM scFv. The first component may comprise an anti-CD3E VH domain such as that of SP34 (i.e., the immune cell binding domain) linked through a 25-mer linker having an MMP2 cleavage site (AIPVSLR; SEQ ID NO: 46) to an inert binding partner VL domain from gantenerumab. The second component may comprise an anti-CD3E VL domain such as that of SP34 (i.e., the immune cell binding domain) linked through a 25-mer linker having an MMP2 cleavage site (AIPVSLR; SEQ ID NO: 46) to an inert binding partner VH domain from clone alpha-MUC1-1 antibody.

In this way, the immune cell binding domains of the first and second components are masked unless cleaved by the tumor-associated protease MMP2. When the first and second components are targeted to the EPCAM-positive tumor, cleavage by MMP2 can mediate release of the inert binding domains (i.e., inert binding partners). In this way, the VH and VL of SP34 could bind and activate a T cell at the site of the cancer. Further, targeting of the attenuated IFN-alpha to the cancer cell by the EPCAM antibody could lead to direct anti-cancer effects. This type of TWICE could mediate anti-cancer effects by an attenuated cytokine and stimulate an anti-cancer immune response.

Similarly, a TWICE could employ IL-15 or an attenuated IL-2 to modulate T-cell activation.

In an analogous fashion, a TWICE could be designed that comprise other attenuated cytokines as complementary functional domains in the first component. A TWICE could also be designed that comprise a complementary functional domain in both the first and second components for an additive effect.

Example 7. TWICE Comprising Various Dimerization Domain Linkers and Various Dimerization Domains To construct examples of TWICE molecules, a well-established anti-EpCAM antibody targeting cancer cells was used. The EpCAM antibody Solitomab (Brischwein K, et al *Mol Immunol.* 43(8):1129-43 (2006)) was chosen, and this antibody was used in the format of an antigen binding fragment (Fab) comprising two chains, a heavy chain consisting of a heavy chain variable plus a CH1 domain, and a light chain consisting of a light chain variable and kappa constant domain.

For initial testing of these TWICE molecules, the VH of the anti-CD3epsilon antibody SP34 was fused to the C-terminus of the heavy chain of the Solitomab Fab, and the VL of the anti-PDL1 antibody Atezolizumab was fused to the C-terminus of the light chain of the Solitomab Fab using flexible linkers of 15 amino acids in length.

As shown in FIG. 6, TWICE molecules may contain a dimerization domain that links the mispaired variable domains and prevents domain swap unless the TWICE are activated proteolytically in the tumor microenvironment. This dimerization domain may be constructed as a heterodimerization to enforce the efficient formation of heterodimers between the VH and VL domains and avoid the formation of homodimers. Several heterodimerization domains have been described in the literature. To test which heterodimerization domains are suitable for engineering TWICE, several TWICE were constructed and expressed using various heterodimerization domains.

First, a TWICE was constructed using a coiled-coil heterodimerization domain as shown in FIG. 7A. Coiled-coils have also been called leucine zippers. Sequences of coiled-coil domains that have been engineered as acid and base coil to form heterodimers are listed in US 2016 0002356 A1 and in U.S. Pat. No. 8,877,893 B2. In the present example, the heavy chain of the TWICE molecule was fused to a basic coil (SEQ ID NO: 201) and the light chain was fused to an acid coil (SEQ ID NO: 202). One of ordinary skill in the art will know that the heavy chain might also be fused to an acid coil and the light chain fused to a basic coil.

Table 12 lists the dimerization domain linkers included in the coiled-coil TWICE constructs. These dimerization domain linkers may contain a sequence that can be cleaved by a protease. Protease cleavage will lead to separation of the dimerization domain from the rest of the TWICE molecule, which allows the complementation of the immune cell binding VH or VL domain between two TWICE by domain swap. In the examples listed in Table 12, several examples of dimerization domain linkers are listed. In some of the examples, the linker contains a sequence that can be cleaved by a matrix metalloprotease in a tumor microenvironment. In other examples, the dimerization domain linker contains a protease site that can be cleaved by Factor Xa (FXa), which can be used to artificially activate TWICE molecules in vitro. In other words, a Factor Xa cleavage site was employed in the examples as a proxy for a protease cleavage site because Factor Xa is convenient to use in the laboratory setting. In some of the examples listed in Table 12, the heavy chain and the light chain of one TWICE molecule comprise the same protease cleavage sequence in their dimerization domain linker, and in others the heavy chain and the light chain of one TWICE molecule comprise different protease cleavage sequences in their dimerization domain linker.

In some of the examples listed in Table 12, the TWICE contains a heterodimeric Fc as a dimerization domain. Here, the lysine repositioning strategy disclosed in WO2017106462A1 was used to construct TWICE with a hetero-Fc dimerization domain. Table 12 shows the dimerization domain linker that were used in the TWICE molecules TWICE191 and TWICE192. The TWICE191 comprises the heavy chain of SEQ ID NO: 171 and the light chain of SEQ ID NO: 172, and the TWICE192 comprises the heavy chain of SEQ ID NO: 173 and the light chain of SEQ ID NO: 174. These TWICE contain the mutations S364K/K409L in the Fc of the heavy chain and K370S/F405K in the Fc of the light chain to promote the formation of a hetero-Fc between the heavy and light chain. Engineering TWICE with a hetero-Fc dimerization domain enables binding to FcRn, the neonatal Fc receptor, which mediates recycling of the molecules and extends their serum half-life. These TWICE examples further contain the N297Q mutation in the Fc, which produces an aglycosylated molecule with impaired effector function.

In another example the Fab constant domains (CH1 and CL) were used as dimerization domains to construct a TWICE molecule. In order to allow for efficient assembly of the heavy and light chain of a TWICE molecule, which also contains a Fab as a cancer targeting moiety, the dimerization domain CH1 and CL were constructed as a CrossFab (FIG. 7A). A CrossFab is a strategy that enables efficient assembly of the two light chains of a bispecific antibody construct by crossover of the constant domains in one of the Fabs such that the VH is linked to the CL and the VL is linked to the CH1 (Schaefer W et a., *Proc Natl Acad Sci USA.* 108(27): 11187-92 (2011)). In the TWICE constructs containing a CrossFab dimerization domain (TWICE200 and TWICE204, see Table 13), the VH of the immune cell engager is linked to a CL domain with a dimerization domain linker sequence, and the VL of the complementary engager is linked to a CH1 domain with the dimerization domain linker sequence. A Factor Xa protease cleavage sequence (Ile-Glu-Gly-Arg) was included in all of the dimerization domain linkers. The full sequence of the TWICE200 comprises the heavy chain of SEQ ID NO: 177 and the light chain of SEQ ID NO:178, and the construct TWICE204 comprises the heavy chain of SEQ ID NO: 179 and the light chain of SEQ ID NO: 180.

In another example, the TWICE was constructed using the IgE CH2 domain as a dimerization domain. The IgE CH2 normally functions as a hinge domain in IgE, but this domain has been used to construct Fab-like molecules with similar binding properties by domain substitution (Cooke et al, *mAbs.* 10(8):1248-1259 (2018)). In the TWICE189 and TWICE190, the IgE CH2 domain was fused to the immune cell engager VH and VL domains using the dimerization domain linker sequences given in Table 12. The dimerization domain linkers contain a Factor Xa cleavage sequence (Ile-Glu-Gly-Arg).

TABLE 12

TWICE constructs encompassing various dimerization domains and linkers

| Construct | Dimerization domain linker (VH) | Dimerization domain linker (VL) | Dimerization domain |
|---|---|---|---|
| TWICE117 | GGGGSIEGRGGGGS (SEQ ID NO: 203) | GGPLGVRGKGGGS (SEQ ID NO: 204) | leucine zipper |
| TWICE193 | GGGGSIEGRGGSGGGS (SEQ ID NO: 205) | GGGGSIEGRGGSGGGS (SEQ ID NO: 205) | leucine zipper |
| TWICE191 | GGGIEGRGGG (SEQ ID NO: 206) | GGGIEGRGGG (SEQ ID NO: 206) | Hetero-Fc |
| TWICE192 | GGGGSIEGRGGG (SEQ ID NO: 207) | GGGGSIEGRGGG (SEQ ID NO: 207) | Hetero-Fc |
| TWICE200 | IEGRG (SEQ ID NO: 208) | GGIEGRG (SEQ ID NO: 209) | CH1/CL |
| TWICE204 | IEGRG (SEQ ID NO: 208) | GGIEGRG (SEQ ID NO: 209) | CH1/CL |
| TWICE189 | GIEGRG (SEQ ID NO: 210) | GIEGRG (SEQ ID NO: 210) | IgE CH2 |
| TWICE190 | GGGIEGRG (SEQ ID NO: 211) | GGGIEGRG (SEQ ID NO: 211) | IgE CH2 |

TABLE 13

Exemplary TWICE

| Molecule | | Heavy chain SEQ ID NO | Light chain SEQ ID NO |
|---|---|---|---|
| TWICE117 | SP34 VH Atezolizumab VL coiled-coil | 165 | 166 |
| TWICE189 | SP34 VH Atezolizumab VL EDH2 | 167 | 168 |
| TWICE190 | SP34 VH Atezolizumab VL 8-mer linker EDH2 | 169 | 170 |
| TWICE191 | SP34 VH Atezolizumab VL Fc | 171 | 172 |
| TWICE192 | SP34 VH Atezolizumab VL G4S-linker Fc | 173 | 174 |
| TWICE193 | SP34 VH Atezolizumab VL 20-mer linker coiled-coil | 175 | 176 |
| TWICE200 | SP34 VH FXa CL Atezolizumab VL FXa CH1 | 177 | 178 |
| TWICE204 | Atezolizumab VH FXa CL SP34VL FXa CH1 | 179 | 180 |
| TWICE277 | SP34 VH Ipilimumab VL Fc | 171 | 181 |
| TWICE278 | Ipilimumab VH SP34 VL Fc | 182 | 183 |
| TWICE281 | SP34 VH Ipilimumab VL coiled-coil | 165 | 184 |
| TWICE282 | Ipilimumab VH SP34 VL coiled-coil | 185 | 186 |
| TWICE283 | Ipilimumab VH Atezolizumab VL coiled-coil | 185 | 166 |
| TWICE284 | Atezolizumab VH IpilimumabVL coiled-coil | 187 | 184 |
| TWICE285 | SP34 VH Ipilimumab VL 20-mer linker coiled-coil | 175 | 188 |
| TWICE286 | Ipilimumab VH -SP34 VL 20-mer linker coiled-coil | 189 | 190 |
| TWICE332 | dsFv SP34 VH Ipilimumab VL Fc | 191 | 192 |
| TWICE335 | dsFv Ipilimumab VH SP34 VL Fc | 193 | 194 |
| CTRL351 | Epcam/Ipilimumab bsAb | 185 | 184 |
| CTRL352 | EpCAM/SP34 bsAb | 175 | 190 |
| CTRL353 | EpCAM/Ipilumumab bsAb | 195 | 196 |
| CTRL354 | EpCAM/Atezolizumab bsAb | 189 | 188 |
| TWICE394 | Theralizumab VH SP34 VL Fc | 195 | 183 |
| TWICE395 | SP34 VH Theralizumab VL Fc | 171 | 196 |
| CTRL396 | EpCAM/Theralizumab bsAB | 195 | 196 |
| CTRL399 | EpCAM/Urelumab bsAb | 197 | 198 |
| TWICE400 | Theralizumab VH Urelumab VL Fc | 195 | 198 |
| TWICE401 | Urelumab VH Theralizumab VL Fc | 197 | 198 |
| CTRL426 | EpCAM/SP34 Fc bsAb | 171 | 183 |
| TWICE431 | SP34 VH dummy VL Fc | 171 | 199 |
| TWICE432 | dummy VH SP34 VL Fc | 200 | 183 |
| CTRL406 | EpCAM/CD16A Fc bsAb | 212 | 213 |
| CTRL437 | EpCAM/OKT3 Fc bsAb | 214 | 215 |
| TWICE440 | OKT3 VH/CD16A VL Fc | 214 | 213 |
| TWICE441 | CD16A VH/OKT3 VL Fc | 212 | 215 |

The TWICE proteins listed in Table 13 were expressed in transient HEK293 cultures (30-50 ml) in shake-flasks by co-transfection of the respective heavy chains and light chains. The expressed proteins were purified from supernatant by FPLC using IMAC columns (Histrap Excel, GE) or in the case of Fc-containing TWICE proteins by protein A columns (MabSelect PrismA, GE). The purified proteins were analyzed by SDS-PAGE and showed bands at the expected molecular weight for all the linkers and dimerization domains tested (FIG. 7B). The expression levels were highest for TWICE with coiled-coil or hetero-Fc dimerization domains.

The TWICE were tested further by cleavage with recombinant FXa protease. In a reaction of 15 µl approximately 1 µg of purified TWICE and 0.1 µg FXa (New England Biolabs #P8010) were incubated in a buffer containing 20 mM Tris-HCl (pH 8.0) with 100 mM NaCl and 2 mM $CaCl_2$ for 1 hour at ambient temperature. The reaction was stopped by addition of 5 µl 4× LDS sample buffer (Thermo Fisher NP0007) and heating to 95° C. for 2 minutes. The samples were then separated by SDS PAGE to analyze cleavage products (FIG. 7C).

The samples TWICE193, TWICE191 and TWICE192, which contain FXa cleavage sequences in both dimerization domain linkers, i.e. in the heavy chain and in the light chain (Table 13), were cleaved completely by FXa (FIG. 7C). The TWICE117, which has a FXa cleavage site in the heavy chain dimerization domain linker and an MMP2 cleavage site in the light chain dimerization domain linker, was cleaved only partially (FIG. 7B). The constructs TWICE200, TWICE204, TWICE189 and TWICE190, which have FXa cleavage sites included in both dimerization domain linkers, were not cleaved by FXa protease under these conditions. This result suggests that the configuration of the dimerization domains (CH1/CL or IgE CH2) or the linker lengths in the constructs TWICE200, TWICE204, TWICE189 and TWICE190, which are 5 to 8 residues in length (Table 12), are not favorable for protease cleavage in these particular constructs. However, the coiled-coil and the hetero-Fc are dimerization domains that are included in the designs TWICE117, TWICE193, TWICE192, and TWICE193, are suitable for the construction of TWICE. The TWICE molecules containing these dimerization domains expressed well and could be activated by cleavage with recombinant protease.

Example 8. TWICE with Various Binding Moieties: Fv Vs Fab

TWICE molecules were engineered with the CD3 antibody SP34 and the CTLA4 antibody Ipilimumab and containing the hetero-Fc dimerization domain. In some examples, the anti-EpCAM antibody Solitomab was used as a Fab (TWICE277 and TWICE278), in other examples this antibody was used as a disulfide-stabilized Fv (dsFv, TWICE332 and TWICE335) by engineering a disulfide between the residue 44 of the VH and residue 100 of the VL (referring to Kabat numbering). The TWICE molecules were expressed and purified by Protein A affinity chromatography as described above, and their ability to bind to EpCAM was tested in an ELISA binding assay. Recombinant soluble EpCAM-His6 protein (produced in-house) was coated on ELISA plates at 5 µg/ml at 4° C. overnight and plates blocked with 1% BSA in PBS. Serial dilutions of TWICE were allowed to bind to EpCAM, and the bound TWICE were detected with a mouse anti-human Fc secondary (JDC-10 Abcam, ab99759). The results (FIGS. 8A-8B) showed that TWICE molecules with Fab or dsFv targeting moieties bound to the antigen with similar binding affinities, with KD ranging from 1.04 nM to 1.65 nM with the dsFv TWICEs, and 1.21 nM to 1.22 nM for the Fab TWICEs. Thus, TWICE molecules can be constructed with different targeting moieties, for example Fab or dsFv, to target cells in the tumor microenvironment.

Example 9. Testing of a CD3/CTLA-4 TWICE in a Bridging ELISA

To test the domain swap and generation of functional paratopes (i.e., paired VH/VL domains) by TWICE pairs, a bridging ELISA assay was developed that measures the ability of TWICE pairs to bind target antigen and immune cell engaging molecules simultaneously. The schematic drawing in FIG. 9A illustrates the principle of this bridging ELISA. Briefly, the ELISA plates are coated with target antigen (recombinant soluble EpCAM, black hexagon) at a concentration of 5 µg/ml overnight. TWICE molecules can be activated by cleavage with FXa as described above, and then added to the plate at a serial dilution. The TWICE can bind to the target antigen with their target binding moiety, which is drawn as Fab (4 grey ovals) in FIG. 9A. Binding to the target antigen (EpCAM) on the plate brings the TWICEs in close proximity, which allows the immune cell binding domain and the complementary binding domain to undergo domain swap and form complete immune cell binding paratopes (black and white ovals in FIG. 9A). The functional complementation is measured by incubation with an antigen that is bound by the immune cell binding domain, such as CD3 (striped triangle in FIG. 9A). The antigen is provided as an Fc-fusion protein (murine IgG2a Fc), and can therefore be detected with an anti-mouse Fc secondary antibody. This detection step by a secondary antibody is omitted in the schematic drawing in FIG. 9A for clarity.

FIG. 9B and FIG. 9C show examples of bridging ELISAs that measure the functional complementation of a TWICE pair by domain swap. In these examples, the TWICE277 and 278 (as described in Table 13) are used, which contain the immune cell binding antibody SP34 that binds CD3epsilon and the complementary antibody Ipilimumab that binds CTLA-4. The VH of the CD3 antibody and the VL of the CTLA-4 antibody are comprised in the TWICE277, and the VL of the anti-CD3 and the VH of the anti-CTLA-4 are comprised in the TWICE278. These examples of TWICE molecules further contain the hetero-Fc dimerization domains and FXa cleavage sites in both dimerization domain linkers. FIG. 9B shows the result from a CD3 bridging ELISA, which measures the ability of TWICE to bind CD3, and FIG. 9C shows the result of a CTLA-4 bridging ELISA, which measures the ability of TWICE to bind CTLA-4. In this experiment, the individual TWICE (277 or 278 alone) did not show binding to CD3 or to CTLA-4 even when activated by cleavage with FXa. Furthermore, when the TWICE 277 and 278 were combined but not activated by cleavage with FXa, the TWICE did not show binding to CD3 or CTLA-4. Only when the TWICE277 and 278 were combined and cleaved by FXa to remove the dimerization domain did they show binding to CD3 or CTLA-4 (diamond symbols in FIGS. 9B and 9C) in a dose-dependent response. These results demonstrate that the TWICE molecules can undergo domain swap and generate functional immune cell binding domains when both TWICE are bound to target antigen. Furthermore, the dimerization domain of these TWICE functions as intended as a locking mechanism that prevents domain swap of TWICE unless the dimerization domain is removed by protease cleavage.

FIGS. 10A-10B show another example of CD3/CTLA-4 TWICE molecules that were tested in a bridging ELISA experiment. The TWICE281 and 282 used in this experiment encompass the same EpCAM targeting and CD3 and CTLA-4 antibodies as TWICE277 and TWICE278 described above, but differ in that they contain a coiled-coil dimerization domain. Furthermore, TWICE281 and 282 contain a FXa cleavage site in the heavy chain and an MMP2 cleavage sequence in the light chain, and the molecules can therefore be activated by cleavage by FXa or MMP2. Similar to the previous experiment, the TWICE277 and 278 showed a dose-response binding curve only when activated by cleavage with FXa (FIGS. 10A and 10B). Without activation by FXa, the TWICE did not bind to either CD3 or CTLA-4. Thus, the hetero-Fc and coiled-coil dimerization domains are both suitable for engineering TWICE. A hetero-Fc may be preferred when an extended serum half-life of the TWICE is desired.

Example 10. CD3/CD28 TWICE

FIGS. 11A-11B show an example of TWICE constructed from the CD3 antibody SP34 and the costimulatory anti-CD28 antibody Theralizumab that were tested in a bridging ELISA experiment (TWICE 394 and 395 from Table 13). These examples of TWICE were again engineered using the hetero-Fc dimerization domain and FXa cleavage sites in both the heavy and light chain linkers. Similar to the previous examples, the TWICE394 and TWICE395 showed binding to immune cell antigens CD3 and CD28 only when they were combined and activated by cleavage (FIGS. 11A and 11B). The individual TWICE did not show binding to either immune cell antigen. Cleavage was again necessary for domain swap and binding, as evidenced by the fact that the uncleaved TWICE did not show any bridging activity (grey squares in FIGS. 11A and 11B).

Example 11. CD28/4-1BB TWICE

FIGS. 12A-12B show an example of TWICE constructed with the antibodies Theralizumab and Urelumab, which bind the co-stimulatory molecules CD28 and CD137 (4-1BB). The TWICE400 and 401 (as shown in Table 13) were constructed using the variable domains of Theralizumab and Urelumab and containing the hetero-Fc dimerization domain and FXa cleavage sites in both linkers. When these molecules were tested in a bridging ELISA format, the TWICE showed binding to CD28 (FIG. 12A) and 4-1BB (FIG. 12B), when the constructs were precleaved with FXa and both TWICE were present. Neither TWICE alone bound to CD28 or to 4-1BB.

Example 12. CTLA-4/PD-L1 TWICE

FIG. 13 shows an example of TWICE constructed with the antibodies Ipilimumab and Atezolizumab, which bind to the checkpoint molecules CTLA-4 and PD-L1, respectively. The TWICE283 contains the VH of Ipilumumab and the VL of Atezolizumab, and the complementary TWICE284 contains the VH of Atezolizumab and the VL of Ipilumumab, as shown in Table 13. These TWICE were designed with a coiled-coil dimerization domain and a FXa cleavage site in the heavy chain. When these TWICE were tested in an EpCAM/PD-L1 bridging ELISA, the TWICE 284 exhibited significant binding to PD-L1 (FIG. 13), even though this TWICE contains only the VH of Atezolizumab, but lacks the cognate Atezolizumab VL. This result suggests that the VH of Atezolizumab is sufficient to mediate antigen binding.

This notion is consistent with the fact that a crystal structure of Atezolizumab in complex with PD-L1 (Lee H T et al. *Sci Rep* 7: 5532-5532 (2017)) reveals that the VL of the antibody makes no significant contact with the antigen and therefore may be dispensable or replaceable for antigen binding. Therefore, Atezolizumab is an example of an antibody that is not suitable for the construction of a TWICE, at least not in conjunction with Ipilimumab, due to the fact that it retains its binding properties in the VH domain when the paratope (i.e., VH/VL pair) is split in a TWICE.

However, as shown in FIGS. 9A-12B, Ipilimumab, SP34, Theralizumab, and Urelumab are exemplary antibodies that do not exhibit binding when the paratope is split, and such antibodies are therefore suitable for the construction of TWICE.

Example 13. Immune Cell Activation by TWICE

The redirection of T cells by TWICE constructs was tested in an in vitro T-cell activation assay. Briefly, colorectal cancer cells (HCT-15) were seeded in 96-well plates at a density of 5,000 cells/well and allowed to adhere overnight. Peripheral blood mononuclear cells (PBMCs) were added at an effector-to-target ratio of 10:1, and the cells were treated with serial dilutions of TWICE molecules. In some of the experiments the TWICE molecules were preactivated by cleavage with FXa protease (NEB # P8010L) prior to the addition to cells.

To quantify T cell activation, secreted interferon gamma was detected in the media 24 hours after addition of TWICE using an IFNgamma ELISA kit (Invitrogen 88-7316-88). The target cell killing was determined 48 hours after the start of treatment using a cytotoxicity assay that quantitatively measures lactate dehydrogenase (LDH) from lysed cancer cells (CytoTox96, Promega). The target cell killing is expressed as specific lysis (%) in the dose-response curves shown in FIGS. 14A-16, which corresponds to the fraction of LDH release compared to cells lysed with a lysis buffer, and subtracting the background LDH release from untreated cells.

FIGS. 14A-14B show the results of a cell killing assay with the TWICE277 and 278, and the TWICE281 and 282 that had been tested in bridging ELISAs before. As described above, these TWICE contain the anti-CD3epsilon engaging antibody SP34 and the CTLA-4 antibody Ipilimumab. TWICE277 and 278 are constructed with a hetero-Fc dimerization domain that is attached to VH or VL through the linker GGGIEGRGGG (SEQ ID NO: 206), which contains the FXa cleavage sequence Ile-Glu-Gly-Arg. In contrast, the TWICE281 and 282 contain coiled-coil dimerization domains with non-identical linkers in the heavy and light chain (FIG. 14A). These TWICE are constructed with a FXa cleavage site in the heavy chain linker GGGGSIEGRGGGGS (SEQ ID NO: 203) and an MMP2 cleavage site in the light chain linker GGPLGVRGKGGGS (SEQ ID NO: 204). The LDH release data from this experiment (FIG. 14B) demonstrated that both TWICE pairs induced a strong killing of cancer cells by PBMCs when the TWICEs were pre-activated by FXa prior to addition to the cells. The TWICE277 and 278 did not induce this killing response without precleavage, which confirms that cleavage is necessary for TWICE activation and domain swap, and is consistent with the data obtained in bridging ELISA experiments with these molecules (FIGS. 9B-9C). However, the TWICE281 and 282, which also required activation by FXa in the bridging ELISA (FIGS. 10A-10B), readily induced the killing of HCT15 cells by PBMCs in a dose dependent manner even when the TWICE were not preactivated.

These results show that the TWICE molecules can be activated by cancer cells, which can cleave the MMP2 site in the light chain linker. Altogether this experiment confirmed that: (1) TWICE can efficiently engage immune cells to kill cancer cells; (2) proteolytic cleavage is necessary for TWICE activation, and (3) a protease produced by cancer cells can activate TWICE molecules.

FIG. 15A-15D show the results of a cleavage assay (FIG. 15A), a T cell activation assay (FIG. 15B), and killing assay (FIGS. 15C-15D) with TWICE 285 and TWICE286, which also contain the anti-CD3epsilon engaging antibody SP34 and the CTLA-4 antibody Ipilimumab. These examples of TWICE are designed with a FXa cleavage site in the dimerization domain linker GGGGSIEGRGGSGGGS (SEQ ID NO: 205) in both the heavy and the light chain, which is longer than the linkers of the examples shown in FIGS. 14A-14B above. These examples of TWICE also contain a coiled-coil dimerization domain.

When the TWICE285 was cleaved with FXa, the molecule produced the expected fragments on SDS-PAGE (FIG. 15A), showing that the TWICE can be preactivated with FXa. The cytokine release and killing data shown in FIG. 15B and FIG. 15C confirmed that the TWICE molecules TWICE285 plus TWICE286 are able to engage and redirect PBMCs against HCT-15 cells when the TWICE were activated by cleavage with FXa protease. Neither TWICE285 nor TWICE286 alone induced the release of interferon gamma by T cells or the killing of cancer cells.

However, when these TWICE were tested together without precleavage in an LDH release experiment, the molecules induced cancer cell lysis irrespective of preactivation by FXa (FIG. 15D). This result is in contrast to the TWICE examples described above, which required cleavage for activation in the bridging ELISA and T cell activation assays. The data therefore establishes that the design of the dimerization domain and linker length are relevant to TWICE activation. The specific longer linker GGGGSIEGRGGSGGGS (SEQ ID NO: 205) of TWICE285 and TWICE286 in conjunction with the coiled-coil dimerization domain present in these constructs may not prevent domain swap in the absence of cleavage.

Example 14. Costimulatory TWICE

Next, the TWICE394 and TWICE395, which engage CD3 and CD28 as shown in Table 13, were tested in a T cell redirection assay (FIG. 16). As described above, these TWICE are constructed from the anti-CD28 antibody Theralizumab and the anti-CD3 epsilon antibody SP34. These molecules can therefore bind to CD3 and CD28 as shown in FIGS. 11A-11B, which provides costimulatory signals to trigger T cell activation. When these TWICE were tested in a T cell killing assay, the TWICE394 and 395 induced robust killing of HCT-15 cancer cells after preactivation with FXa, but showed no activity without prior cleavage.

In order to test the stimulatory signal from engagement of CD28 and CD3 by TWICE, a protocol was developed to exhaust T cells prior to testing TWICE activity. For T-cell activation and exhaustion, prostate cancer cells (PC-3) were seeded in a 6-well plate at a density of 150,000 cells/well and allowed to adhere overnight. Peripheral blood mononuclear cells (PBMCs) were added at an effector-to-target ratio of 10:1 and cells were treated with two-component T cell engagers based on SEQ ID NOs: 168 and 169 of U.S. Ser. No. 10/035,856B2 at a concentration of 100 nM. This two-component system works similar to a CD3 bispecific antibody in that T cells are engaged to kill cancer cells. However, it has an advantage over a conventional bispecific antibody for pre-activation because the molecules cannot bind to CD3 in solution and can therefore easily be removed by washing the PBMCs. The PBMCs were analyzed 48 hours after the preactivation by flow cytometry, revealing the treatment induced robust upregulation of activation and exhaustion markers on CD3+ cells (FIG. 17A) demonstrating preactivation and exhaustion. Such preactivated immune cells may be more reflective of the immune cells in a tumor microenvironment than unstimulated PBMCs, because tumor-infiltrating lymphocytes are known to be exhausted and to display increased expression of exhaustion markers (Baitsch L et al. *Trends Immunol.* 33(7):364-72 (2012)).

The pre-activated PBMCs were subsequently used in a redirection assay against colorectal cancer cells (HCT-15) as described above to test the potency of TWICE molecules to trigger T cell activation, except the effector to target ratio was modified to 1:4 in this assay. FIG. 17B shows the results of this T cell activation assay. The TWICE394 and TWICE395, which bind CD3 and CD28, induced robust activation of exhausted T cells as measured by the IFN gamma secretion. The TWICE277 and TWICE278, which bind CD3 and CTLA-4, also induced IFNgamma secretion, albeit to lower levels than TWICE394 and TWICE395. A pair of control TWICE, which contain the CD3 antibody VH and VL domains paired with non-functional VH and VL domains (SEQ ID NOs: 199 and 200), were also included in this assay. The control TWICE431 plus TWICE432 produced low levels of interferon gamma in this redirection experiment with exhausted T cells. Altogether, these results are consistent with a recent publication that showed co-stimulatory activation of CD28 together with CD3 by a trispecific antibody generates a superior T cell activation over either stimulus alone, and may amount to a stronger anti-tumor immune response (Wu, L., Seung, E., Xu, L. et al. Trispecific antibodies enhance the therapeutic efficacy of tumor-directed T cells through T cell receptor co-stimulation. Nat Cancer (published online Nov. 18, 2019) doi: 10.1038/s43018-019-0004-z). Consistent with this observation, the present data suggest that TWICE can potently stimulate exhausted T cells, and the additive effect of co-stimulation or checkpoint blockade can induce a stronger response than CD3 engagement alone. However, contrary to the published trispecific antibody, the TWICE can deliver these co-stimulatory signals in an activatable fashion.

Example 15. TWICE Engaging NK Cells Through CD16A

In another example, TWICE were engineered to engage natural killer (NK) cells using an antibody against CD16A. The anti-CD16A antibody used to construct these TWICE molecules has been evaluated in clinical trials (NCT01221571) in the molecule AFM13, a bispecific antibody targeting CD30 and CD16A. For evaluating this antibody in a TWICE pair, the anti-CD16A antibody was combined with the anti-CD3 antibody OKT3 to generate the TWICE molecules TWICE440 and TWICE441, which comprise the hetero-Fc dimerization domain and FXa cleavage sites in the dimerization domain linkers.

The TWICE molecules were first tested in a CD16A bridging ELISA, similar to the bridging ELISA experiments described above. The TWICE440 and 441 showed the expected binding to CD16A only when both TWICE were present and preactivated with FXa protease (FIG. 18A). As seen with other TWICE molecules, precleavage of the TWICE was necessary, and the uncleaved TWICE did not exhibit binding to CD16A in this bridging ELISA assay. Furthermore, the individual TWICE molecules did not show binding to CD16A even when they were precleaved by FXa. The anti-CD16A antibody derived from AFM13 is therefore suitable for use in TWICE, as the halves of the split paratope (i.e. the VH and VL) are not binding to antigen when they are separated in TWICE.

The TWICE440 and 441 were subsequently tested in a redirection assay using HCT15 colon cancer cells and NK cells. As described above for redirection assays performed with PBMCs described above, the cancer cells were seeded in 96-well plates at 5000 cells/well and allowed to adhere overnight. Next, purified NK cells (Stem Cell Technologies, Cat#70036) were added to the cancer cells at an effector-to-target ratio of 20:1, and preactivated TWICE were added to the wells at various concentrations. Target cell killing was determined by measurement of LDH release 24 hours after addition of TWICE using a cytotoxicity assay that quantitatively measures LDH from lysed cancer cells (CytoTox96, Promega). The results of this NK cell redirection assay are shown in FIG. 18B. In this experiment a control bispecific antibody targeting EpCAM and CD16a (CTRL406) induced the release of LDH from cancer cells demonstrating killing by NK cells.

A control bispecific antibody targeting EpCAM and CD3 also induced LDH release, although to a lesser extent than the CD16a/EpCAM bispecific antibody, possibly due to the presence of some NKT cells. The TWICE440 and 441 induced robust NK redirection and cancer cell killing, which was similar to the amount of killing observed with the CD16a/EpCAM bispecific antibody, demonstrating that TWICE molecules can be engineered to engage NK cells via a CD16a antibody. The engagement of NK cells via the anti-CD16 antibody can induce cancer cell killing.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A kit or composition for treating cancer in a patient comprising:
   a. a first component comprising a targeted immune cell binding agent comprising:
      i. a first targeting moiety that binds a tumor antigen expressed by the cancer;
      ii. a first immune cell binding domain capable of immune cell binding activity when the first immune cell binding domain is bound to a second immune cell binding domain, wherein the second immune cell binding domain is not part of the first component, and wherein the first immune cell binding domain is either a VH domain or VL domain; and
      iii. a first complementary binding domain capable of binding to a complementary antigen when the first complementary binding domain is bound to a second complementary binding domain, wherein
         (1) the second complementary binding domain is not part of the first component,
         (2) when the first immune cell binding domain is a VH domain the first complementary binding domain is a VL domain,
         (3) when the first immune cell binding domain is a VL domain, the first complementary binding domain is a VH domain, and
         (4) wherein the first complementary binding domain is a binding partner for the first immune cell binding domain, such that the first immune cell binding domain does not bind to the second immune cell binding domain unless the first immune cell binding domain is not bound to the first complementary domain; and:
   b. a second component comprising a targeted immune cell binding agent comprising:
      i. a second targeting moiety that binds a tumor antigen expressed by the cancer or an antigen expressed by a tumor microenvironment cell;
      ii. a second immune cell binding domain capable of immune cell binding activity when the second immune cell binding domain is bound to the first immune cell binding domain, wherein the second immune cell binding domain is a VH if the first immune cell binding domain is a VL and wherein the second immune cell binding domain is a VL if the first immune cell binding domain is a VH; and
      iii. a second complementary binding domain capable of binding to a complementary antigen when the second complementary binding domain is bound to the first complementary binding domain, wherein
         (1) when the second immune cell binding domain is a VH domain the second complementary binding domain is a VL domain,
         (2) when the second immune cell binding domain is a VL domain, the second complementary binding domain is a VH domain, and
         (3) wherein the second complementary binding domain is a binding partner for the second immune cell binding domain, such that the second immune cell binding domain does not bind to the first immune cell binding domain unless the second immune cell binding domain is not bound to the second complementary domain.

2. The kit or composition of claim 1, wherein the first immune cell binding domain is bound to the first complementary binding domain by a first dimerization domain and a second dimerization domain, wherein:
   a. the first dimerization domain is attached to the first immune cell binding domain by a first linker;
   b. the second dimerization domain is attached to the first complementary binding domain by a second linker; and
   c. the first and/or second linker is a cleavable linker.

3. The kit or composition of claim 1, wherein the second immune cell binding domain is bound to the second complementary binding domain by a first dimerization domain and a second dimerization domain, wherein:
   a. the first dimerization domain is attached to the second immune cell binding domain by a first linker;
   b. the second dimerization domain is attached to the second complementary binding domain by a second linker; and
   c. the first and/or second linker is a cleavable linker.

4. The kit or composition of claim 2, wherein the first and second linkers are cleavable linkers; optionally wherein the protease cleavage sites of the first and/or second cleavable linkers are cleaved by a protease expressed by a cancer cell or a cell in a tumor microenvironment.

5. The kit or composition of claim 2, wherein the first and second linkers are from 5 to 30 amino acids in length.

6. The kit or composition of claim 5, wherein the first and second linkers are from 8 to 16 amino acids in length.

7. The kit or composition of claim 2, wherein the first and second dimerization domains are both:
   a. leucine zippers;
   b. immunoglobulin domains; or
   c. T-cell receptor (TCR) domains.

8. The kit or composition of claim 7, wherein the first and second dimerization domains are both immunoglobulin domains.

9. The kit or composition of claim 1, wherein the first complementary binding domain and the second complementary binding domain are, when bound to each other, capable of binding the cancer; optionally wherein the first complementary binding domain and the second complementary binding domain are, when bound to each other, capable of binding an immune checkpoint molecule, RANK or RANKL, or a cell-death-inducing antigen.

10. The kit or composition of claim 1, wherein the first complementary binding domain and the second complementary binding domain are, when bound to each other, capable of binding a T cell, a macrophage, or a natural killer cell.

11. The kit or composition of claim 10, wherein the first complementary binding domain and the second complementary binding domain are, when bound to each other, capable of binding a T cell; optionally wherein the first complementary binding domain and the second complementary binding domain are, when bound to each other, capable of binding CD3, programmed cell death protein 1 (PD-1), cytotoxic T-lymphocyte-associated protein 4 (CTLA-4), T-cell immunoglobulin and mucin-domain 3 (TIM-3), lymphocyte-activation gene 3 (LAG-3), killer-cell immunoglobulin-like receptor (KIR), CD28, CD137, OX40, CD27, GITR (TNFRSF18), TIGIT, or inducible T-cell costimulatory (ICOS).

12. The kit or composition of claim 10, wherein the first complementary binding domain and the second complementary binding domain are, when bound to each other, capable of binding a natural killer cell; optionally wherein the first complementary binding domain and the second complementary binding domain are, when bound to each other, capable of binding CD16A.

13. The kit or composition of claim 1, wherein the first immune cell binding domain and the second immune cell binding domain are, when bound to each other, capable of binding a T cell, a macrophage, or a natural killer cell.

14. The kit or composition of claim 13, wherein the first immune cell binding domain and the second immune cell binding domain are, when bound to each other, capable of binding a T cell; optionally wherein the first immune cell binding domain and the second immune cell binding domain are, when bound to each other, capable of binding CD3, the T-cell receptor, programmed cell death protein 1 (PD-1), cytotoxic T-lymphocyte-associated protein 4 (CTLA-4), T-cell immunoglobulin and mucin-domain 3 (TIM-3), lymphocyte-activation gene 3 (LAG-3), killer-cell immunoglobulin-like receptor (KIR), CD28, CD137, OX40, CD27, GITR (TNFRSF18), TIGIT, or inducible T-cell costimulatory (ICOS).

15. The kit or composition of claim 13, wherein the first immune cell binding domain and the second immune cell binding domain are, when bound to each other, capable of binding a natural killer cell; optionally wherein the first immune cell binding domain and the second immune binding domain are, when bound to each other, capable of binding CD16A.

16. The kit or composition of claim 1, wherein the first and/or second targeting moiety comprises an antibody or antigen binding fragment thereof; optionally wherein the first and/or second targeting moiety comprises an antibody or antigen binding fragment thereof that binds α4-integrin; A33; ACVRL 1/ALK1; ADAM17; ALK; APRIL; BCMA; C242; CA125; Cadherin-19; CAIX; CanAg; Carbonic Anhydrase IX; CCN1; CCR4; CD123; CD133; CD137 (4-1BB); CD138/Syndecan1; CD19; CD2; CD20; CD22; CD30; CD33; CD37; CD38; CD4; CD40; CD44; CD45; CD48; CD5; CD52; CD56; CD59; CD70; CD70b; CD71; CD74; CD79b; CD80; CD86; CD98; CEA; CEACAM; CEACAM1; CK8; c-Kit; CLDN1; CLDN18; CLDN18.2; CLDN6; c-met/HGFR; c-RET; Cripto; CTLA-4; CXCR4; DKK-1; DLL3; DLL4; TRAIL-R2/DR5; DRS; EGFL7; EGFR; EGFRvIII; endoglin; ENPP3; EpCAM; EphA2; Episialin; FAP; FGFR1; FGFR2; FGFR3; FGFR4; fibronectin extra-domain B; FLT-3; flt4; folate receptor 1; GCC; GD2; GD3; Glypican-3; Glypicans; GM3; GPNMB; GPR49; GRP78; Her2/Neu; HER3/ERBB3; HLA-DR; ICAM-1; IGF-1R; IGFR; IL-3Ra; Integrin α5β1; Integrin α6β4; Integrin αV; Integrin αVβ3; Lewis Y; Lewis y/b antigen; LFL2; LIV-1; Ly6E; MCP-1; Mesothelin; MMP-9; MUC1; MUC18; MUC5A; MUC5AC; Myostatin; NaPi2b; Neuropilin 1; NGcGM3; NRP1; P-cadherin; PCLA; PD-1; PDG-FRa; PD-L1; PD-L2; Phosphatidylserine; PIVKA-II; PLVAP; PRLR; Progastrin; PSCA; PSMA; RANKL; RG1; Siglec-15; SLAMF6; SLAMF7; SLC44A4, STEAP-1; TACSTD-2; Tenascin C; TPBG; TRAIL-R1/DR4; TROP-2; TWEAKR; TYRP1; VANGL2; VEGF; VEGF-C; VEGFR-2; or VEGF-R2.

17. The kit or composition of claim 1, wherein the second targeting moiety binds an antigen expressed by a tumor microenvironment cell; optionally wherein the tumor microenvironment cell is a fibroblast or macrophage.

18. The kit or composition of claim 17, wherein the antigen expressed by a fibroblast is fibroblast activation protein or the antigen expressed by a macrophage is MAC-1/CD11b or sideroflexin 3.

19. A method of treating cancer expressing a tumor antigen that binds the first targeting moiety and/or second targeting moiety in a patient comprising administering the composition of claim 1 to the patient; optionally wherein the cancer expressing a tumor antigen that binds the first and/or second targeting moiety is any one of breast cancer, ovarian cancer, endometrial cancer, cervical cancer, bladder cancer, renal cancer, melanoma, lung cancer, prostate cancer, testicular cancer, thyroid cancer, brain cancer, esophageal cancer, gastric cancer, pancreatic cancer, colorectal cancer, liver cancer, leukemia, myeloma, Non-Hodgkin's lymphoma, Hodgkin lymphoma, acute myeloid leukemia, acute lymphoblastic leukemia, chronic lymphoblastic leukemia, lymphoproliferative disorder, myelodysplastic disorder, myeloproliferative disease or premalignant disease.

20. A method of targeting immune cells to cancer expressing a tumor antigen that binds both the first and/or second targeting moiety in a patient comprising administering the composition of claim 1 to the patient.

21. A method of targeting immune cells to cancer expressing two tumor antigens, wherein one tumor antigen binds the first targeting moiety and one tumor antigen binds the second targeting moiety, in a patient comprising administering the composition of claim 1 to the patient.

* * * * *

```
                       SEQUENCE LISTING

<160> NUMBER OF SEQ ID NOS: 215

<210> SEQ ID NO 1
  <211> LENGTH: 8
  <212> TYPE: PRT
  <213> ORGANISM: Artificial Sequence
  <220> FEATURE:
  <223> OTHER INFORMATION: ADAM28 cleavage site

<400> SEQUENCE: 1

Lys Pro Ala Lys Phe Phe Arg Leu
  1               5

<210> SEQ ID NO 2
  <211> LENGTH: 8
  <212> TYPE: PRT
  <213> ORGANISM: Artificial Sequence
  <220> FEATURE:
  <223> OTHER INFORMATION: ADAM28 cleavage site

<400> SEQUENCE: 2

Asp Pro Ala Lys Phe Phe Arg Leu
  1               5

<210> SEQ ID NO 3
  <211> LENGTH: 8
  <212> TYPE: PRT
  <213> ORGANISM: Artificial Sequence
  <220> FEATURE:
  <223> OTHER INFORMATION: ADAM28 cleavage site

<400> SEQUENCE: 3

Lys Pro Met Lys Phe Phe Arg Leu
  1               5

<210> SEQ ID NO 4
  <211> LENGTH: 8
  <212> TYPE: PRT
  <213> ORGANISM: Artificial Sequence
  <220> FEATURE:
  <223> OTHER INFORMATION: ADAM28 cleavage site
```

```
<400> SEQUENCE: 4

Leu Pro Ala Lys Phe Phe Arg Leu
1               5

<210> SEQ ID NO 5
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 5

Leu Pro Met Lys Phe Phe Arg Leu
1               5

<210> SEQ ID NO 6
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 6

Lys Pro Ala Met Phe Phe Arg Leu
1               5

<210> SEQ ID NO 7
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 7

Tyr Pro Ala Lys Phe Phe Arg Leu
1               5

<210> SEQ ID NO 8
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 8

Lys Trp Ala Lys Phe Phe Arg Leu
1               5

<210> SEQ ID NO 9
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 9

Asp Pro Met Lys Phe Phe Arg Leu
1               5

<210> SEQ ID NO 10
<211> LENGTH: 8
<212> TYPE: PRT
<213> ORGANISM: Artificial Sequence
<220> FEATURE:
<223> OTHER INFORMATION: ADAM28 cleavage site
```

```
<400> SEQUENCE: 10

Asp Pro Ala Met Phe Phe Arg Leu
1               5

<210> SEQ ID NO 11
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 11

Asp Pro Met Met Phe Phe Arg Leu
1               5

<210> SEQ ID NO 12
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 12

Lys Met Ala Met Phe Phe Arg Leu
1               5

<210> SEQ ID NO 13
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 13

Lys Met Ala Met Phe Phe Ile Met
1               5

<210> SEQ ID NO 14
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 14

Lys Pro Ala Met Phe Phe Ile Met
1               5

<210> SEQ ID NO 15
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 15

Leu Pro Ala Met Phe Phe Arg Leu
1               5

<210> SEQ ID NO 16
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 16
```

```
Leu Pro Met Met Phe Phe Arg Leu
1               5

<210> SEQ ID NO 17
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 17

Leu Met Ala Met Phe Phe Arg Leu
1               5

<210> SEQ ID NO 18
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 18

Leu Met Ala Met Phe Phe Ile Met
1               5

<210> SEQ ID NO 19
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 19

Leu Pro Ala Met Phe Phe Ile Met
1               5

<210> SEQ ID NO 20
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 20

Leu Pro Ala Met Phe Phe Tyr Met
1               5

<210> SEQ ID NO 21
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 21

Lys Pro Met Met Phe Phe Arg Leu
1               5

<210> SEQ ID NO 22
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 22
```

Lys Pro Ala Lys Phe Phe Tyr Met
1               5

<210> SEQ ID NO 23
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 23

Lys Pro Ala Lys Phe Phe Ile Met
1               5

<210> SEQ ID NO 24
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 24

Ile Pro Met Lys Phe Phe Arg Leu
1               5

<210> SEQ ID NO 25
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 25

Ile Pro Ala Met Phe Phe Arg Leu
1               5

<210> SEQ ID NO 26
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 26

Ile Pro Met Met Phe Phe Arg Leu
1               5

<210> SEQ ID NO 27
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 27

Ile Met Ala Met Phe Phe Arg Leu
1               5

<210> SEQ ID NO 28
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 28

Ile Met Ala Met Phe Phe Ile Met

```
1               5

<210> SEQ ID NO 29
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 29

Ile Pro Ala Met Phe Phe Ile Met
1               5

<210> SEQ ID NO 30
<211> LENGTH: 8
<212> TYPE: PRT
<213> ORGANISM: Artificial Sequence
<220> FEATURE:
<223> OTHER INFORMATION: ADAM28 cleavage site

<400> SEQUENCE: 30

Ile Pro Ala Met Phe Phe Tyr Met
1               5

<210> SEQ ID NO 31
<211> LENGTH: 2
<212> TYPE: PRT
<213> ORGANISM: Artificial Sequence
<220> FEATURE:
<223> OTHER INFORMATION: cathepsin B cleavage site

<400> SEQUENCE: 31

Phe Arg
1

<210> SEQ ID NO 32
<211> LENGTH: 2
<212> TYPE: PRT
<213> ORGANISM: Artificial Sequence
<220> FEATURE:
<223> OTHER INFORMATION: cathepsin B cleavage site

<400> SEQUENCE: 32

Phe Lys
1

<210> SEQ ID NO 33
<211> LENGTH: 2
<212> TYPE: PRT
<213> ORGANISM: Artificial Sequence
<220> FEATURE:
<223> OTHER INFORMATION: cathepsin B cleavage site

<400> SEQUENCE: 33

Val Ala
1

<210> SEQ ID NO 34
<211> LENGTH: 2
<212> TYPE: PRT
<213> ORGANISM: Artificial Sequence
<220> FEATURE:
<223> OTHER INFORMATION: cathepsin B cleavage site

<400> SEQUENCE: 34

Val Arg
1
```

<210> SEQ ID NO 35
<211> LENGTH: 2
<212> TYPE: PRT
<213> ORGANISM: Artificial Sequence
<220> FEATURE:
<223> OTHER INFORMATION: cathepsin B cleavage site
<220> FEATURE:
<221> NAME/KEY: misc_feature
<222> LOCATION: (2)..(2)
<223> OTHER INFORMATION: Xaa is citrulline

<400> SEQUENCE: 35

Val Xaa
1

<210> SEQ ID NO 36
<211> LENGTH: 8
<212> TYPE: PRT
<213> ORGANISM: Artificial Sequence
<220> FEATURE:
<223> OTHER INFORMATION: cathepsin B cleavage site

<400> SEQUENCE: 36

His Leu Val Glu Ala Leu Tyr Leu
1               5

<210> SEQ ID NO 37
<211> LENGTH: 12
<212> TYPE: PRT
<213> ORGANISM: Artificial Sequence
<220> FEATURE:
<223> OTHER INFORMATION: cathepsin B cleavage site

<400> SEQUENCE: 37

Ser Leu Leu Lys Ser Arg Met Val Pro Asn Phe Asn
1               5                   10

<210> SEQ ID NO 38
<211> LENGTH: 12
<212> TYPE: PRT
<213> ORGANISM: Artificial Sequence
<220> FEATURE:
<223> OTHER INFORMATION: cathepsin B cleavage site

<400> SEQUENCE: 38

Ser Leu Leu Ile Ala Arg Arg Met Pro Asn Phe Asn
1               5                   10

<210> SEQ ID NO 39
<211> LENGTH: 4
<212> TYPE: PRT
<213> ORGANISM: Artificial Sequence
<220> FEATURE:
<223> OTHER INFORMATION: cathepsin B cleavage site

<400> SEQUENCE: 39

Lys Lys Phe Ala
1

<210> SEQ ID NO 40
<211> LENGTH: 4
<212> TYPE: PRT
<213> ORGANISM: Artificial Sequence
<220> FEATURE:
<223> OTHER INFORMATION: cathepsin B cleavage site

<400> SEQUENCE: 40

```
Ala Phe Lys Lys
1

<210> SEQ ID NO 41
<211> LENGTH: 3
<212> TYPE: PRT
<213> ORGANISM: Artificial Sequence
<220> FEATURE:
<223> OTHER INFORMATION: cathepsin B cleavage site

<400> SEQUENCE: 41

Gln Gln Gln
1

<210> SEQ ID NO 42
<211> LENGTH: 9
<212> TYPE: PRT
<213> ORGANISM: Artificial Sequence
<220> FEATURE:
<223> OTHER INFORMATION: cathepsin D cleavage site

<400> SEQUENCE: 42

Pro Arg Ser Phe Phe Arg Leu Gly Lys
1               5

<210> SEQ ID NO 43
<211> LENGTH: 12
<212> TYPE: PRT
<213> ORGANISM: Artificial Sequence
<220> FEATURE:
<223> OTHER INFORMATION: cathepsin D cleavage site

<400> SEQUENCE: 43

Ser Gly Val Val Ile Ala Thr Val Ile Val Ile Thr
1               5                   10

<210> SEQ ID NO 44
<211> LENGTH: 3
<212> TYPE: PRT
<213> ORGANISM: Artificial Sequence
<220> FEATURE:
<223> OTHER INFORMATION: cathepsin K cleavage site

<400> SEQUENCE: 44

Gly Gly Pro
1

<210> SEQ ID NO 45
<211> LENGTH: 12
<212> TYPE: PRT
<213> ORGANISM: Artificial Sequence
<220> FEATURE:
<223> OTHER INFORMATION: MMP1 cleavage site

<400> SEQUENCE: 45

Ser Leu Gly Pro Gln Gly Ile Trp Gly Gln Phe Asn
1               5                   10

<210> SEQ ID NO 46
<211> LENGTH: 7
<212> TYPE: PRT
<213> ORGANISM: Artificial Sequence
<220> FEATURE:
<223> OTHER INFORMATION: MMP2 cleavage site

<400> SEQUENCE: 46
```

```
Ala Ile Pro Val Ser Leu Arg
1               5

<210> SEQ ID NO 47
<211> LENGTH: 12
<212> TYPE: PRT
<213> ORGANISM: Artificial Sequence
<220> FEATURE:
<223> OTHER INFORMATION: MMP2 cleavage site

<400> SEQUENCE: 47

Ser Leu Pro Leu Gly Leu Trp Ala Pro Asn Phe Asn
1               5                   10

<210> SEQ ID NO 48
<211> LENGTH: 8
<212> TYPE: PRT
<213> ORGANISM: Artificial Sequence
<220> FEATURE:
<223> OTHER INFORMATION: MMP2 cleavage site

<400> SEQUENCE: 48

His Pro Val Gly Leu Leu Ala Arg
1               5

<210> SEQ ID NO 49
<211> LENGTH: 8
<212> TYPE: PRT
<213> ORGANISM: Artificial Sequence
<220> FEATURE:
<223> OTHER INFORMATION: MMP2 cleavage site

<400> SEQUENCE: 49

Gly Pro Leu Gly Val Arg Gly Lys
1               5

<210> SEQ ID NO 50
<211> LENGTH: 8
<212> TYPE: PRT
<213> ORGANISM: Artificial Sequence
<220> FEATURE:
<223> OTHER INFORMATION: MMP2 cleavage site

<400> SEQUENCE: 50

Gly Pro Leu Gly Leu Trp Ala Gln
1               5

<210> SEQ ID NO 51
<211> LENGTH: 8
<212> TYPE: PRT
<213> ORGANISM: Artificial Sequence
<220> FEATURE:
<223> OTHER INFORMATION: MMP3 cleavage site

<400> SEQUENCE: 51

Ser Thr Ala Val Ile Val Ser Ala
1               5

<210> SEQ ID NO 52
<211> LENGTH: 8
<212> TYPE: PRT
<213> ORGANISM: Artificial Sequence
<220> FEATURE:
<223> OTHER INFORMATION: MMP7 cleavage site

<400> SEQUENCE: 52

Gly Pro Leu Gly Leu Ala Arg Lys
```

```
1               5
```

<210> SEQ ID NO 53
<211> LENGTH: 8
<212> TYPE: PRT
<213> ORGANISM: Artificial Sequence
<220> FEATURE:
<223> OTHER INFORMATION: MMP7 cleavage site

<400> SEQUENCE: 53

```
Arg Pro Leu Ala Leu Trp Arg Ser
1               5
```

<210> SEQ ID NO 54
<211> LENGTH: 12
<212> TYPE: PRT
<213> ORGANISM: Artificial Sequence
<220> FEATURE:
<223> OTHER INFORMATION: MMP7 cleavage site

<400> SEQUENCE: 54

```
Ser Leu Arg Pro Leu Ala Leu Trp Arg Ser Phe Asn
1               5                   10
```

<210> SEQ ID NO 55
<211> LENGTH: 6
<212> TYPE: PRT
<213> ORGANISM: Artificial Sequence
<220> FEATURE:
<223> OTHER INFORMATION: MMP2/9 cleavage site

<400> SEQUENCE: 55

```
Gly Ile Leu Gly Val Pro
1               5
```

<210> SEQ ID NO 56
<211> LENGTH: 8
<212> TYPE: PRT
<213> ORGANISM: Artificial Sequence
<220> FEATURE:
<223> OTHER INFORMATION: MMP2/9 cleavage site

<400> SEQUENCE: 56

```
Gly Pro Leu Gly Ile Ala Gly Gln
1               5
```

<210> SEQ ID NO 57
<211> LENGTH: 8
<212> TYPE: PRT
<213> ORGANISM: Artificial Sequence
<220> FEATURE:
<223> OTHER INFORMATION: MMP9 cleavage site

<400> SEQUENCE: 57

```
Ala Val Arg Trp Leu Leu Thr Ala
1               5
```

<210> SEQ ID NO 58
<211> LENGTH: 7
<212> TYPE: PRT
<213> ORGANISM: Artificial Sequence
<220> FEATURE:
<223> OTHER INFORMATION: MMP9 cleavage site

<400> SEQUENCE: 58

```
Pro Leu Gly Leu Tyr Ala Leu
1               5
```

<210> SEQ ID NO 59
<211> LENGTH: 9
<212> TYPE: PRT
<213> ORGANISM: Artificial Sequence
<220> FEATURE:
<223> OTHER INFORMATION: MMP9 cleavage site

<400> SEQUENCE: 59

Gly Pro Gln Gly Ile Ala Gly Gln Arg
1               5

<210> SEQ ID NO 60
<211> LENGTH: 8
<212> TYPE: PRT
<213> ORGANISM: Artificial Sequence
<220> FEATURE:
<223> OTHER INFORMATION: MMP9 cleavage site

<400> SEQUENCE: 60

Lys Pro Val Ser Leu Ser Tyr Arg
1               5

<210> SEQ ID NO 61
<211> LENGTH: 8
<212> TYPE: PRT
<213> ORGANISM: Artificial Sequence
<220> FEATURE:
<223> OTHER INFORMATION: MMP11 cleavage site

<400> SEQUENCE: 61

Ala Ala Ala Thr Ser Ile Ala Met
1               5

<210> SEQ ID NO 62
<211> LENGTH: 8
<212> TYPE: PRT
<213> ORGANISM: Artificial Sequence
<220> FEATURE:
<223> OTHER INFORMATION: MMP11 cleavage site

<400> SEQUENCE: 62

Ala Ala Gly Ala Met Phe Leu Glu
1               5

<210> SEQ ID NO 63
<211> LENGTH: 12
<212> TYPE: PRT
<213> ORGANISM: Artificial Sequence
<220> FEATURE:
<223> OTHER INFORMATION: MMP13 cleavage site

<400> SEQUENCE: 63

Gly Pro Gln Gly Leu Ala Gly Gln Arg Gly Ile Val
1               5                   10

<210> SEQ ID NO 64
<211> LENGTH: 5
<212> TYPE: PRT
<213> ORGANISM: Artificial Sequence
<220> FEATURE:
<223> OTHER INFORMATION: MMP14 cleavage site

<400> SEQUENCE: 64

Pro Arg His Leu Arg
1               5

<210> SEQ ID NO 65
<211> LENGTH: 12
<212> TYPE: PRT
<213> ORGANISM: Artificial Sequence
<220> FEATURE:
<223> OTHER INFORMATION: MMP14 cleavage site

<400> SEQUENCE: 65

Pro Gln Gly Leu Leu Gly Ala Pro Gly Ile Leu Gly
1               5                   10

<210> SEQ ID NO 66
<211> LENGTH: 8
<212> TYPE: PRT
<213> ORGANISM: Artificial Sequence
<220> FEATURE:
<223> OTHER INFORMATION: MMP14 cleavage site

<400> SEQUENCE: 66

Pro Arg Ser Ala Lys Glu Leu Arg
1               5

<210> SEQ ID NO 67
<211> LENGTH: 6
<212> TYPE: PRT
<213> ORGANISM: Artificial Sequence
<220> FEATURE:
<223> OTHER INFORMATION: PSA / KLK3

<400> SEQUENCE: 67

His Ser Ser Lys Leu Gln
1               5

<210> SEQ ID NO 68
<211> LENGTH: 5
<212> TYPE: PRT
<213> ORGANISM: Artificial Sequence
<220> FEATURE:
<223> OTHER INFORMATION: PSA / KLK3

<400> SEQUENCE: 68

Ser Ser Lys Leu Gln
1               5

<210> SEQ ID NO 69
<211> LENGTH: 4
<212> TYPE: PRT
<213> ORGANISM: Artificial Sequence
<220> FEATURE:
<223> OTHER INFORMATION: KLK4

<400> SEQUENCE: 69

Arg Gln Gln Arg
1

<210> SEQ ID NO 70
<211> LENGTH: 3
<212> TYPE: PRT
<213> ORGANISM: Artificial Sequence
<220> FEATURE:
<223> OTHER INFORMATION: TMPRSS2

<400> SEQUENCE: 70

Gly Gly Arg
1

```
<210> SEQ ID NO 71
<211> LENGTH: 3
<212> TYPE: PRT
<213> ORGANISM: Artificial Sequence
<220> FEATURE:
<223> OTHER INFORMATION: Legumain

<400> SEQUENCE: 71

Ala Ala Asn
1

<210> SEQ ID NO 72
<211> LENGTH: 3
<212> TYPE: PRT
<213> ORGANISM: Artificial Sequence
<220> FEATURE:
<223> OTHER INFORMATION: ST14 (Matriptase)

<400> SEQUENCE: 72

Gln Ala Arg
1

<210> SEQ ID NO 73
<211> LENGTH: 8
<212> TYPE: PRT
<213> ORGANISM: Artificial Sequence
<220> FEATURE:
<223> OTHER INFORMATION: C1s cleavage site

<400> SEQUENCE: 73

Tyr Leu Gly Arg Ser Tyr Lys Val
1               5

<210> SEQ ID NO 74
<211> LENGTH: 6
<212> TYPE: PRT
<213> ORGANISM: Artificial Sequence
<220> FEATURE:
<223> OTHER INFORMATION: C1s cleavage site
<220> FEATURE:
<221> NAME/KEY: misc_feature
<222> LOCATION: (6)..(6)
<223> OTHER INFORMATION: Xaa can be any naturally occurring amino acid

<400> SEQUENCE: 74

Met Gln Leu Gly Arg Xaa
1               5

<210> SEQ ID NO 75
<211> LENGTH: 8
<212> TYPE: PRT
<213> ORGANISM: Artificial Sequence
<220> FEATURE:
<223> OTHER INFORMATION: MASP2 cleavage site

<400> SEQUENCE: 75

Ser Leu Gly Arg Lys Ile Gln Ile
1               5

<210> SEQ ID NO 76
<211> LENGTH: 9
<212> TYPE: PRT
<213> ORGANISM: Artificial Sequence
<220> FEATURE:
<223> OTHER INFORMATION: C2a and Bb cleavage site

<400> SEQUENCE: 76

Gly Leu Ala Arg Ser Asn Leu Asp Glu
```

```
1               5

<210> SEQ ID NO 77
<211> LENGTH: 8
<212> TYPE: PRT
<213> ORGANISM: Artificial Sequence
<220> FEATURE:
<223> OTHER INFORMATION: uPa cleavage site

<400> SEQUENCE: 77

Thr Tyr Ser Arg Ser Arg Tyr Leu
1               5

<210> SEQ ID NO 78
<211> LENGTH: 12
<212> TYPE: PRT
<213> ORGANISM: Artificial Sequence
<220> FEATURE:
<223> OTHER INFORMATION: uPa cleavage site

<400> SEQUENCE: 78

Lys Lys Ser Pro Gly Arg Val Val Gly Gly Ser Val
1               5                   10

<210> SEQ ID NO 79
<211> LENGTH: 8
<212> TYPE: PRT
<213> ORGANISM: Artificial Sequence
<220> FEATURE:
<223> OTHER INFORMATION: uPa cleavage site

<400> SEQUENCE: 79

Asn Ser Gly Arg Ala Val Thr Tyr
1               5

<210> SEQ ID NO 80
<211> LENGTH: 3
<212> TYPE: PRT
<213> ORGANISM: Artificial Sequence
<220> FEATURE:
<223> OTHER INFORMATION: uPa cleavage site

<400> SEQUENCE: 80

Ala Phe Lys
1

<210> SEQ ID NO 81
<211> LENGTH: 12
<212> TYPE: PRT
<213> ORGANISM: Artificial Sequence
<220> FEATURE:
<223> OTHER INFORMATION: tissue-type plasminogen activator (tPA)

<400> SEQUENCE: 81

Gly Gly Ser Gly Gln Arg Gly Arg Lys Ala Leu Glu
1               5                   10

<210> SEQ ID NO 82
<211> LENGTH: 10
<212> TYPE: PRT
<213> ORGANISM: Artificial Sequence
<220> FEATURE:
<223> OTHER INFORMATION: ADAM10

<400> SEQUENCE: 82

Pro Arg Tyr Glu Ala Tyr Lys Met Gly Lys
1               5                   10
```

```
<210> SEQ ID NO 83
<211> LENGTH: 5
<212> TYPE: PRT
<213> ORGANISM: Artificial Sequence
<220> FEATURE:
<223> OTHER INFORMATION: ADAM12

<400> SEQUENCE: 83

Leu Ala Gln Ala Phe
1               5

<210> SEQ ID NO 84
<211> LENGTH: 11
<212> TYPE: PRT
<213> ORGANISM: Artificial Sequence
<220> FEATURE:
<223> OTHER INFORMATION: ADAM17

<400> SEQUENCE: 84

Glu His Ala Asp Leu Leu Ala Val Val Ala Lys
1               5                   10

<210> SEQ ID NO 85
<211> LENGTH: 5
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 85

Gly Gly Gly Gly Ser
1               5

<210> SEQ ID NO 86
<211> LENGTH: 4
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 86

Gly Gly Gly Ser
1

<210> SEQ ID NO 87
<211> LENGTH: 2
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 87

Gly Ser
1

<210> SEQ ID NO 88
<211> LENGTH: 5
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 88
```

```
Gly Ser Gly Gly Ser
1               5

<210> SEQ ID NO 89
<211> LENGTH: 4
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 89

Gly Gly Ser Gly
1

<210> SEQ ID NO 90
<211> LENGTH: 5
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 90

Gly Gly Ser Gly Gly
1               5

<210> SEQ ID NO 91
<211> LENGTH: 5
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 91

Gly Ser Gly Ser Gly
1               5

<210> SEQ ID NO 92
<211> LENGTH: 5
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 92

Gly Ser Gly Gly Gly
1               5

<210> SEQ ID NO 93
<211> LENGTH: 5
<212> TYPE: PRT
<213> ORGANISM: Artificial Sequence
<220> FEATURE:
<223> OTHER INFORMATION: flexible amino acid linker (may be presented in
      repeating fashion)

<400> SEQUENCE: 93

Gly Gly Gly Ser Gly
1               5

<210> SEQ ID NO 94
<211> LENGTH: 5
<212> TYPE: PRT
<213> ORGANISM: Artificial Sequence
```

<220> FEATURE:
<223> OTHER INFORMATION: flexible amino acid linker (may be presented in
      repeating fashion)

<400> SEQUENCE: 94

Gly Ser Ser Ser Gly
1               5

<210> SEQ ID NO 95
<211> LENGTH: 51
<212> TYPE: RNA
<213> ORGANISM: Artificial Sequence
<220> FEATURE:
<223> OTHER INFORMATION: Anti-EGFR aptamer (tight binder with Kd=2.4 nM)

<400> SEQUENCE: 95
ugccgcuaua augcacggau uuaaucgccg uagaaaagca gucaaagcc g         51

<210> SEQ ID NO 96
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 96
uggcgcuaaa uagcacggaa auaaucgccg uagaaaagca gucaaagcc g         51

<210> SEQ ID NO 97
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 97
ugcuaguaua ucgcacggau uuaaucgccg uagaaaagca gucaaagcc g         51

<210> SEQ ID NO 98
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 98
ugccgccaua ucacacggau uuaaucgccg uagaaaagca gucaaagcc g         51

<210> SEQ ID NO 99
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 99
uuccgcugua uaacacggac uuaaucgccg uaguaaagca gucaaagcc g         51

<210> SEQ ID NO 100
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 100
ugucgcucua uugcacggau uuaaucgccg uagaaaagca gucaaagcc g         51

<210> SEQ ID NO 101
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 101
ugcugcuuua ucccacauau uuuuuccccu cauaacaaua uuucucccc c         51

<210> SEQ ID NO 102
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (45)..(45)
<223> OTHER INFORMATION: n is a, c, g, or u
<220> FEATURE:
<221> NAME/KEY: misc_feature
<222> LOCATION: (47)..(47)
<223> OTHER INFORMATION: n is a, c, g, or u

<400> SEQUENCE: 102
ugcngcuaua ucgcncguau uuaaucgccg uagaaaagca gucnangcc g         51

<210> SEQ ID NO 103
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 103
ugcaaagaaa acgcacguau uuaaucgccg uaguaaagca gucaaagcc g         51

<210> SEQ ID NO 104
<211> LENGTH: 53
<212> TYPE: RNA
<213> ORGANISM: Artificial Sequence
<220> FEATURE:
<223> OTHER INFORMATION: Anti-EGFR aptamer

<400> SEQUENCE: 104
ugcaucacua ucgaaccuau uuaauccacc aaaauaauug caaguccaua cuc      53

<210> SEQ ID NO 105
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (5)..(6)
<223> OTHER INFORMATION: n is a, c, g, or u
<220> FEATURE:
<221> NAME/KEY: misc_feature

```
<222> LOCATION: (17)..(17)
<223> OTHER INFORMATION: n is a, c, g, or u
<220> FEATURE:
<221> NAME/KEY: misc_feature
<222> LOCATION: (48)..(48)
<223> OTHER INFORMATION: n is a, c, g, or u

<400> SEQUENCE: 105
ugccnnaaua acacacnuau auaaucgccg uacaaaauca ugucaaancc g          51

<210> SEQ ID NO 106
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 106
ugcagcugua uugcacguau uuaaucgccg uagaaaagca gucaaagcc g           51

<210> SEQ ID NO 107
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 107
uuccgauaau cccgcguacu aaaucaccau agucaacaau uccaaccuc             50

<210> SEQ ID NO 108
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 108
uccacuauau cacacguauu uaaucgccgu agaaaagcau gucaaagccg            50

<210> SEQ ID NO 109
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 109
ucccucaacc ucgcuacuau uuaaucgccg uagaaaagca gucaaagcc u           51

<210> SEQ ID NO 110
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 110
ugccgcuaua ucacacgaau uuaaucgccg uagaaaagca gucaaagcc g           51

<210> SEQ ID NO 111
<211> LENGTH: 51
<212> TYPE: RNA
<213> ORGANISM: Artificial Sequence
<220> FEATURE:
<223> OTHER INFORMATION: Anti-EGFR aptamer
```

```
<400> SEQUENCE: 111
agccccuaga acacacggau uuaaucgccg uagaaaagca gucaaagcc g         51

<210> SEQ ID NO 112
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 112
ugccaauaua uaacacggaa uuaaucgccg uagaaaagca gucaaagcc g         51

<210> SEQ ID NO 113
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 113
ugccgcuaua gcgcacggau uuaaucgccg uagaaaagca gucaaagcc g         51

<210> SEQ ID NO 114
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 114
ugcagauaua ugucacucau uaaucccgu auaaaaacau aacuaagcuc            50

<210> SEQ ID NO 115
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 115
uguagcugua uugcacacau uaaaucgccg uaguaaagca gucaaagcc g         51

<210> SEQ ID NO 116
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 116
uaccaauaua ucgccacaca uaaucgccgu agaaaagcau gucaaagccg           50

<210> SEQ ID NO 117
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 117
ugccgcuaug cccacggaau uuaaucgccg uagaaaaaca gucaaaguc g         51

<210> SEQ ID NO 118
<211> LENGTH: 51
```

```
<212> TYPE: RNA
<213> ORGANISM: Artificial Sequence
<220> FEATURE:
<223> OTHER INFORMATION: Anti-EGFR aptamer

<400> SEQUENCE: 118
ugccgcuauu uagcacggau uaaaucgccg uagaaaagca ugucaaagcc g          51

<210> SEQ ID NO 119
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (45)..(45)
<223> OTHER INFORMATION: n is a, c, g, or u

<400> SEQUENCE: 119
ugccgcuauu uagcacggau uaaaucgccg uagaaaagca ugucnaagcc g          51

<210> SEQ ID NO 120
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (41)..(41)
<223> OTHER INFORMATION: n is a, c, g, or u

<400> SEQUENCE: 120
uguaguaaua ugacacggau uuaaucgccg uagaaaagca ngucaaagcc u          51

<210> SEQ ID NO 121
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 121
ugucgccauu acgcacggau uuaaucgccg uagaaaagca ugucaaagcc g          51

<210> SEQ ID NO 122
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 122 ugccccaaa cuacacaaau uuaaucgccg uauaaaagca ugucaaagcc g          51

<210> SEQ ID NO 123
<211> LENGTH: 49
<212> TYPE: RNA
<213> ORGANISM: Artificial Sequence
<220> FEATURE:
<223> OTHER INFORMATION: Anti-EGFR aptamer

<400> SEQUENCE: 123
ugcacuaucu cacacguacu aaucgccgua uaaaagcaug ucaaagccg             49

<210> SEQ ID NO 124
```

```
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 124
ugucgcaaua auacacuaau uuaaucgccg uagaaaagca ugucaaagcc g          51

<210> SEQ ID NO 125
<211> LENGTH: 49
<212> TYPE: RNA
<213> ORGANISM: Artificial Sequence
<220> FEATURE:
<223> OTHER INFORMATION: Anti-EGFR aptamer

<400> SEQUENCE: 125
ugcaacaaua uagcacguau uuaaucgccg uaguaaagca ugucaaagg             49

<210> SEQ ID NO 126
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 126
cuaccacaaa ucccacauau uuaaucuccc aaucaaaucu guccauucc c          51

<210> SEQ ID NO 127
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 127
ugcccuaaac ucacacggau auaaucgccg uagaaaagca ugucaaagcc g          51

<210> SEQ ID NO 128
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 128
uugucguaug ucacacguau uaaaucgccg uauaaaagca ugucaaagcc g          51

<210> SEQ ID NO 129
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 129
uuccgcuaua acacacggag aaaaucgccg uaguaaagca ugucaaagcc g          51

<210> SEQ ID NO 130
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 130
```
ugccgauaua acgcacggau auaaucgccg uagaaaagca ugucaaagcc g    51

<210> SEQ ID NO 131
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 131
ugccauuaua cagcacggau uuaaucgccg uagaaaagca ugucaaagcc g    51

<210> SEQ ID NO 132
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 132
uccagaaaua ugcacacauu uaaucgccgu agaaaagcau gucaaagccg    50

<210> SEQ ID NO 133
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 133
uccgcuaaac aacacggaua caaucgccgu agaaaagcau guccaagccg    50

<210> SEQ ID NO 134
<211> LENGTH: 49
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (46)..(48)
<223> OTHER INFORMATION: n is a, c, g, or u

<400> SEQUENCE: 134
ugcacuaucu cacacguacu aaucgccgua uaaaagcaug ucaaannng    49

<210> SEQ ID NO 135
<211> LENGTH: 50
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (3)..(3)
<223> OTHER INFORMATION: n is a, c, g, or u
<220> FEATURE:
<221> NAME/KEY: misc_feature
<222> LOCATION: (6)..(6)
<223> OTHER INFORMATION: n is a, c, g, or u
<220> FEATURE:
<221> NAME/KEY: misc_feature
<222> LOCATION: (8)..(10)
<223> OTHER INFORMATION: n is a, c, g, or u
<220> FEATURE:
<221> NAME/KEY: misc_feature
<222> LOCATION: (21)..(21)
<223> OTHER INFORMATION: n is a, c, g, or u
<220> FEATURE:

```
<221> NAME/KEY: misc_feature
<222> LOCATION: (45)..(45)
<223> OTHER INFORMATION: n is a, c, g, or u

<400> SEQUENCE: 135
aungcnannn uacacguauu naaucgccgu agaaaagcau gucanagccg            50

<210> SEQ ID NO 136
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 136
ugcugcuaua uugcaauuuu uuaaacuaag uagaaaacca uguacaaguc g          51

<210> SEQ ID NO 137
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 137
ugucgccaua uugcacggau uuaaucgccg uagaaaagca uguccaagcc g          51

<210> SEQ ID NO 138
<211> LENGTH: 52
<212> TYPE: RNA
<213> ORGANISM: Artificial Sequence
<220> FEATURE:
<223> OTHER INFORMATION: Anti-EGFR aptamer

<400> SEQUENCE: 138
ugccguuaua acccacggaa uuuaaccucc guagaaaagc augucaaagc cg         52

<210> SEQ ID NO 139
<211> LENGTH: 52
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (40)..(40)
<223> OTHER INFORMATION: n is a, c, g, or u

<400> SEQUENCE: 139
ugugaauaua uaucacggau uuaaucgccg uauaaaagcn augucaaagc cg         52

<210> SEQ ID NO 140
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (10)..(11)
<223> OTHER INFORMATION: n is a, c, g, or u
<220> FEATURE:
<221> NAME/KEY: misc_feature
<222> LOCATION: (13)..(13)
<223> OTHER INFORMATION: n is a, c, g, or u

<400> SEQUENCE: 140
ugccgauaun nancacggau uuaaucgccg uagaaaagca uguccaagcc g          51
```

```
<210> SEQ ID NO 141
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 141
ugucacuaaa uugcacguau auaaucgccg uaguaagcau gucaaagccg         50

<210> SEQ ID NO 142
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 142
ugcaaccaua aagcacguaa uaaaucgccg uauauaagca ugucaaagcc g       51

<210> SEQ ID NO 143
<211> LENGTH: 50
<212> TYPE: RNA
<213> ORGANISM: Artificial Sequence
<220> FEATURE:
<223> OTHER INFORMATION: Anti-EGFR aptamer

<400> SEQUENCE: 143
ugccgcuaua uagcacguau uaaucgccgu aguaaagcau gucaaagccg         50

<210> SEQ ID NO 144
<211> LENGTH: 52
<212> TYPE: RNA
<213> ORGANISM: Artificial Sequence
<220> FEATURE:
<223> OTHER INFORMATION: Anti-EGFR aptamer

<400> SEQUENCE: 144
ugccgcuaua gcacacggaa uuuaaucgcc guaguaaagc augucaaagc cg      52

<210> SEQ ID NO 145
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (15)..(15)
<223> OTHER INFORMATION: n is a, c, g, or u
<220> FEATURE:
<221> NAME/KEY: misc_feature
<222> LOCATION: (45)..(45)
<223> OTHER INFORMATION: n is a, c, g, or u

<400> SEQUENCE: 145
ugcagguaua uaacncggau uuaaucgccg uagaaaagca ugucnaagcc g       51

<210> SEQ ID NO 146
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 146
```
ugcuccuaua acacacggau uuaaucgccg uagaaaagca uguccaagcc g    51

<210> SEQ ID NO 147
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 147
ugcccguaau ugcacggauu uaaucgccgu agaaaagcau guccaagccg g    51

<210> SEQ ID NO 148
<211> LENGTH: 51
<212> TYPE: RNA
<213> ORGANISM: Artificial Sequence
<220> FEATURE:
<223> OTHER INFORMATION: Anti-EGFR aptamer
<220> FEATURE:
<221> NAME/KEY: misc_feature
<222> LOCATION: (12)..(12)
<223> OTHER INFORMATION: n is a, c, g, or u
<220> FEATURE:
<221> NAME/KEY: misc_feature
<222> LOCATION: (44)..(44)
<223> OTHER INFORMATION: n is a, c, g, or u

<400> SEQUENCE: 148
acucccuaua ungcaacuac auaaucgccg uaaauaagca uguncaagcc g    51

<210> SEQ ID NO 149
<211> LENGTH: 54
<212> TYPE: RNA
<213> ORGANISM: Artificial Sequence
<220> FEATURE:
<223> OTHER INFORMATION: Anti-EGFR aptamer

<400> SEQUENCE: 149
ugaagcuaga ucacacuaaa uuaaucgccg uagaaaagca gucaaaaaa gccg    54

<210> SEQ ID NO 150
<211> LENGTH: 52
<212> TYPE: RNA
<213> ORGANISM: Artificial Sequence
<220> FEATURE:
<223> OTHER INFORMATION: Anti-EGFR aptamer

<400> SEQUENCE: 150
ugacucuuua uccccguac auuauucacc gaaccaaagc auuaccaucc cc    52

<210> SEQ ID NO 151
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 151
ugacgcccua acacacguau auaaucgccg uagaaaagca gucaaagcc g    51

<210> SEQ ID NO 152
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 152

-continued ugucgcaaaa uagcacguau uuaaucgccg uagaaaagca uguccaagcc g        51

<210> SEQ ID NO 153
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 153
ugaguguaua auucacguau uuaaucgccg uagaaaagca ugucaaagcc g        51

<210> SEQ ID NO 154
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 154
ugcuacuaua ucguagguaa cuaaucgccc uacaaacuca cucuaaaacc g        51

<210> SEQ ID NO 155
<211> LENGTH: 53
<212> TYPE: RNA
<213> ORGANISM: Artificial Sequence
<220> FEATURE:
<223> OTHER INFORMATION: Anti-EGFR aptamer

<400> SEQUENCE: 155
uuacgcuaua ucacacggaa uuuuaaucgc cguagaaaag cauguccaag ccg      53

<210> SEQ ID NO 156
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 156
cccaucugua cuacaggaau uuaaucgccg uagaaaagca uguccaagcc g        51

<210> SEQ ID NO 157
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 157
ugcccauaaa uagcacggau uuaaucgccg uagaaaagca uguccaagcc g        51

<210> SEQ ID NO 158
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 158
ugccgcaaua acauacacau auaaucgccg uagaaaagca ugucaaagcc g        51

<210> SEQ ID NO 159
<211> LENGTH: 51
<212> TYPE: RNA

```
<213> ORGANISM: Artificial Sequence
<220> FEATURE:
<223> OTHER INFORMATION: Anti-EGFR aptamer

<400> SEQUENCE: 159
ugcaacuaua ucgcacguau guaaucgccg uagaaaaagc augucaaagc c        51

<210> SEQ ID NO 160
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 160
uuccgcuaua uagcacggaa uuaaucgccg uagaaaagca uguccaagcc g        51

<210> SEQ ID NO 161
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 161
uuccgcuaag ucacacgaaa uuaaucgccg uagaaaagca uguccaagcc g        51

<210> SEQ ID NO 162
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 162
uguagcaaua ucacacguaa uuaaucgccg uauauaagca ugucaaagcc g        51

<210> SEQ ID NO 163
<211> LENGTH: 51
<212> TYPE: RNA
<213> ORGANISM: Artificial Sequence
<220> FEATURE:
<223> OTHER INFORMATION: Anti-EGFR aptamer

<400> SEQUENCE: 163
ugccguuaua uaucacggau uuaaucgccg uagaaaagca uguccaagcc g        51

<210> SEQ ID NO 164
<211> LENGTH: 49
<212> TYPE: RNA
<213> ORGANISM: Artificial Sequence
<220> FEATURE:
<223> OTHER INFORMATION: Anti-EGFR aptamer

<400> SEQUENCE: 164
uaacacauau aucaaguaac uuaucuccuu aguaaccauc uccaagccg          49

<210> SEQ ID NO 165
<211> LENGTH: 416
<212> TYPE: PRT
<213> ORGANISM: Artificial Sequence
<220> FEATURE:
<223> OTHER INFORMATION: Anti-EpCAM VH-CH1, SP34 VH, FXa, basic coil

<400> SEQUENCE: 165

Glu Val Gln Leu Leu Glu Gln Ser Gly Ala Glu Leu Val Arg Pro Gly
```

```
               1               5                  10                 15
               Thr Ser Val Lys Ile Ser Cys Lys Ala Ser Gly Tyr Ala Phe Thr Asn
                           20                  25                 30

Tyr Trp Leu Gly Trp Val Lys Gln Arg Pro Gly His Gly Leu Glu Trp
                           35                  40                 45

Ile Gly Asp Ile Phe Pro Ser Gly Asn Ile His Tyr Asn Glu Lys
                    50                  55                 60

Phe Lys Gly Lys Ala Thr Leu Thr Ala Asp Lys Ser Ser Thr Ala
               65                  70                  75                 80

Tyr Met Gln Leu Ser Ser Leu Thr Phe Glu Asp Ser Ala Val Tyr Phe
                               85                  90                 95

Cys Ala Arg Leu Arg Asn Trp Asp Glu Pro Met Asp Tyr Trp Gly Gln
                           100                 105                110

Gly Thr Thr Val Thr Val Ser Ser Ala Ser Thr Lys Gly Pro Ser Val
                           115                 120                125

Phe Pro Leu Ala Pro Ser Ser Lys Ser Thr Ser Gly Gly Thr Ala Ala
                           130                 135                140

Leu Gly Cys Leu Val Lys Asp Tyr Phe Pro Glu Pro Val Thr Val Ser
               145                 150                 155                160

Trp Asn Ser Gly Ala Leu Thr Ser Gly Val His Thr Phe Pro Ala Val
                           165                 170                175

Leu Gln Ser Ser Gly Leu Tyr Ser Leu Ser Ser Val Val Thr Val Pro
                           180                 185                190

Ser Ser Ser Leu Gly Thr Gln Thr Tyr Ile Cys Asn Val Asn His Lys
                           195                 200                205

Pro Ser Asn Thr Lys Val Asp Lys Lys Val Glu Pro Lys Ser Cys Asp
               210                 215                 220

Lys Thr His Thr Gly Gly Gly Ser Gly Gly Gly Ser Glu Val
               225                 230                 235                240

Gln Leu Val Glu Ser Gly Gly Gly Leu Val Lys Pro Gly Gly Ser Leu
                           245                 250                255

Arg Leu Ser Cys Ala Ala Ser Gly Phe Thr Phe Asn Thr Tyr Ala Met
                           260                 265                270

Asn Trp Val Arg Gln Ala Pro Gly Lys Gly Leu Glu Trp Val Ala Arg
                           275                 280                285

Ile Arg Ser Lys Tyr Asn Asn Tyr Ala Thr Tyr Tyr Ala Asp Ser Val
                           290                 295                300

Lys Gly Arg Phe Thr Ile Ser Arg Asp Asp Ser Lys Asn Ser Leu Tyr
               305                 310                 315                320

Leu Gln Met Asn Ser Leu Lys Thr Glu Asp Thr Ala Val Tyr Tyr Cys
                           325                 330                335

Val Arg His Gly Asn Phe Gly Asn Ser Tyr Val Ser Trp Phe Ala Tyr
                           340                 345                350

Trp Gly Gln Gly Thr Leu Val Thr Val Ser Ser Gly Gly Gly Gly Ser
                           355                 360                365

Ile Glu Gly Arg Gly Gly Gly Ser Lys Asn Ala Gln Cys Lys Lys
                    370                 375                380

Lys Leu Gln Ala Leu Lys Lys Lys Asn Ala Gln Leu Lys Trp Lys Leu
               385                 390                 395                400

Gln Ala Leu Lys Lys Lys Leu Ala Gln Gly His His His His His
                           405                 410                415

<210> SEQ ID NO 166
```

<211> LENGTH: 387
<212> TYPE: PRT
<213> ORGANISM: Artificial Sequence
<220> FEATURE:
<223> OTHER INFORMATION: REPLACE

<400> SEQUENCE: 166

| | | | | | | | | | | | | | | |
|---|---|---|---|---|---|---|---|---|---|---|---|---|---|---|
| Glu | Leu | Val | Met | Thr | Gln | Ser | Pro | Ser | Ser | Leu | Thr | Val | Thr | Ala | Gly |
| 1 | | | | 5 | | | | | 10 | | | | | 15 | |
| Glu | Lys | Val | Thr | Met | Ser | Cys | Lys | Ser | Ser | Gln | Ser | Leu | Leu | Asn | Ser |
| | | | 20 | | | | | 25 | | | | | 30 | | |
| Gly | Asn | Gln | Lys | Asn | Tyr | Leu | Thr | Trp | Tyr | Gln | Gln | Lys | Pro | Gly | Gln |
| | | 35 | | | | | 40 | | | | | 45 | | | |
| Pro | Pro | Lys | Leu | Leu | Ile | Tyr | Trp | Ala | Ser | Thr | Arg | Glu | Ser | Gly | Val |
| 50 | | | | | 55 | | | | | 60 | | | | | |
| Pro | Asp | Arg | Phe | Thr | Gly | Ser | Gly | Ser | Gly | Thr | Asp | Phe | Thr | Leu | Thr |
| 65 | | | | | 70 | | | | | 75 | | | | | 80 |
| Ile | Ser | Ser | Val | Gln | Ala | Glu | Asp | Leu | Ala | Val | Tyr | Tyr | Cys | Gln | Asn |
| | | | | 85 | | | | | 90 | | | | | 95 | |
| Asp | Tyr | Ser | Tyr | Pro | Leu | Thr | Phe | Gly | Ala | Gly | Thr | Lys | Leu | Glu | Ile |
| | | | 100 | | | | | 105 | | | | | 110 | | |
| Lys | Arg | Thr | Val | Ala | Ala | Pro | Ser | Val | Phe | Ile | Phe | Pro | Pro | Ser | Asp |
| | | 115 | | | | | 120 | | | | | 125 | | | |
| Glu | Gln | Leu | Lys | Ser | Gly | Thr | Ala | Ser | Val | Val | Cys | Leu | Leu | Asn | Asn |
| 130 | | | | | 135 | | | | | 140 | | | | | |
| Phe | Tyr | Pro | Arg | Glu | Ala | Lys | Val | Gln | Trp | Lys | Val | Asp | Asn | Ala | Leu |
| 145 | | | | | 150 | | | | | 155 | | | | | 160 |
| Gln | Ser | Gly | Asn | Ser | Gln | Glu | Ser | Val | Thr | Glu | Gln | Asp | Ser | Lys | Asp |
| | | | | 165 | | | | | 170 | | | | | 175 | |
| Ser | Thr | Tyr | Ser | Leu | Ser | Ser | Thr | Leu | Thr | Leu | Ser | Lys | Ala | Asp | Tyr |
| | | | 180 | | | | | 185 | | | | | 190 | | |
| Glu | Lys | His | Lys | Val | Tyr | Ala | Cys | Glu | Val | Thr | His | Gln | Gly | Leu | Ser |
| | | 195 | | | | | 200 | | | | | 205 | | | |
| Ser | Pro | Val | Thr | Lys | Ser | Phe | Asn | Arg | Gly | Glu | Cys | Gly | Gly | Gly | Gly |
| 210 | | | | | 215 | | | | | 220 | | | | | |
| Ser | Gly | Gly | Gly | Gly | Ser | Gly | Gly | Gly | Gly | Ser | Asp | Ile | Gln | Met | Thr |
| 225 | | | | | 230 | | | | | 235 | | | | | 240 |
| Gln | Ser | Pro | Ser | Ser | Leu | Ser | Ala | Ser | Val | Gly | Asp | Arg | Val | Thr | Ile |
| | | | | 245 | | | | | 250 | | | | | 255 | |
| Thr | Cys | Arg | Ala | Ser | Gln | Asp | Val | Ser | Thr | Ala | Val | Ala | Trp | Tyr | Gln |
| | | | 260 | | | | | 265 | | | | | 270 | | |
| Gln | Lys | Pro | Gly | Lys | Ala | Pro | Lys | Leu | Leu | Ile | Tyr | Ser | Ala | Ser | Phe |
| | | 275 | | | | | 280 | | | | | 285 | | | |
| Leu | Tyr | Ser | Gly | Val | Pro | Ser | Arg | Phe | Ser | Gly | Gly | Ser | Gly | Gly | Thr |
| 290 | | | | | 295 | | | | | 300 | | | | | |
| Asp | Phe | Thr | Leu | Thr | Ile | Ser | Ser | Leu | Gln | Pro | Glu | Asp | Phe | Ala | Thr |
| 305 | | | | | 310 | | | | | 315 | | | | | 320 |
| Tyr | Tyr | Cys | Gln | Gln | Tyr | Leu | Tyr | His | Pro | Ala | Thr | Phe | Gly | Gln | Gly |
| | | | | 325 | | | | | 330 | | | | | 335 | |
| Thr | Lys | Val | Glu | Ile | Lys | Gly | Gly | Pro | Leu | Gly | Val | Arg | Gly | Lys | Gly |
| | | | 340 | | | | | 345 | | | | | 350 | | |
| Gly | Gly | Ser | Glu | Asn | Ala | Gln | Cys | Glu | Lys | Glu | Leu | Gln | Ala | Leu | Glu |
| | | 355 | | | | | 360 | | | | | 365 | | | |
| Lys | Glu | Asn | Ala | Gln | Leu | Glu | Trp | Glu | Leu | Gln | Ala | Leu | Glu | Lys | Glu |
| 370 | | | | | 375 | | | | | 380 | | | | | |

Leu Ala Gln
385

<210> SEQ ID NO 167
<211> LENGTH: 475
<212> TYPE: PRT
<213> ORGANISM: Artificial Sequence
<220> FEATURE:
<223> OTHER INFORMATION: Anti-EpCAM VH-CH1, SP34 VH, FXa, IgE CH2

<400> SEQUENCE: 167

```
Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Gly Gly Gly Ser Glu Val
225                 230                 235                 240

Gln Leu Val Glu Ser Gly Gly Gly Leu Val Lys Pro Gly Gly Ser Leu
                245                 250                 255

Arg Leu Ser Cys Ala Ala Ser Gly Phe Thr Phe Asn Thr Tyr Ala Met
            260                 265                 270

Asn Trp Val Arg Gln Ala Pro Gly Lys Gly Leu Glu Trp Val Ala Arg
        275                 280                 285

Ile Arg Ser Lys Tyr Asn Asn Tyr Ala Thr Tyr Tyr Ala Asp Ser Val
    290                 295                 300

Lys Gly Arg Phe Thr Ile Ser Arg Asp Asp Ser Lys Asn Ser Leu Tyr
305                 310                 315                 320

Leu Gln Met Asn Ser Leu Lys Thr Glu Asp Thr Ala Val Tyr Tyr Cys
                325                 330                 335

Val Arg His Gly Asn Phe Gly Asn Ser Tyr Val Ser Trp Phe Ala Tyr
            340                 345                 350
```

-continued

```
Trp Gly Gln Gly Thr Leu Val Thr Val Ser Ser Gly Ile Glu Gly Arg
            355                 360                 365

Gly Pro Pro Thr Val Lys Ile Leu Gln Ser Ser Cys Asp Gly Gly
            370                 375                 380

His Phe Pro Pro Thr Ile Gln Leu Leu Cys Leu Val Ser Gly Tyr Thr
385                 390                 395                 400

Pro Gly Thr Ile Gln Ile Thr Trp Leu Glu Asp Gly Gln Val Met Asp
            405                 410                 415

Val Asp Leu Ser Thr Ala Ser Thr Thr Gln Glu Gly Glu Leu Ala Ser
            420                 425                 430

Thr Gln Ser Glu Leu Thr Leu Ser Gln Lys His Trp Leu Ser Asp Arg
            435                 440                 445

Thr Tyr Thr Cys Gln Val Thr Tyr Gln Gly His Thr Phe Glu Asp Ser
450                 455                 460

Thr Lys Lys Cys Ala His His His His His
465                 470                 475

<210> SEQ ID NO 168
<211> LENGTH: 450
<212> TYPE: PRT
<213> ORGANISM: Artificial Sequence
<220> FEATURE:
<223> OTHER INFORMATION: Anti-EpCAM VL-CL, Atezolizumab VL, FXa, IgE CH2

<400> SEQUENCE: 168

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Asp Ile Gln Met Thr
225                 230                 235                 240
```

```
Gln Ser Pro Ser Ser Leu Ser Ala Ser Val Gly Asp Arg Val Thr Ile
            245                 250                 255

Thr Cys Arg Ala Ser Gln Asp Val Ser Thr Ala Val Ala Trp Tyr Gln
            260                 265                 270

Gln Lys Pro Gly Lys Ala Pro Lys Leu Leu Ile Tyr Ser Ala Ser Phe
            275                 280                 285

Leu Tyr Ser Gly Val Pro Ser Arg Phe Ser Gly Ser Gly Ser Gly Thr
            290                 295                 300

Asp Phe Thr Leu Thr Ile Ser Ser Leu Gln Pro Glu Asp Phe Ala Thr
305                 310                 315                 320

Tyr Tyr Cys Gln Gln Tyr Leu Tyr His Pro Ala Thr Phe Gly Gln Gly
            325                 330                 335

Thr Lys Val Glu Ile Lys Gly Gly Ile Glu Gly Arg Gly Pro Pro
            340                 345                 350

Thr Val Lys Ile Leu Gln Ser Ser Cys Asp Gly Gly Gly His Phe Pro
            355                 360                 365

Pro Thr Ile Gln Leu Leu Cys Leu Val Ser Gly Tyr Thr Pro Gly Thr
            370                 375                 380

Ile Gln Ile Thr Trp Leu Glu Asp Gly Gln Val Met Asp Val Asp Leu
385                 390                 395                 400

Ser Thr Ala Ser Thr Thr Gln Glu Gly Glu Leu Ala Ser Thr Gln Ser
            405                 410                 415

Glu Leu Thr Leu Ser Gln Lys His Trp Leu Ser Asp Arg Thr Tyr Thr
            420                 425                 430

Cys Gln Val Thr Tyr Gln Gly His Thr Phe Glu Asp Ser Thr Lys Lys
            435                 440                 445

Cys Ala
450

<210> SEQ ID NO 169
<211> LENGTH: 477
<212> TYPE: PRT
<213> ORGANISM: Artificial Sequence
<220> FEATURE:
<223> OTHER INFORMATION: Anti-EpCAM VH-CH1, SP34 VH, FXa, IgE CH2

<400> SEQUENCE: 169

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
            35                  40                  45

Ile Gly Asp Ile Phe Pro Gly Ser Gly Asn Ile His Tyr Asn Glu Lys
        50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
            85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140
```

-continued

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Gly Gly Ser Glu Val
225                 230                 235                 240

Gln Leu Val Glu Ser Gly Gly Gly Leu Val Lys Pro Gly Gly Ser Leu
                245                 250                 255

Arg Leu Ser Cys Ala Ala Ser Gly Phe Thr Phe Asn Thr Tyr Ala Met
            260                 265                 270

Asn Trp Val Arg Gln Ala Pro Gly Lys Gly Leu Glu Trp Val Ala Arg
        275                 280                 285

Ile Arg Ser Lys Tyr Asn Asn Tyr Ala Thr Tyr Tyr Ala Asp Ser Val
    290                 295                 300

Lys Gly Arg Phe Thr Ile Ser Arg Asp Asp Ser Lys Asn Ser Leu Tyr
305                 310                 315                 320

Leu Gln Met Asn Ser Leu Lys Thr Glu Asp Thr Ala Val Tyr Tyr Cys
                325                 330                 335

Val Arg His Gly Asn Phe Gly Asn Ser Tyr Val Ser Trp Phe Ala Tyr
            340                 345                 350

Trp Gly Gln Gly Thr Leu Val Thr Val Ser Ser Gly Gly Gly Ile Glu
        355                 360                 365

Gly Arg Gly Pro Pro Thr Val Lys Ile Leu Gln Ser Ser Cys Asp Gly
    370                 375                 380

Gly Gly His Phe Pro Pro Thr Ile Gln Leu Leu Cys Leu Val Ser Gly
385                 390                 395                 400

Tyr Thr Pro Gly Thr Ile Gln Ile Thr Trp Leu Glu Asp Gly Gln Val
                405                 410                 415

Met Asp Val Asp Leu Ser Thr Ala Ser Thr Thr Gln Glu Gly Glu Leu
            420                 425                 430

Ala Ser Thr Gln Ser Glu Leu Thr Leu Ser Gln Lys His Trp Leu Ser
        435                 440                 445

Asp Arg Thr Tyr Thr Cys Gln Val Thr Tyr Gln Gly His Thr Phe Glu
    450                 455                 460

Asp Ser Thr Lys Lys Cys Ala His His His His His
465                 470                 475
```

<210> SEQ ID NO 170
<211> LENGTH: 578
<212> TYPE: PRT
<213> ORGANISM: Artificial Sequence
<220> FEATURE:
<223> OTHER INFORMATION: Anti-EpCAM VL-CL, Atezolizumab VL, FXa, IgE CH2

<400> SEQUENCE: 170

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30
```

```
Gly Asn Gln Lys Asn Tyr Leu Thr Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys Gly Gly Gly Gly
                210                 215                 220

Ser Gly Gly Gly Gly Ser Gly Gly Gly Gly Ser Asp Ile Gln Met Thr
225                 230                 235                 240

Gln Ser Pro Ser Ser Leu Ser Ala Ser Val Gly Asp Arg Val Thr Ile
                245                 250                 255

Thr Cys Arg Ala Ser Gln Asp Val Ser Thr Ala Val Ala Trp Tyr Gln
                260                 265                 270

Gln Lys Pro Gly Lys Ala Pro Lys Leu Leu Ile Tyr Ser Ala Ser Phe
                275                 280                 285

Leu Tyr Ser Gly Val Pro Ser Arg Phe Ser Gly Ser Gly Ser Gly Thr
                290                 295                 300

Asp Phe Thr Leu Thr Ile Ser Ser Leu Gln Pro Glu Asp Phe Ala Thr
305                 310                 315                 320

Tyr Tyr Cys Gln Gln Tyr Leu Tyr His Pro Ala Thr Phe Gly Gln Gly
                325                 330                 335

Thr Lys Val Glu Ile Lys Gly Gly Gly Ile Glu Gly Arg Gly Gly Gly
                340                 345                 350

Asp Lys Thr His Thr Cys Pro Pro Cys Pro Ala Pro Glu Leu Leu Gly
                355                 360                 365

Gly Pro Ser Val Phe Leu Phe Pro Pro Lys Pro Lys Asp Thr Leu Met
370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Gln Ser Thr Tyr
                420                 425                 430

Arg Val Val Ser Val Leu Thr Val Leu His Gln Asp Trp Leu Asn Gly
                435                 440                 445
```

Lys Glu Tyr Lys Cys Lys Val Ser Asn Lys Ala Leu Pro Ala Pro Ile
            450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Asp Glu Leu Thr Lys Asn Gln Val Ser
                485                 490                 495

Leu Thr Cys Leu Val Ser Gly Phe Tyr Pro Ser Asp Ile Ala Val Glu
            500                 505                 510

Trp Glu Ser Asn Gly Gln Pro Glu Asn Asn Tyr Lys Thr Thr Pro Pro
            515                 520                 525

Val Leu Asp Ser Asp Gly Ser Phe Lys Leu Tyr Ser Lys Leu Thr Val
530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
            565                 570                 575

Pro Gly

<210> SEQ ID NO 171
<211> LENGTH: 599
<212> TYPE: PRT
<213> ORGANISM: Artificial Sequence
<220> FEATURE:
<223> OTHER INFORMATION: Anti-EpCAM VH-CH1, SP34 VH, FXa, Fc

<400> SEQUENCE: 171

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Gly Gly Ser Glu Val

```
            225                 230                 235                 240
        Gln Leu Val Glu Ser Gly Gly Leu Val Lys Pro Gly Gly Ser Leu
                        245                 250                 255

Arg Leu Ser Cys Ala Ala Ser Gly Phe Thr Phe Asn Thr Tyr Ala Met
                        260                 265                 270

Asn Trp Val Arg Gln Ala Pro Gly Lys Gly Leu Glu Trp Val Ala Arg
                        275                 280                 285

Ile Arg Ser Lys Tyr Asn Asn Tyr Ala Thr Tyr Tyr Ala Asp Ser Val
                290                 295                 300

Lys Gly Arg Phe Thr Ile Ser Arg Asp Asp Ser Lys Asn Ser Leu Tyr
        305                 310                 315                 320

Leu Gln Met Asn Ser Leu Lys Thr Glu Asp Thr Ala Val Tyr Tyr Cys
                        325                 330                 335

Val Arg His Gly Asn Phe Gly Asn Ser Tyr Val Ser Trp Phe Ala Tyr
                        340                 345                 350

Trp Gly Gln Gly Thr Leu Val Thr Val Ser Ser Gly Gly Gly Ile Glu
                        355                 360                 365

Gly Arg Gly Gly Gly Asp Lys Thr His Thr Cys Pro Pro Cys Pro Ala
                370                 375                 380

Pro Glu Leu Leu Gly Gly Pro Ser Val Phe Leu Phe Pro Pro Lys Pro
        385                 390                 395                 400

Lys Asp Thr Leu Met Ile Ser Arg Thr Pro Glu Val Thr Cys Val Val
                        405                 410                 415

Val Asp Val Ser His Glu Asp Pro Glu Val Lys Phe Asn Trp Tyr Val
                        420                 425                 430

Asp Gly Val Glu Val His Asn Ala Lys Thr Lys Pro Arg Glu Glu Gln
                435                 440                 445

Tyr Gln Ser Thr Tyr Arg Val Val Ser Val Leu Thr Val Leu His Gln
                    450                 455                 460

Asp Trp Leu Asn Gly Lys Glu Tyr Lys Cys Lys Val Ser Asn Lys Ala
        465                 470                 475                 480

Leu Pro Ala Pro Ile Glu Lys Thr Ile Ser Lys Ala Lys Gly Gln Pro
                        485                 490                 495

Arg Glu Pro Gln Val Tyr Thr Leu Pro Pro Ser Arg Asp Glu Leu Thr
                        500                 505                 510

Lys Asn Gln Val Lys Leu Thr Cys Leu Val Lys Gly Phe Tyr Pro Ser
                        515                 520                 525

Asp Ile Ala Val Glu Trp Glu Ser Asn Gly Gln Pro Glu Asn Asn Tyr
                530                 535                 540

Lys Thr Thr Pro Pro Val Leu Asp Ser Asp Gly Ser Phe Phe Leu Tyr
        545                 550                 555                 560

Ser Leu Leu Thr Val Asp Lys Ser Arg Trp Gln Gln Gly Asn Val Phe
                        565                 570                 575

Ser Cys Ser Val Met His Glu Ala Leu His Asn His Tyr Thr Gln Lys
                        580                 585                 590

Ser Leu Ser Leu Ser Pro Gly
                        595

<210> SEQ ID NO 172
<211> LENGTH: 578
<212> TYPE: PRT
<213> ORGANISM: Artificial Sequence
<220> FEATURE:
<223> OTHER INFORMATION: Anti-EpCAM VL-CL, Atezolizumab VL, FXa, Fc
```

```
<400> SEQUENCE: 172

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Asp Ile Gln Met Thr
225                 230                 235                 240

Gln Ser Pro Ser Ser Leu Ser Ala Ser Val Gly Asp Arg Val Thr Ile
                245                 250                 255

Thr Cys Arg Ala Ser Gln Asp Val Ser Thr Ala Val Ala Trp Tyr Gln
            260                 265                 270

Gln Lys Pro Gly Lys Ala Pro Lys Leu Leu Ile Tyr Ser Ala Ser Phe
        275                 280                 285

Leu Tyr Ser Gly Val Pro Ser Arg Phe Ser Gly Ser Gly Ser Gly Thr
    290                 295                 300

Asp Phe Thr Leu Thr Ile Ser Ser Leu Gln Pro Glu Asp Phe Ala Thr
305                 310                 315                 320

Tyr Tyr Cys Gln Gln Tyr Leu Tyr His Pro Ala Thr Phe Gly Gln Gly
                325                 330                 335

Thr Lys Val Glu Ile Lys Gly Gly Ile Glu Gly Arg Gly Gly Gly
            340                 345                 350

Asp Lys Thr His Thr Cys Pro Pro Cys Pro Ala Pro Glu Leu Leu Gly
        355                 360                 365

Gly Pro Ser Val Phe Leu Phe Pro Pro Lys Pro Lys Asp Thr Leu Met
    370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415
```

```
His Asn Ala Lys Thr Lys Pro Arg Glu Glu Gln Tyr Gln Ser Thr Tyr
            420                 425                 430

Arg Val Val Ser Val Leu Thr Val Leu His Gln Asp Trp Leu Asn Gly
            435                 440                 445

Lys Glu Tyr Lys Cys Lys Val Ser Asn Lys Ala Leu Pro Ala Pro Ile
450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Asp Glu Leu Thr Lys Asn Gln Val Ser
            485                 490                 495

Leu Thr Cys Leu Val Ser Gly Phe Tyr Pro Ser Asp Ile Ala Val Glu
            500                 505                 510

Trp Glu Ser Asn Gly Gln Pro Glu Asn Asn Tyr Lys Thr Thr Pro Pro
            515                 520                 525

Val Leu Asp Ser Asp Gly Ser Phe Lys Leu Tyr Ser Lys Leu Thr Val
            530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
            565                 570                 575

Pro Gly

<210> SEQ ID NO 173
<211> LENGTH: 601
<212> TYPE: PRT
<213> ORGANISM: Artificial Sequence
<220> FEATURE:
<223> OTHER INFORMATION: Anti-EpCAM VH-CH1, SP34 VH, FXa, Fc

<400> SEQUENCE: 173

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

-continued

```
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Gly Gly Gly Ser Gly Gly Gly Ser Glu Val
225                 230                 235                 240
Gln Leu Val Glu Ser Gly Gly Leu Val Lys Pro Gly Gly Ser Leu
            245                 250                 255
Arg Leu Ser Cys Ala Ala Ser Gly Phe Thr Phe Asn Thr Tyr Ala Met
                260                 265                 270
Asn Trp Val Arg Gln Ala Pro Gly Lys Gly Leu Glu Trp Val Ala Arg
            275                 280                 285
Ile Arg Ser Lys Tyr Asn Asn Tyr Ala Thr Tyr Tyr Ala Asp Ser Val
            290                 295                 300
Lys Gly Arg Phe Thr Ile Ser Arg Asp Asp Ser Lys Asn Ser Leu Tyr
305                 310                 315                 320
Leu Gln Met Asn Ser Leu Lys Thr Glu Asp Thr Ala Val Tyr Tyr Cys
                325                 330                 335
Val Arg His Gly Asn Phe Gly Asn Ser Tyr Val Ser Trp Phe Ala Tyr
                340                 345                 350
Trp Gly Gln Gly Thr Leu Val Thr Val Ser Ser Gly Gly Gly Gly Ser
            355                 360                 365
Ile Glu Gly Arg Gly Gly Asp Lys Thr His Thr Cys Pro Pro Cys
            370                 375                 380
Pro Ala Pro Glu Leu Leu Gly Gly Pro Ser Val Phe Leu Phe Pro Pro
385                 390                 395                 400
Lys Pro Lys Asp Thr Leu Met Ile Ser Arg Thr Pro Glu Val Thr Cys
                405                 410                 415
Val Val Val Asp Val Ser His Glu Asp Pro Glu Val Lys Phe Asn Trp
                420                 425                 430
Tyr Val Asp Gly Val Glu Val His Asn Ala Lys Thr Lys Pro Arg Glu
            435                 440                 445
Glu Gln Tyr Gln Ser Thr Tyr Arg Val Val Ser Val Leu Thr Val Leu
            450                 455                 460
His Gln Asp Trp Leu Asn Gly Lys Glu Tyr Lys Cys Lys Val Ser Asn
465                 470                 475                 480
Lys Ala Leu Pro Ala Pro Ile Glu Lys Thr Ile Ser Lys Ala Lys Gly
                485                 490                 495
Gln Pro Arg Glu Pro Gln Val Tyr Thr Leu Pro Pro Ser Arg Asp Glu
            500                 505                 510
Leu Thr Lys Asn Gln Val Lys Leu Thr Cys Leu Val Lys Gly Phe Tyr
            515                 520                 525
Pro Ser Asp Ile Ala Val Glu Trp Glu Ser Asn Gly Gln Pro Glu Asn
530                 535                 540
Asn Tyr Lys Thr Thr Pro Pro Val Leu Asp Ser Asp Gly Ser Phe Phe
545                 550                 555                 560
Leu Tyr Ser Leu Leu Thr Val Asp Lys Ser Arg Trp Gln Gln Gly Asn
                565                 570                 575
Val Phe Ser Cys Ser Val Met His Glu Ala Leu His Asn His Tyr Thr
                580                 585                 590
Gln Lys Ser Leu Ser Leu Ser Pro Gly
            595                 600
```

<210> SEQ ID NO 174
<211> LENGTH: 580
<212> TYPE: PRT
<213> ORGANISM: Artificial Sequence
<220> FEATURE:
<223> OTHER INFORMATION: Anti-EpCAM VL-CL, Atezolizumab VL, FXa, Fc

<400> SEQUENCE: 174

```
Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Asp Ile Gln Met Thr
225                 230                 235                 240

Gln Ser Pro Ser Ser Leu Ser Ala Ser Val Gly Asp Arg Val Thr Ile
                245                 250                 255

Thr Cys Arg Ala Ser Gln Asp Val Ser Thr Ala Val Ala Trp Tyr Gln
            260                 265                 270

Gln Lys Pro Gly Lys Ala Pro Lys Leu Leu Ile Tyr Ser Ala Ser Phe
        275                 280                 285

Leu Tyr Ser Gly Val Pro Ser Arg Phe Ser Gly Ser Gly Ser Gly Thr
    290                 295                 300

Asp Phe Thr Leu Thr Ile Ser Ser Leu Gln Pro Glu Asp Phe Ala Thr
305                 310                 315                 320

Tyr Tyr Cys Gln Gln Tyr Leu Tyr His Pro Ala Thr Phe Gly Gln Gly
                325                 330                 335

Thr Lys Val Glu Ile Lys Gly Gly Gly Ser Ile Glu Gly Arg Gly
            340                 345                 350

Gly Gly Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
```

```
            370                 375                 380
Leu Met Ile Ser Arg Thr Pro Glu Val Thr Cys Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Gln Tyr Gln Ser
            420                 425                 430

Thr Tyr Arg Val Val Ser Val Leu Thr Val Leu His Gln Asp Trp Leu
            435                 440                 445

Asn Gly Lys Glu Tyr Lys Cys Lys Val Ser Asn Lys Ala Leu Pro Ala
    450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Asp Glu Leu Thr Lys Asn Gln
                485                 490                 495

Val Ser Leu Thr Cys Leu Val Ser Gly Phe Tyr Pro Ser Asp Ile Ala
            500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Lys Leu Tyr Ser Lys Leu
530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly
            580

<210> SEQ ID NO 175
<211> LENGTH: 418
<212> TYPE: PRT
<213> ORGANISM: Artificial Sequence
<220> FEATURE:
<223> OTHER INFORMATION: Anti-EpCAM VH-CH1, SP34 VH, FXa, basic coil

<400> SEQUENCE: 175

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
```

```
                    145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
210                 215                 220
Lys Thr His Thr Gly Gly Gly Ser Gly Gly Gly Ser Glu Val
225                 230                 235                 240
Gln Leu Val Glu Ser Gly Gly Leu Val Lys Pro Gly Gly Ser Leu
                245                 250                 255
Arg Leu Ser Cys Ala Ala Ser Gly Phe Thr Phe Asn Thr Tyr Ala Met
                260                 265                 270
Asn Trp Val Arg Gln Ala Pro Gly Lys Gly Leu Glu Trp Val Ala Arg
                275                 280                 285
Ile Arg Ser Lys Tyr Asn Asn Tyr Ala Thr Tyr Tyr Ala Asp Ser Val
                290                 295                 300
Lys Gly Arg Phe Thr Ile Ser Arg Asp Asp Ser Lys Asn Ser Leu Tyr
305                 310                 315                 320
Leu Gln Met Asn Ser Leu Lys Thr Glu Asp Thr Ala Val Tyr Tyr Cys
                325                 330                 335
Val Arg His Gly Asn Phe Gly Asn Ser Tyr Val Ser Trp Phe Ala Tyr
                340                 345                 350
Trp Gly Gln Gly Thr Leu Val Thr Val Ser Ser Gly Gly Gly Gly Ser
                355                 360                 365
Ile Glu Gly Arg Gly Gly Ser Gly Gly Ser Lys Asn Ala Gln Cys
                370                 375                 380
Lys Lys Lys Leu Gln Ala Leu Lys Lys Lys Asn Ala Gln Leu Lys Trp
385                 390                 395                 400
Lys Leu Gln Ala Leu Lys Lys Lys Leu Ala Gln Gly His His His His
                405                 410                 415
His His

<210> SEQ ID NO 176
<211> LENGTH: 390
<212> TYPE: PRT
<213> ORGANISM: Artificial Sequence
<220> FEATURE:
<223> OTHER INFORMATION: Anti-EpCAM VL-CL, Atezolizumab VL, FXa, acid
      coil

<400> SEQUENCE: 176

Glu Leu Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
                20                  25                  30
Gly Asn Gln Lys Asn Tyr Leu Thr Trp Tyr Gln Gln Lys Pro Gly Gln
            35                  40                  45
Pro Pro Lys Leu Leu Ile Tyr Trp Ala Ser Thr Arg Glu Ser Gly Val
        50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
```

```
                    85                  90                  95
Asp Tyr Ser Tyr Pro Leu Thr Phe Gly Ala Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Asp Ile Gln Met Thr
225                 230                 235                 240

Gln Ser Pro Ser Ser Leu Ser Ala Ser Val Gly Asp Arg Val Thr Ile
                245                 250                 255

Thr Cys Arg Ala Ser Gln Asp Val Ser Thr Ala Val Ala Trp Tyr Gln
            260                 265                 270

Gln Lys Pro Gly Lys Ala Pro Lys Leu Leu Ile Tyr Ser Ala Ser Phe
        275                 280                 285

Leu Tyr Ser Gly Val Pro Ser Arg Phe Ser Gly Ser Gly Ser Gly Thr
    290                 295                 300

Asp Phe Thr Leu Thr Ile Ser Ser Leu Gln Pro Glu Asp Phe Ala Thr
305                 310                 315                 320

Tyr Tyr Cys Gln Gln Tyr Leu Tyr His Pro Ala Thr Phe Gly Gln Gly
                325                 330                 335

Thr Lys Val Glu Ile Lys Gly Gly Gly Gly Ser Ile Glu Gly Arg Gly
            340                 345                 350

Gly Ser Gly Gly Ser Glu Asn Ala Gln Cys Glu Lys Glu Leu Gln
        355                 360                 365

Ala Leu Glu Lys Glu Asn Ala Gln Leu Glu Trp Glu Leu Gln Ala Leu
    370                 375                 380

Glu Lys Glu Leu Ala Gln
385                 390

<210> SEQ ID NO 177
<211> LENGTH: 467
<212> TYPE: PRT
<213> ORGANISM: Artificial Sequence
<220> FEATURE:
<223> OTHER INFORMATION: Anti-EpCAM VL-CL, SP34 VH, FXa, Ckappa

<400> SEQUENCE: 177

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
```

```
              50                  55                  60
Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys Gly Gly Gly Gly
            210                 215                 220

Ser Gly Gly Gly Gly Ser Gly Gly Gly Gly Ser Glu Val Gln Leu Val
225                 230                 235                 240

Glu Ser Gly Gly Gly Leu Val Lys Pro Gly Gly Ser Leu Arg Leu Ser
                245                 250                 255

Cys Ala Ala Ser Gly Phe Thr Phe Asn Thr Tyr Ala Met Asn Trp Val
            260                 265                 270

Arg Gln Ala Pro Gly Lys Gly Leu Glu Trp Val Ala Arg Ile Arg Ser
            275                 280                 285

Lys Tyr Asn Asn Tyr Ala Thr Tyr Tyr Ala Asp Ser Val Lys Gly Arg
            290                 295                 300

Phe Thr Ile Ser Arg Asp Asp Ser Lys Asn Ser Leu Tyr Leu Gln Met
305                 310                 315                 320

Asn Ser Leu Lys Thr Glu Asp Thr Ala Val Tyr Tyr Cys Val Arg His
                325                 330                 335

Gly Asn Phe Gly Asn Ser Tyr Val Ser Trp Phe Ala Tyr Trp Gly Gln
            340                 345                 350

Gly Thr Leu Val Thr Val Ser Ser Ile Glu Gly Arg Gly Pro Ser Val
            355                 360                 365

Phe Ile Phe Pro Pro Ser Asp Glu Gln Leu Lys Ser Gly Thr Ala Ser
370                 375                 380

Val Val Cys Leu Leu Asn Asn Phe Tyr Pro Arg Glu Ala Lys Val Gln
385                 390                 395                 400

Trp Lys Val Asp Asn Ala Leu Gln Ser Gly Asn Ser Gln Glu Ser Val
                405                 410                 415

Thr Glu Gln Asp Ser Lys Asp Ser Thr Tyr Ser Leu Ser Ser Thr Leu
            420                 425                 430

Thr Leu Ser Lys Ala Asp Tyr Glu Lys His Lys Val Tyr Ala Cys Glu
            435                 440                 445

Val Thr His Gln Gly Leu Ser Ser Pro Val Thr Lys Ser Phe Asn Arg
            450                 455                 460

Gly Glu Cys
465
```

<210> SEQ ID NO 178
<211> LENGTH: 456
<212> TYPE: PRT
<213> ORGANISM: Artificial Sequence
<220> FEATURE:
<223> OTHER INFORMATION: Anti-EpCAM VH-CH1, Atezolizumab VL, FXa, CH1, 6His

<400> SEQUENCE: 178

```
Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Gly Gly Ser Asp Ile
225                 230                 235                 240

Gln Met Thr Gln Ser Pro Ser Ser Leu Ser Ala Ser Val Gly Asp Arg
                245                 250                 255

Val Thr Ile Thr Cys Arg Ala Ser Gln Asp Val Ser Thr Ala Val Ala
            260                 265                 270

Trp Tyr Gln Gln Lys Pro Gly Lys Ala Pro Lys Leu Leu Ile Tyr Ser
        275                 280                 285

Ala Ser Phe Leu Tyr Ser Gly Val Pro Ser Arg Phe Ser Gly Ser Gly
    290                 295                 300

Ser Gly Thr Asp Phe Thr Leu Thr Ile Ser Ser Leu Gln Pro Glu Asp
305                 310                 315                 320

Phe Ala Thr Tyr Tyr Cys Gln Gln Tyr Leu Tyr His Pro Ala Thr Phe
                325                 330                 335

Gly Gln Gly Thr Lys Val Glu Ile Lys Gly Gly Ile Glu Gly Arg Gly
            340                 345                 350

Pro Ser Val Phe Pro Leu Ala Pro Ser Ser Lys Ser Thr Ser Gly Gly
```

```
            355                 360                 365
Thr Ala Ala Leu Gly Cys Leu Val Lys Asp Tyr Phe Pro Glu Pro Val
            370                 375                 380
Thr Val Ser Trp Asn Ser Gly Ala Leu Thr Ser Gly Val His Thr Phe
385                 390                 395                 400
Pro Ala Val Leu Gln Ser Ser Gly Leu Tyr Ser Leu Ser Ser Val Val
            405                 410                 415
Thr Val Pro Ser Ser Ser Leu Gly Thr Gln Thr Tyr Ile Cys Asn Val
            420                 425                 430
Asn His Lys Pro Ser Asn Thr Lys Val Asp Lys Lys Val Glu Pro Lys
            435                 440                 445
Ser Cys His His His His His His
            450                 455

<210> SEQ ID NO 179
<211> LENGTH: 460
<212> TYPE: PRT
<213> ORGANISM: Artificial Sequence
<220> FEATURE:
<223> OTHER INFORMATION: Anti-EpCAM VL-CL, Atezolizumab VH, FXa, Ckappa

<400> SEQUENCE: 179

Glu Leu Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp Tyr Ser Tyr Pro Leu Thr Phe Gly Ala Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys Gly Gly Gly Gly
    210                 215                 220
Ser Gly Gly Gly Gly Ser Gly Gly Gly Ser Glu Val Gln Leu Val
225                 230                 235                 240
Glu Ser Gly Gly Gly Leu Val Gln Pro Gly Gly Ser Leu Arg Leu Ser
                245                 250                 255
Cys Ala Ala Ser Gly Phe Thr Phe Ser Asp Ser Trp Ile His Trp Val
```

```
            260                 265                 270
Arg Gln Ala Pro Gly Lys Gly Leu Glu Trp Val Ala Trp Ile Ser Pro
        275                 280                 285

Tyr Gly Gly Ser Thr Tyr Tyr Ala Asp Ser Val Lys Gly Arg Phe Thr
        290                 295                 300

Ile Ser Ala Asp Thr Ser Lys Asn Thr Ala Tyr Leu Gln Met Asn Ser
305                 310                 315                 320

Leu Arg Ala Glu Asp Thr Ala Val Tyr Tyr Cys Ala Arg Arg His Trp
                325                 330                 335

Pro Gly Gly Phe Asp Tyr Trp Gly Gln Gly Thr Leu Val Thr Val Ser
            340                 345                 350

Ser Ile Glu Gly Arg Gly Pro Ser Val Phe Ile Phe Pro Pro Ser Asp
        355                 360                 365

Glu Gln Leu Lys Ser Gly Thr Ala Ser Val Val Cys Leu Leu Asn Asn
        370                 375                 380

Phe Tyr Pro Arg Glu Ala Lys Val Gln Trp Lys Val Asp Asn Ala Leu
385                 390                 395                 400

Gln Ser Gly Asn Ser Gln Glu Ser Val Thr Glu Gln Asp Ser Lys Asp
                405                 410                 415

Ser Thr Tyr Ser Leu Ser Ser Thr Leu Thr Leu Ser Lys Ala Asp Tyr
            420                 425                 430

Glu Lys His Lys Val Tyr Ala Cys Glu Val Thr His Gln Gly Leu Ser
        435                 440                 445

Ser Pro Val Thr Lys Ser Phe Asn Arg Gly Glu Cys
        450                 455                 460

<210> SEQ ID NO 180
<211> LENGTH: 458
<212> TYPE: PRT
<213> ORGANISM: Artificial Sequence
<220> FEATURE:
<223> OTHER INFORMATION: Anti-EpCAM VH-CH1, SP34 VL, FXa, CH1, 6His

<400> SEQUENCE: 180

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
```

```
                    165                 170                 175
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His Thr Gly Gly Gly Ser Gly Gly Gly Ser Gln Ala
225                 230                 235             240

Val Val Thr Gln Glu Pro Ser Leu Thr Val Ser Pro Gly Gly Thr Val
            245                 250                 255

Thr Leu Thr Cys Arg Ser Ser Thr Gly Ala Val Thr Ala Ser Asn Tyr
            260                 265                 270

Ala Asn Trp Val Gln Gln Lys Pro Gly Gln Ala Pro Arg Gly Leu Ile
            275                 280                 285

Gly Gly Thr Asn Lys Arg Ala Pro Trp Thr Pro Ala Arg Phe Ser Gly
            290                 295                 300

Ser Leu Leu Gly Gly Lys Ala Ala Leu Thr Ile Thr Gly Ala Gln Ala
305                 310                 315                 320

Glu Asp Glu Ala Asp Tyr Tyr Cys Ala Leu Trp Tyr Ser Asn Leu Trp
            325                 330                 335

Val Phe Gly Gly Gly Thr Lys Leu Thr Val Leu Gly Ile Glu Gly
            340                 345                 350

Arg Gly Pro Ser Val Phe Pro Leu Ala Pro Ser Ser Lys Ser Thr Ser
            355                 360                 365

Gly Gly Thr Ala Ala Leu Gly Cys Leu Val Lys Asp Tyr Phe Pro Glu
            370                 375                 380

Pro Val Thr Val Ser Trp Asn Ser Gly Ala Leu Thr Ser Gly Val His
385                 390                 395                 400

Thr Phe Pro Ala Val Leu Gln Ser Ser Gly Leu Tyr Ser Leu Ser Ser
            405                 410                 415

Val Val Thr Val Pro Ser Ser Ser Leu Gly Thr Gln Thr Tyr Ile Cys
            420                 425                 430

Asn Val Asn His Lys Pro Ser Asn Thr Lys Val Asp Lys Lys Val Glu
            435                 440                 445

Pro Lys Ser Cys His His His His His His
            450                 455

<210> SEQ ID NO 181
<211> LENGTH: 579
<212> TYPE: PRT
<213> ORGANISM: Artificial Sequence
<220> FEATURE:
<223> OTHER INFORMATION: Anti-EpCAM VL-CL, Ipilimumab VL, FXa, Fc

<400> SEQUENCE: 181

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
            50                  55                  60

Pro Asp Arg Phe Thr Gly Ser Gly Ser Gly Thr Asp Phe Thr Leu Thr
```

-continued

```
                65                  70                  75                  80
        Ile Ser Ser Val Gln Ala Glu Asp Leu Ala Val Tyr Tyr Cys Gln Asn
                            85                  90                  95

Asp Tyr Ser Tyr Pro Leu Thr Phe Gly Ala Gly Thr Lys Leu Glu Ile
                        100                 105                 110

Lys Arg Thr Val Ala Ala Pro Ser Val Phe Ile Phe Pro Pro Ser Asp
                        115                 120                 125

Glu Gln Leu Lys Ser Gly Thr Ala Ser Val Val Cys Leu Leu Asn Asn
                130                 135                 140

Phe Tyr Pro Arg Glu Ala Lys Val Gln Trp Lys Val Asp Asn Ala Leu
        145                 150                 155                 160

Gln Ser Gly Asn Ser Gln Glu Ser Val Thr Glu Gln Asp Ser Lys Asp
                        165                 170                 175

Ser Thr Tyr Ser Leu Ser Ser Thr Leu Thr Leu Ser Lys Ala Asp Tyr
                        180                 185                 190

Glu Lys His Lys Val Tyr Ala Cys Glu Val Thr His Gln Gly Leu Ser
                        195                 200                 205

Ser Pro Val Thr Lys Ser Phe Asn Arg Gly Glu Cys Gly Gly Gly Gly
                        210                 215                 220

Ser Gly Gly Gly Gly Ser Gly Gly Gly Gly Ser Glu Ile Val Leu Thr
        225                 230                 235                 240

Gln Ser Pro Gly Thr Leu Ser Leu Ser Pro Gly Glu Arg Ala Thr Leu
                        245                 250                 255

Ser Cys Arg Ala Ser Gln Ser Val Gly Ser Ser Tyr Leu Ala Trp Tyr
                        260                 265                 270

Gln Gln Lys Pro Gly Gln Ala Pro Arg Leu Leu Ile Tyr Gly Ala Phe
                        275                 280                 285

Ser Arg Ala Thr Gly Ile Pro Asp Arg Phe Ser Gly Ser Gly Ser Gly
                        290                 295                 300

Thr Asp Phe Thr Leu Thr Ile Ser Arg Leu Glu Pro Glu Asp Phe Ala
        305                 310                 315                 320

Val Tyr Tyr Cys Gln Gln Tyr Gly Ser Ser Pro Trp Thr Phe Gly Gln
                        325                 330                 335

Gly Thr Lys Val Glu Ile Lys Gly Gly Gly Ile Glu Gly Arg Gly Gly
                        340                 345                 350

Gly Asp Lys Thr His Thr Cys Pro Pro Cys Pro Ala Pro Glu Leu Leu
                        355                 360                 365

Gly Gly Pro Ser Val Phe Leu Phe Pro Pro Lys Pro Lys Asp Thr Leu
                        370                 375                 380

Met Ile Ser Arg Thr Pro Glu Val Thr Cys Val Val Val Asp Val Ser
        385                 390                 395                 400

His Glu Asp Pro Glu Val Lys Phe Asn Trp Tyr Val Asp Gly Val Glu
                        405                 410                 415

Val His Asn Ala Lys Thr Lys Pro Arg Glu Glu Gln Tyr Gln Ser Thr
                        420                 425                 430

Tyr Arg Val Val Ser Val Leu Thr Val Leu His Gln Asp Trp Leu Asn
                        435                 440                 445

Gly Lys Glu Tyr Lys Cys Lys Val Ser Asn Lys Ala Leu Pro Ala Pro
                        450                 455                 460

Ile Glu Lys Thr Ile Ser Lys Ala Lys Gly Gln Pro Arg Glu Pro Gln
        465                 470                 475                 480

Val Tyr Thr Leu Pro Pro Ser Arg Asp Glu Leu Thr Lys Asn Gln Val
                        485                 490                 495
```

```
Ser Leu Thr Cys Leu Val Ser Gly Phe Tyr Pro Ser Asp Ile Ala Val
            500                 505                 510

Glu Trp Glu Ser Asn Gly Gln Pro Glu Asn Asn Tyr Lys Thr Thr Pro
515                 515                 520                 525

Pro Val Leu Asp Ser Asp Gly Ser Phe Lys Leu Tyr Ser Lys Leu Thr
            530                 535                 540

Val Asp Lys Ser Arg Trp Gln Gln Gly Asn Val Phe Ser Cys Ser Val
545                 550                 555                 560

Met His Glu Ala Leu His Asn His Tyr Thr Gln Lys Ser Leu Ser Leu
            565                 570                 575

Ser Pro Gly

<210> SEQ ID NO 182
<211> LENGTH: 592
<212> TYPE: PRT
<213> ORGANISM: Artificial Sequence
<220> FEATURE:
<223> OTHER INFORMATION: Anti-EpCAM VH-CH1, Ipilimumab VH, FXa, Fc

<400> SEQUENCE: 182

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Gly Ser Gly Gly Gly Gly Ser Gln Val
225                 230                 235                 240

Gln Leu Val Glu Ser Gly Gly Val Val Gln Pro Gly Arg Ser Leu
                245                 250                 255

Arg Leu Ser Cys Ala Ala Ser Gly Phe Thr Phe Ser Ser Tyr Thr Met
            260                 265                 270
```

His Trp Val Arg Gln Ala Pro Gly Lys Gly Leu Glu Trp Val Thr Phe
            275                 280                 285
Ile Ser Tyr Asp Gly Asn Asn Lys Tyr Tyr Ala Asp Ser Val Lys Gly
            290                 295                 300
Arg Phe Thr Ile Ser Arg Asp Asn Ser Lys Asn Thr Leu Tyr Leu Gln
305                 310                 315                 320
Met Asn Ser Leu Arg Ala Glu Asp Thr Ala Ile Tyr Tyr Cys Ala Arg
            325                 330                 335
Thr Gly Trp Leu Gly Pro Phe Asp Tyr Trp Gly Gln Gly Thr Leu Val
            340                 345                 350
Thr Val Ser Ser Gly Gly Gly Ile Glu Gly Arg Gly Gly Asp Lys
            355                 360                 365
Thr His Thr Cys Pro Pro Cys Pro Ala Pro Glu Leu Leu Gly Gly Pro
            370                 375                 380
Ser Val Phe Leu Phe Pro Pro Lys Pro Lys Asp Thr Leu Met Ile Ser
385                 390                 395                 400
Arg Thr Pro Glu Val Thr Cys Val Val Val Asp Val Ser His Glu Asp
            405                 410                 415
Pro Glu Val Lys Phe Asn Trp Tyr Val Asp Gly Val Glu Val His Asn
            420                 425                 430
Ala Lys Thr Lys Pro Arg Glu Glu Gln Tyr Gln Ser Thr Tyr Arg Val
            435                 440                 445
Val Ser Val Leu Thr Val Leu His Gln Asp Trp Leu Asn Gly Lys Glu
450                 455                 460
Tyr Lys Cys Lys Val Ser Asn Lys Ala Leu Pro Ala Pro Ile Glu Lys
465                 470                 475                 480
Thr Ile Ser Lys Ala Lys Gly Gln Pro Arg Glu Pro Gln Val Tyr Thr
            485                 490                 495
Leu Pro Pro Ser Arg Asp Glu Leu Thr Lys Asn Gln Val Lys Leu Thr
            500                 505                 510
Cys Leu Val Lys Gly Phe Tyr Pro Ser Asp Ile Ala Val Glu Trp Glu
            515                 520                 525
Ser Asn Gly Gln Pro Glu Asn Asn Tyr Lys Thr Thr Pro Pro Val Leu
530                 535                 540
Asp Ser Asp Gly Ser Phe Phe Leu Tyr Ser Leu Leu Thr Val Asp Lys
545                 550                 555                 560
Ser Arg Trp Gln Gln Gly Asn Val Phe Ser Cys Ser Val Met His Glu
            565                 570                 575
Ala Leu His Asn His Tyr Thr Gln Lys Ser Leu Ser Leu Ser Pro Gly
            580                 585                 590

<210> SEQ ID NO 183
<211> LENGTH: 580
<212> TYPE: PRT
<213> ORGANISM: Artificial Sequence
<220> FEATURE:
<223> OTHER INFORMATION: Anti-EpCAM VL-CL, SP34 VL, FXa, Fc

<400> SEQUENCE: 183

Glu Leu Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
            35                  40                  45

-continued

```
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp Tyr Ser Tyr Pro Leu Thr Phe Gly Ala Gly Thr Lys Leu Glu Ile
            100                 105                 110
Lys Arg Thr Val Ala Ala Pro Ser Val Phe Ile Phe Pro Pro Ser Asp
        115                 120                 125
Glu Gln Leu Lys Ser Gly Thr Ala Ser Val Val Cys Leu Leu Asn Asn
    130                 135                 140
Phe Tyr Pro Arg Glu Ala Lys Val Gln Trp Lys Val Asp Asn Ala Leu
145                 150                 155                 160
Gln Ser Gly Asn Ser Gln Glu Ser Val Thr Glu Gln Asp Ser Lys Asp
                165                 170                 175
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys Gly Gly Gly Gly
    210                 215                 220
Ser Gly Gly Gly Gly Ser Gly Gly Gly Gly Ser Gln Ala Val Val Thr
225                 230                 235                 240
Gln Glu Pro Ser Leu Thr Val Ser Pro Gly Gly Thr Val Thr Leu Thr
                245                 250                 255
Cys Arg Ser Ser Thr Gly Ala Val Thr Ala Ser Asn Tyr Ala Asn Trp
            260                 265                 270
Val Gln Gln Lys Pro Gly Gln Ala Pro Arg Gly Leu Ile Gly Gly Thr
        275                 280                 285
Asn Lys Arg Ala Pro Trp Thr Pro Ala Arg Phe Ser Gly Ser Leu Leu
    290                 295                 300
Gly Gly Lys Ala Ala Leu Thr Ile Thr Gly Ala Gln Ala Glu Asp Glu
305                 310                 315                 320
Ala Asp Tyr Tyr Cys Ala Leu Trp Tyr Ser Asn Leu Trp Val Phe Gly
                325                 330                 335
Gly Gly Thr Lys Leu Thr Val Leu Gly Gly Ile Glu Gly Arg Gly
            340                 345                 350
Gly Gly Asp Lys Thr His Thr Cys Pro Pro Cys Pro Ala Pro Glu Leu
        355                 360                 365
Leu Gly Gly Pro Ser Val Phe Leu Phe Pro Pro Lys Pro Lys Asp Thr
    370                 375                 380
Leu Met Ile Ser Arg Thr Pro Glu Val Thr Cys Val Val Val Asp Val
385                 390                 395                 400
Ser His Glu Asp Pro Glu Val Lys Phe Asn Trp Tyr Val Asp Gly Val
                405                 410                 415
Glu Val His Asn Ala Lys Thr Lys Pro Arg Glu Glu Gln Tyr Gln Ser
            420                 425                 430
Thr Tyr Arg Val Val Ser Val Leu Thr Val Leu His Gln Asp Trp Leu
        435                 440                 445
Asn Gly Lys Glu Tyr Lys Cys Lys Val Ser Asn Lys Ala Leu Pro Ala
    450                 455                 460
Pro Ile Glu Lys Thr Ile Ser Lys Ala Lys Gly Gln Pro Arg Glu Pro
```

```
                465                 470                 475                 480
Gln Val Tyr Thr Leu Pro Pro Ser Arg Asp Glu Leu Thr Lys Asn Gln
                485                 490                 495

Val Ser Leu Thr Cys Leu Val Ser Gly Phe Tyr Pro Ser Asp Ile Ala
                500                 505                 510

Val Glu Trp Glu Ser Asn Gly Gln Pro Glu Asn Asn Tyr Lys Thr Thr
                515                 520                 525

Pro Pro Val Leu Asp Ser Asp Gly Ser Phe Lys Leu Tyr Ser Lys Leu
                530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly
                580

<210> SEQ ID NO 184
<211> LENGTH: 388
<212> TYPE: PRT
<213> ORGANISM: Artificial Sequence
<220> FEATURE:
<223> OTHER INFORMATION: Anti-EpCAM VL-CL, Ipilimumab VL, MMP2, acid
      coil

<400> SEQUENCE: 184

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
                100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Glu Ile Val Leu Thr
225                 230                 235                 240
```

```
Gln Ser Pro Gly Thr Leu Ser Leu Ser Pro Gly Glu Arg Ala Thr Leu
                245                 250                 255

Ser Cys Arg Ala Ser Gln Ser Val Gly Ser Ser Tyr Leu Ala Trp Tyr
            260                 265                 270

Gln Gln Lys Pro Gly Gln Ala Pro Arg Leu Leu Ile Tyr Gly Ala Phe
        275                 280                 285

Ser Arg Ala Thr Gly Ile Pro Asp Arg Phe Ser Gly Ser Gly Ser Gly
    290                 295                 300

Thr Asp Phe Thr Leu Thr Ile Ser Arg Leu Glu Pro Glu Asp Phe Ala
305                 310                 315                 320

Val Tyr Tyr Cys Gln Gln Tyr Gly Ser Ser Pro Trp Thr Phe Gly Gln
                325                 330                 335

Gly Thr Lys Val Glu Ile Lys Gly Gly Pro Leu Gly Val Arg Gly Lys
            340                 345                 350

Gly Gly Gly Ser Glu Asn Ala Gln Cys Glu Lys Glu Leu Gln Ala Leu
        355                 360                 365

Glu Lys Glu Asn Ala Gln Leu Glu Trp Glu Leu Gln Ala Leu Glu Lys
    370                 375                 380

Glu Leu Ala Gln
385

<210> SEQ ID NO 185
<211> LENGTH: 409
<212> TYPE: PRT
<213> ORGANISM: Artificial Sequence
<220> FEATURE:
<223> OTHER INFORMATION: Anti-EpCAM VH-CH1, Ipilimuab VH, FXa, basic
      coil

<400> SEQUENCE: 185

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Val Glu Pro Lys Ser Cys Asp
    210                 215                 220

Lys Thr His Thr Gly Gly Gly Gly Ser Gly Gly Gly Gly Ser Gln Val
225                 230                 235                 240

Gln Leu Val Glu Ser Gly Gly Val Val Gln Pro Gly Arg Ser Leu
                245                 250                 255

Arg Leu Ser Cys Ala Ala Ser Gly Phe Thr Phe Ser Ser Tyr Thr Met
                260                 265                 270

His Trp Val Arg Gln Ala Pro Gly Lys Gly Leu Glu Trp Val Thr Phe
            275                 280                 285

Ile Ser Tyr Asp Gly Asn Asn Lys Tyr Tyr Ala Asp Ser Val Lys Gly
    290                 295                 300

Arg Phe Thr Ile Ser Arg Asp Asn Ser Lys Asn Thr Leu Tyr Leu Gln
305                 310                 315                 320

Met Asn Ser Leu Arg Ala Glu Asp Thr Ala Ile Tyr Tyr Cys Ala Arg
                325                 330                 335

Thr Gly Trp Leu Gly Pro Phe Asp Tyr Trp Gly Gln Gly Thr Leu Val
                340                 345                 350

Thr Val Ser Ser Gly Gly Gly Gly Ser Ile Glu Gly Arg Gly Gly Gly
                355                 360                 365

Gly Ser Lys Asn Ala Gln Cys Lys Lys Lys Leu Gln Ala Leu Lys Lys
    370                 375                 380

Lys Asn Ala Gln Leu Lys Trp Lys Leu Gln Ala Leu Lys Lys Lys Leu
385                 390                 395                 400

Ala Gln Gly His His His His His His
                405

<210> SEQ ID NO 186
<211> LENGTH: 389
<212> TYPE: PRT
<213> ORGANISM: Artificial Sequence
<220> FEATURE:
<223> OTHER INFORMATION: Anti-EpCAM VL-CL, SP34 VL, MMP2, acid coil

<400> SEQUENCE: 186

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys Gly Gly Gly
            210                 215                 220

Ser Gly Gly Gly Gly Ser Gly Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Arg Ser Ser Thr Gly Ala Val Thr Ala Ser Asn Tyr Ala Asn Trp
                260                 265                 270

Val Gln Gln Lys Pro Gly Gln Ala Pro Arg Gly Leu Ile Gly Gly Thr
                275                 280                 285

Asn Lys Arg Ala Pro Trp Thr Pro Ala Arg Phe Ser Gly Ser Leu Leu
                290                 295                 300

Gly Gly Lys Ala Ala Leu Thr Ile Thr Gly Ala Gln Ala Glu Asp Glu
305                 310                 315                 320

Ala Asp Tyr Tyr Cys Ala Leu Trp Tyr Ser Asn Leu Trp Val Phe Gly
                325                 330                 335

Gly Gly Thr Lys Leu Thr Val Leu Gly Gly Pro Leu Gly Val Arg Gly
                340                 345                 350

Lys Gly Gly Ser Glu Asn Ala Gln Cys Glu Lys Glu Leu Gln Ala
                355                 360                 365

Leu Glu Lys Glu Asn Ala Gln Leu Glu Trp Glu Leu Gln Ala Leu Glu
370                 375                 380

Lys Glu Leu Ala Gln
385

<210> SEQ ID NO 187
<211> LENGTH: 409
<212> TYPE: PRT
<213> ORGANISM: Artificial Sequence
<220> FEATURE:
<223> OTHER INFORMATION: Anti-EpCAM VH-CH1, Atezolizumab VH, FXa, basic
      coil

<400> SEQUENCE: 187

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
                20                  25                  30

Tyr Trp Leu Gly Trp Val Lys Gln Arg Pro Gly His Gly Leu Glu Trp
            35                  40                  45

Ile Gly Asp Ile Phe Pro Gly Ser Gly Asn Ile His Tyr Asn Glu Lys
        50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
                100                 105                 110

Gly Thr Thr Val Thr Val Ser Ser Ala Ser Thr Lys Gly Pro Ser Val
```

```
              115                 120                 125
Phe Pro Leu Ala Pro Ser Ser Lys Ser Thr Ser Gly Gly Thr Ala Ala
            130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Gly Gly Gly Gly Ser Gly Gly Gly Gly Ser Glu Val
225                 230                 235                 240
Gln Leu Val Glu Ser Gly Gly Gly Leu Val Gln Pro Gly Gly Ser Leu
                245                 250                 255
Arg Leu Ser Cys Ala Ala Ser Gly Phe Thr Phe Ser Asp Ser Trp Ile
            260                 265                 270
His Trp Val Arg Gln Ala Pro Gly Lys Gly Leu Glu Trp Val Ala Trp
        275                 280                 285
Ile Ser Pro Tyr Gly Gly Ser Thr Tyr Tyr Ala Asp Ser Val Lys Gly
290                 295                 300
Arg Phe Thr Ile Ser Ala Asp Thr Ser Lys Asn Thr Ala Tyr Leu Gln
305                 310                 315                 320
Met Asn Ser Leu Arg Ala Glu Asp Thr Ala Val Tyr Tyr Cys Ala Arg
                325                 330                 335
Arg His Trp Pro Gly Gly Phe Asp Tyr Trp Gly Gln Gly Thr Leu Val
            340                 345                 350
Thr Val Ser Ser Gly Gly Gly Gly Ser Ile Glu Gly Arg Gly Gly Gly
        355                 360                 365
Gly Ser Lys Asn Ala Gln Cys Lys Lys Lys Leu Gln Ala Leu Lys Lys
370                 375                 380
Lys Asn Ala Gln Leu Lys Trp Lys Leu Gln Ala Leu Lys Lys Lys Leu
385                 390                 395                 400
Ala Gln Gly His His His His His His
                405

<210> SEQ ID NO 188
<211> LENGTH: 391
<212> TYPE: PRT
<213> ORGANISM: Artificial Sequence
<220> FEATURE:
<223> OTHER INFORMATION: Anti-EpCAM VL-CL, Ipilimumab VL, FXa, acid coil

<400> SEQUENCE: 188

Glu Leu Val Met Thr Gln Ser Pro Ser Ser Leu Thr Val Thr Ala Gly
1               5                   10                  15
Glu Lys Val Thr Met Ser Cys Lys Ser Ser Gln Ser Leu Leu Asn Ser
            20                  25                  30
Gly Asn Gln Lys Asn Tyr Leu Thr Trp Tyr Gln Gln Lys Pro Gly Gln
        35                  40                  45
Pro Pro Lys Leu Leu Ile Tyr Trp Ala Ser Thr Arg Glu Ser Gly Val
    50                  55                  60
Pro Asp Arg Phe Thr Gly Ser Gly Ser Gly Thr Asp Phe Thr Leu Thr
```

65                  70                  75                  80
Ile Ser Ser Val Gln Ala Glu Asp Leu Ala Val Tyr Tyr Cys Gln Asn
                    85                  90                  95

Asp Tyr Ser Tyr Pro Leu Thr Phe Gly Ala Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys Gly Gly Gly Gly
        210                 215                 220

Ser Gly Gly Gly Gly Ser Gly Gly Gly Gly Ser Glu Ile Val Leu Thr
225                 230                 235                 240

Gln Ser Pro Gly Thr Leu Ser Leu Ser Pro Gly Glu Arg Ala Thr Leu
                245                 250                 255

Ser Cys Arg Ala Ser Gln Ser Val Gly Ser Ser Tyr Leu Ala Trp Tyr
                260                 265                 270

Gln Gln Lys Pro Gly Gln Ala Pro Arg Leu Leu Ile Tyr Gly Ala Phe
            275                 280                 285

Ser Arg Ala Thr Gly Ile Pro Asp Arg Phe Ser Gly Ser Gly Ser Gly
        290                 295                 300

Thr Asp Phe Thr Leu Thr Ile Ser Arg Leu Glu Pro Glu Asp Phe Ala
305                 310                 315                 320

Val Tyr Tyr Cys Gln Gln Tyr Gly Ser Ser Pro Trp Thr Phe Gly Gln
                325                 330                 335

Gly Thr Lys Val Glu Ile Lys Gly Gly Gly Ser Ile Glu Gly Arg
                340                 345                 350

Gly Gly Ser Gly Gly Gly Ser Glu Asn Ala Gln Cys Glu Lys Glu Leu
            355                 360                 365

Gln Ala Leu Glu Lys Glu Asn Ala Gln Leu Glu Trp Glu Leu Gln Ala
        370                 375                 380

Leu Glu Lys Glu Leu Ala Gln
385                 390

<210> SEQ ID NO 189
<211> LENGTH: 411
<212> TYPE: PRT
<213> ORGANISM: Artificial Sequence
<220> FEATURE:
<223> OTHER INFORMATION: Anti-EpCAM VH-CH1, Ipilimumab VH, FXa, basic
      coil

<400> SEQUENCE: 189

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
                20                  25                  30

```
Tyr Trp Leu Gly Trp Val Lys Gln Arg Pro His Gly Leu Glu Trp
             35                  40                  45
Ile Gly Asp Ile Phe Pro Gly Ser Gly Asn Ile His Tyr Asn Glu Lys
 50                  55                  60
Phe Lys Gly Lys Ala Thr Leu Thr Ala Asp Lys Ser Ser Ser Thr Ala
 65                  70                  75                  80
Tyr Met Gln Leu Ser Ser Leu Thr Phe Glu Asp Ser Ala Val Tyr Phe
                 85                  90                  95
Cys Ala Arg Leu Arg Asn Trp Asp Glu Pro Met Asp Tyr Trp Gly Gln
            100                 105                 110
Gly Thr Thr Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
210                 215                 220
Lys Thr His Thr Gly Gly Gly Gly Ser Gly Gly Gly Gly Ser Gln Val
225                 230                 235                 240
Gln Leu Val Glu Ser Gly Gly Gly Val Val Gln Pro Gly Arg Ser Leu
                245                 250                 255
Arg Leu Ser Cys Ala Ala Ser Gly Phe Thr Phe Ser Ser Tyr Thr Met
            260                 265                 270
His Trp Val Arg Gln Ala Pro Gly Lys Gly Leu Glu Trp Val Thr Phe
        275                 280                 285
Ile Ser Tyr Asp Gly Asn Asn Lys Tyr Tyr Ala Asp Ser Val Lys Gly
290                 295                 300
Arg Phe Thr Ile Ser Arg Asp Asn Ser Lys Asn Thr Leu Tyr Leu Gln
305                 310                 315                 320
Met Asn Ser Leu Arg Ala Glu Asp Thr Ala Ile Tyr Tyr Cys Ala Arg
                325                 330                 335
Thr Gly Trp Leu Gly Pro Phe Asp Tyr Trp Gly Gln Gly Thr Leu Val
            340                 345                 350
Thr Val Ser Ser Gly Gly Gly Gly Ser Ile Glu Gly Arg Gly Gly Ser
        355                 360                 365
Gly Gly Gly Ser Lys Asn Ala Gln Cys Lys Lys Leu Gln Ala Leu
            370                 375                 380
Lys Lys Lys Asn Ala Gln Leu Lys Trp Lys Leu Gln Ala Leu Lys Lys
385                 390                 395                 400
Lys Leu Ala Gln Gly His His His His His
            405                 410

<210> SEQ ID NO 190
<211> LENGTH: 392
<212> TYPE: PRT
<213> ORGANISM: Artificial Sequence
<220> FEATURE:
<223> OTHER INFORMATION: Anti-EpCAM VL-CL, SP34 VL, FXa, acid coil
```

<400> SEQUENCE: 190

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Arg Ser Ser Thr Gly Ala Val Thr Ala Ser Asn Tyr Ala Asn Trp
            260                 265                 270

Val Gln Gln Lys Pro Gly Gln Ala Pro Arg Gly Leu Ile Gly Gly Thr
        275                 280                 285

Asn Lys Arg Ala Pro Trp Thr Pro Ala Arg Phe Ser Gly Ser Leu Leu
    290                 295                 300

Gly Gly Lys Ala Ala Leu Thr Ile Thr Gly Ala Gln Ala Glu Asp Glu
305                 310                 315                 320

Ala Asp Tyr Tyr Cys Ala Leu Trp Tyr Ser Asn Leu Trp Val Phe Gly
                325                 330                 335

Gly Gly Thr Lys Leu Thr Val Leu Gly Gly Gly Gly Ser Ile Glu Gly
            340                 345                 350

Arg Gly Gly Ser Gly Gly Gly Ser Glu Asn Ala Gln Cys Glu Lys Glu
        355                 360                 365

Leu Gln Ala Leu Glu Lys Glu Asn Ala Gln Leu Glu Trp Glu Leu Gln
    370                 375                 380

Ala Leu Glu Lys Glu Leu Ala Gln
385                 390

<210> SEQ ID NO 191
<211> LENGTH: 490
<212> TYPE: PRT
<213> ORGANISM: Artificial Sequence
<220> FEATURE:
<223> OTHER INFORMATION: Anti-EpCAM VH 44Cys, Sp34 VH, FXa, Fc

<400> SEQUENCE: 191

```
Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Cys Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Gly Gly Ser Gly Gly Gly Gly
        115                 120                 125

Ser Glu Val Gln Leu Val Glu Ser Gly Gly Gly Leu Val Lys Pro Gly
    130                 135                 140

Gly Ser Leu Arg Leu Ser Cys Ala Ala Ser Gly Phe Thr Phe Asn Thr
145                 150                 155                 160

Tyr Ala Met Asn Trp Val Arg Gln Ala Pro Gly Lys Gly Leu Glu Trp
                165                 170                 175

Val Ala Arg Ile Arg Ser Lys Tyr Asn Asn Tyr Ala Thr Tyr Tyr Ala
            180                 185                 190

Asp Ser Val Lys Gly Arg Phe Thr Ile Ser Arg Asp Asp Ser Lys Asn
        195                 200                 205

Ser Leu Tyr Leu Gln Met Asn Ser Leu Lys Thr Glu Asp Thr Ala Val
    210                 215                 220

Tyr Tyr Cys Val Arg His Gly Asn Phe Gly Asn Ser Tyr Val Ser Trp
225                 230                 235                 240

Phe Ala Tyr Trp Gly Gln Gly Thr Leu Val Thr Val Ser Ser Gly Gly
                245                 250                 255

Gly Ile Glu Gly Arg Gly Gly Gly Asp Lys Thr His Thr Cys Pro Pro
            260                 265                 270

Cys Pro Ala Pro Glu Leu Leu Gly Gly Pro Ser Val Phe Leu Phe Pro
        275                 280                 285

Pro Lys Pro Lys Asp Thr Leu Met Ile Ser Arg Thr Pro Glu Val Thr
    290                 295                 300

Cys Val Val Val Asp Val Ser His Glu Asp Pro Glu Val Lys Phe Asn
305                 310                 315                 320

Trp Tyr Val Asp Gly Val Glu Val His Asn Ala Lys Thr Lys Pro Arg
                325                 330                 335

Glu Glu Gln Tyr Gln Ser Thr Tyr Arg Val Val Ser Val Leu Thr Val
            340                 345                 350

Leu His Gln Asp Trp Leu Asn Gly Lys Glu Tyr Lys Cys Lys Val Ser
        355                 360                 365

Asn Lys Ala Leu Pro Ala Pro Ile Glu Lys Thr Ile Ser Lys Ala Lys
```

```
                370                 375                 380
Gly Gln Pro Arg Glu Pro Gln Val Tyr Thr Leu Pro Pro Ser Arg Asp
385                 390                 395                 400

Glu Leu Thr Lys Asn Gln Val Lys Leu Thr Cys Leu Val Lys Gly Phe
                405                 410                 415

Tyr Pro Ser Asp Ile Ala Val Glu Trp Glu Ser Asn Gly Gln Pro Glu
                420                 425                 430

Asn Asn Tyr Lys Thr Thr Pro Pro Val Leu Asp Ser Asp Gly Ser Phe
                435                 440                 445

Phe Leu Tyr Ser Leu Leu Thr Val Asp Lys Ser Arg Trp Gln Gln Gly
            450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly
                485                 490

<210> SEQ ID NO 192
<211> LENGTH: 467
<212> TYPE: PRT
<213> ORGANISM: Artificial Sequence
<220> FEATURE:
<223> OTHER INFORMATION: Anti-EpCAM VL 100 Cys, Ipilimumab VL, FXa, Fc

<400> SEQUENCE: 192

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Cys Gly Thr Lys Leu Glu Ile
                100                 105                 110

Lys Gly Gly Gly Gly Ser Gly Gly Gly Ser Glu Ile Val Leu Thr
            115                 120                 125

Gln Ser Pro Gly Thr Leu Ser Leu Ser Pro Gly Glu Arg Ala Thr Leu
        130                 135                 140

Ser Cys Arg Ala Ser Gln Ser Val Gly Ser Ser Tyr Leu Ala Trp Tyr
145                 150                 155                 160

Gln Gln Lys Pro Gly Gln Ala Pro Arg Leu Leu Ile Tyr Gly Ala Phe
                165                 170                 175

Ser Arg Ala Thr Gly Ile Pro Asp Arg Phe Ser Gly Ser Gly Ser Gly
            180                 185                 190

Thr Asp Phe Thr Leu Thr Ile Ser Arg Leu Glu Pro Glu Asp Phe Ala
        195                 200                 205

Val Tyr Tyr Cys Gln Gln Tyr Gly Ser Ser Pro Trp Thr Phe Gly Gln
        210                 215                 220

Gly Thr Lys Val Glu Ile Lys Gly Gly Gly Ile Glu Gly Arg Gly Gly
225                 230                 235                 240

Gly Asp Lys Thr His Thr Cys Pro Pro Cys Pro Ala Pro Glu Leu Leu
```

-continued

```
                245                 250                 255
Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Gln Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Asp Glu Leu Thr Lys Asn Gln Val
    370                 375                 380

Ser Leu Thr Cys Leu Val Ser Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Lys Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly
465

<210> SEQ ID NO 193
<211> LENGTH: 483
<212> TYPE: PRT
<213> ORGANISM: Artificial Sequence
<220> FEATURE:
<223> OTHER INFORMATION: Anti-EpCAM VH 44 Cys, Ipilimumab VH, FXa, Fc

<400> SEQUENCE: 193

Glu Val Gln Leu Leu Glu Gln Ser Gly Ala Glu Leu Val Arg Pro Gly
1               5                  10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Cys Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Gly Gly Gly Ser Gly Gly Gly Gly
        115                 120                 125

Ser Gln Val Gln Leu Val Glu Ser Gly Gly Gly Val Val Gln Pro Gly
```

```
                130                 135                 140
Arg Ser Leu Arg Leu Ser Cys Ala Ala Ser Gly Phe Thr Phe Ser Ser
145                 150                 155                 160

Tyr Thr Met His Trp Val Arg Gln Ala Pro Gly Lys Gly Leu Glu Trp
                165                 170                 175

Val Thr Phe Ile Ser Tyr Asp Gly Asn Asn Lys Tyr Tyr Ala Asp Ser
            180                 185                 190

Val Lys Gly Arg Phe Thr Ile Ser Arg Asp Asn Ser Lys Asn Thr Leu
                195                 200                 205

Tyr Leu Gln Met Asn Ser Leu Arg Ala Glu Asp Thr Ala Ile Tyr Tyr
            210                 215                 220

Cys Ala Arg Thr Gly Trp Leu Gly Pro Phe Asp Tyr Trp Gly Gln Gly
225                 230                 235                 240

Thr Leu Val Thr Val Ser Ser Gly Gly Gly Ile Glu Gly Arg Gly Gly
                245                 250                 255

Gly Asp Lys Thr His Thr Cys Pro Pro Cys Pro Ala Pro Glu Leu Leu
            260                 265                 270

Gly Gly Pro Ser Val Phe Leu Phe Pro Pro Lys Pro Lys Asp Thr Leu
            275                 280                 285

Met Ile Ser Arg Thr Pro Glu Val Thr Cys Val Val Val Asp Val Ser
    290                 295                 300

His Glu Asp Pro Glu Val Lys Phe Asn Trp Tyr Val Asp Gly Val Glu
305                 310                 315                 320

Val His Asn Ala Lys Thr Lys Pro Arg Glu Glu Gln Tyr Gln Ser Thr
                325                 330                 335

Tyr Arg Val Val Ser Val Leu Thr Val Leu His Gln Asp Trp Leu Asn
            340                 345                 350

Gly Lys Glu Tyr Lys Cys Lys Val Ser Asn Lys Ala Leu Pro Ala Pro
        355                 360                 365

Ile Glu Lys Thr Ile Ser Lys Ala Lys Gly Gln Pro Arg Glu Pro Gln
    370                 375                 380

Val Tyr Thr Leu Pro Pro Ser Arg Asp Glu Leu Thr Lys Asn Gln Val
385                 390                 395                 400

Lys Leu Thr Cys Leu Val Lys Gly Phe Tyr Pro Ser Asp Ile Ala Val
                405                 410                 415

Glu Trp Glu Ser Asn Gly Gln Pro Glu Asn Asn Tyr Lys Thr Thr Pro
            420                 425                 430

Pro Val Leu Asp Ser Asp Gly Ser Phe Phe Leu Tyr Ser Leu Leu Thr
            435                 440                 445

Val Asp Lys Ser Arg Trp Gln Gln Gly Asn Val Phe Ser Cys Ser Val
450                 455                 460

Met His Glu Ala Leu His Asn His Tyr Thr Gln Lys Ser Leu Ser Leu
465                 470                 475                 480

Ser Pro Gly

<210> SEQ ID NO 194
<211> LENGTH: 468
<212> TYPE: PRT
<213> ORGANISM: Artificial Sequence
<220> FEATURE:
<223> OTHER INFORMATION: Anti-EpCAM VL 100 Cys, SP34 VL, FXa, Fc

<400> SEQUENCE: 194

Glu Leu Val Met Thr Gln Ser Pro Ser Ser Leu Thr Val Thr Ala Gly
1               5                   10                  15
```

```
Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Cys Gln Asn
                85                  90                  95

Asp Tyr Ser Tyr Pro Leu Thr Phe Gly Cys Gly Thr Lys Leu Glu Ile
            100                 105                 110

Lys Gly Gly Gly Gly Ser Gly Gly Gly Ser Gln Ala Val Val Thr
            115                 120                 125

Gln Glu Pro Ser Leu Thr Val Ser Pro Gly Gly Thr Val Thr Leu Thr
    130                 135                 140

Cys Arg Ser Ser Thr Gly Ala Val Thr Ala Ser Asn Tyr Ala Asn Trp
145                 150                 155                 160

Val Gln Gln Lys Pro Gly Gln Ala Pro Arg Gly Leu Ile Gly Gly Thr
                165                 170                 175

Asn Lys Arg Ala Pro Trp Thr Pro Ala Arg Phe Ser Gly Ser Leu Leu
            180                 185                 190

Gly Gly Lys Ala Ala Leu Thr Ile Thr Gly Ala Gln Ala Glu Asp Glu
            195                 200                 205

Ala Asp Tyr Tyr Cys Ala Leu Trp Tyr Ser Asn Leu Trp Val Phe Gly
210                 215                 220

Gly Gly Thr Lys Leu Thr Val Leu Gly Gly Ile Glu Gly Arg Gly
225                 230                 235                 240

Gly Gly Asp Lys Thr His Thr Cys Pro Pro Cys Pro Ala Pro Glu Leu
            245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Gln Ser
305                 310                 315                 320

Thr Tyr Arg Val Val Ser Val Leu Thr Val Leu His Gln Asp Trp Leu
            325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Ser Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Lys Leu Tyr Ser Lys Leu
            420                 425                 430
```

-continued

```
Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly
465

<210> SEQ ID NO 195
<211> LENGTH: 411
<212> TYPE: PRT
<213> ORGANISM: Artificial Sequence
<220> FEATURE:
<223> OTHER INFORMATION: Anti-EpCAM VH-CH1, Theralizumab VH, FXa, Fc

<400> SEQUENCE: 195

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Gly Gly Gly Gly Ser Glu Val
225                 230                 235                 240

Gln Leu Val Glu Ser Gly Gly Leu Val Gln Pro Gly Gly Ser Leu
                245                 250                 255

Arg Leu Ser Cys Ala Ala Ser Gly Phe Thr Phe Ser Asp Ser Trp Ile
            260                 265                 270

His Trp Val Arg Gln Ala Pro Gly Lys Gly Leu Glu Trp Val Ala Trp
        275                 280                 285

Ile Ser Pro Tyr Gly Gly Ser Thr Tyr Tyr Ala Asp Ser Val Lys Gly
    290                 295                 300

Arg Phe Thr Ile Ser Ala Asp Thr Ser Lys Asn Thr Ala Tyr Leu Gln
305                 310                 315                 320
```

```
Met Asn Ser Leu Arg Ala Glu Asp Thr Ala Val Tyr Tyr Cys Ala Arg
            325                 330                 335

Arg His Trp Pro Gly Gly Phe Asp Tyr Trp Gly Gln Gly Thr Leu Val
        340                 345                 350

Thr Val Ser Ser Gly Gly Gly Gly Ser Ile Glu Gly Arg Gly Gly Ser
            355                 360                 365

Gly Gly Gly Ser Lys Asn Ala Gln Cys Lys Lys Leu Gln Ala Leu
        370                 375                 380

Lys Lys Lys Asn Ala Gln Leu Lys Trp Lys Leu Gln Ala Leu Lys Lys
385                 390                 395                 400

Lys Leu Ala Gln Gly His His His His His His
            405                 410

<210> SEQ ID NO 196
<211> LENGTH: 578
<212> TYPE: PRT
<213> ORGANISM: Artificial Sequence
<220> FEATURE:
<223> OTHER INFORMATION: Anti-EpCAM VL-CL, Theralizumab VL, FXa, Fc

<400> SEQUENCE: 196

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Asp Ile Gln Met Thr
225                 230                 235                 240

Gln Ser Pro Ser Ser Leu Ser Ala Ser Val Gly Asp Arg Val Thr Ile
                245                 250                 255

Thr Cys His Ala Ser Gln Asn Ile Tyr Val Trp Leu Asn Trp Tyr Gln
            260                 265                 270
```

```
Gln Lys Pro Gly Lys Ala Pro Lys Leu Leu Ile Tyr Lys Ala Ser Asn
            275                 280                 285

Leu His Thr Gly Val Pro Ser Arg Phe Ser Gly Ser Gly Ser Gly Thr
    290                 295                 300

Asp Phe Thr Leu Thr Ile Ser Ser Leu Gln Pro Glu Asp Phe Ala Thr
305                 310                 315                 320

Tyr Tyr Cys Gln Gln Gly Gln Thr Tyr Pro Tyr Thr Phe Gly Gly Gly
                325                 330                 335

Thr Lys Val Glu Ile Lys Gly Gly Ile Glu Gly Arg Gly Gly Gly
            340                 345                 350

Asp Lys Thr His Thr Cys Pro Pro Cys Pro Ala Pro Glu Leu Leu Gly
            355                 360                 365

Gly Pro Ser Val Phe Leu Phe Pro Pro Lys Pro Lys Asp Thr Leu Met
    370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Gln Ser Thr Tyr
            420                 425                 430

Arg Val Val Ser Val Leu Thr Val Leu His Gln Asp Trp Leu Asn Gly
        435                 440                 445

Lys Glu Tyr Lys Cys Lys Val Ser Asn Lys Ala Leu Pro Ala Pro Ile
    450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Asp Glu Leu Thr Lys Asn Gln Val Ser
                485                 490                 495

Leu Thr Cys Leu Val Ser Gly Phe Tyr Pro Ser Asp Ile Ala Val Glu
            500                 505                 510

Trp Glu Ser Asn Gly Gln Pro Glu Asn Tyr Lys Thr Thr Pro Pro
        515                 520                 525

Val Leu Asp Ser Asp Gly Ser Phe Lys Leu Tyr Ser Lys Leu Thr Val
    530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
                565                 570                 575

Pro Gly

<210> SEQ ID NO 197
<211> LENGTH: 595
<212> TYPE: PRT
<213> ORGANISM: Artificial Sequence
<220> FEATURE:
<223> OTHER INFORMATION: Anti-EpCAM VH-CH1, Urelumab VH, FXa, Fc

<400> SEQUENCE: 197

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
```

-continued

```
            50                  55                  60
Phe Lys Gly Lys Ala Thr Leu Thr Ala Asp Lys Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Gly Gly Gly Gly Ser Gly Gly Gly Gly Ser Gln Val
225                 230                 235                 240

Gln Leu Gln Gln Trp Gly Ala Gly Leu Leu Lys Pro Ser Glu Thr Leu
                245                 250                 255

Ser Leu Thr Cys Ala Val Tyr Gly Gly Ser Phe Ser Gly Tyr Tyr Trp
                260                 265                 270

Ser Trp Ile Arg Gln Ser Pro Glu Lys Gly Leu Glu Trp Ile Gly Glu
            275                 280                 285

Ile Asn His Gly Gly Tyr Val Thr Tyr Asn Pro Ser Leu Glu Ser Arg
            290                 295                 300

Val Thr Ile Ser Val Asp Thr Ser Lys Asn Gln Phe Ser Leu Lys Leu
305                 310                 315                 320

Ser Ser Val Thr Ala Ala Asp Thr Ala Val Tyr Tyr Cys Ala Arg Asp
                325                 330                 335

Tyr Gly Pro Gly Asn Tyr Asp Trp Tyr Phe Asp Leu Trp Gly Arg Gly
                340                 345                 350

Thr Leu Val Thr Val Ser Ser Gly Gly Gly Ile Glu Gly Arg Gly Gly
                355                 360                 365

Gly Asp Lys Thr His Thr Cys Pro Pro Cys Pro Ala Pro Glu Leu Leu
            370                 375                 380

Gly Gly Pro Ser Val Phe Leu Phe Pro Pro Lys Pro Lys Asp Thr Leu
385                 390                 395                 400

Met Ile Ser Arg Thr Pro Glu Val Thr Cys Val Val Val Asp Val Ser
                405                 410                 415

His Glu Asp Pro Glu Val Lys Phe Asn Trp Tyr Val Asp Gly Val Glu
                420                 425                 430

Val His Asn Ala Lys Thr Lys Pro Arg Glu Glu Gln Tyr Gln Ser Thr
            435                 440                 445

Tyr Arg Val Val Ser Val Leu Thr Val Leu His Gln Asp Trp Leu Asn
            450                 455                 460

Gly Lys Glu Tyr Lys Cys Lys Val Ser Asn Lys Ala Leu Pro Ala Pro
465                 470                 475                 480
```

```
Ile Glu Lys Thr Ile Ser Lys Ala Lys Gly Gln Pro Arg Glu Pro Gln
                485                 490                 495

Val Tyr Thr Leu Pro Pro Ser Arg Asp Glu Leu Thr Lys Asn Gln Val
            500                 505                 510

Lys Leu Thr Cys Leu Val Lys Gly Phe Tyr Pro Ser Asp Ile Ala Val
        515                 520                 525

Glu Trp Glu Ser Asn Gly Gln Pro Glu Asn Asn Tyr Lys Thr Thr Pro
    530                 535                 540

Pro Val Leu Asp Ser Asp Gly Ser Phe Phe Leu Tyr Ser Leu Leu Thr
545                 550                 555                 560

Val Asp Lys Ser Arg Trp Gln Gln Gly Asn Val Phe Ser Cys Ser Val
                565                 570                 575

Met His Glu Ala Leu His Asn His Tyr Thr Gln Lys Ser Leu Ser Leu
            580                 585                 590

Ser Pro Gly
        595

<210> SEQ ID NO 198
<211> LENGTH: 578
<212> TYPE: PRT
<213> ORGANISM: Artificial Sequence
<220> FEATURE:
<223> OTHER INFORMATION: Anti-EpCAM VL-CL, Urelumab VL, FXa, Fc

<400> SEQUENCE: 198

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
    210                 215                 220

Ser Gly Gly Gly Gly Ser Gly Gly Gly Gly Ser Asp Ile Gln Met Thr
225                 230                 235                 240
```

```
Gln Ser Pro Ser Ser Leu Ser Ala Ser Val Gly Asp Arg Val Thr Ile
                245                 250                 255

Thr Cys His Ala Ser Gln Asn Ile Tyr Val Trp Leu Asn Trp Tyr Gln
            260                 265                 270

Gln Lys Pro Gly Lys Ala Pro Lys Leu Leu Ile Tyr Lys Ala Ser Asn
        275                 280                 285

Leu His Thr Gly Val Pro Ser Arg Phe Ser Gly Ser Gly Ser Gly Thr
    290                 295                 300

Asp Phe Thr Leu Thr Ile Ser Ser Leu Gln Pro Glu Asp Phe Ala Thr
305                 310                 315                 320

Tyr Tyr Cys Gln Gln Gly Gln Thr Tyr Pro Tyr Thr Phe Gly Gly Gly
                325                 330                 335

Thr Lys Val Glu Ile Lys Gly Gly Gly Ile Glu Gly Arg Gly Gly Gly
            340                 345                 350

Asp Lys Thr His Thr Cys Pro Pro Cys Pro Ala Pro Glu Leu Leu Gly
        355                 360                 365

Gly Pro Ser Val Phe Leu Phe Pro Pro Lys Pro Lys Asp Thr Leu Met
    370                 375                 380

Ile Ser Arg Thr Pro Glu Val Thr Cys Val Val Val Asp Val Ser His
385                 390                 395                 400

Glu Asp Pro Glu Val Lys Phe Asn Trp Tyr Val Asp Gly Val Glu Val
                405                 410                 415

His Asn Ala Lys Thr Lys Pro Arg Glu Glu Gln Tyr Gln Ser Thr Tyr
            420                 425                 430

Arg Val Val Ser Val Leu Thr Val Leu His Gln Asp Trp Leu Asn Gly
        435                 440                 445

Lys Glu Tyr Lys Cys Lys Val Ser Asn Lys Ala Leu Pro Ala Pro Ile
    450                 455                 460

Glu Lys Thr Ile Ser Lys Ala Lys Gly Gln Pro Arg Glu Pro Gln Val
465                 470                 475                 480

Tyr Thr Leu Pro Pro Ser Arg Asp Glu Leu Thr Lys Asn Gln Val Ser
                485                 490                 495

Leu Thr Cys Leu Val Ser Gly Phe Tyr Pro Ser Asp Ile Ala Val Glu
            500                 505                 510

Trp Glu Ser Asn Gly Gln Pro Glu Asn Asn Tyr Lys Thr Thr Pro Pro
        515                 520                 525

Val Leu Asp Ser Asp Gly Ser Phe Lys Leu Tyr Ser Lys Leu Thr Val
    530                 535                 540

Asp Lys Ser Arg Trp Gln Gln Gly Asn Val Phe Ser Cys Ser Val Met
545                 550                 555                 560

His Glu Ala Leu His Asn His Tyr Thr Gln Lys Ser Leu Ser Leu Ser
                565                 570                 575

Pro Gly

<210> SEQ ID NO 199
<211> LENGTH: 580
<212> TYPE: PRT
<213> ORGANISM: Artificial Sequence
<220> FEATURE:
<223> OTHER INFORMATION: Anti-EpCAM VL-CL, Dummy VL, FXa, Fc

<400> SEQUENCE: 199

Glu Leu Val Met Thr Gln Ser Pro Ser Ser Leu Thr Val Thr Ala Gly
1               5                   10                  15
```

-continued

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Gly Gly Gly Gly
210                 215                 220

Ser Gly Gly Gly Gly Ser Gly Gly Gly Gly Ser Gln Ala Val Val Thr
225                 230                 235                 240

Gln Glu Pro Ser Leu Thr Val Ser Pro Gly Gly Thr Val Thr Leu Thr
                245                 250                 255

Cys Arg Ser Ser Thr Gly Ala Val Thr Thr Ser Asn Tyr Ala Asn Trp
            260                 265                 270

Val Gln Gln Lys Pro Gly Gln Ala Pro Arg Gly Leu Ile Gly Gly Thr
        275                 280                 285

Asn Lys Arg Ala Pro Trp Thr Pro Ala Arg Phe Ser Gly Ser Leu Leu
290                 295                 300

Gly Gly Lys Ala Ala Leu Thr Ile Thr Gly Ala Gln Ala Glu Asp Glu
305                 310                 315                 320

Ala Asp Tyr Tyr Cys Ala Leu Trp Tyr Ser Asn Leu Ala Val Phe Gly
                325                 330                 335

Gly Gly Thr Lys Leu Thr Val Leu Gly Gly Gly Ile Glu Gly Arg Gly
            340                 345                 350

Gly Gly Asp Lys Thr His Thr Cys Pro Pro Cys Pro Ala Pro Glu Leu
        355                 360                 365

Leu Gly Gly Pro Ser Val Phe Leu Phe Pro Pro Lys Pro Lys Asp Thr
370                 375                 380

Leu Met Ile Ser Arg Thr Pro Glu Val Thr Cys Val Val Val Asp Val
385                 390                 395                 400

Ser His Glu Asp Pro Glu Val Lys Phe Asn Trp Tyr Val Asp Gly Val
                405                 410                 415

Glu Val His Asn Ala Lys Thr Lys Pro Arg Glu Glu Gln Tyr Gln Ser
            420                 425                 430

Thr Tyr Arg Val Val Ser Val Leu Thr Val Leu His Gln Asp Trp Leu

```
            435                 440                 445
Asn Gly Lys Glu Tyr Lys Cys Lys Val Ser Asn Lys Ala Leu Pro Ala
450                 455                 460

Pro Ile Glu Lys Thr Ile Ser Lys Ala Lys Gly Gln Pro Arg Glu Pro
465                 470                 475                 480

Gln Val Tyr Thr Leu Pro Pro Ser Arg Asp Glu Leu Thr Lys Asn Gln
                    485                 490                 495

Val Ser Leu Thr Cys Leu Val Ser Gly Phe Tyr Pro Ser Asp Ile Ala
                500                 505                 510

Val Glu Trp Glu Ser Asn Gly Gln Pro Glu Asn Asn Tyr Lys Thr Thr
            515                 520                 525

Pro Pro Val Leu Asp Ser Asp Gly Ser Phe Lys Leu Tyr Ser Lys Leu
        530                 535                 540

Thr Val Asp Lys Ser Arg Trp Gln Gln Gly Asn Val Phe Ser Cys Ser
545                 550                 555                 560

Val Met His Glu Ala Leu His Asn His Tyr Thr Gln Lys Ser Leu Ser
                565                 570                 575

Leu Ser Pro Gly
            580

<210> SEQ ID NO 200
<211> LENGTH: 600
<212> TYPE: PRT
<213> ORGANISM: Artificial Sequence
<220> FEATURE:
<223> OTHER INFORMATION: Anti-EpCAM VH-CH1, Dummy VH, FXa, Fc

<400> SEQUENCE: 200

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
```

```
            210                 215                 220
Lys Thr His Thr Gly Gly Gly Ser Gly Gly Gly Ser Glu Val
225                 230                 235                 240

Gln Leu Val Glu Ser Gly Gly Leu Val Gln Pro Gly Gly Ser Leu
                245                 250                 255

Arg Leu Ser Cys Ala Ala Ser Gly Phe Thr Phe Ser Ser Tyr Ala Met
                260                 265                 270

Asn Trp Val Arg Gln Ala Pro Gly Lys Gly Leu Glu Trp Val Ala Arg
            275                 280                 285

Ile Ser Gly Ser Gly Gly Ser Thr Tyr Tyr Ala Asp Ser Val Lys Asp
        290                 295                 300

Arg Phe Thr Ile Ser Arg Asp Asp Ser Lys Asn Ser Leu Tyr Leu Gln
305                 310                 315                 320

Met Asn Ser Leu Lys Thr Glu Asp Thr Ala Val Tyr Tyr Cys Val Arg
                325                 330                 335

Gly Lys Gly Asn Thr His Lys Pro Tyr Gly Tyr Val Arg Tyr Phe Asp
                340                 345                 350

Val Trp Gly Gln Gly Thr Leu Val Thr Val Ser Ser Gly Gly Gly Ile
            355                 360                 365

Glu Gly Arg Gly Gly Gly Asp Lys Thr His Thr Cys Pro Pro Cys Pro
370                 375                 380

Ala Pro Glu Leu Leu Gly Gly Pro Ser Val Phe Leu Phe Pro Pro Lys
385                 390                 395                 400

Pro Lys Asp Thr Leu Met Ile Ser Arg Thr Pro Glu Val Thr Cys Val
                405                 410                 415

Val Val Asp Val Ser His Glu Asp Pro Glu Val Lys Phe Asn Trp Tyr
                420                 425                 430

Val Asp Gly Val Glu Val His Asn Ala Lys Thr Lys Pro Arg Glu Glu
            435                 440                 445

Gln Tyr Gln Ser Thr Tyr Arg Val Val Ser Val Leu Thr Val Leu His
        450                 455                 460

Gln Asp Trp Leu Asn Gly Lys Glu Tyr Lys Cys Lys Val Ser Asn Lys
465                 470                 475                 480

Ala Leu Pro Ala Pro Ile Glu Lys Thr Ile Ser Lys Ala Lys Gly Gln
                485                 490                 495

Pro Arg Glu Pro Gln Val Tyr Thr Leu Pro Pro Ser Arg Asp Glu Leu
                500                 505                 510

Thr Lys Asn Gln Val Lys Leu Thr Cys Leu Val Lys Gly Phe Tyr Pro
            515                 520                 525

Ser Asp Ile Ala Val Glu Trp Glu Ser Asn Gly Gln Pro Glu Asn Asn
        530                 535                 540

Tyr Lys Thr Thr Pro Pro Val Leu Asp Ser Asp Gly Ser Phe Phe Leu
545                 550                 555                 560

Tyr Ser Leu Leu Thr Val Asp Lys Ser Arg Trp Gln Gln Gly Asn Val
                565                 570                 575

Phe Ser Cys Ser Val Met His Glu Ala Leu His Asn His Tyr Thr Gln
                580                 585                 590

Lys Ser Leu Ser Leu Ser Pro Gly
            595                 600

<210> SEQ ID NO 201
<211> LENGTH: 32
<212> TYPE: PRT
<213> ORGANISM: Artificial Sequence
```

```
<220> FEATURE:
<223> OTHER INFORMATION: Basic coil

<400> SEQUENCE: 201

Lys Asn Ala Gln Cys Lys Lys Leu Gln Ala Leu Lys Lys Asn
1               5                   10                  15

Ala Gln Leu Lys Trp Lys Leu Gln Ala Leu Lys Lys Leu Ala Gln
            20                  25                  30

<210> SEQ ID NO 202
<211> LENGTH: 32
<212> TYPE: PRT
<213> ORGANISM: Artificial Sequence
<220> FEATURE:
<223> OTHER INFORMATION: Acid coil

<400> SEQUENCE: 202

Glu Asn Ala Gln Cys Glu Lys Glu Leu Gln Ala Leu Glu Lys Glu Asn
1               5                   10                  15

Ala Gln Leu Glu Trp Glu Leu Gln Ala Leu Glu Lys Glu Leu Ala Gln
            20                  25                  30

<210> SEQ ID NO 203
<211> LENGTH: 14
<212> TYPE: PRT
<213> ORGANISM: Artificial Sequence
<220> FEATURE:
<223> OTHER INFORMATION: Leucine zipper sequence

<400> SEQUENCE: 203

Gly Gly Gly Gly Ser Ile Glu Gly Arg Gly Gly Gly Gly Ser
1               5                   10

<210> SEQ ID NO 204
<211> LENGTH: 13
<212> TYPE: PRT
<213> ORGANISM: Artificial Sequence
<220> FEATURE:
<223> OTHER INFORMATION: Leucine zipper sequence

<400> SEQUENCE: 204

Gly Gly Pro Leu Gly Val Arg Gly Lys Gly Gly Gly Ser
1               5                   10

<210> SEQ ID NO 205
<211> LENGTH: 16
<212> TYPE: PRT
<213> ORGANISM: Artificial Sequence
<220> FEATURE:
<223> OTHER INFORMATION: Leucine zipper sequence

<400> SEQUENCE: 205

Gly Gly Gly Gly Ser Ile Glu Gly Arg Gly Gly Ser Gly Gly Gly Ser
1               5                   10                  15

<210> SEQ ID NO 206
<211> LENGTH: 10
<212> TYPE: PRT
<213> ORGANISM: Artificial Sequence
<220> FEATURE:
<223> OTHER INFORMATION: Hetero Fc sequence

<400> SEQUENCE: 206

Gly Gly Gly Ile Glu Gly Arg Gly Gly Gly
1               5                   10
```

<210> SEQ ID NO 207
<211> LENGTH: 12
<212> TYPE: PRT
<213> ORGANISM: Artificial Sequence
<220> FEATURE:
<223> OTHER INFORMATION: Hetero Fc sequence

<400> SEQUENCE: 207

Gly Gly Gly Gly Ser Ile Glu Gly Arg Gly Gly Gly
1               5                   10

<210> SEQ ID NO 208
<211> LENGTH: 5
<212> TYPE: PRT
<213> ORGANISM: Artificial Sequence
<220> FEATURE:
<223> OTHER INFORMATION: CH1 sequence

<400> SEQUENCE: 208

Ile Glu Gly Arg Gly
1               5

<210> SEQ ID NO 209
<211> LENGTH: 7
<212> TYPE: PRT
<213> ORGANISM: Artificial Sequence
<220> FEATURE:
<223> OTHER INFORMATION: CL sequence

<400> SEQUENCE: 209

Gly Gly Ile Glu Gly Arg Gly
1               5

<210> SEQ ID NO 210
<211> LENGTH: 6
<212> TYPE: PRT
<213> ORGANISM: Artificial Sequence
<220> FEATURE:
<223> OTHER INFORMATION: IgE CH2 sequence

<400> SEQUENCE: 210

Gly Ile Glu Gly Arg Gly
1               5

<210> SEQ ID NO 211
<211> LENGTH: 8
<212> TYPE: PRT
<213> ORGANISM: Artificial Sequence
<220> FEATURE:
<223> OTHER INFORMATION: IgE CH2 sequence

<400> SEQUENCE: 211

Gly Gly Gly Ile Glu Gly Arg Gly
1               5

<210> SEQ ID NO 212
<211> LENGTH: 593
<212> TYPE: PRT
<213> ORGANISM: Artificial Sequence
<220> FEATURE:
<223> OTHER INFORMATION: Anti-EpCAM VH-CH1, OKT3 VH, FXa, Fc

<400> SEQUENCE: 212

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn

```
                    20                  25                  30
Tyr Trp Leu Gly Trp Val Lys Gln Arg Pro Gly His Gly Leu Glu Trp
                35                  40                  45
Ile Gly Asp Ile Phe Pro Gly Ser Gly Asn Ile His Tyr Asn Glu Lys
 50                  55                  60
Phe Lys Gly Lys Ala Thr Leu Thr Ala Asp Lys Ser Ser Ser Thr Ala
 65                  70                  75                  80
Tyr Met Gln Leu Ser Ser Leu Thr Phe Glu Asp Ser Ala Val Tyr Phe
                85                  90                  95
Cys Ala Arg Leu Arg Asn Trp Asp Glu Pro Met Asp Tyr Trp Gly Gln
                100                 105                 110
Gly Thr Thr Val Thr Val Ser Ser Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr Gly Gly Gly Ser Gly Gly Gly Ser Asp Val
225                 230                 235                 240
Gln Leu Val Gln Ser Gly Ala Glu Val Lys Lys Pro Gly Ala Ser Val
                245                 250                 255
Lys Val Ser Cys Lys Ala Ser Gly Tyr Thr Phe Thr Arg Tyr Thr Met
                260                 265                 270
His Trp Val Arg Gln Ala Pro Gly Gln Gly Leu Glu Trp Ile Gly Tyr
                275                 280                 285
Ile Asn Pro Ser Arg Gly Tyr Thr Asn Tyr Ala Asp Ser Val Lys Gly
                290                 295                 300
Arg Phe Thr Ile Thr Thr Asp Lys Ser Thr Ser Thr Ala Tyr Met Glu
305                 310                 315                 320
Leu Ser Ser Leu Arg Ser Glu Asp Thr Ala Thr Tyr Tyr Cys Ala Arg
                325                 330                 335
Tyr Tyr Asp Asp His Tyr Cys Leu Asp Tyr Trp Gly Gln Gly Thr Thr
                340                 345                 350
Val Thr Val Ser Ser Gly Gly Ile Glu Gly Arg Gly Gly Gly Asp
                355                 360                 365
Lys Thr His Thr Cys Pro Pro Cys Pro Ala Pro Glu Leu Leu Gly Gly
                370                 375                 380
Pro Ser Val Phe Leu Phe Pro Pro Lys Pro Lys Asp Thr Leu Met Ile
385                 390                 395                 400
Ser Arg Thr Pro Glu Val Thr Cys Val Val Val Asp Val Ser His Glu
                405                 410                 415
Asp Pro Glu Val Lys Phe Asn Trp Tyr Val Asp Gly Val Glu Val His
                420                 425                 430
Asn Ala Lys Thr Lys Pro Arg Glu Glu Gln Tyr Gln Ser Thr Tyr Arg
                435                 440                 445
```

Val Val Ser Val Leu Thr Val Leu His Gln Asp Trp Leu Asn Gly Lys
    450                 455                 460

Glu Tyr Lys Cys Lys Val Ser Asn Lys Ala Leu Pro Ala Pro Ile Glu
465                 470                 475                 480

Lys Thr Ile Ser Lys Ala Lys Gly Gln Pro Arg Glu Pro Gln Val Tyr
                485                 490                 495

Thr Leu Pro Pro Ser Arg Asp Glu Leu Thr Lys Asn Gln Val Lys Leu
                500                 505                 510

Thr Cys Leu Val Lys Gly Phe Tyr Pro Ser Asp Ile Ala Val Glu Trp
                515                 520                 525

Glu Ser Asn Gly Gln Pro Glu Asn Asn Tyr Lys Thr Thr Pro Pro Val
                530                 535                 540

Leu Asp Ser Asp Gly Ser Phe Phe Leu Tyr Ser Leu Leu Thr Val Asp
545                 550                 555                 560

Lys Ser Arg Trp Gln Gln Gly Asn Val Phe Ser Cys Ser Val Met His
                565                 570                 575

Glu Ala Leu His Asn His Tyr Thr Gln Lys Ser Leu Ser Leu Ser Pro
                580                 585                 590

Gly

<210> SEQ ID NO 213
<211> LENGTH: 577
<212> TYPE: PRT
<213> ORGANISM: Artificial Sequence
<220> FEATURE:
<223> OTHER INFORMATION: Anti-EpCAM VL-CL, OKT3 VL, FXa, Fc

<400> SEQUENCE: 213

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys Gly Gly Gly
210                 215                 220

Ser Gly Gly Gly Ser Gly Gly Gly Ser Asp Ile Val Leu Thr
225                 230                 235                 240

Gln Ser Pro Ala Thr Leu Ser Leu Ser Pro Gly Glu Arg Ala Thr Leu
                245                 250                 255

Ser Cys Arg Ala Ser Gln Ser Val Ser Tyr Met Asn Trp Tyr Gln Gln
                260                 265                 270

Lys Pro Gly Lys Ala Pro Lys Arg Trp Ile Tyr Asp Thr Ser Lys Val
            275                 280                 285

Ala Ser Gly Val Pro Ala Arg Phe Ser Gly Ser Gly Ser Gly Thr Asp
            290                 295                 300

Tyr Ser Leu Thr Ile Asn Ser Leu Glu Ala Glu Asp Ala Ala Thr Tyr
305                 310                 315                 320

Tyr Cys Gln Gln Trp Ser Ser Asn Pro Leu Thr Phe Gly Gly Gly Thr
                325                 330                 335

Lys Val Glu Ile Lys Gly Gly Gly Ile Glu Gly Arg Gly Gly Asp
            340                 345                 350

Lys Thr His Thr Cys Pro Pro Cys Pro Ala Pro Glu Leu Leu Gly Gly
            355                 360                 365

Pro Ser Val Phe Leu Phe Pro Pro Lys Pro Lys Asp Thr Leu Met Ile
370                 375                 380

Ser Arg Thr Pro Glu Val Thr Cys Val Val Val Asp Val Ser His Glu
385                 390                 395                 400

Asp Pro Glu Val Lys Phe Asn Trp Tyr Val Asp Gly Val Glu Val His
                405                 410                 415

Asn Ala Lys Thr Lys Pro Arg Glu Glu Gln Tyr Gln Ser Thr Tyr Arg
            420                 425                 430

Val Val Ser Val Leu Thr Val Leu His Gln Asp Trp Leu Asn Gly Lys
            435                 440                 445

Glu Tyr Lys Cys Lys Val Ser Asn Lys Ala Leu Pro Ala Pro Ile Glu
450                 455                 460

Lys Thr Ile Ser Lys Ala Lys Gly Gln Pro Arg Glu Pro Gln Val Tyr
465                 470                 475                 480

Thr Leu Pro Pro Ser Arg Asp Glu Leu Thr Lys Asn Gln Val Ser Leu
                485                 490                 495

Thr Cys Leu Val Ser Gly Phe Tyr Pro Ser Asp Ile Ala Val Glu Trp
            500                 505                 510

Glu Ser Asn Gly Gln Pro Glu Asn Asn Tyr Lys Thr Thr Pro Pro Val
            515                 520                 525

Leu Asp Ser Asp Gly Ser Phe Lys Leu Tyr Ser Lys Leu Thr Val Asp
530                 535                 540

Lys Ser Arg Trp Gln Gln Gly Asn Val Phe Ser Cys Ser Val Met His
545                 550                 555                 560

Glu Ala Leu His Asn His Tyr Thr Gln Lys Ser Leu Ser Leu Ser Pro
                565                 570                 575

Gly

<210> SEQ ID NO 214
<211> LENGTH: 594
<212> TYPE: PRT
<213> ORGANISM: Artificial Sequence
<220> FEATURE:
<223> OTHER INFORMATION: Anti-EpCAM VH-CH1, anti-CD16A VH, FXa, Fc

```
<400> SEQUENCE: 214

Glu Val Gln Leu Leu Glu Gln Ser Gly Ala Glu Leu Val Arg Pro Gly
1               5                   10                  15

Thr Ser Val Lys Ile Ser Cys Lys Ala Ser Gly Tyr Ala Phe Thr Asn
            20                  25                  30

Tyr Trp Leu Gly Trp Val Lys Gln Arg Pro Gly His Gly Leu Glu Trp
        35                  40                  45

Ile Gly Asp Ile Phe Pro Gly Ser Gly Asn Ile His Tyr Asn Glu Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Phe Glu Asp Ser Ala Val Tyr Phe
                85                  90                  95

Cys Ala Arg Leu Arg Asn Trp Asp Glu Pro Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Gly Gly Gly Ser Gly Gly Gly Ser Gln Val
225                 230                 235                 240

Gln Leu Val Gln Ser Gly Ala Glu Val Lys Lys Pro Gly Glu Ser Leu
                245                 250                 255

Lys Val Ser Cys Lys Ala Ser Gly Tyr Thr Phe Thr Ser Tyr Tyr Met
            260                 265                 270

His Trp Val Arg Gln Ala Pro Gly Gln Gly Leu Glu Trp Met Gly Ile
        275                 280                 285

Ile Asn Pro Ser Gly Gly Ser Thr Ser Tyr Ala Gln Lys Phe Gln Gly
    290                 295                 300

Arg Val Thr Met Thr Arg Asp Thr Ser Thr Ser Thr Val Tyr Met Glu
305                 310                 315                 320

Leu Ser Ser Leu Arg Ser Glu Asp Thr Ala Val Tyr Tyr Cys Ala Arg
                325                 330                 335

Gly Ser Ala Tyr Tyr Tyr Asp Phe Ala Asp Tyr Trp Gly Gln Gly Thr
            340                 345                 350

Leu Val Thr Val Ser Ser Gly Gly Ile Glu Gly Arg Gly Gly Gly
        355                 360                 365

Asp Lys Thr His Thr Cys Pro Pro Cys Pro Ala Pro Glu Leu Leu Gly
    370                 375                 380

Gly Pro Ser Val Phe Leu Phe Pro Pro Lys Pro Lys Asp Thr Leu Met
385                 390                 395                 400

Ile Ser Arg Thr Pro Glu Val Thr Cys Val Val Val Asp Val Ser His
                405                 410                 415
```

Glu Asp Pro Glu Val Lys Phe Asn Trp Tyr Val Asp Gly Val Glu Val
            420                 425                 430

His Asn Ala Lys Thr Lys Pro Arg Glu Glu Gln Tyr Gln Ser Thr Tyr
            435                 440                 445

Arg Val Val Ser Val Leu Thr Val Leu His Gln Asp Trp Leu Asn Gly
450                 455                 460

Lys Glu Tyr Lys Cys Lys Val Ser Asn Lys Ala Leu Pro Ala Pro Ile
465                 470                 475                 480

Glu Lys Thr Ile Ser Lys Ala Lys Gly Gln Pro Arg Glu Pro Gln Val
            485                 490                 495

Tyr Thr Leu Pro Pro Ser Arg Asp Glu Leu Thr Lys Asn Gln Val Lys
            500                 505                 510

Leu Thr Cys Leu Val Lys Gly Phe Tyr Pro Ser Asp Ile Ala Val Glu
            515                 520                 525

Trp Glu Ser Asn Gly Gln Pro Glu Asn Asn Tyr Lys Thr Thr Pro Pro
            530                 535                 540

Val Leu Asp Ser Asp Gly Ser Phe Phe Leu Tyr Ser Leu Leu Thr Val
545                 550                 555                 560

Asp Lys Ser Arg Trp Gln Gln Gly Asn Val Phe Ser Cys Ser Val Met
            565                 570                 575

His Glu Ala Leu His Asn His Tyr Thr Gln Lys Ser Leu Ser Leu Ser
            580                 585                 590

Pro Gly

<210> SEQ ID NO 215
<211> LENGTH: 577
<212> TYPE: PRT
<213> ORGANISM: Artificial Sequence
<220> FEATURE:
<223> OTHER INFORMATION: Anti-EpCAM VL-CL, anti-CD16A VL, FXa, Fc

<400> SEQUENCE: 215

Glu Leu Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

```
Ser Thr Tyr Ser Leu Ser Ser Thr Leu Thr Leu Ser Lys Ala Asp Tyr
            180                 185                 190
Glu Lys His Lys Val Tyr Ala Cys Glu Val Thr His Gln Gly Leu Ser
        195                 200                 205
Ser Pro Val Thr Lys Ser Phe Asn Arg Gly Glu Cys Gly Gly Gly Gly
    210                 215                 220
Ser Gly Gly Gly Gly Ser Gly Gly Gly Gly Ser Ser Tyr Val Leu Thr
225                 230                 235                 240
Gln Pro Ser Ser Val Ser Val Ala Pro Gly Gln Thr Ala Thr Ile Ser
                245                 250                 255
Cys Gly Gly His Asn Ile Gly Ser Lys Asn Val His Trp Tyr Gln Gln
            260                 265                 270
Arg Pro Gly Gln Ser Pro Val Leu Val Ile Tyr Gln Asp Asn Lys Arg
        275                 280                 285
Pro Ser Gly Ile Pro Glu Arg Phe Ser Gly Ser Asn Ser Gly Asn Thr
    290                 295                 300
Ala Thr Leu Thr Ile Ser Gly Thr Gln Ala Met Asp Glu Ala Asp Tyr
305                 310                 315                 320
Tyr Cys Gln Val Trp Asp Asn Tyr Ser Val Leu Phe Gly Gly Gly Thr
                325                 330                 335
Lys Leu Thr Val Leu Gly Gly Gly Ile Glu Gly Arg Gly Gly Gly Asp
            340                 345                 350
Lys Thr His Thr Cys Pro Pro Cys Pro Ala Pro Glu Leu Leu Gly Gly
        355                 360                 365
Pro Ser Val Phe Leu Phe Pro Pro Lys Pro Lys Asp Thr Leu Met Ile
    370                 375                 380
Ser Arg Thr Pro Glu Val Thr Cys Val Val Val Asp Val Ser His Glu
385                 390                 395                 400
Asp Pro Glu Val Lys Phe Asn Trp Tyr Val Asp Gly Val Glu Val His
                405                 410                 415
Asn Ala Lys Thr Lys Pro Arg Glu Glu Gln Tyr Gln Ser Thr Tyr Arg
            420                 425                 430
Val Val Ser Val Leu Thr Val Leu His Gln Asp Trp Leu Asn Gly Lys
        435                 440                 445
Glu Tyr Lys Cys Lys Val Ser Asn Lys Ala Leu Pro Ala Pro Ile Glu
    450                 455                 460
Lys Thr Ile Ser Lys Ala Lys Gly Gln Pro Arg Glu Pro Gln Val Tyr
465                 470                 475                 480
Thr Leu Pro Pro Ser Arg Asp Glu Leu Thr Lys Asn Gln Val Ser Leu
                485                 490                 495
Thr Cys Leu Val Ser Gly Phe Tyr Pro Ser Asp Ile Ala Val Glu Trp
            500                 505                 510
Glu Ser Asn Gly Gln Pro Glu Asn Asn Tyr Lys Thr Thr Pro Pro Val
        515                 520                 525
Leu Asp Ser Asp Gly Ser Phe Lys Leu Tyr Ser Lys Leu Thr Val Asp
    530                 535                 540
Lys Ser Arg Trp Gln Gln Gly Asn Val Phe Ser Cys Ser Val Met His
545                 550                 555                 560
Glu Ala Leu His Asn His Tyr Thr Gln Lys Ser Leu Ser Leu Ser Pro
                565                 570                 575
Gly
```